United States Patent
Zhou

(10) Patent No.: US 11,541,391 B2
(45) Date of Patent: Jan. 3, 2023

(54) MAGNETIC SEPARATION DEVICE AND METHOD OF USE

(71) Applicant: Yuchen Zhou, San Jose, CA (US)

(72) Inventor: Yuchen Zhou, San Jose, CA (US)

(73) Assignee: Applied Cells Inc., Santa Clara, CA (US)

( * ) Notice: Subject to any disclaimer, the term of this patent is extended or adjusted under 35 U.S.C. 154(b) by 691 days.

(21) Appl. No.: 16/565,164

(22) Filed: Sep. 9, 2019

(65) Prior Publication Data

US 2020/0001298 A1 Jan. 2, 2020

Related U.S. Application Data

(63) Continuation of application No. 15/911,116, filed on Mar. 3, 2018, now Pat. No. 10,449,553, which is a
(Continued)

(51) Int. Cl.
*B01L 3/00* (2006.01)
*B03C 1/033* (2006.01)
(Continued)

(52) U.S. Cl.
CPC ........ *B01L 3/502753* (2013.01); *A61K 38/27* (2013.01); *B01D 21/283* (2013.01);
(Continued)

(58) Field of Classification Search
CPC ......... B01L 3/502753; B01L 3/502715; B01L 3/50273; B01L 3/502761; B01L 2200/027; B01L 2200/0647; B01L 2200/0652; B01L 2200/0668; B01L 2300/021; B01L 2300/0861; B01L 2300/0864; B01L 2400/043; B01L 2400/0436; B01L 2400/0439; B01L 2400/0457; B01L 2400/0487; B01L 2400/0496; A61K 38/27; B01D 21/283; B01D 35/06; B01F 31/86;
(Continued)

(56) References Cited

U.S. PATENT DOCUMENTS 4,759,775 A 7/1988 Peterson et al.
5,902,489 A 5/1999 Yusada et al.
(Continued)

FOREIGN PATENT DOCUMENTS

WO 2009132151 10/2009

OTHER PUBLICATIONS

Petersson et al., Separation of lipids from blood utilizing ultrasonic standing waves in microfludic channels, Analyst, 2004, 938-943, vol. 129.
(Continued)

*Primary Examiner* — Benjamin R Whatley
*Assistant Examiner* — Jean Caraballo-Leon
(74) *Attorney, Agent, or Firm* — Bing K. Yen

(57) ABSTRACT

The current invention relates to the method and apparatus to magnetically separate biological entities with magnetic labels from a fluid sample. The claimed magnetic separation device removes biological entities with magnetic labels from its fluidic solution by using a soft-magnetic center pole with two soft-magnetic side poles. The claimed device further includes processes to dissociate entities conglomerate after magnetic separation.

20 Claims, 93 Drawing Sheets

Related U.S. Application Data continuation of application No. 15/911,115, filed on Mar. 3, 2018.

(51) Int. Cl.

| | | |
|---|---|---|
| *B03C 1/28* | (2006.01) | |
| *B03C 1/30* | (2006.01) | |
| *G01N 1/40* | (2006.01) | |
| *G01N 33/49* | (2006.01) | |
| *B01D 21/28* | (2006.01) | |
| *B01F 11/02* | (2006.01) | |
| *G01N 33/543* | (2006.01) | |
| *G01N 35/00* | (2006.01) | |
| *A61K 38/27* | (2006.01) | |
| *C12Q 1/6806* | (2018.01) | |
| *B03C 1/005* | (2006.01) | |
| *B01D 35/06* | (2006.01) | |
| *G01N 27/74* | (2006.01) | |
| *B03C 1/23* | (2006.01) | |
| *G01N 15/00* | (2006.01) | |
| *B01F 31/86* | (2022.01) | |

(52) U.S. Cl.
CPC .............. *B01D 35/06* (2013.01); *B01F 31/86* (2022.01); *B01L 3/50273* (2013.01); *B01L 3/502715* (2013.01); *B01L 3/502761* (2013.01); *B03C 1/005* (2013.01); *B03C 1/0332* (2013.01); *B03C 1/23* (2013.01); *B03C 1/288* (2013.01); *B03C 1/30* (2013.01); *C12Q 1/6806* (2013.01); *G01N 1/4077* (2013.01); *G01N 15/00* (2013.01); *G01N 27/745* (2013.01); *G01N 33/491* (2013.01); *G01N 33/54326* (2013.01); *G01N 33/54333* (2013.01); *G01N 35/0098* (2013.01); *B01L 2200/027* (2013.01); *B01L 2200/0647* (2013.01); *B01L 2200/0652* (2013.01); *B01L 2200/0668* (2013.01); *B01L 2300/021* (2013.01); *B01L 2300/0861* (2013.01); *B01L 2300/0864* (2013.01); *B01L 2400/043* (2013.01); *B01L 2400/0436* (2013.01); *B01L 2400/0439* (2013.01); *B01L 2400/0457* (2013.01); *B01L 2400/0487* (2013.01); *B01L 2400/0496* (2013.01); *B03C 2201/18* (2013.01); *B03C 2201/20* (2013.01); *B03C 2201/26* (2013.01); *G01N 2035/00554* (2013.01)

(58) Field of Classification Search
CPC ......... B03C 1/005; B03C 1/0332; B03C 1/23; B03C 1/288; B03C 1/30; B03C 2201/18; B03C 2201/20; B03C 2201/26; B03C 1/01; C12Q 1/6806; G01N 1/4077; G01N 15/00; G01N 27/745; G01N 33/491; G01N 33/54326; G01N 33/54333; G01N 35/0098; G01N 2035/00554; G01N 2015/1006; G01N 2015/1486; G01N 2015/149; G01N 15/1459; C12M 23/16; C12M 47/04; C12M 47/06; C12N 5/00; C12N 15/1003; C12N 2509/10
See application file for complete search history.

(56) References Cited

U.S. PATENT DOCUMENTS

| | | |
|---|---|---|
| 5,972,721 A | 10/1999 | Bruno et al. |
| 6,216,538 B1 | 4/2001 | Yasuda et al. |
| 6,254,830 B1 | 7/2001 | Pivarnik et al. |
| 6,929,750 B2 | 8/2005 | Laurell et al. |
| 7,348,185 B2 | 3/2008 | Yamamichi |
| 7,474,184 B1* | 1/2009 | Humphries ........... B03C 1/0332 436/526 |
| 7,781,202 B2 | 8/2010 | Yamamichi |
| 8,273,302 B2 | 9/2012 | Takahashi et al. |
| 8,309,408 B2 | 11/2012 | Ward et al. |
| 8,573,060 B2 | 11/2013 | Huang et al. |
| 8,636,906 B2 | 1/2014 | Stein |
| 8,956,536 B2 | 2/2015 | Yu et al. |
| 8,986,944 B2 | 3/2015 | Yamanishi et al. |
| 9,095,494 B2 | 8/2015 | Warner et al. |
| 9,109,197 B2 | 8/2015 | Yasuda et al. |
| 9,217,131 B2 | 12/2015 | Lamish et al. |
| 9,272,234 B2 | 3/2016 | Lipkens et al. |
| 9,476,855 B2 | 10/2016 | Ward et al. |
| 9,510,998 B2 | 12/2016 | Warner et al. |
| 9,513,205 B2 | 12/2016 | Yu et al. |
| 9,551,643 B2 | 1/2017 | Warner et al. |
| 9,656,263 B2 | 5/2017 | Laurell et al. |
| 9,725,690 B2 | 8/2017 | Presz et al. |
| 9,745,569 B2 | 8/2017 | Lipkens et al. |
| 9,796,956 B2 | 10/2017 | Lipkens et al. |
| 9,835,540 B2 | 12/2017 | Yu et al. |
| 9,885,642 B2 | 2/2018 | Yu |
| 10,045,913 B2 | 8/2018 | Warner et al. |
| 10,052,431 B2 | 8/2018 | Dreschel et al. |
| 10,173,220 B2 | 1/2019 | Middlebrook et al. |
| 10,444,125 B2 | 10/2019 | Yu |
| 10,677,695 B2 | 6/2020 | Koyata et al. |
| 10,710,006 B2 | 7/2020 | Lipkens et al. |
| 10,724,029 B2 | 7/2020 | Lipkens et al. |
| 2004/0069708 A1 | 4/2004 | Laurell et al. |
| 2005/0106064 A1 | 5/2005 | Laurell et al. |
| 2006/0094051 A1 | 5/2006 | Lee et al. |
| 2006/0240572 A1 | 10/2006 | Carron et al. |
| 2007/0182517 A1 | 8/2007 | Humphries et al. |
| 2008/0160630 A1 | 7/2008 | Liu et al. |
| 2009/0052273 A1 | 2/2009 | Sarvazyan |
| 2010/0317093 A1 | 12/2010 | Turewicz et al. |
| 2011/0033922 A1 | 2/2011 | Landers et al. |
| 2012/0100546 A1 | 4/2012 | Lowery et al. |
| 2012/0122731 A1 | 5/2012 | Soh et al. |
| 2012/0295302 A1 | 11/2012 | Lamish et al. |
| 2013/0265054 A1 | 10/2013 | Lowery et al. |
| 2013/0330739 A1 | 12/2013 | Yu |
| 2014/0120570 A1* | 5/2014 | Yu ........................... B03C 1/288 210/695 |
| 2014/0231315 A1 | 8/2014 | Laurell et al. |
| 2015/0010939 A1 | 1/2015 | Warner et al. |
| 2015/0177111 A1 | 6/2015 | Warmer et al. |
| 2015/0253226 A1 | 9/2015 | Augustsson et al. |
| 2015/0308971 A1 | 10/2015 | Bisgaard et al. |
| 2016/0252445 A1 | 9/2016 | Yu et al. |
| 2018/0348097 A1 | 12/2018 | Abbott et al. |

OTHER PUBLICATIONS

Jonsson et al., Particle separation using ultrasound can radically reduce embolic load to brain after cardiac surgery, The Annals of Thoracic Surgery, 2004, 1572-1578, vol. 78.

Petrov et al., Electrically controlled integrated optical filter, Technical Physics Letters, 2004, 120-122, vol. 30.

Xia et al., Combined microfluidic-micromagnetic separation of living cells in continuous flow, Biomedical Microdevices, 2006, 299-308, vol. 8.

Radisic et al., Micro- and nanotechnology in cell separation, International Journal of Nanomedicine, 2006, 3-14, vol. 1.

Pamme et al., Continuous sorting of magnetic cells via on-chip free-flow magnetophoresis, Lab on a Chip, 2006, 974-980, vol. 6.

Laurell et al., Chip integrated strategies for acoustic separation and manipulation of cells and particles, Chemical Society Reviews, 2007, 492-506, vol. 36.

Riethdorf et al., Detection of circulating tumor cells in peripheral blood of patients with metastatic breast cancer: A validation study of the CellSearch system, Clinical Cancer Research, 2007, 920-928, vol. 13.

(56) References Cited

OTHER PUBLICATIONS

June, Carl H., Adoptive T cell therapy for cancer in the clinic, The Journal of Clinical Investigation, 2007, 1466-1476, vol. 117.
Pamme, Nicole, Continuous flow separations in microfluidic devices, Lab on a Chip, 2007, 1644-1659, vol. 7.
Riley et al., Human T regulatory cell therapy: Take a billion or so and call me in the morning, Immunity, 2009, 656-665, vol. 30.
Tsutsui et al., Cell separation by non-inertial force fields in microfluidic systems, Mechanics Research Communications, 2009, 92-103, vol. 36.
Lenshof, Andreas, Acoustic standing wave manipulation of particles and cells in microfluidic chips, Doctoral Thesis, 2009, Lund University, Lund, Sweden.
Yu et al., Circulating tumor cells: approaches to isolation and characterization, The Journal of Cell Biology, 2018, 373-382, vol. 192.
Utz et al., Microfluidic waves, Lab on a Chip, 2011, 3846-3854, vol. 11.
Dykes et al., Efficient removal of platelets from peripheral blood progenitor cell products using a novel micro-chip based acoustophoretic platform, PLOS One, 2011, e23074, vol. 6.
Augustsson et al., Microfluidic label-free enrichment of prostate cancer cells in blood based on acoustophoresis, Analytical Chemistry, 2012, 7954-7962, vol. 84.
Kandilov et al., The national market for medicare clinical laboratory testing: implications for payment reform, Medicare & Medicaid Research Review, 2012, e1-e21, vol. 2.
Barnkob et al., Acoustic radiation- and streaming-induced microparticle velocities determined by micro-PIV in an ultrasound symmetry plane. Physical Review E, 2012, 056307, vol. 86.
Tajudin et al., Integrated acoustic immunoaffinity-capture (IAI) platform for detection of PSA from whole blood samples, Lab on a Chip, 2013, 1790-1796, vol. 13.
Burguillos et al., Microchannel acoustophoresis does not impact survival or function of microglia, leukocytes or tumor cells, PLOS One, 2013, e64233, vol. 8.
Singh et al., Manufacture of clinical-grade CD 19-specific T cells stably expressing chimeric antigen receptor using sleeping beauty system and artificial antigen presenting cells, PLOS One, 2013, e64138, vol. 8.
Lenshof et al., Efficient purification of CD4+ lymphocytes from peripheral blood progenitor cell products using affinity bead acoustophoresis, Cytometry Part A, 2014, 933-941, vol. 85A.
Ilie et al., "Sentinel" circulating tumor cells allow early diagnosis of lung cancer in patients with chronic obstructive pulmonary disease, PLOS One, 2014, e111597, vol. 9.
Matsueda et al., Immunotherapy in gastric cancer, World Journal of Gastroenterology, 2014, 1657-1666, vol. 20.
Grenvall et al., Concurrent isolation of lymphocytes and granulocytes using prefocused free flow acoustophoresis, Analytical Chemistry, 2015, 5596-5604, vol. 87.
Jakobsson et al., Thousand-fold volumetric concentration of live cells with a recirculating acoustofluidic device, Analytical Chemistry, 2015, 8497-8502, vol. 87.
Fong et al., A microfluidic platform for precision small-volume sample processing and its use to size separate biological particles with an acoustic microdevice, Journal of Visualized Experiments, 2015, e53051, vol. 105.
Shields et al., Microfluidic cell sorting: a review of the advances in the separation of cells from debulking to rare cell isolation, Lab on a Chip, 2015, 1230-1249, vol. 15.
Temiz et al., Lab-on-a-chip devices: how to close and plug the lab?, Microelectronic Engineering, 2015, 156-175, vol. 132.
Hahn et al., A numerically efficient damping model for acoustic resonances in microfluidic cavities, Physics of Fluids, 2015, 062005, vol. 27.
Poruk et al., Circulating tumor cell phenotype predicts recurrence and survival in pancreatic adenocarcinoma, Annals of Surgery, 2016, 1073-1081, vol. 264.
Jansson et al., Prognostic impact of circulating tumor cell apoptosis and clusters in serial blood samples from patients with metastatic breast cancer in a prospective observational cohort, BMC Cancer, 2016, 433, vol. 16.
Banys-Paluchowski et al., Circulating tumor cells in breast cancer—current status and perspectives, Critical Reviews in Oncology/Hematology, 2016, 22-29, vol. 97.
Urbansky et al., Affinity-bead-mediated enrichment of CD8+ lymphocytes from peripheral blood progenitor cell products using acoustophoresis, Micromachines, 2016, 101, vol. 7.
Chen et al., Cancer statistics in China, 2015, CA: A Cancer Journal for Clinicians, 2016, 115-132, vol. 66.
Magnusson et al., Clinical-scale cell-surface-marker independent acoustic microfluidic enrichment of tumor cells from blood, Analytical Chemistry, 2017, 11954-11961, vol. 89.
Boffa et al., Cellular expression of PD-L1 in the peripheral blood of lung cancer patients is associated with worse survival, Cancer Epidemiology, Biomarkers & Prevention, 2017, 1139-1145, vol. 26.
Cui, Mingyang, Particle enrichment in longitudinal standing bulk acoustic wave microfluidics, Master Thesis, 2017, Washington University, St. Louis, Missouri.
Eyer et al., Single-cell deep phenotyping of IgG-secreting cells for high-resolution immune monitoring, Nature Biotechnology, 2017, 977-982, vol. 35.
Fachin et al., Monolithic chip for high-throughput blood cell depletion to sort rare circulating tumor cells, Scientific Reports, 2017, 10936, vol. 7.
Cushing et al., Reducing WBC background in cancer cell separation products by negative acoustic contrast particle immunoacoustophoresis, Analytica Chimica Acta, 2018, 256-264, vol. 1000.
Vormittag et al., A guide to manufacturing CAR T cell therapies, Current Opinion in Biotechnology, 2018, 164-181, vol. 53.
Yu et al., An integrated enrichment system to facilitate isolation and molecular characterization of single cancer cells from whole blood, Cytometry Part A, 2018, 1226-1233, vol. 93A.
Leipold et al., Comparison of CyTOF assays across sites: Results of a six-center pilot study, Journal of Immunological Methods, 2018, 37-43, vol. 453.
Abdlaty et al., Hyperspectral imaging: comparison of acousto-optic and liquid crystal tunable filters, Proceedings of SPIE, Medical Imaging 2018: Physics of Medical Imaging, 105732P, vol. 10573.
Bhagwat et al., An integrated flow cytometry-based platform for isolation and molecular characterization of circulating tumor single cells and clusters, Scientific Reports, 2018, 5035, vol. 8.
U.S. Appl. No. 11/900,370, filed Mar. 12, 2009, Zhou, Yuchen.
Nilsson et al., Acoustic control of suspended particles in micro fluidic chips, Lab on a Chip, 2004, 131-135, vol. 4.
Petersson et al., Free flow acoustophoresis: microfluidic-based mode of particle and cell separation, Analytical Chemistry, 2007, 5117-5123, vol. 79.
Adams et al., Integrated acoustic and magnetic separation in microfluidic channels, Applied Physics Letters, 2009, 254103, vol. 95.
Adams et al., Tunable acoustophoretic band-pass particle sorter, Applied Physics Letters, 2010, 064103, vol. 97.
Guldiken et al., Sheathless size-based acoustic particle separation, Sensors, 2012, 905-922, vol. 12.
Glynne-Jones et al., Acoustofluidic 23: acoustic manipulation combined with other force fields, Lab on a Chip, 2013, 1003-1010, vol. 13.
Sajeesh et al., Particle separation and sorting in microfluidic devices: a review, Microfluidic Nanofluidic, 2014, 1-52, vol. 17.
Watarai, Hitoshi, Continuous separation principles using external microaction forces, Annual Review of Analytical Chemistry, 2013, 353-378, vol. 6.
Yasutaka et al., Dual-stage actuator for HDD achieving high-accuracy positioning and wide-bandwidth servo control, Toshiba Review, 2011, vol. 66.
Antfolk et al., Label-free single-cell separation and imaging of cancer cells using an integrated microfluidic system, 2017, 46507, vol. 7.

(56) References Cited

OTHER PUBLICATIONS

Ott et al., An ongoing analysis of a phase IB study of the personal neoantigen vaccine NEO-PV-01 + Nivolumab in patients with metastatic melanoma, NSCLC and bladder cancer, Handout from ESMO Congress, Munich, 2018.

Second-generation micro actuator for better head-positioning accuracy, Hitachi Global Storage Technology Tech Brief, 2017.

\* cited by examiner

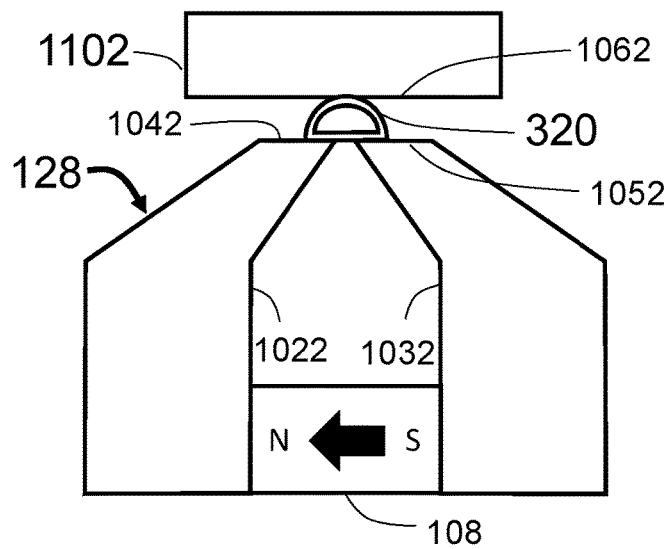
FIG. 20A
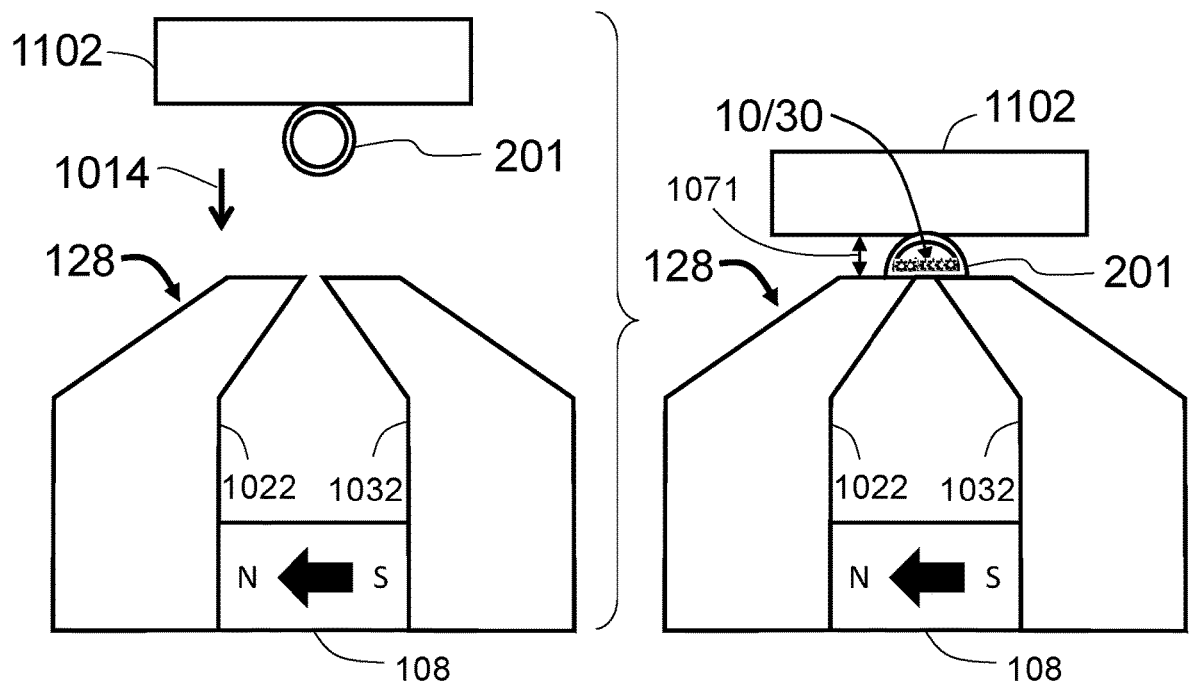
FIG. 20B
FIG. 20C

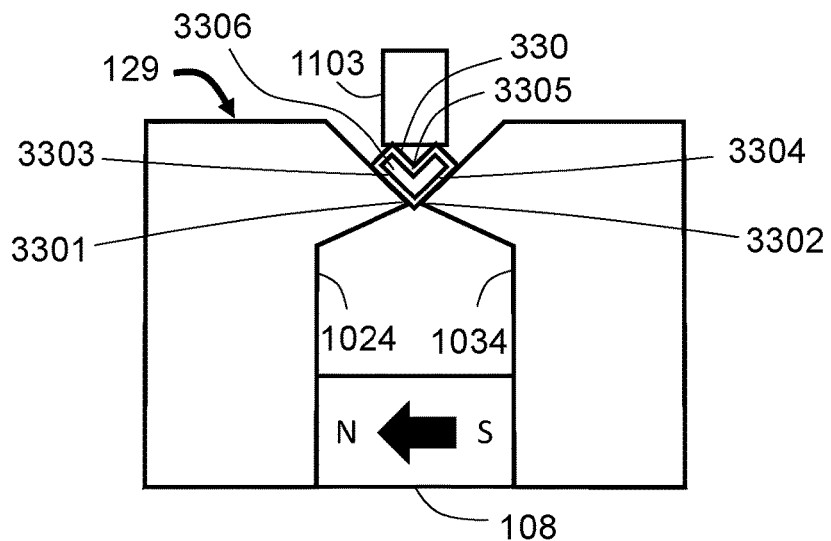
*FIG. 21A*
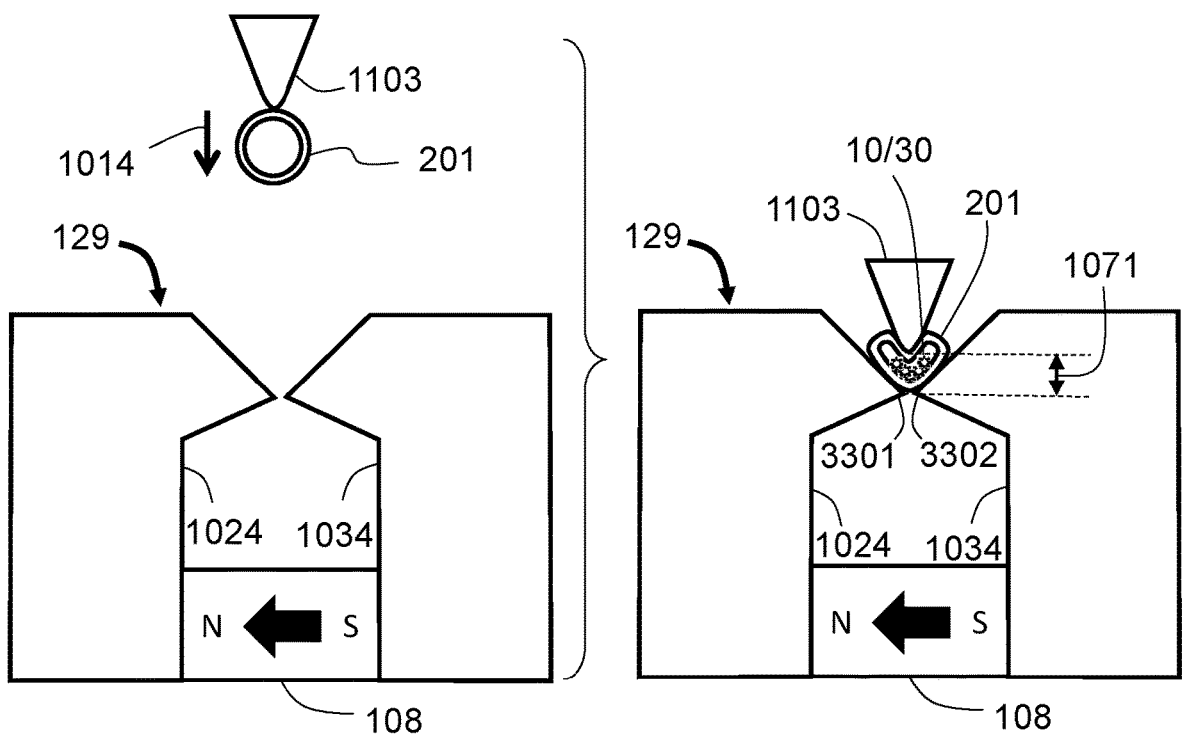
*FIG. 21B*  *FIG. 21C*

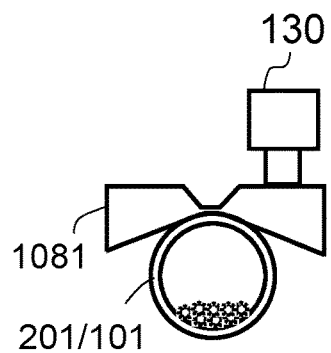
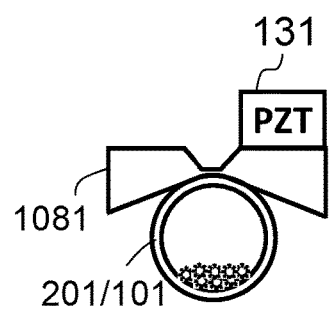
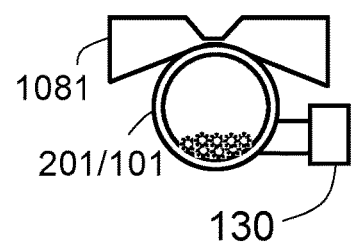
*FIG. 23A*     *FIG. 23B*     *FIG. 23C*
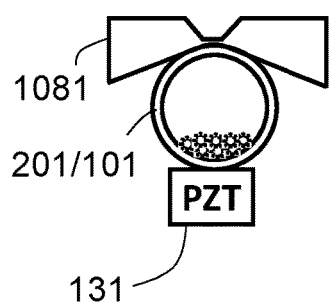
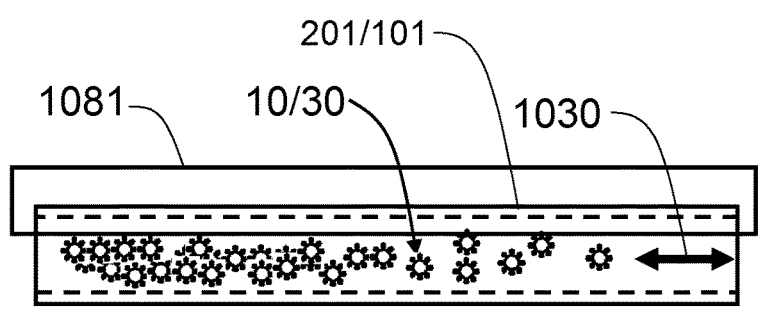
*FIG. 23D*     *FIG. 23E*

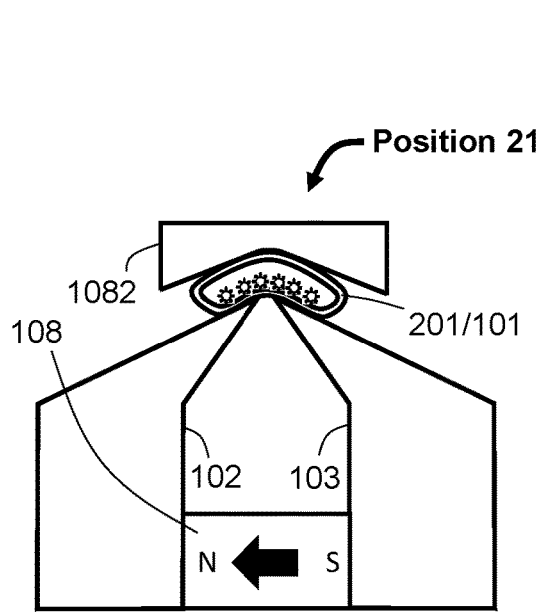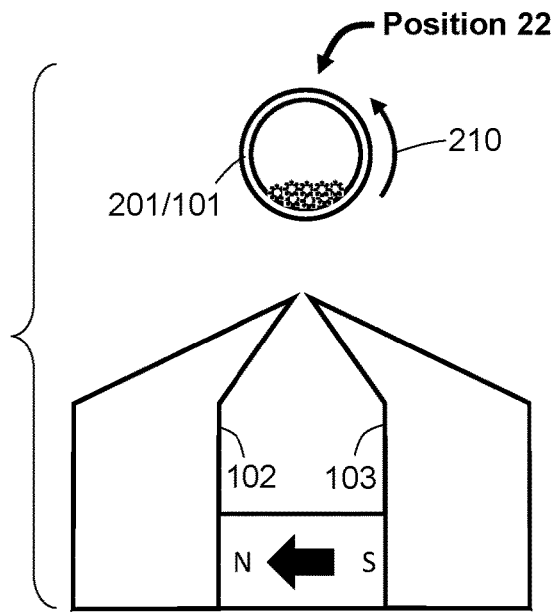
FIG. 26A  FIG. 26B
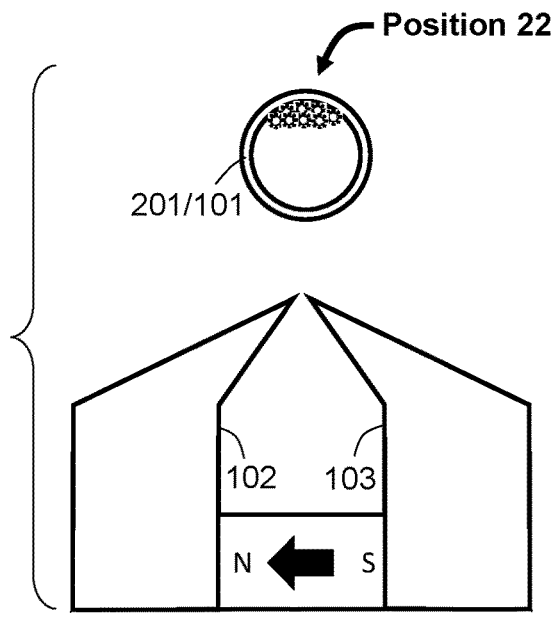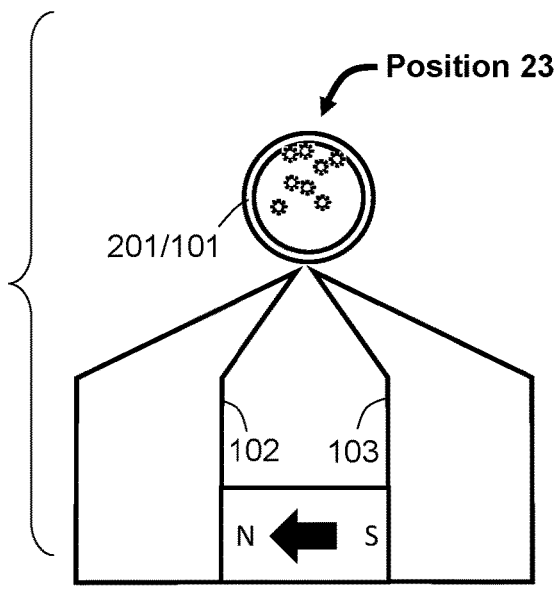
FIG. 26C  FIG. 26D

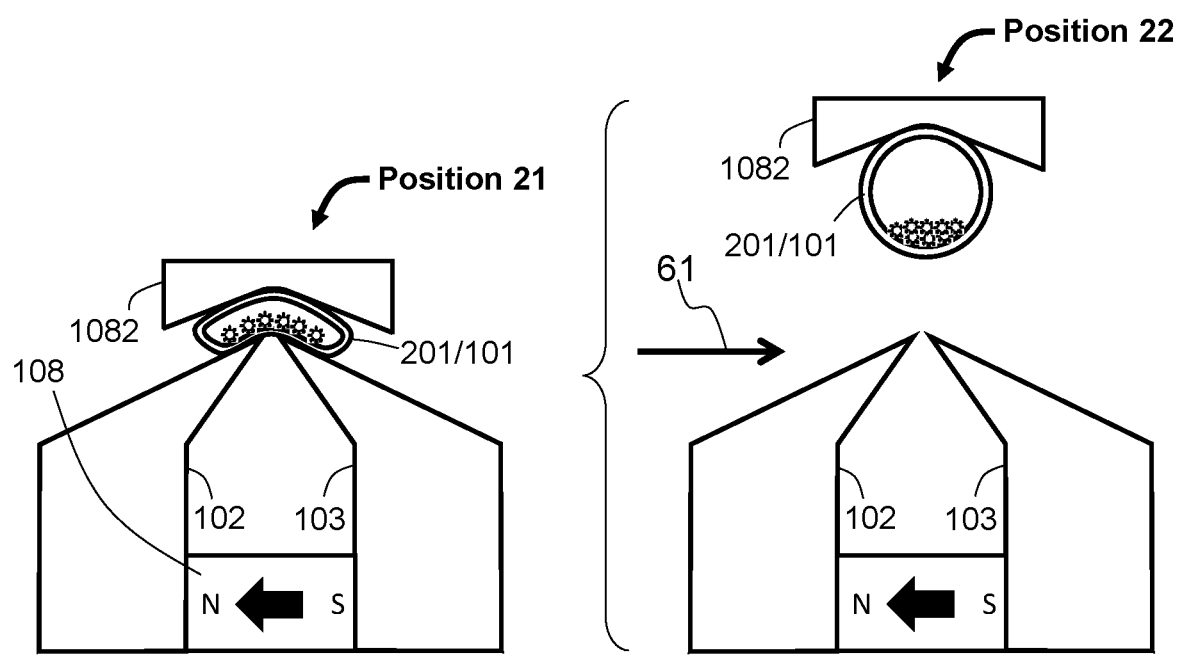
FIG. 27A
FIG. 27B
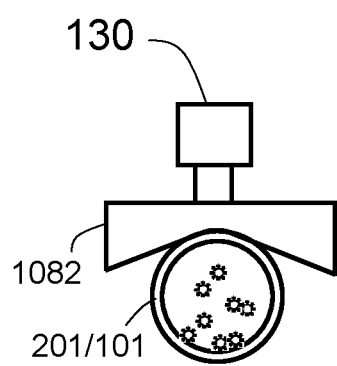
FIG. 27C
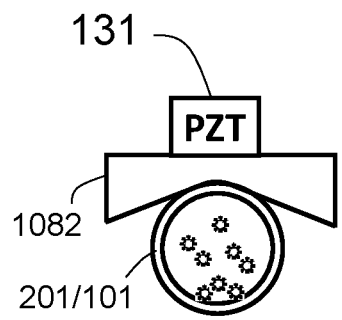
FIG. 27D

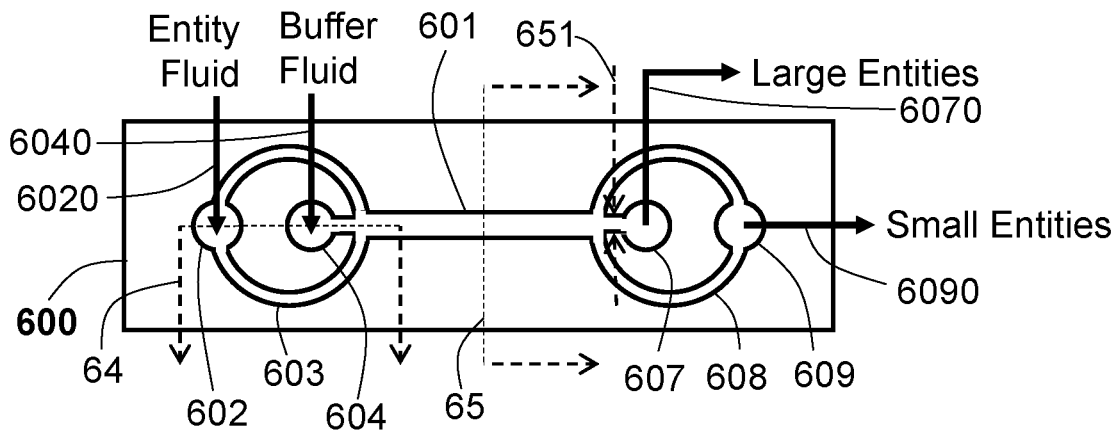
*FIG. 38A*
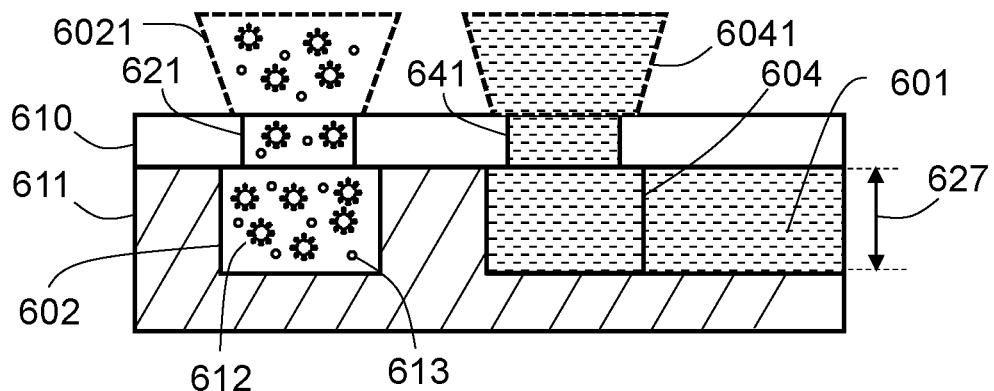
*FIG. 38B*
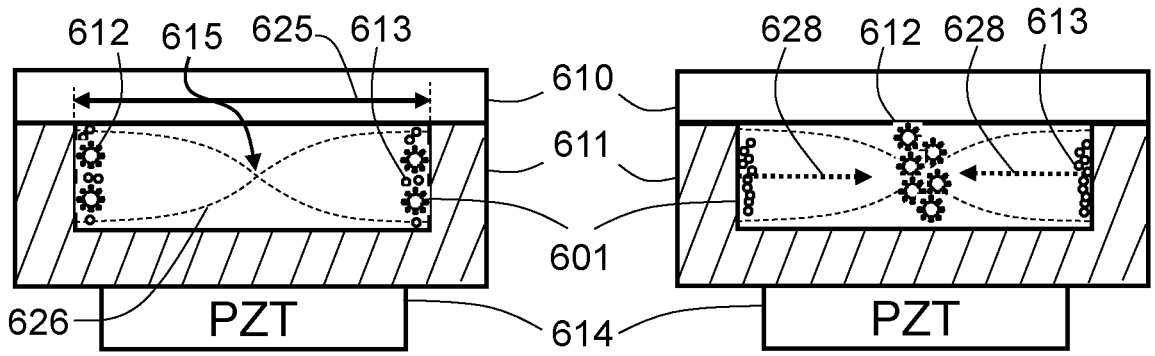
*FIG. 38C*                    *FIG. 38D*

5806

Add into target sample magnetic labels hybridized with antibodies or ligands, which specifically bind to surface antigens or receptors on target cells or entities,

58061

Add into target sample magnetic labels and fluorescent labels which are hybridized with antibodies or ligands, and specifically bind to same or different surface antigens or receptors on target cells or entities

Incubate target sample to form magnetic labels binding to target cells or entities

58071

Incubate target sample to form magnetic labels and fluorescent labels binding to target cells or entities

*FIG. 76B*

MAGNETIC SEPARATION DEVICE AND METHOD OF USE

BACKGROUND

The current invention generally relates to methods and apparatus to separate biological entities, including cells, bacteria and molecules from human blood, body tissue, body fluid and other human related biological samples. The disclosed methods and apparatus may also be utilized to separate biological entities from animal and plant samples. More particularly, the current invention relates to the methods and apparatus for achieving separation of biological entities using one or more of a micro-fluidic separation device/chip ("UFL"), and one or more of a magnetic separation device ("MAG"), individually or in combination. For description purpose, "cells" will be used predominantly hereafter as a typical representation of biological entities in general. However, it is understood that the methods and apparatus disclosed in this invention may be readily applied to other biological entities without limitation.

Separation of biological entities from a fluid base solution, for example separating a specific type of white blood cell from human blood, typically involves a first step of identifying the target biological entities with specificity, and followed by a second step of physical extraction of the identified target biological entities from the fluid base solution. In human blood, different types of biological cells may have various types of surface antigens or surface receptors, which are also referred to as surface markers in this invention. Certain surface markers on a given type of cell may be unique to said type of cell and may be used to identify said type of cell from blood sample with specificity.

FIG. 1A through FIG. 1C show examples of identifying or labeling target cells 1 using superparamagnetic labels 2 ("SPLs") as in FIG. 1A, using optical fluorescent labels 3 ("OFLs") as in FIG. 1B, and using both the SPLs 2 and OFLs 3 together as in FIG. 1C.

In FIG. 1A, cell 1 has surface markers 11. SPLs 2 are conjugated with surface antibodies or ligands, also referred to as "probes" 21, which specifically bind to the surface markers 11 of cell 1. Large quantity of SPLs 2 having probes 21 are put into the solution where cell 1 resides. After incubation processes 9, a plurality of SPLs 2 are bound to cell 1 surface with probes 21 selectively bound to surface markers 11 with specificity. Thus, cells 1 is magnetically identified or labeled by SPLs 2, i.e. magnetically labeled cell 10. A magnetic field with sufficient field gradient may be applied to cell 10 to produce a physical force on the SPLs 2 attached to the cell 10 surface. With sufficient strength, the physical force working through the SPLs 2 on cell 10 may be used to separate and physically remove cell 10 from its liquid solution.

In FIG. 1B, cell 1 has surface markers 12. OFLs 3 are conjugated with probes 22, which specifically bind to the surface markers 12 of cell 1. Large quantity of OFLs 3 having probes 22 are put into the solution where cell 1 resides. After incubation processes 9, a plurality of OFLs 3 are bound to cell 1 surface with probes 22 selectively bound to surface markers 12 with specificity. Thus, cells 1 is optically identified or labeled by OFLs 3, i.e. optically labeled cell 20. By using an optical based cell separation system, cell 1 may be separated from its liquid solution based on the optical signal that OFL 3 produces under an excitation light. One type of such optical based cell separation system is a flow cytometer, wherein a liquid solution is streamed through a conduit within said flow cytometer as a continuous flow. At least one excitation light source produces a light spot upon said liquid flow through said conduit at a first optical wavelength. In the presence of OFL 3 in the light spot, OFL3 is excited by first wavelength and radiates optical light at a second wavelength. When cell 1 with bound OFLs 3 passes said light spot within said flow, OFLs 3 bound to cell 1 radiate optical signal in second wavelength. The strength of said optical signal as well as duration while cell 1 passes the light spot may be used to identify the presence of cell 1 by the flow cytometer, which then diverts cell 1 into a second liquid flow path or mechanically removes cell 1 from the liquid flow, thus separating cell 1 from the fluid base. In practice, OFL 3 bound to cell 1 may be various types of fluorescent dyes or quantum dots, producing excited optical light at multiple wavelengths. A plurality of excitation light sources may also be used in the same flow cytometer system to produce excitation light spots at different locations of the liquid flow with different excitation light wavelength. Combination of various wavelengths produced by OFL 3 on same cell 1 may be used to increase specificity of separation of cell 1, especially when a combination of various types of surface markers 12 is needed to specifically identify a sub-category target cell 1 population from a major category of same type of cells, for example CD4-T cells from other white blood cells.

In FIG. 1C, cell 1 has both surface markers 11 and 12. SPLs 2 conjugated with probes 21 and OFLs 3 conjugated with probes 22 are both bound to cell 1 surface after incubation processes 9 to form magnetically and optically labeled cell 30. Cell 30 allows for separation of cell 30 with a combination of a magnetic separation and an optical based cell separation system. The magnetic separation through SPLs 2 may provide a fast first stage separation of cell category including cell 30, while the optical separation through OFLs 3 may provide a second stage separation of cell 30 after magnetic separation with more specificity. Alternatively, cell 30 may be separated via OFLs 3 in a first stage and via SPLs 2 in a second stage. In either case, SPLs 2 and OFLs 3 together may help increase speed, efficiency and specificity in separation of cell 1 compared with FIG. 1A and FIG. 1B.

FIG. 2A shows an example of conventional magnetic separation through SPL 2. In a container 5, liquid solution 6 contains cells 10 of FIG. 1A or cells 30 of FIG. 1C that are bound with a plurality of SPLs 2 on cell surface. Magnet 4, preferably a permanent magnet, is positioned in proximity to wall of container 5. Magnet 4 has a magnetization represented by arrow 41 indicating a north pole ("N") and a south pole ("S") on top and bottom surfaces of the magnet 4. Magnetic field produced by the magnetization 41 in the solution 6 is higher at the container 5 wall directly opposing the N surface of the magnet 4, and lower at locations within solution 6 further away from the magnet 4, thus creating a magnetic field gradient pointing towards the magnet 4 within the solution 6. SPLs 2 bound to cells 10/30 are superparamagnetic, which means that SPLs 2 are effectively non-magnetic in the absence of magnetic field, but will gain magnetic moment in the presence of the magnetic field produced by the magnet 4. With the magnetic moment of SPLs 2 and the magnetic field gradient from magnet 4, cells 10/30 will be pulled by the force produced by the magnetic field from magnet 4 towards magnet 4. After sufficient time 7, cells 10/30 may be depleted from solution 6 and form conglomerate at inside surface of the container 5 wall opposing magnet 4. In conventional practice, solution 6 may be removed from container 5, while maintaining magnet 4 position relative to container 5 thus cells 10/30 are retained as conglomerate against container 5 inside surface. Afterwards, magnet 4 may be removed from container 5. With absence of magnetic field, conglomerate of cells 10/30, together with any non-bound free SPLs 2 in the conglomerate, should self-demagnetize over an extensive period of time to become non-magnetic and cells 10/30 may be removed from container 5 as individual cells 10/30.

Conventional method as shown in FIG. 2A has limitations in actual applications. For the SPL 2 to be superparamagnetic, the size of the fundamental superparamagnetic particles ("SPN") contained in SPL 2, for example iron oxide particles, should be in the range of 10 nm (nanometer) to 30 nm. A smaller particle size makes the particles more effectively superparamagnetic but harder to gain magnetic moment in the presence of magnetic field, while a larger particle size makes the particles more difficult to become non-magnetic when magnetic field is removed. SPL 2 is typically composed of SPNs dispersed in a non-magnetic matrix. For example, certain SPL 2 is a solid sphere formed by SPNs evenly mixed within a polymer base, typically has a size larger than 1 µm. In another case, SPL 2 is a solid bead formed by SPNs mixed within an oxide or nitride base, for example iron oxide nanoparticles mixed in silicon oxide base, which can have a size of a few hundred nanometers or tens of nanometers. For the cells 10/30 of FIG. 2A to be suitable for additional cellular processes, including cell culture and cell analysis, SPL 2 size is desired to be smaller than the cell itself, which is usually a few micrometers. Thus, SPL 2 with sub-micrometer size (<1 µm) is desired. SPL 2 size less than 500 nm is more preferred. SPL 2 size less than 200 nm is most preferred. However, when SPL 2 average size is smaller, variation of SPL 2 size becomes larger statistically. FIG. 2B shows an example plot of single SPL 2 magnetic moment in the presence of an applied magnetic field. Solid curve 22 indicates SPL 2 having a population nominal size, or average size, where SPL 2 magnetic moment increases with higher magnetic field. With magnetic field strength increasing from 0 to Hs, nominal size SPL magnetic moment increases with field strength in a linear trend at beginning, until reaching a saturation region where magnetic moment plateaus to Ms, which is determined by the saturation moment of the SPN material within the SPL 2. For SPL 2 with a smaller size than nominal size, curve 23 indicates that at the same magnetic field strength, smaller size SPL 2 gains a lower moment, and thus experiences a lower magnetic force, and requires a higher field to reach saturation magnetic moment Ms. For a larger size SPL 2 than nominal size, curve 24 indicates larger size SPL 2 is easier to saturate to Ms with a lower field and gains a higher moment at the same magnetic field strength.

Now referring back to FIG. 2A, for SPL 2 with sub-micrometer size that is suitable for cell separation and cellular processes, conventional method of FIG. 2A has the limitation of not being able to produce high magnetic field strength and strong magnetic field gradient in solution 6 at locations further away from the container 5 wall opposing magnet 4N surface. Therefore, smaller size SPL 2 of curve 23 of FIG. 2B at farther end of the container 5 from magnet 4 may be difficult to magnetize by magnetic field and experiences smaller force to move the cells 10/30 towards magnet 4. To reach complete depletion of cells 10/30 in solution 6 within container 5, it may require a significant amount of time. Meanwhile, volume of container 5 is limited also due to magnetic field strength from magnet 4, which may not be sufficient to magnetize the smaller SPL 2 of curve 23 of FIG. 2B at large container 5 sizes. Besides the overall process being slow, another drawback of conventional method of FIG. 2A is that the operation as described in FIG. 2A typically involves air exposure of cell 10/30 conglomerate during the steps of solution removal and later removal of cells 10/30 from container 5. Such air exposure poses challenge in achieving sterile separation of cells 10/30 for clinical purpose, as well as risk of cell 10/30 damage or death that negatively affects further cellular processes of cells 10/30.

FIG. 3A shows another example of magnetic separation of cells 10/30 with SPL 2 in prior art. In FIG. 3A, solution 6 containing cells 10/30 is passed through a column 31 that is filled with ferromagnetic or ferrimagnetic spheres 36. By applying a magnetic field across the column with magnets 32 and 33, where dashed lines 34 indicates applied magnetic field direction, spheres 36 may be magnetized by the field and produce localized magnetic field in gaps between neighboring spheres 36. Such local field and field gradient between spheres 36 gaps may be strong, due to the small dimensions of the gaps, to effectively magnetize SPL 2 of all sizes when SPL 2 in solution 6 passes through the gaps between the spheres 36 during a downward flow of solution 6 as indicated by arrow 35, where SPL 2 may be attracted to various spheres 36 surface and separated from the solution 6. Prior art of FIG. 3A may effectively avoid the air exposure issue of FIG. 2A, and may have a higher separation speed of cells 10/30 than FIG. 2A during the flow 35. However, an intrinsic issue of FIG. 3A method is that with the spheres 36 being ferromagnetic or ferrimagnetic and is much larger in size than cells 10/30, magnetic domains in spheres 36 will exist even after removal of magnets 32 and 33 from the column 31. Such magnetic domains, and domain walls between the domains, will inevitably produce local magnetic fields around the surfaces of the spheres 36, which will keep the SPLs 2 on cells 10/30 magnetized and strongly attract the cells 10/30 when magnets 32 and 33 are removed. Therefore, the cells 10/30 are inherently more difficult to be removed from the column 31 in FIG. 3A than FIG. 2A. Cell 10/30 loss due to incomplete removal from column 31 after separation is inherently high. In certain prior art method, a pressurized high speed buffer flow may be used to force wash the cells 10/30 from the spheres in column 36. However, such forced flow will inevitably cause mechanical damage to the cells and will still leave behind significant percentage of cells 10/30 in column 31 due to the strong domain wall field of spheres 36. Besides cell 10/30 loss, another intrinsic issue of FIG. 3A method is introducing spheres 36 as foreign materials in the flow of solution 6, which is not desirable for sterile process needed for clinical applications.

FIG. 3B shows another prior art similar to method of FIG. 3A, except mesh 37 made of ferromagnetic or ferrimagnetic wires are introduced in the column 31 instead of spheres or blocks 36. When magnetic field 34 is applied by the magnets 32 and 33, wires of mesh 37 are magnetized and adjacent wires of mesh 37 produce local magnetic field around the wires. Clearances between wires of the mesh allow fluid 6 to flow in direction 35 within the column. When cells 10/30 are in proximity to wires of mesh 37, cells 10/30 may be attracted to the wire surface due to the local magnetic field and field gradient produced by the wires of the mesh 37. Compared to FIG. 3A prior art, FIG. 3B may adjust size of wires and size of clearance of mesh 37 to tradeoff between cell 10/30 separation speed and cell loss in column. However, in practice, due to the gap between spheres 36 is much smaller than clearance size in mesh 37, cell 10/30 separation speed in FIG. 3B is slower than FIG. 3A, while FIG. 3B still has the same cell loss issue of FIG. 3A, where domains in the wires of mesh 37 maintains SPL 2 magnetic moment after magnets 32 and 33 are removed and cells 10/30 are attracted to the wires by the domain and domain wall. Cell 10/30 loss due to the magnetic domains in wires of mesh 37 also exists in FIG. 3B. Additionally, FIG. 3B is same as FIG. 3A in introducing mesh 37 as foreign materials in the flow of solution 6, which is not desirable for sterile process.

FIG. 3C shows another prior art, where magnets 32 and 33 are each attached with a soft magnetic flux guide 38 with an apex. The flux guides 38 produce localized magnetic field between the apexes of the guides 38 with high field strength and high gradient close to the apexes. FIG. 3C shows the cross-sectional view of the conduit 39, which is intrinsically a circular tubing. The solution 6 containing cells 10/30 flows along the tubing 39 length in the direction perpendicular to the cross-section view. Tubing 39 is positioned on one side of the gap of the apexes. Magnetic field lines 34 exhibit a higher density closer to the gap, indicating both higher magnetic field strength and higher magnetic field gradient towards the gap. Magnetic field 34 produces effective force on cells 10/30 in solution 6 and pulls the cells 10/30 from solution 6 towards the tubing 39 inside wall that is closest to the apexes of the guides 38. Prior art of FIG. 3C when compared to prior art of FIG. 3A and FIG. 3B has the advantages of: (1) not introducing foreign material in the flow path; (2) when magnets 32 and 33 are removed from tubing together with guides 38, there is no ferromagnetic or ferrimagnetic sphere 36 or mesh 37 in the tubing, thus avoiding the domain structures related loss of cells 10/30.

However, prior art of FIG. 3C also has intrinsic deficiencies. First deficiency is the flow speed of solution 6, or flow rate, in the tubing 39 is limited by the prior art design of FIG. 3C. The separation speed of cells 10/30 in the prior art of FIG. 3C is not sufficient for many applications. Circular tubing conduit 39 as shown in FIG. 3C experiences high field and high field gradient at lower end of tubing 39, where cells 10/30 closer to the lower end of tubing 39 may experience a high force that pulls them to move towards the tubing 39 lower wall inner surface much faster. However, for the cells 10/30 closer to the top end of the tubing 39, due to the narrow wedge gap and position of the tubing 39 being on one side of the gap, magnetic field and gradient is significantly lower than the lower end. Thus cells 10/30 closer to the top end of the tubing 39 experience a much smaller force and move to lower end of tubing 39 at a much slower speed. For a limited length of the tubing 39 in the perpendicular to cross-sectional view direction, all cells 10/30 within the fluid 6 flowing through the tubing 39 need to be separated from solution 6 to form a conglomerate on the inside surface of the tubing close to the apexes before solution 6 exits the tubing 39. Due to slower speed of cells 10/30 moving from top of the tubing 39, flow rate of solution 6 needs to be slow such that it can allow enough time for all the cells 10/30 near top of tubing 39 to be attracted into the conglomerate. If solution 6 flows through the tubing 39 at higher speeds, it will cause incomplete separation of cells 10/30 from solution. Such limitation on flow rate due to the circular design of tubing 39, where tubing top end being further away from high field and high gradient apexes, cannot be cured by a smaller size tubing 39. A smaller cross-sectional size circular tubing 39 will bring the top end of the tubing 39 closer to the wedge gap. However, due to the smaller cross-section size, volume of solution 6 flowing through the tubing 39 in a unit time frame, i.e. flow rate of solution 6, will reduce when flow speed of solution 6 is maintained. To maintain the same flow rate as in a larger tubing 39, solution 6 flow speed needs to increase, which then gives less time for cells 10/30 at top end of smaller size tubing 39 to move to the conglomerate site, and offsets the effect of small size tubing 39.

A second deficiency of FIG. 3C prior art is the inability to dissociate individual cells 10/30 from conglomerate of cells 10/30 and non-bound free SPL 2, as the conglomerate will not self-demagnetize with ease after magnets 32 and 33, together will guides 38, are removed from tubing 39 in actual applications. Demagnetization of SPL 2 relies on the SPNs within SPL 2 being effectively nanoparticles. However, as the conglomerate forms an effectively larger body of superparamagnetic material, the SPNs within SPL 2 experiences magneto-static field from a large number of closely packed SPNs from neighboring SPLs 2 in the conglomerate, which reduces the super-paramagnetic nature of the SPNs. In one case, the SPL 2 of cells 10/30 within conglomerate requires extensive time to self-demagnetize, which is not practical for many applications. In another case, the conglomerate won't self-demagnetize due to the SPN being more ferromagnetic in conglomerate form, which is undesirable. High pressure flushing as utilized in FIG. 3A is not effective in FIG. 3C, as majority of the circular tubing 39 inner area is occupied by empty space, while conglomerate is compacted on the lower end of tubing 39. Such flush will mainly flow through the top section of the tubing 39 without producing enough friction force on the conglomerate of cells 10/30 to remove the cells 10/30 from the tubing 39 lower wall. As prior art does not provide an effective method to dissociate conglomerate and remove cells 10/30 from tubing 39, such deficiency of FIG. 3C prior art is limiting its application.

Prior art is limited either in causing cell loss and introducing foreign materials in the flow path, or limited in the flow rate of solution 6 and the ability to extract separated cells from conglomerate with an effective dissociation method.

It is desired to have a method and an apparatus that can achieve high flow rate magnetic separation of cells 10/30 without introducing foreign material in the flow path of the biological solution, and are able to dissociate cells 10/30 from conglomerate in a practically short time without damaging the cells.

SUMMARY OF THE INVENTION

This invention describes novel methods and novel magnetic separation devices ("MAG") that are able to: (1) separate biological entities bound with SPLs from biological solution with high flow rate, without exposure of biological entities to air, and without introducing foreign material in the flow path of the biological solution carrying the biological entities; (2) dissociate the biological entities from the magnetically separated conglomerate.

This invention further describes novel methods and novel micro-fluidic separation devices ("UFL") that separate biological entities from biological solutions based on the size of the biological entities.

This invention further describes novel methods and novel apparatus using MAG and UFL individually and in combination to separate biological entities from biological solutions for various separation applications.

This invention further describes methods of pre-symptom early tumor detection and methods of using MAG and UFL during the process of tumor detection.

The methods, components and apparatus as disclosed by this invention may be utilized to separate biological entities, including cells, bacteria and molecules, from human blood, human body tissue, human bones, human body fluid, human hairs, other human related biological samples, as well as biological entities from animal and plant samples alike without limitation.

BRIEF DESCRIPTION OF THE DRAWINGS

FIG. 20A illustrates cross-sectional view of the eighth embodiment of MAG with a rotated "D" shape rigid channel in separation position.

FIG. 20B illustrates cross-sectional view of the eighth embodiment of MAG with a flexible channel.

FIG. 20C illustrates cross-sectional view of the eighth embodiment of MAG having a flexible channel in separation position with cells being separated.

FIG. 21A illustrates cross-sectional view of the ninth embodiment of MAG having a "V" shape rigid channel in separation position.

FIG. 21B illustrates cross-sectional view of the ninth embodiment of MAG with a flexible channel.

FIG. 21C illustrates cross-sectional view of the ninth embodiment of MAG having a flexible channel in separation position with cells being separated.

FIG. 23A illustrates mechanical vibration is applied to a flexible channel holder by a motor after cells are magnetically separated inside the flexible channel.

FIG. 23B illustrates ultrasound vibration is applied to a flexible channel holder by a piezoelectric transducer ("PZT") after cells are magnetically separated inside the flexible channel.

FIG. 23C illustrates mechanical vibration being applied to a flexible channel by a motor after cells are magnetically separated inside the flexible channel.

FIG. 23D illustrates ultrasound vibration being applied to a flexible channel by a PZT after cells are magnetically separated inside the flexible channel.

FIG. 23E is a side view of the flexible channel of FIG. 22D.

FIG. 26A illustrates the third embodiment of MAG having a flexible channel in separation position with cells being separated.

FIG. 26B illustrates the flexible channel of FIG. 26A departing from MAG and rotating.

FIG. 26C illustrates the conglomerate of separated cells in the flexible channel of FIG. 26B being rotated to top end of the flexible channel.

FIG. 26D illustrates the flexible channel of FIG. 26C moving to demagnetization position.

FIG. 27A illustrates the third embodiment of MAG having a flexible channel in separation position with cells being separated.

FIG. 27B illustrates the flexible channel and its holder of FIG. 27A departing from MAG.

FIG. 27C illustrates mechanical vibration being applied to the channel holder by a motor.

FIG. 27D illustrates ultrasound vibration being applied to the channel holder by a PZT.

FIG. 38A is a top-down view of a micro-fluidic chip ("UFL").

FIG. 38B is a cross-sectional view of a portion of the FIG. 38A UFL including entity fluid inlet, buffer fluid inlet, and part of the UFL.

FIG. 38C is a schematic diagram illustrating a single fluidic pressure node created between two side walls of the UFL of FIG. 38A by ultrasound vibration generated by a PZT.

FIG. 38D is a schematic diagram illustrating the fluid acoustic wave of FIG. 38C causing larger size entities to move around center of the UFL.

FIG. 59B illustrates fluidic lines of FIG. 59A being connected to, or attached with, various fluidic devices to realize sample processing through a single MAG.

FIG. 60A illustrates example of closed and disposable fluidic lines for sample processing through a single UFL.

FIG. 60B illustrates fluidic lines of FIG. 60A being connected to, or attached with, various fluidic devices to realize sample processing through a single UFL.

FIG. 61A illustrates replacement of peristaltic pumps of FIG. 56B with pressurized chambers on input sample bags to drive fluid through fluidic lines.

FIG. 61B illustrates replacement of peristaltic pumps of FIG. 56B with vacuum chambers on output sample bags to drive fluid through fluidic lines.

FIG. 62A illustrates replacement of peristaltic pumps of FIG. 57B with pressurized chambers on input sample bags to drive fluid through fluidic lines.

FIG. 62B illustrates replacement of peristaltic pumps of FIG. 57B with vacuum chambers on output sample bags to drive fluid through fluidic lines.

FIG. 63A illustrates replacement of peristaltic pumps of FIG. 58B with pressurized chambers on input sample bags to drive fluid through fluidic lines.

FIG. 63B illustrates replacement of peristaltic pumps of FIG. 58B with vacuum chambers on output sample bags to drive fluid through fluidic lines.

FIG. 64A illustrates replacement of peristaltic pumps of FIG. 59B with pressurized chambers on input sample bags to drive fluid through fluidic lines.

FIG. 64B illustrates replacement of peristaltic pumps of FIG. 59B with vacuum chambers on output sample bags to drive fluid through fluidic lines.

FIG. 65A illustrates replacement of peristaltic pumps of FIG. 60B with pressurized chambers on input sample bags to drive fluid through fluidic lines.

Figure 60A:
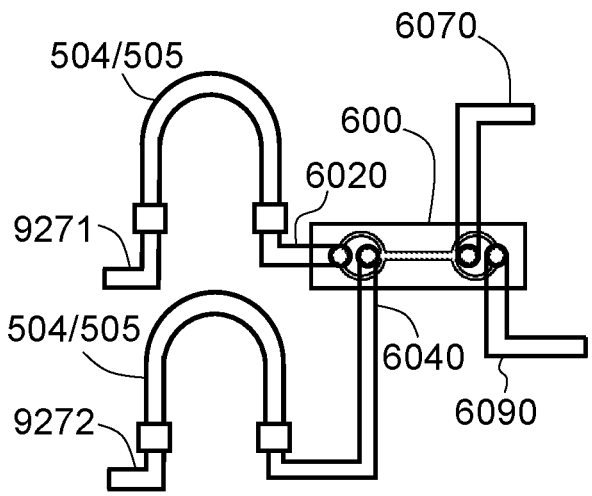
Figure 60B:
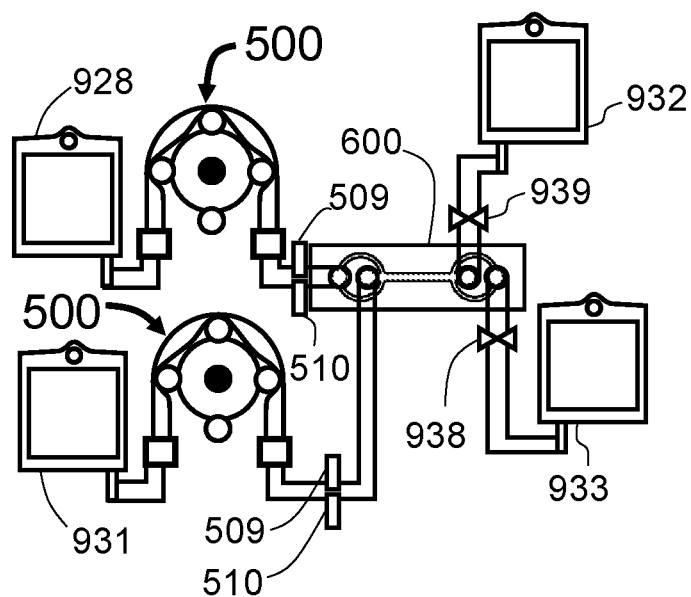
Figure 65A:
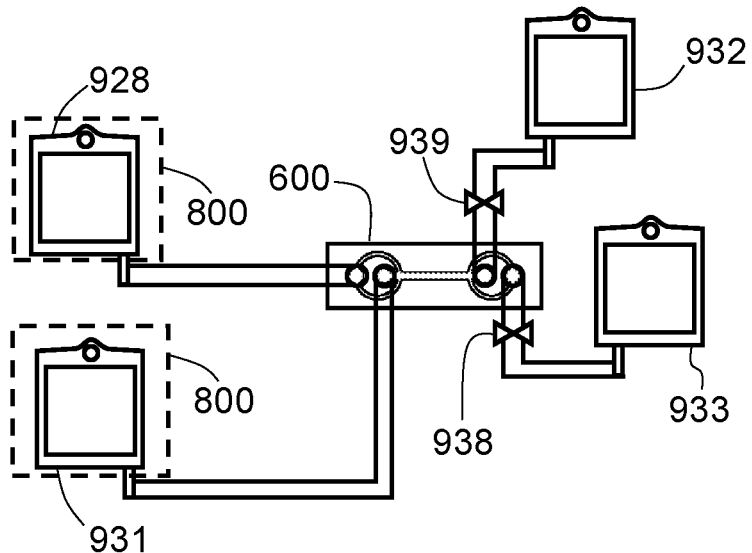
Figure 65B:
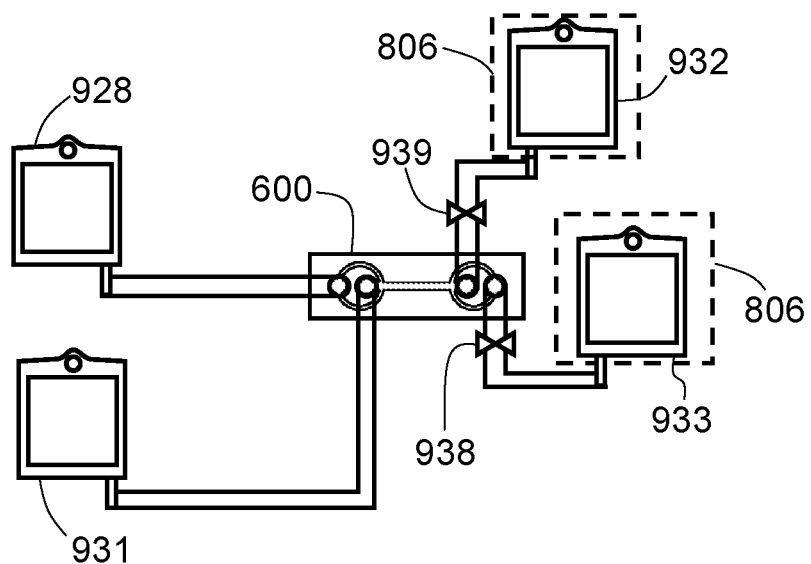

FIG. 65B illustrates replacement of peristaltic pumps of FIG. 60B with vacuum chambers on output sample bags to drive fluid through fluidic lines.

Figure 66:
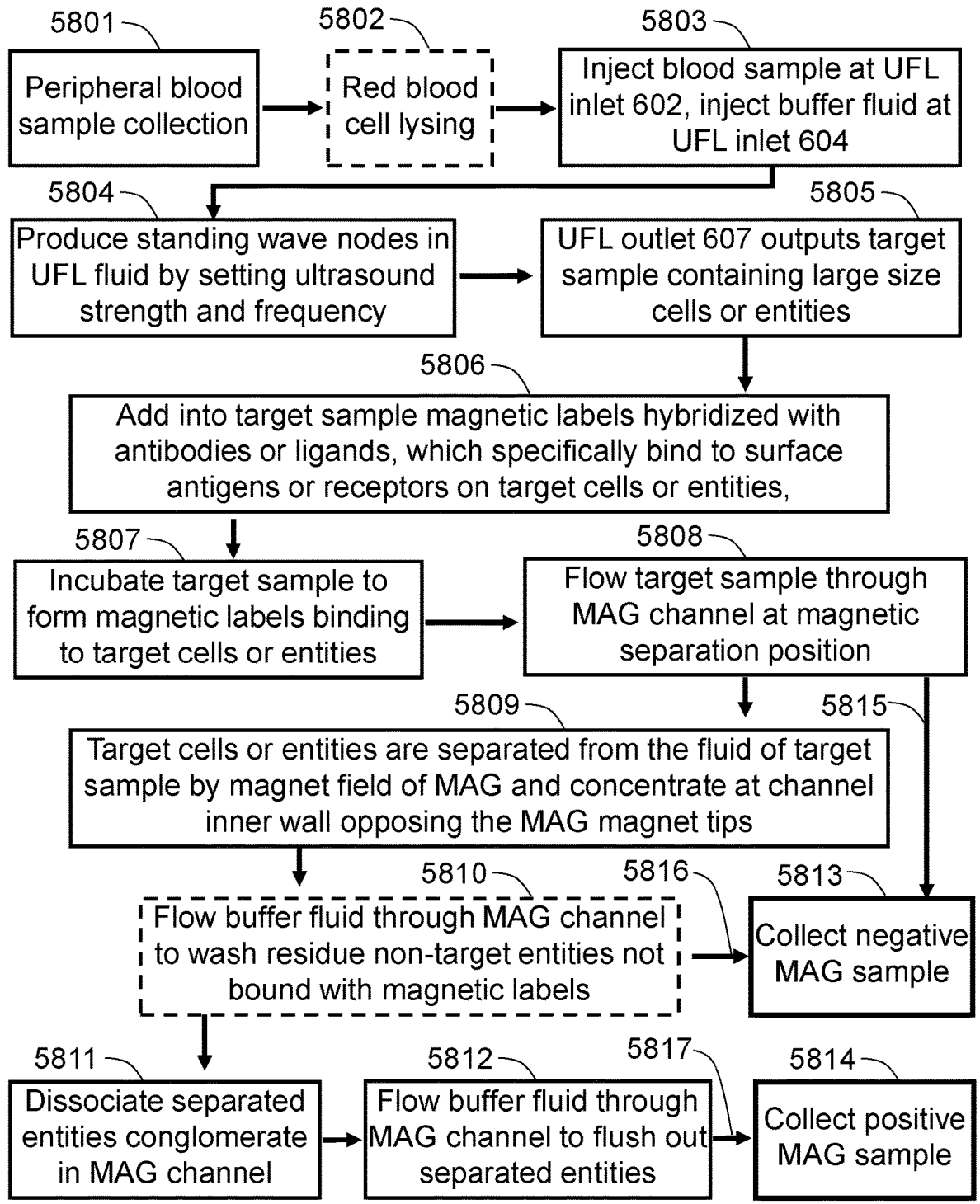

FIG. 66 illustrates a first process flow to separate biological entities from peripheral blood using UFL and MAG.

Figure 67:
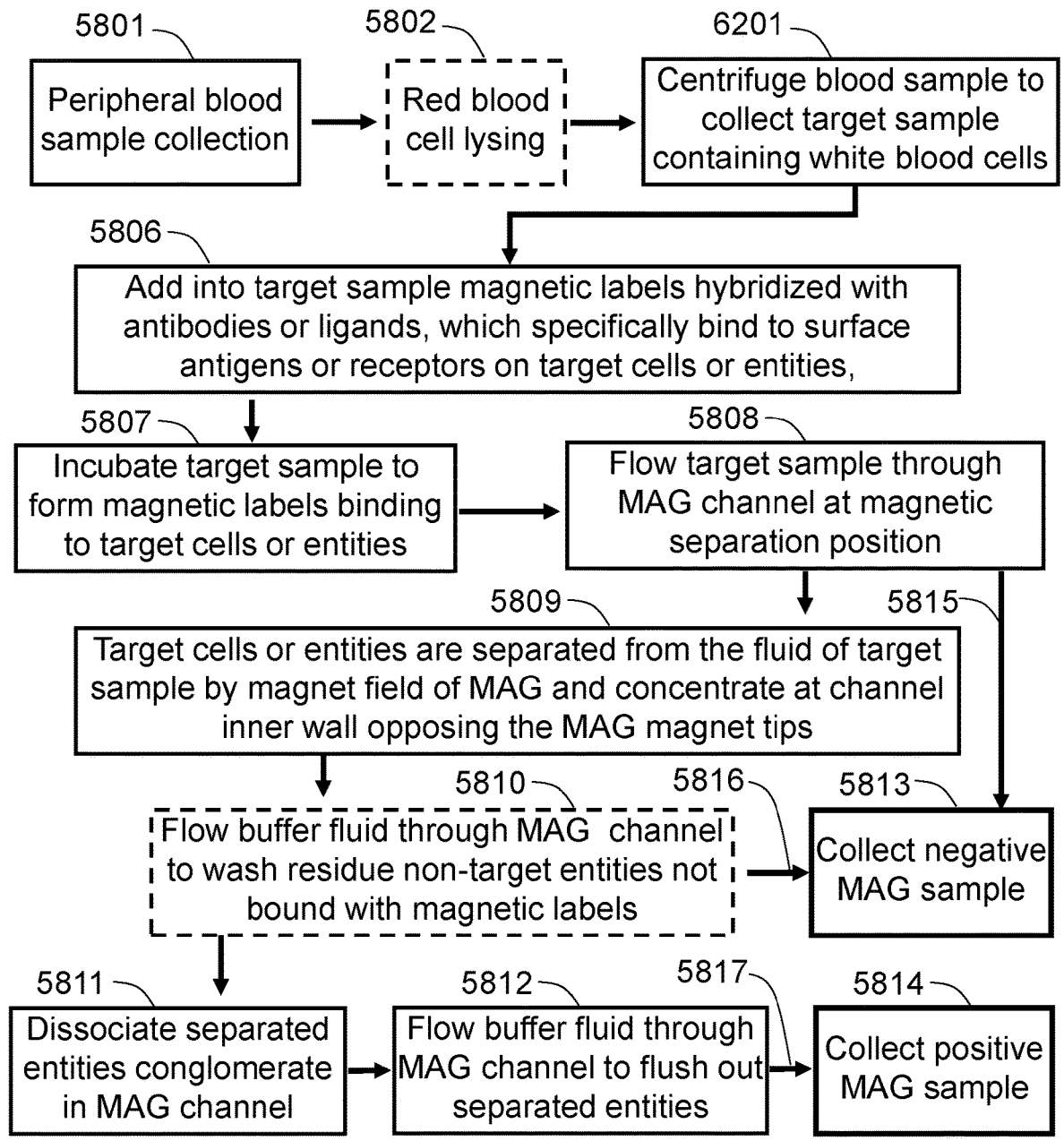

FIG. 67 illustrates a second process flow to separate biological entities from peripheral blood using MAG.

Figure 68:
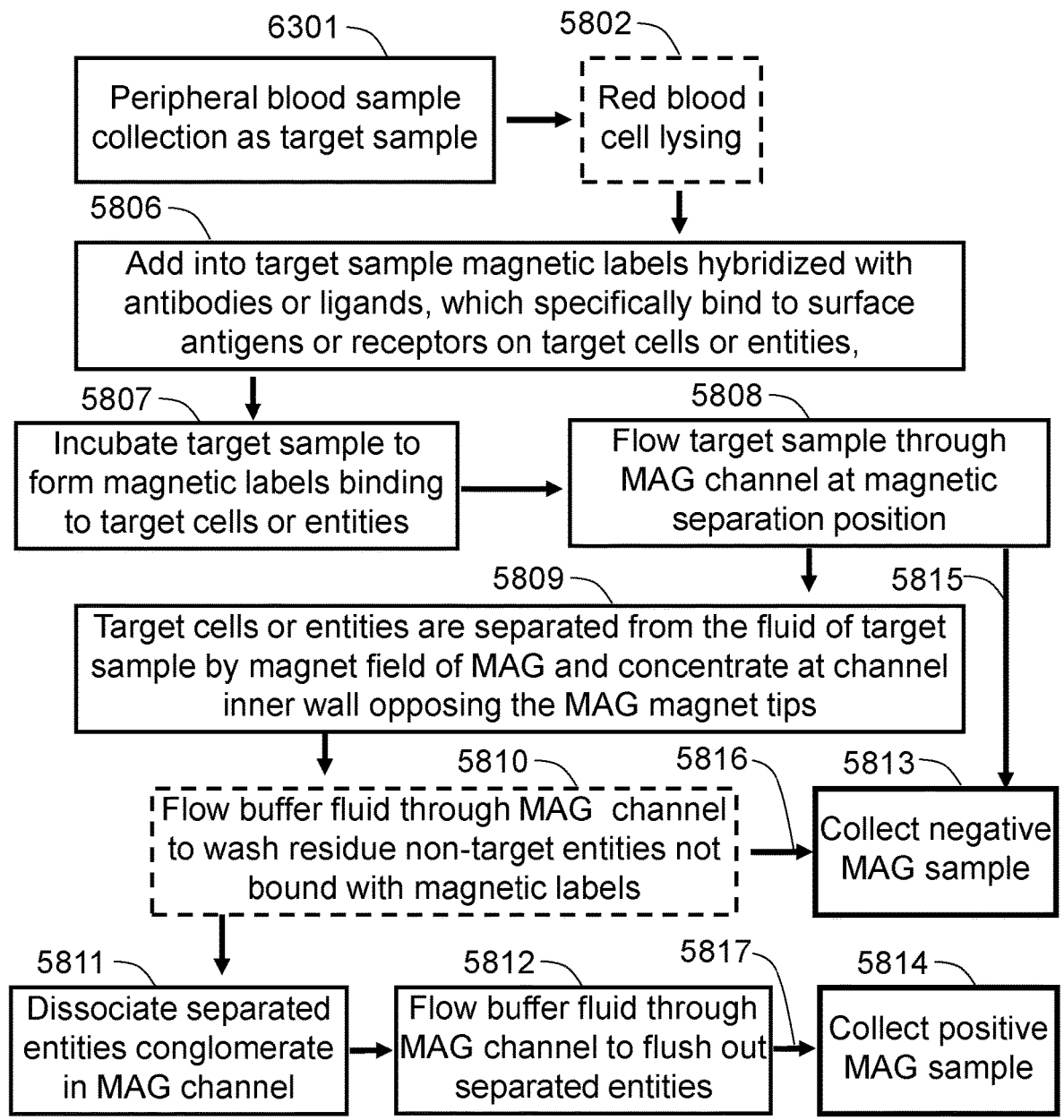

FIG. 68 illustrates a third process flow to separate biological entities from peripheral blood using MAG.

Figure 69:
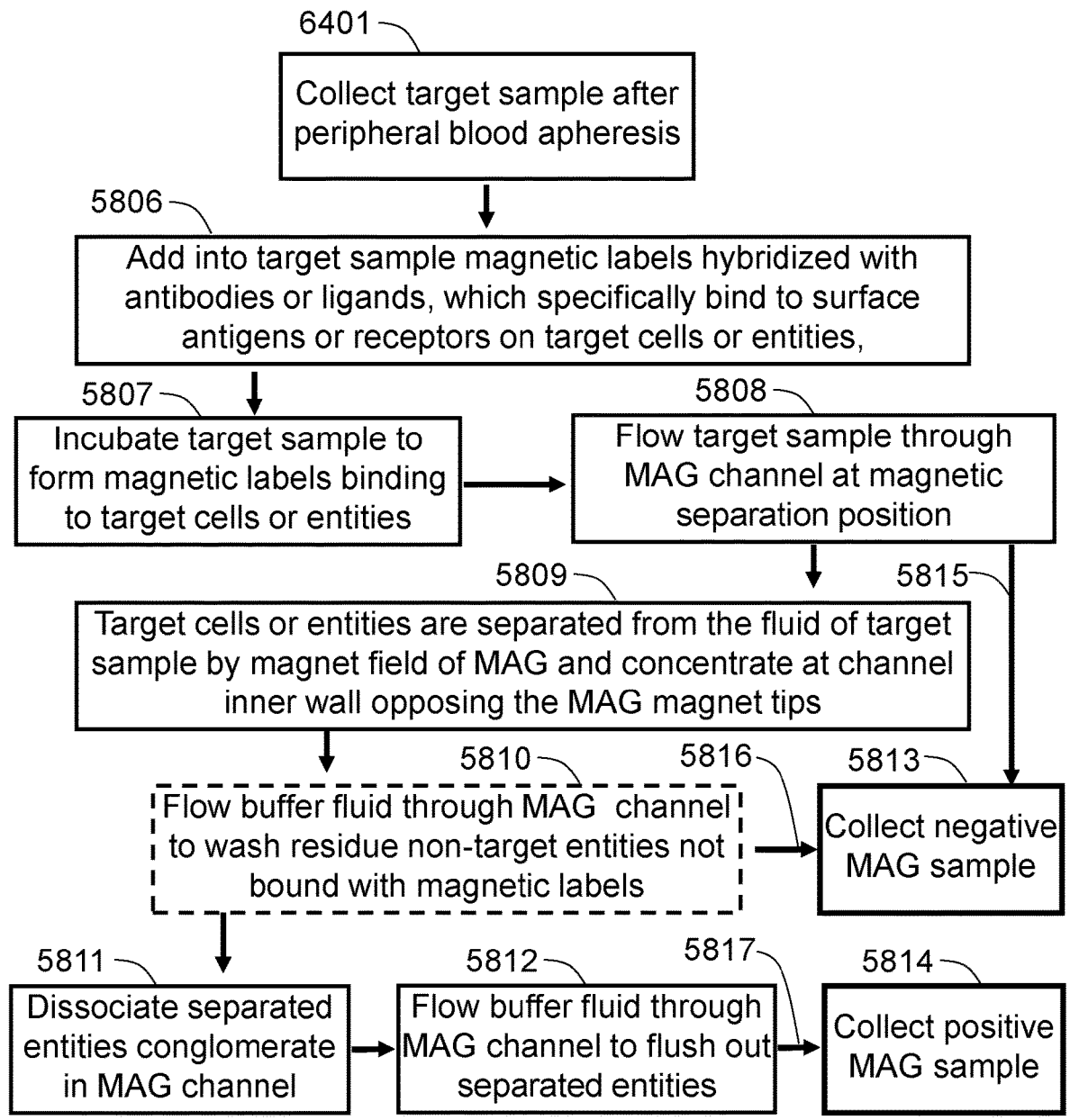

FIG. 69 illustrates a fourth process flow to separate biological entities from peripheral blood using MAG.

Figure 70:
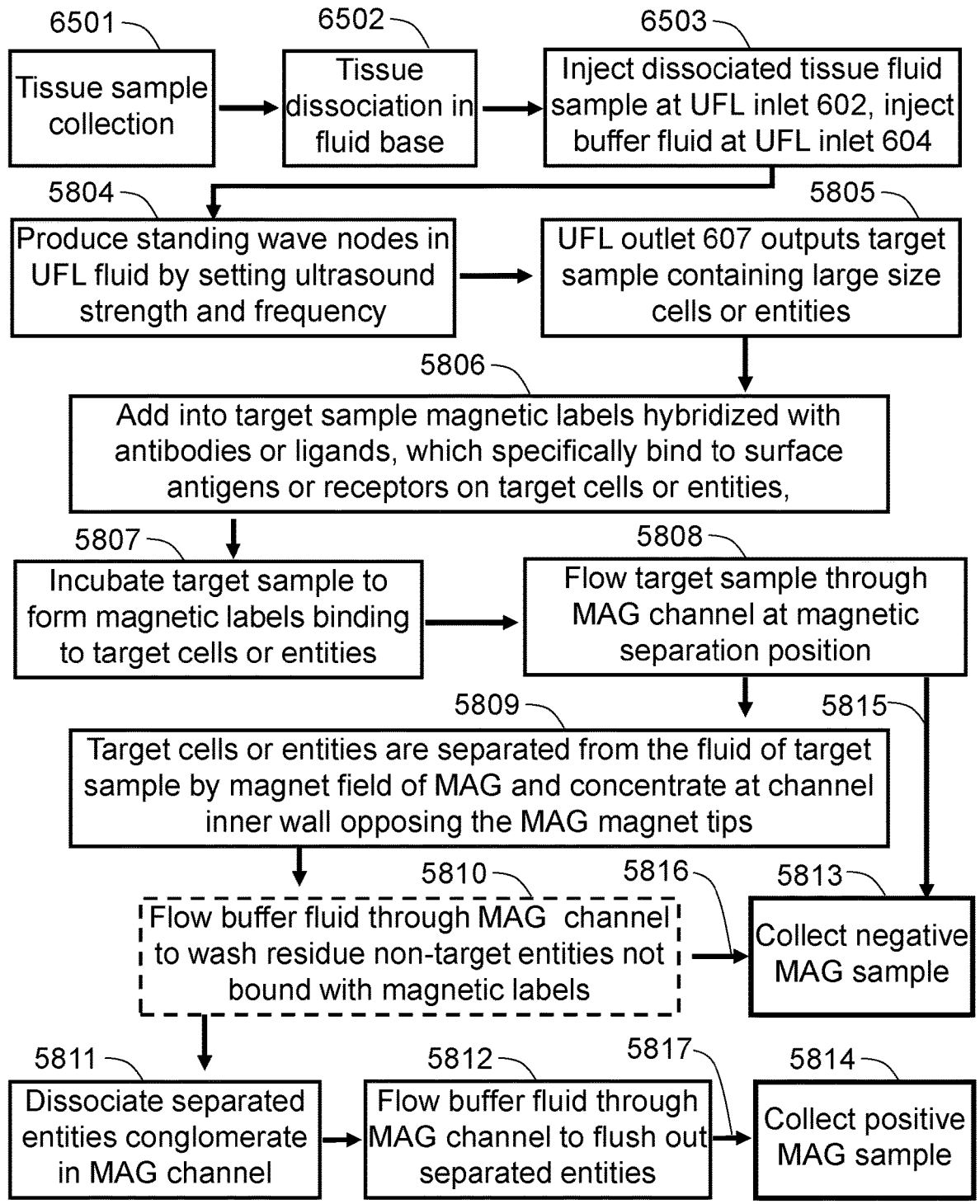

FIG. 70 illustrates a fifth process flow to separate biological entities from tissue sample using UFL and MAG.

Figure 71:
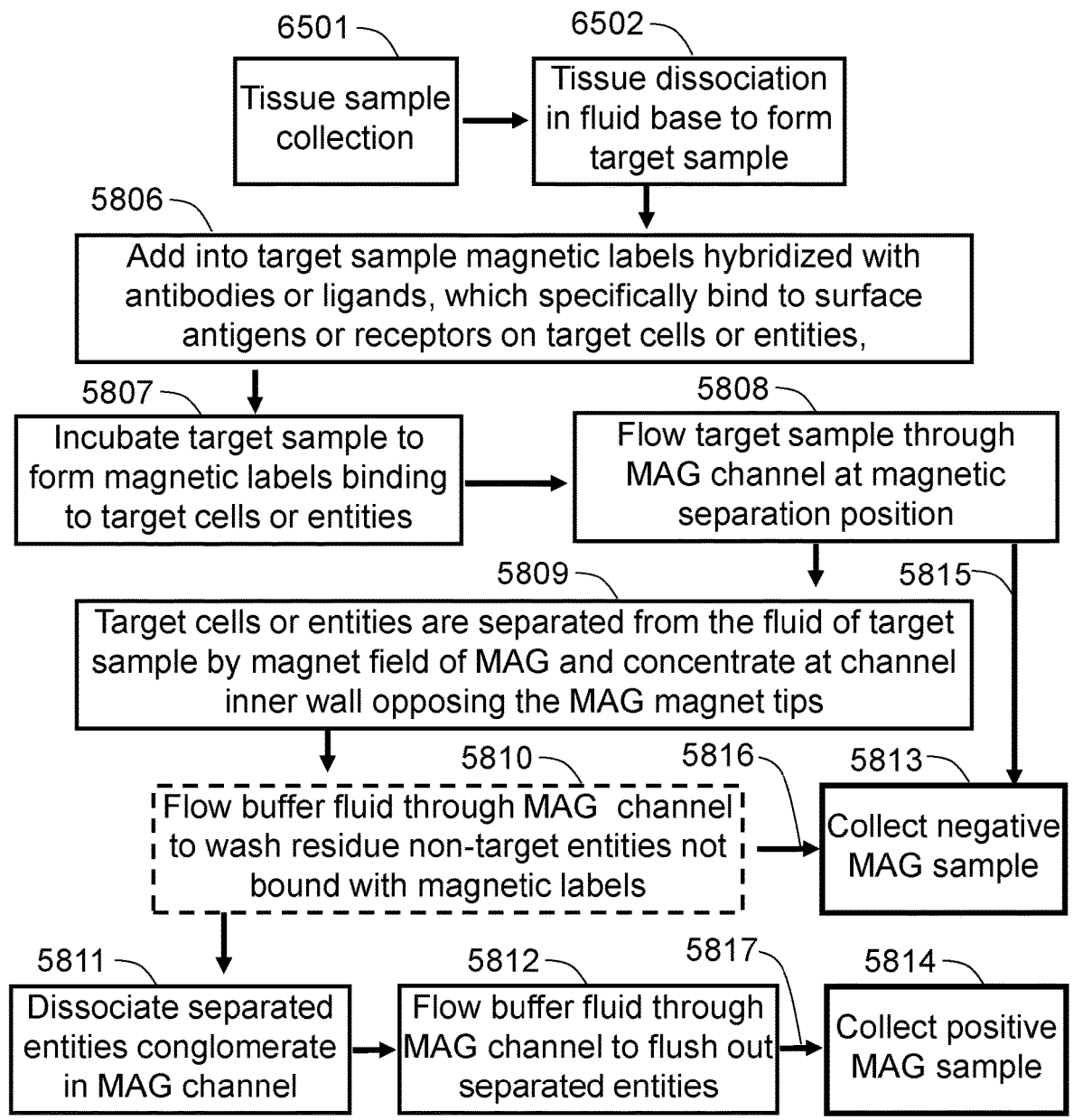

FIG. 71 illustrates a sixth process flow to separate biological entities from tissue sample using MAG.

Figure 72:
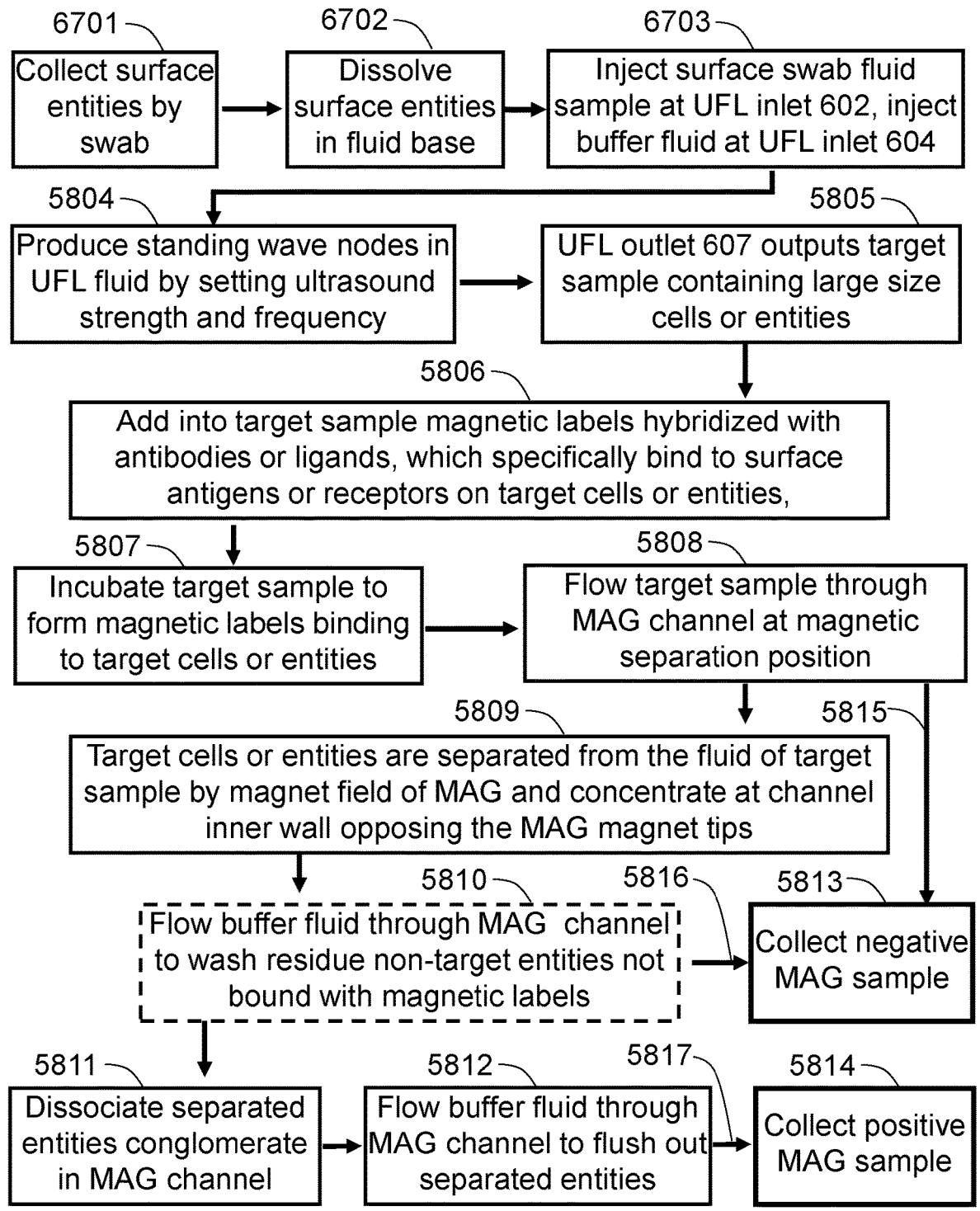

FIG. 72 illustrates a seventh process flow to separate biological entities from surface swab sample using UFL and MAG.

Figure 73:
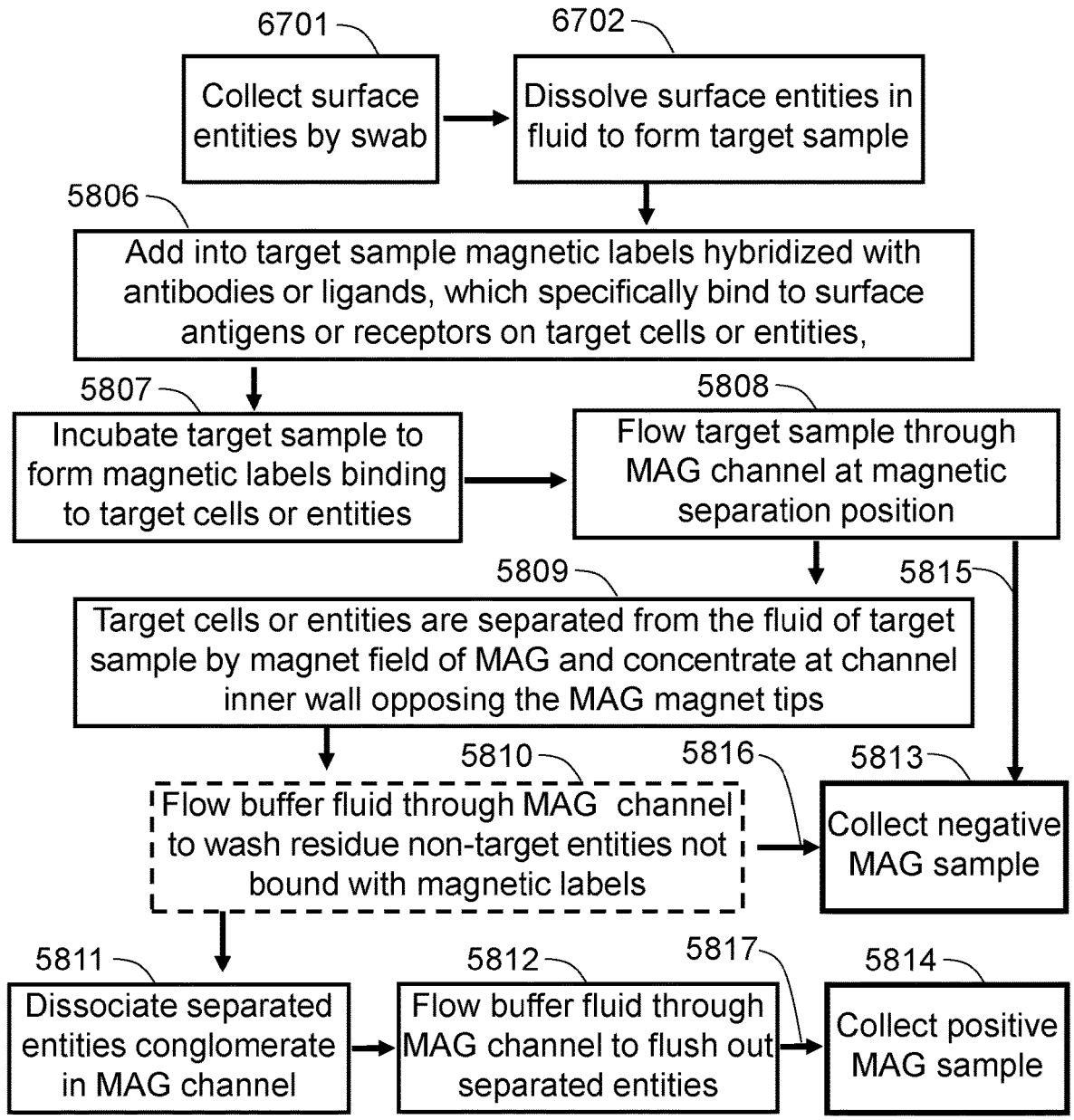

FIG. 73 illustrates an eighth process flow to separate biological entities from surface swab sample using MAG.

Figure 74:
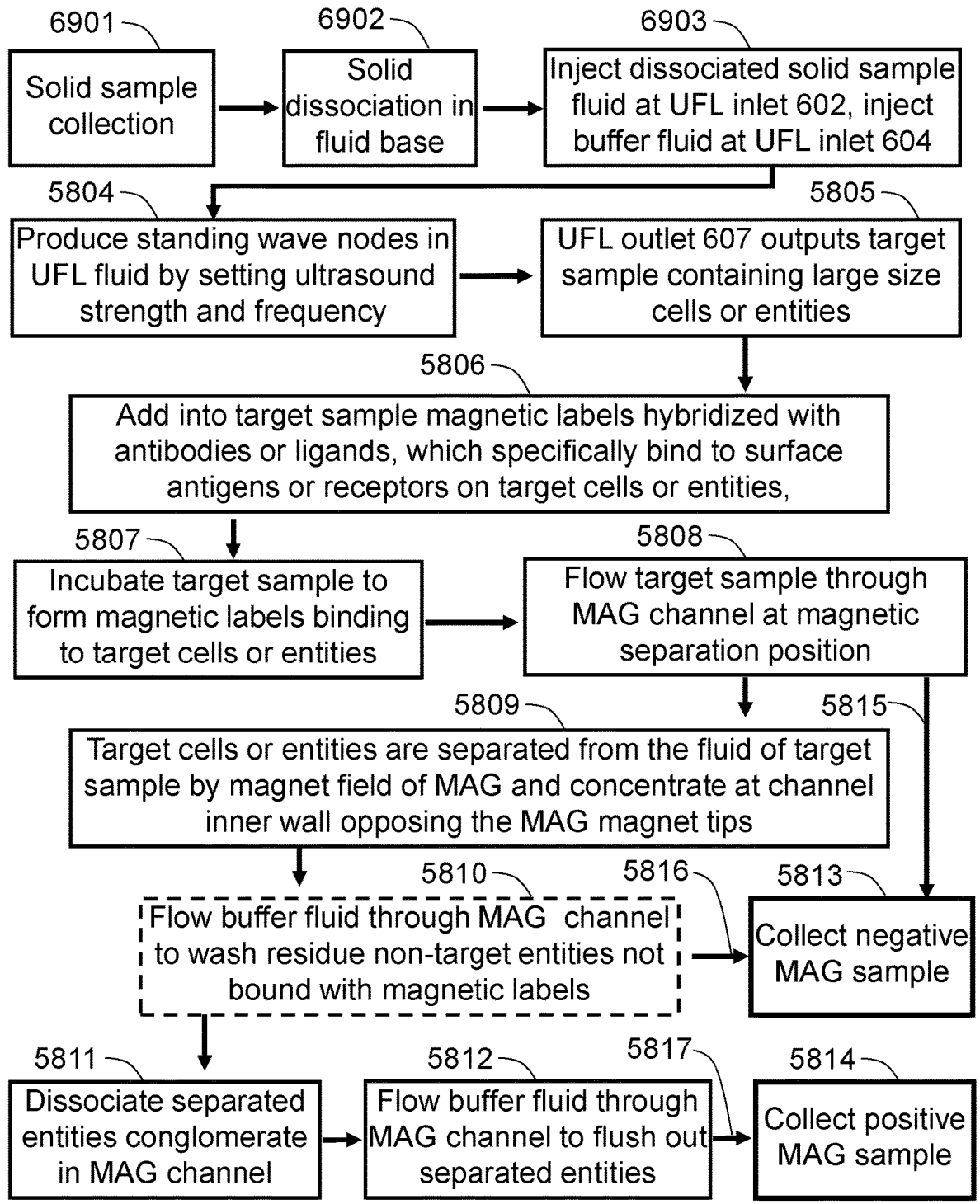

FIG. 74 illustrates a ninth process flow to separate biological entities from solid sample using UFL and MAG.

Figure 75:
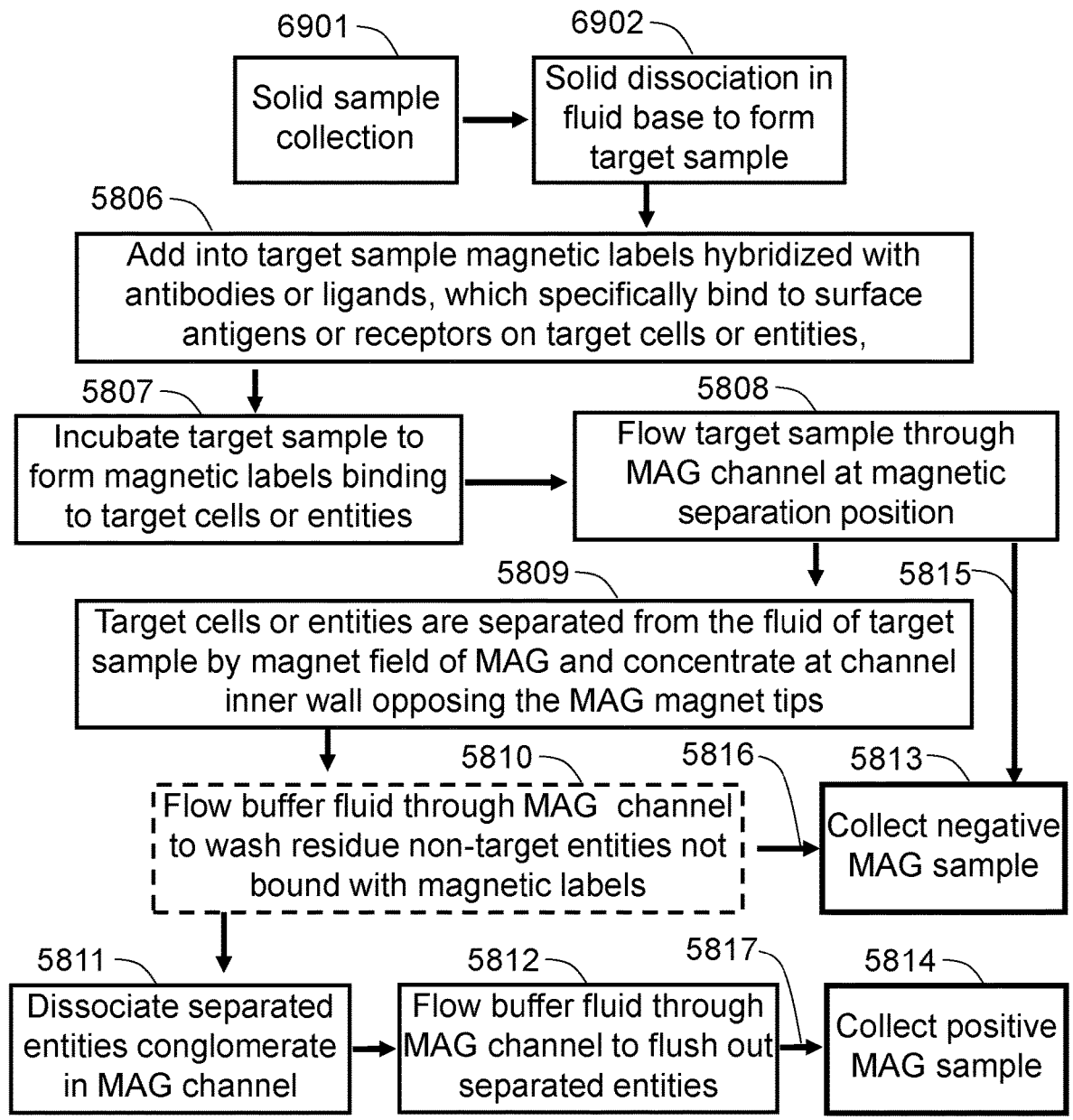

FIG. 75 illustrates a tenth process flow to separate biological entities from solid sample using MAG.

FIG. 76A illustrates addition of both magnetic and fluorescent labels into fluid samples for specific binding to target cells or entities.

FIG. 76B illustrates incubation of both magnetic and fluorescent labels at same time to form specific binding to target cells or entities.

Figure 77A:
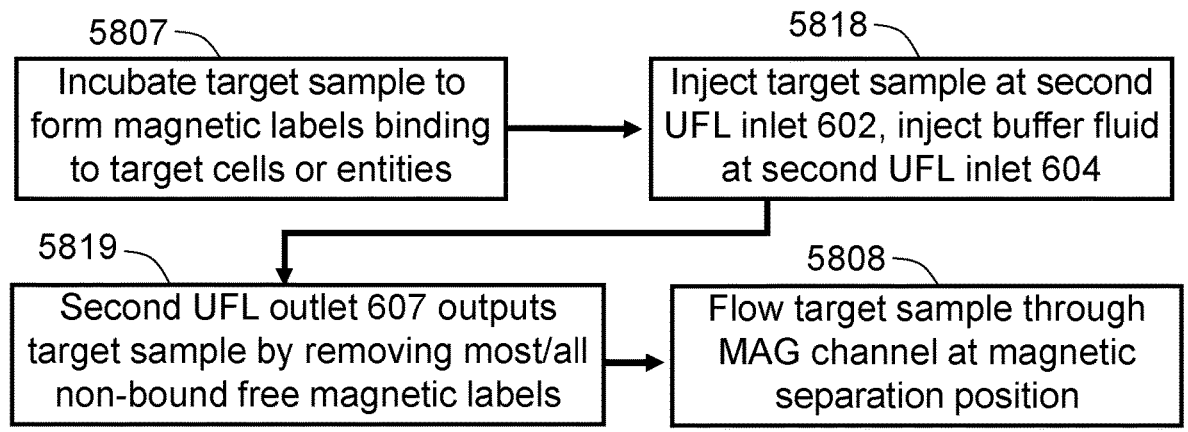

FIG. 77A illustrates process of removing non-bound free magnetic labels from sample fluid by UFL before magnetic separation by MAG.

Figure 77B:
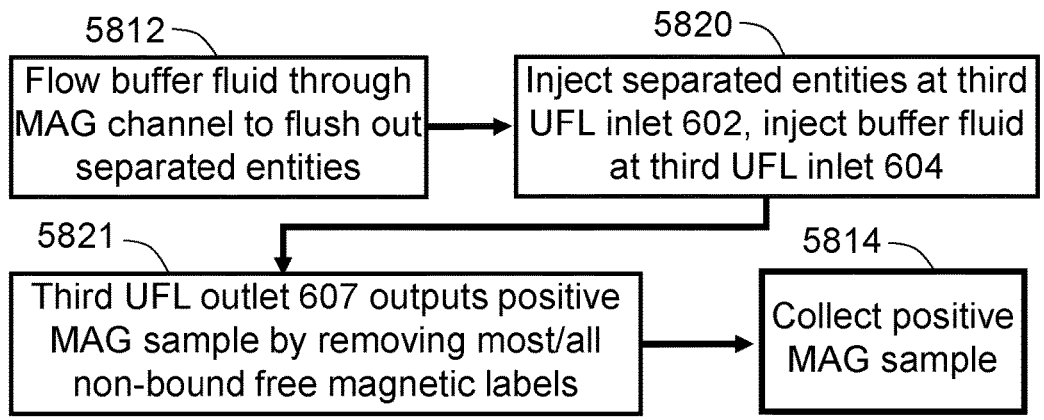

FIG. 77B illustrates process of removing non-bound free magnetic labels from sample fluid by UFL after magnetic separation by MAG.

Figure 78A:
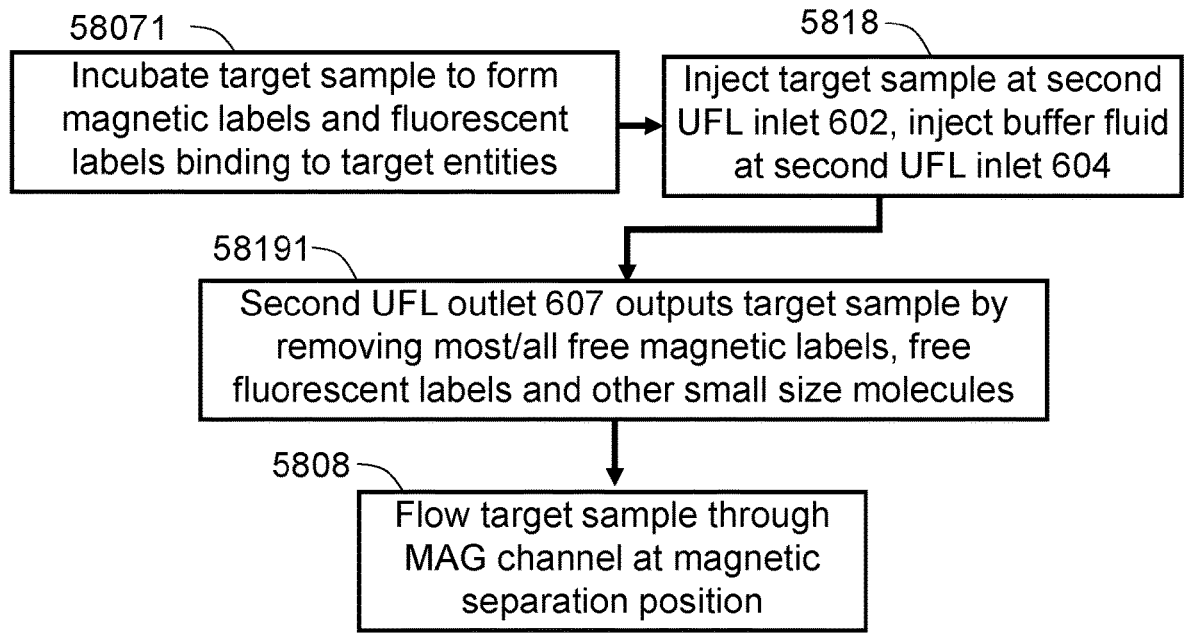

FIG. 78A illustrates process of removing non-bound free magnetic labels and free fluorescent labels from sample fluid by UFL before magnetic separation by MAG.

Figure 78B:
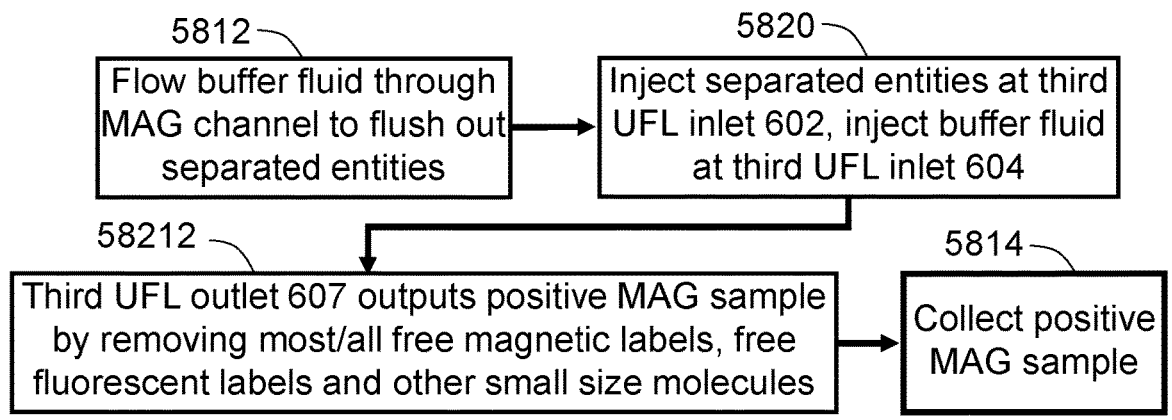

FIG. 78B illustrates process of removing non-bound free magnetic labels and free fluorescent labels from sample fluid by UFL after magnetic separation by MAG.

Figure 79:
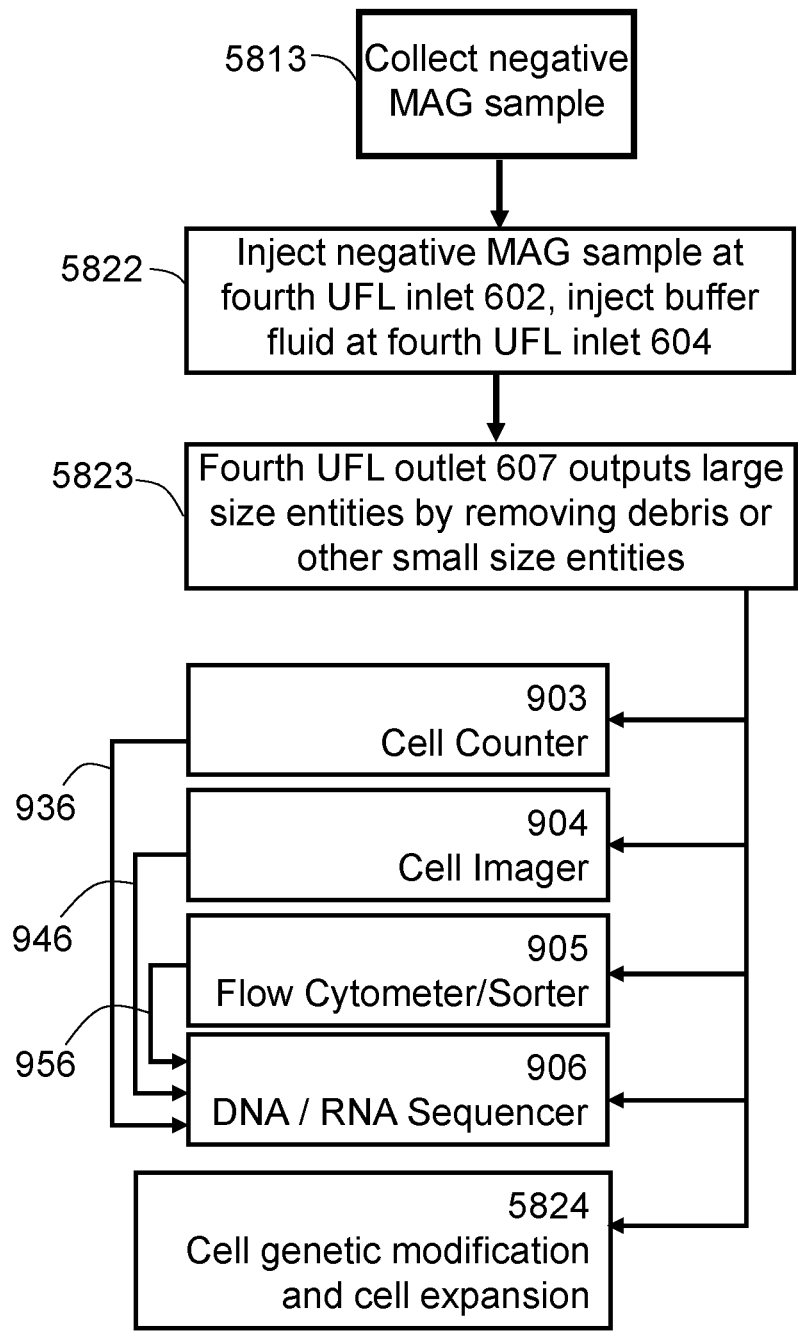

FIG. 79 illustrates continued process of negative MAG sample through UFL and various cell processing devices and procedures.

Figure 80:
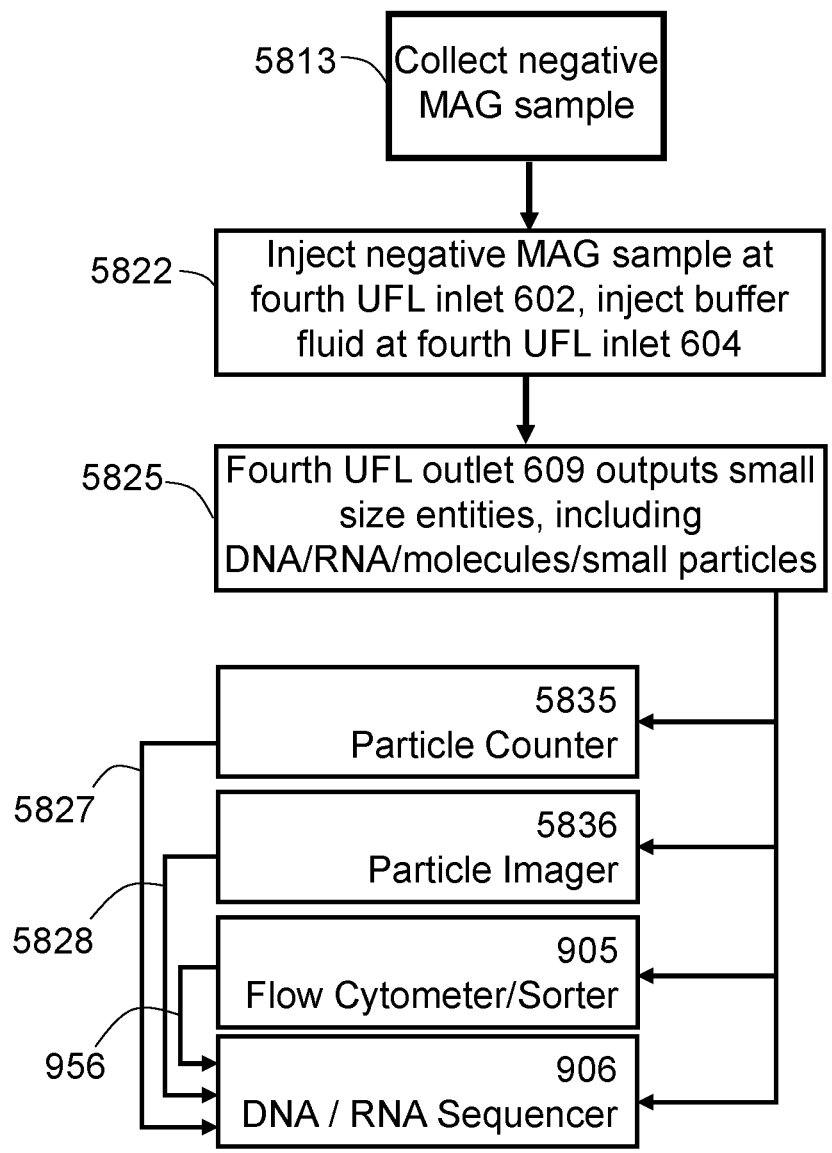

FIG. 80 illustrates continued process of negative MAG sample through UFL and various particle or molecule processing devices.

Figure 81:
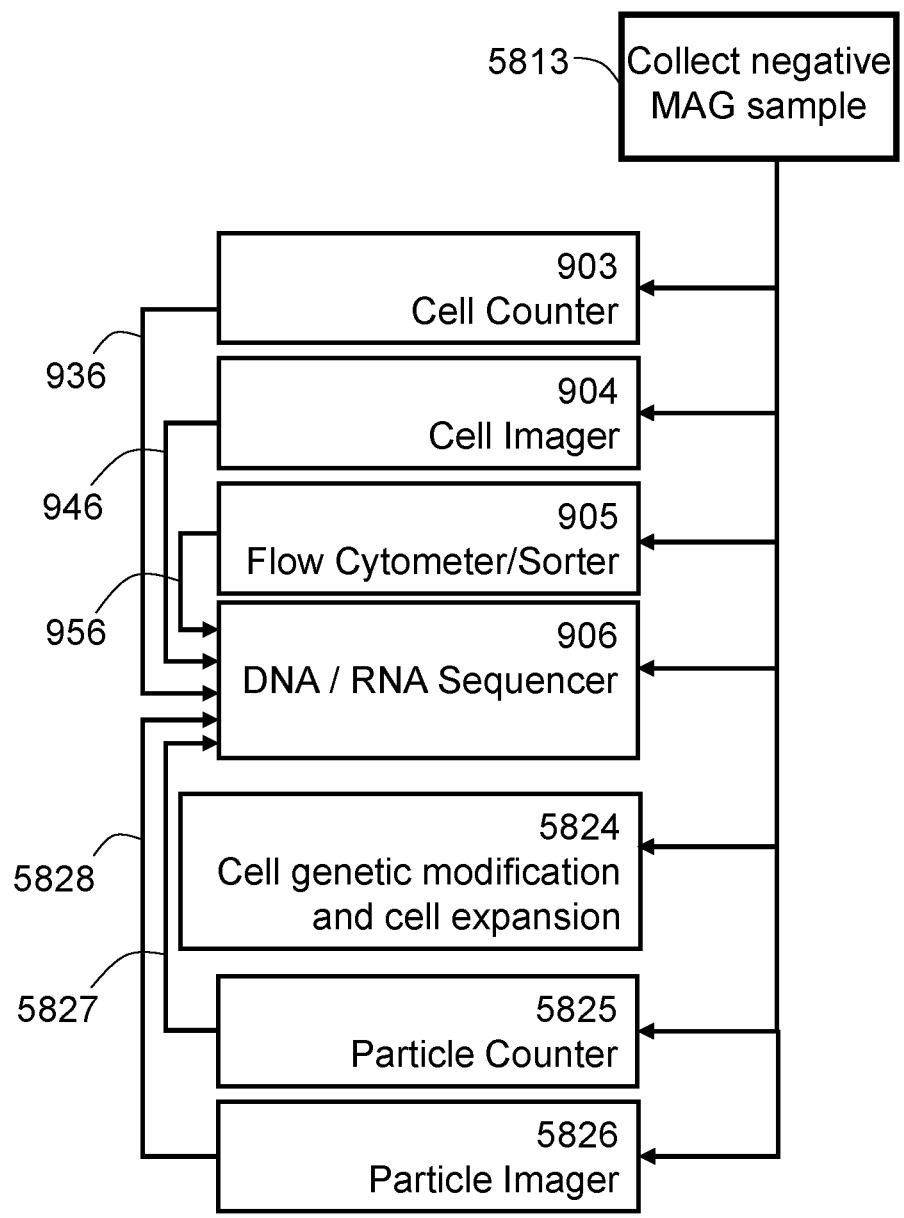

FIG. 81 illustrates entity analysis of negative MAG sample after MAG separation into various analyzing devices.

Figure 82:
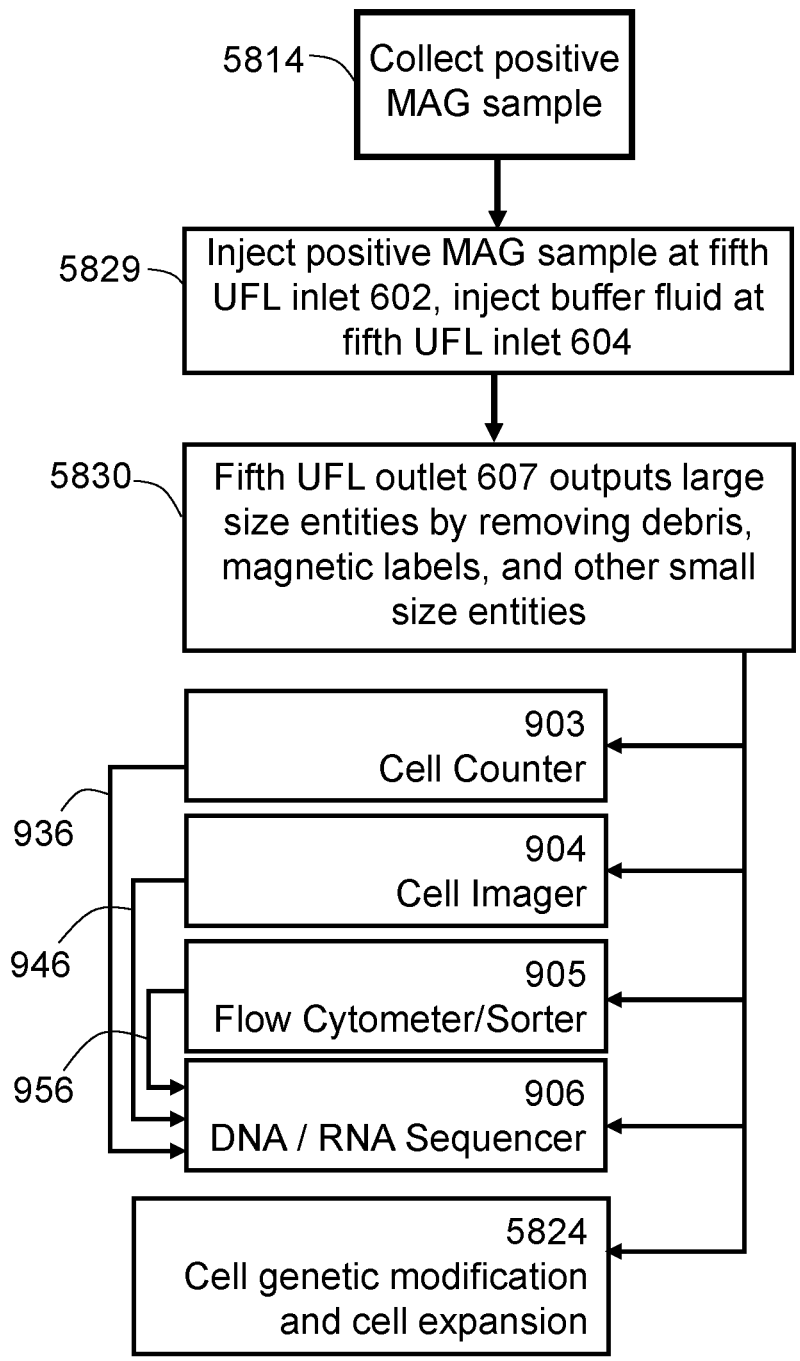

FIG. 82 illustrates continued process of positive MAG sample through UFL and various cell processing devices and procedures.

Figure 83:
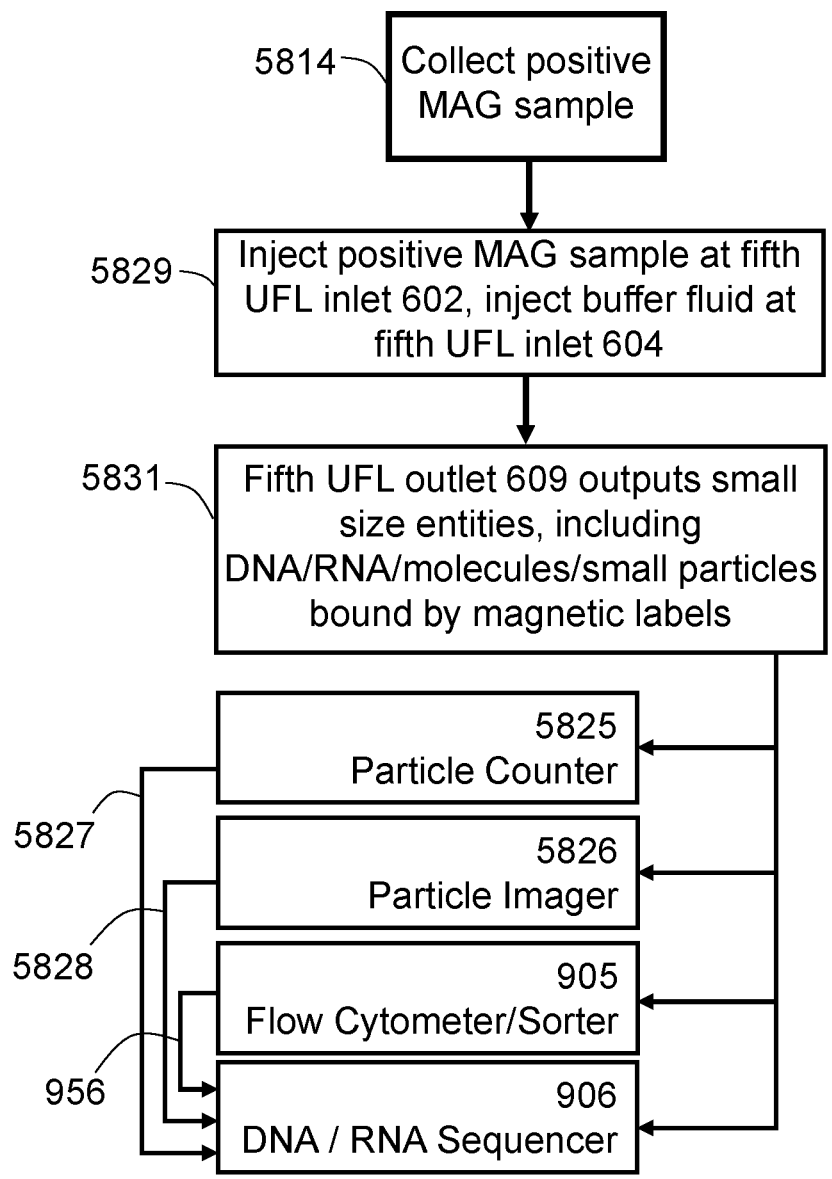

FIG. 83 illustrates continued process of positive MAG sample through UFL and various particle or molecule processing devices.

Figure 84:
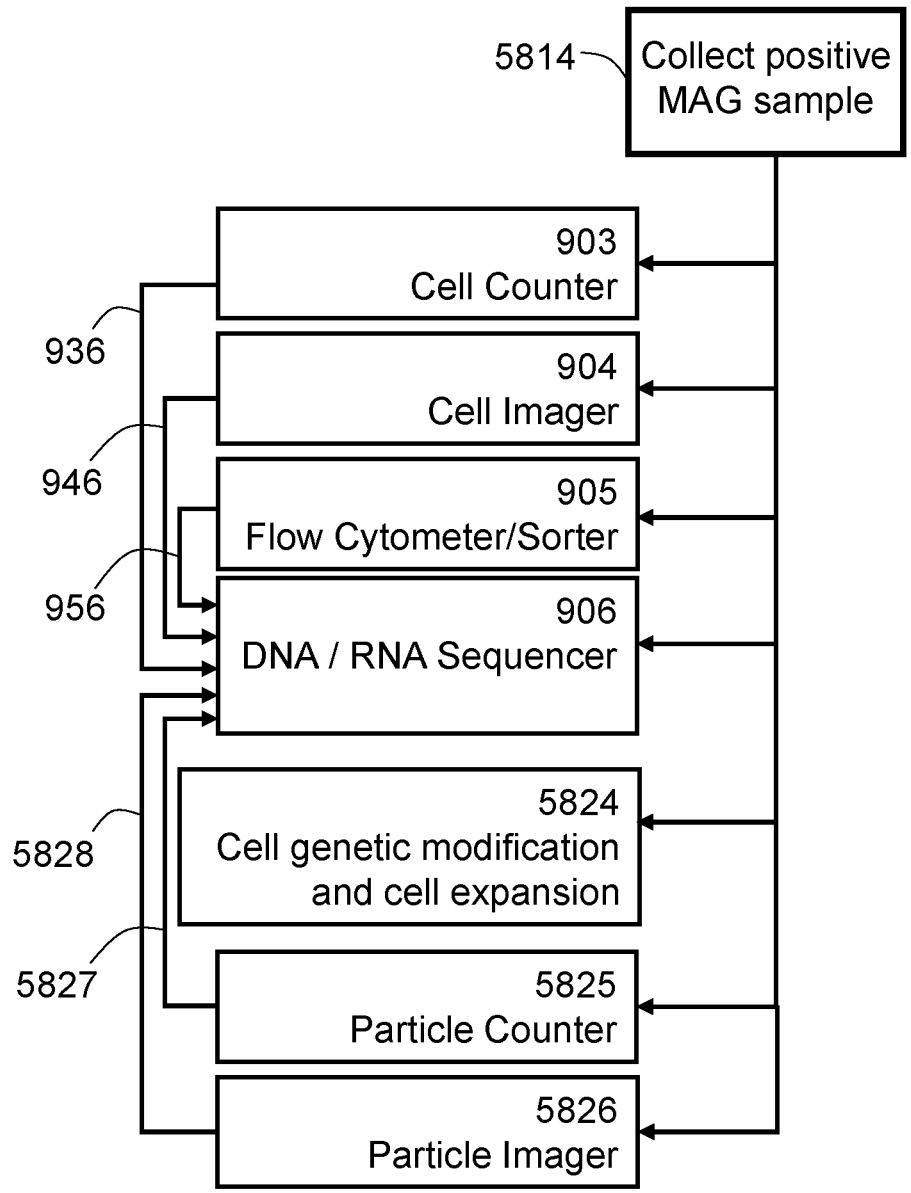

FIG. 84 illustrates entity analysis of positive MAG sample after MAG separation into various analyzing devices.

Figure 85A:
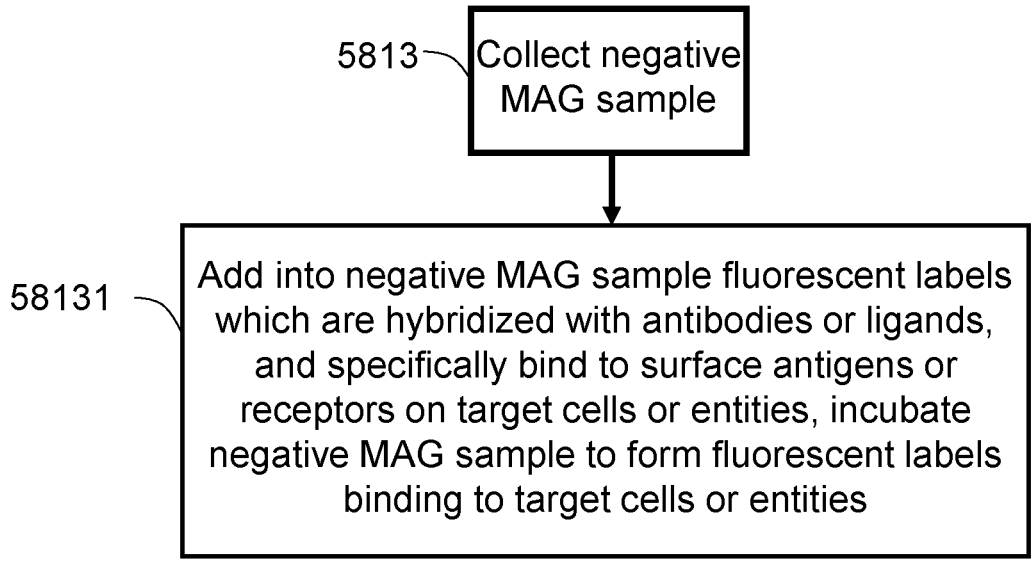

FIG. 85A illustrates adding fluorescent labels to specifically bind to target entities within negative MAG sample immediately after negative MAG sample collection.

Figure 85B:
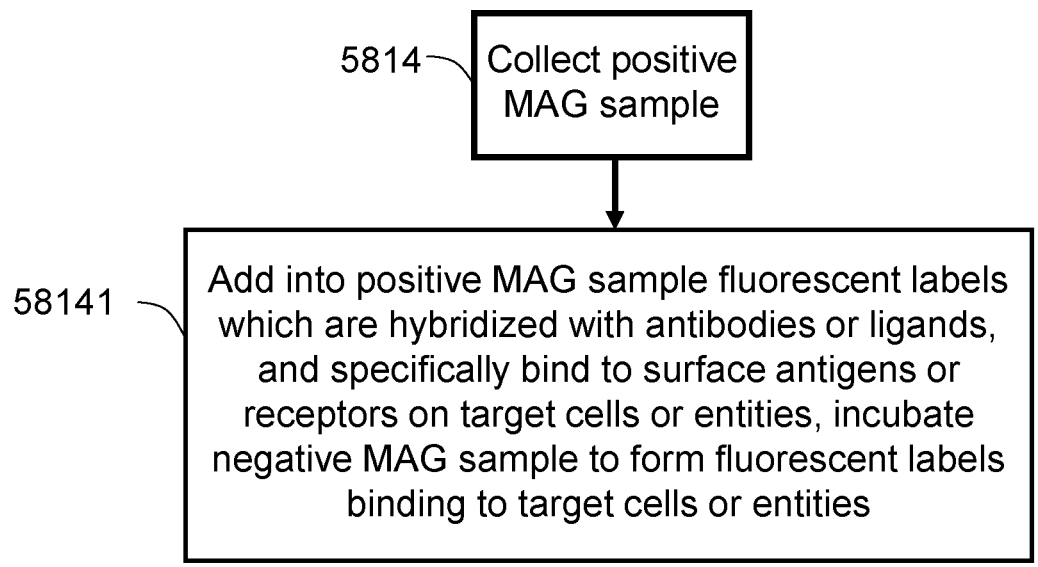

FIG. 85B illustrates adding fluorescent labels to specifically bind to target entities within positive MAG sample immediately after positive MAG sample collection.

Figure 86A:
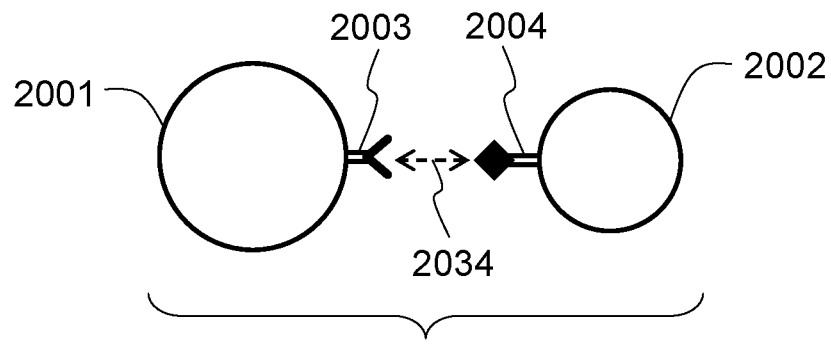
Figure 86B:
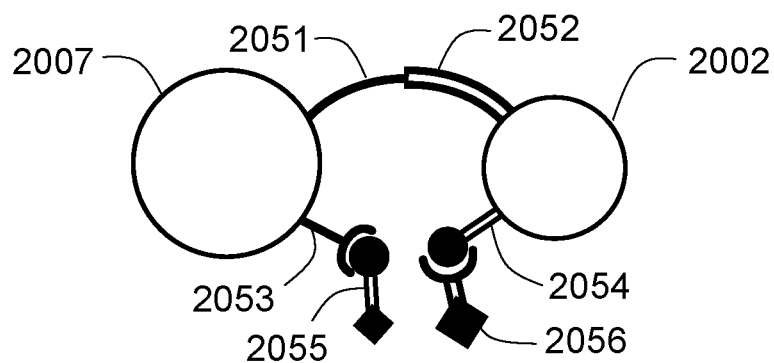
Figure 86C:
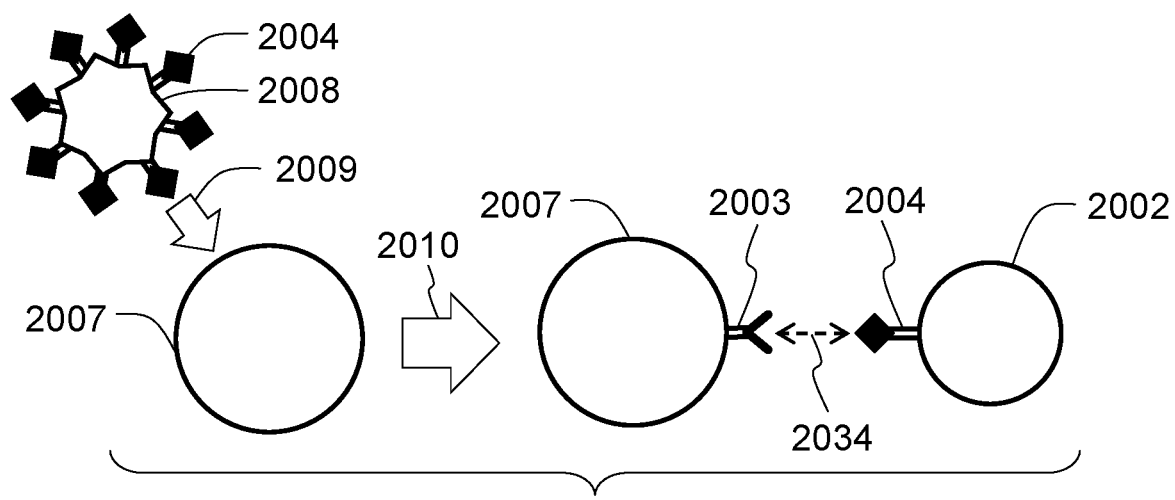
Figure 87:
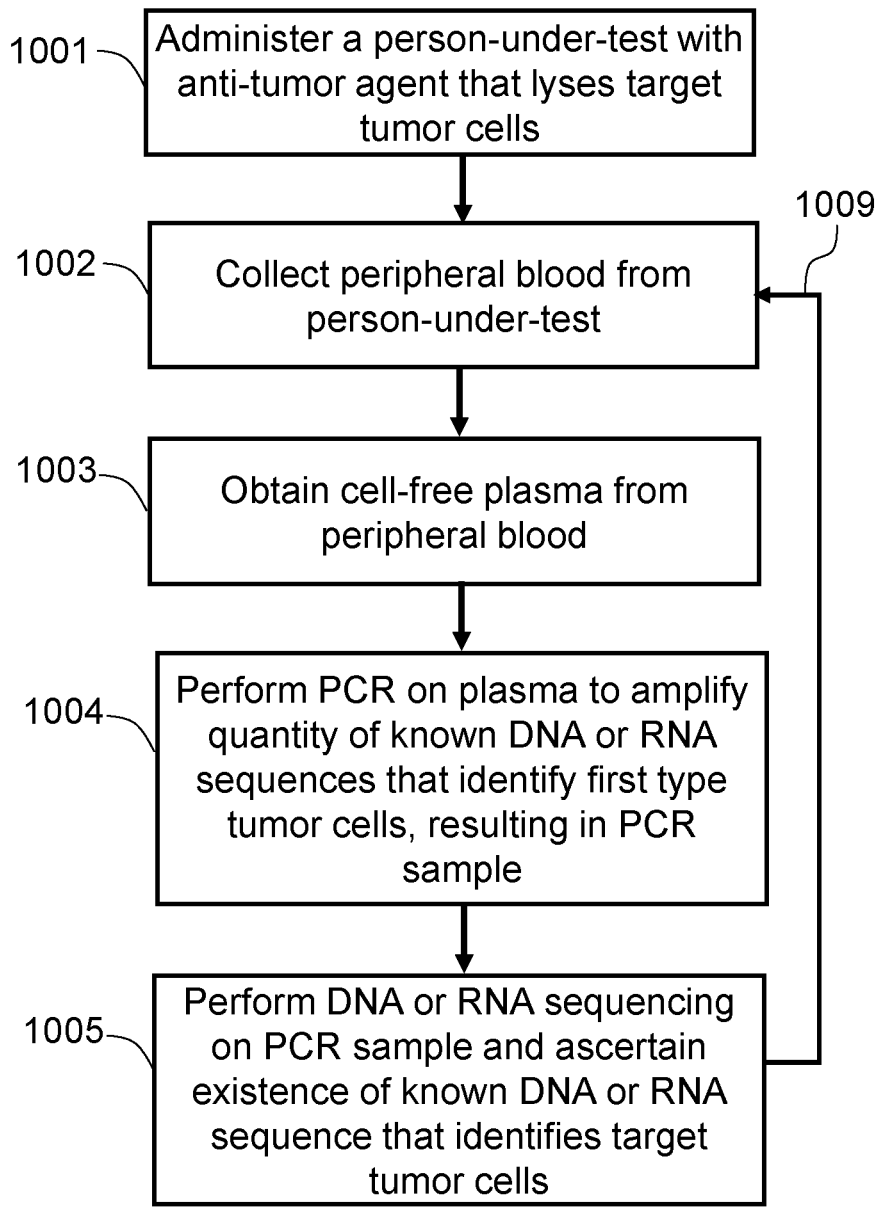
Figure 88:
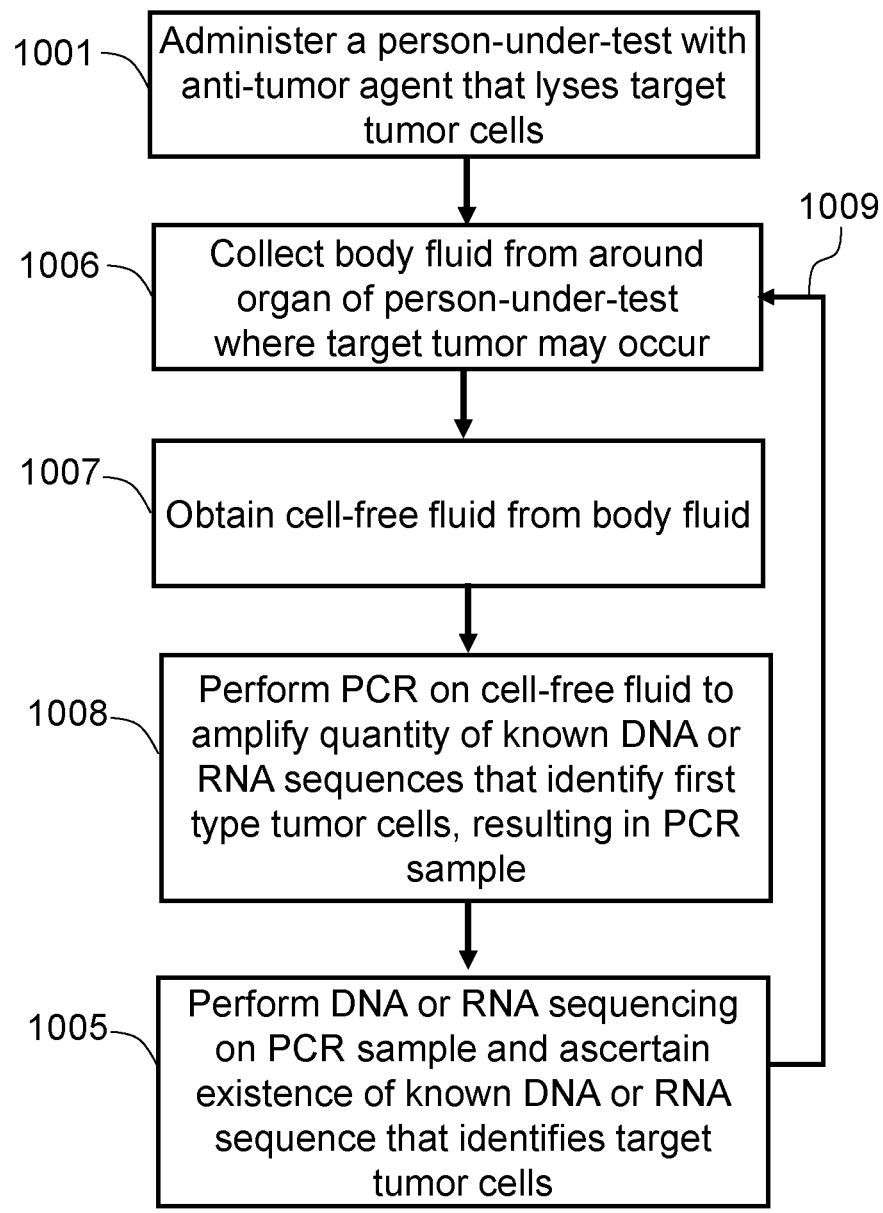
Figure 89:
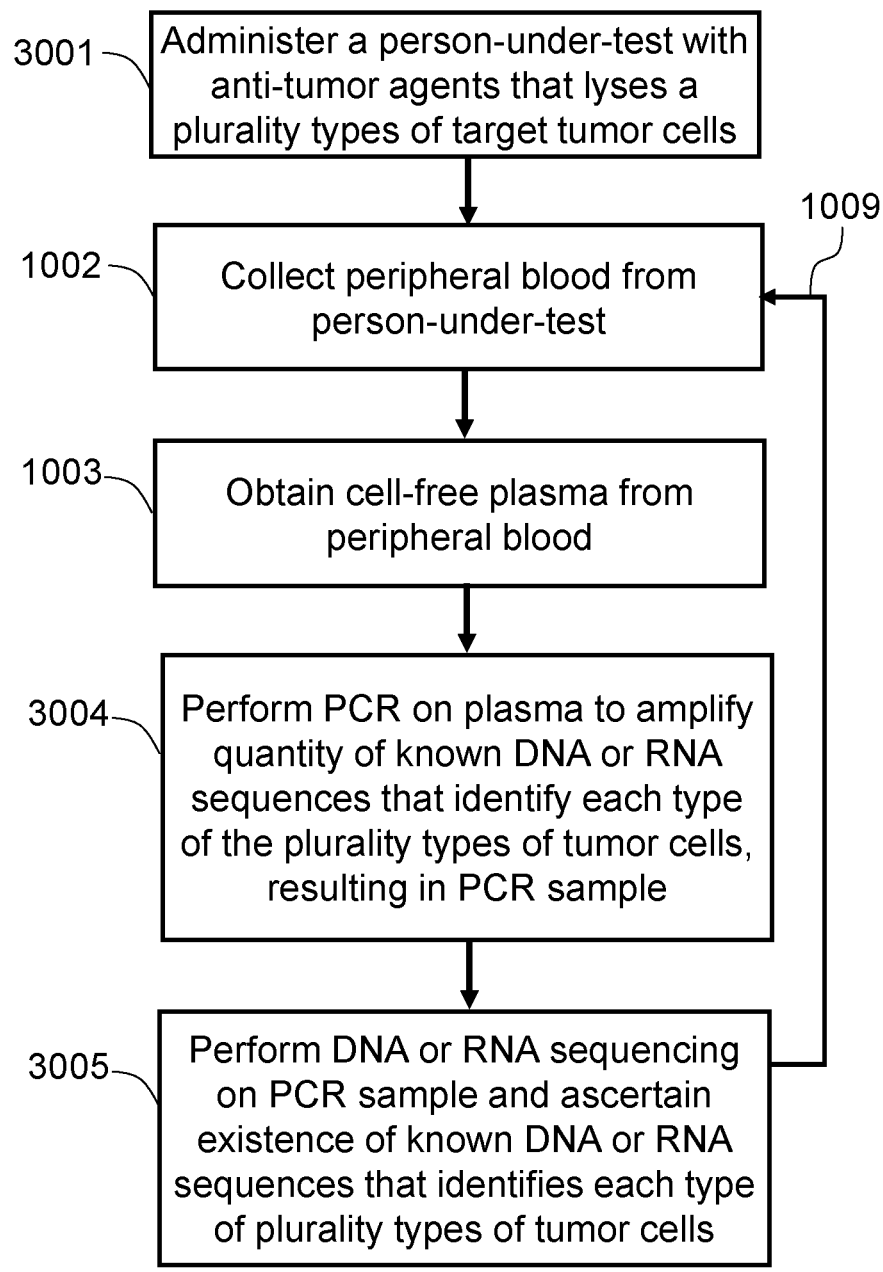
Figure 90:
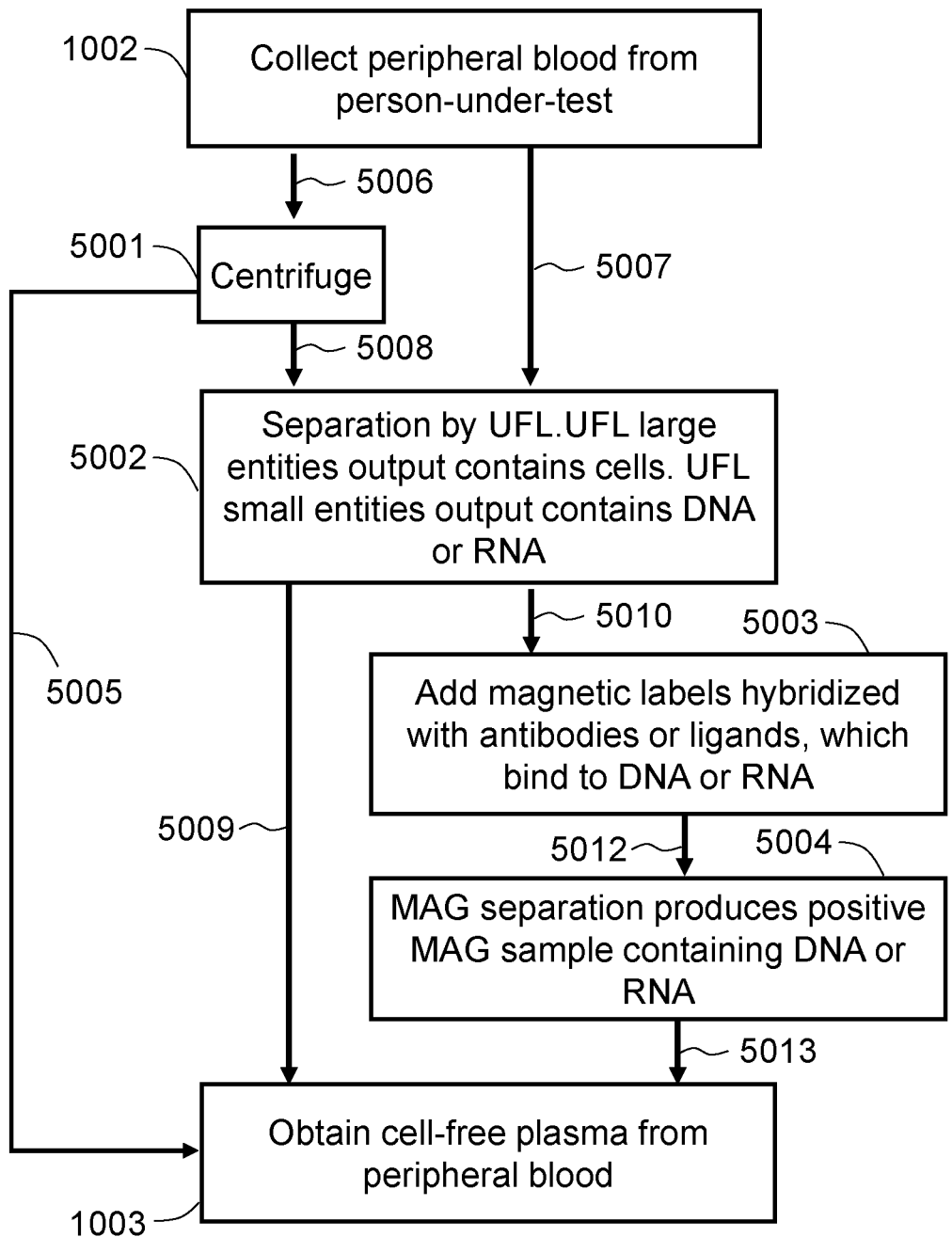
Figure 91:
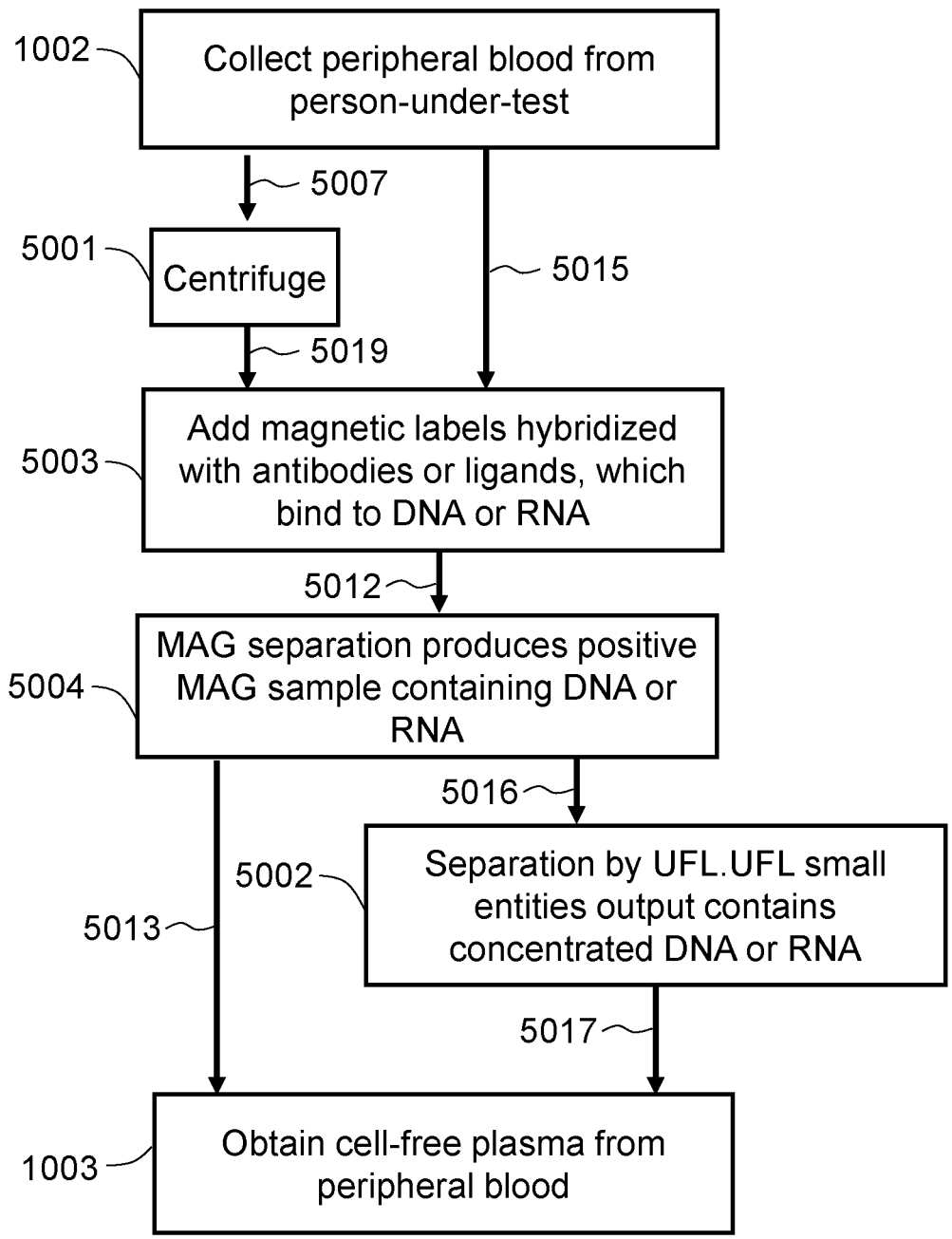
Figure 92:
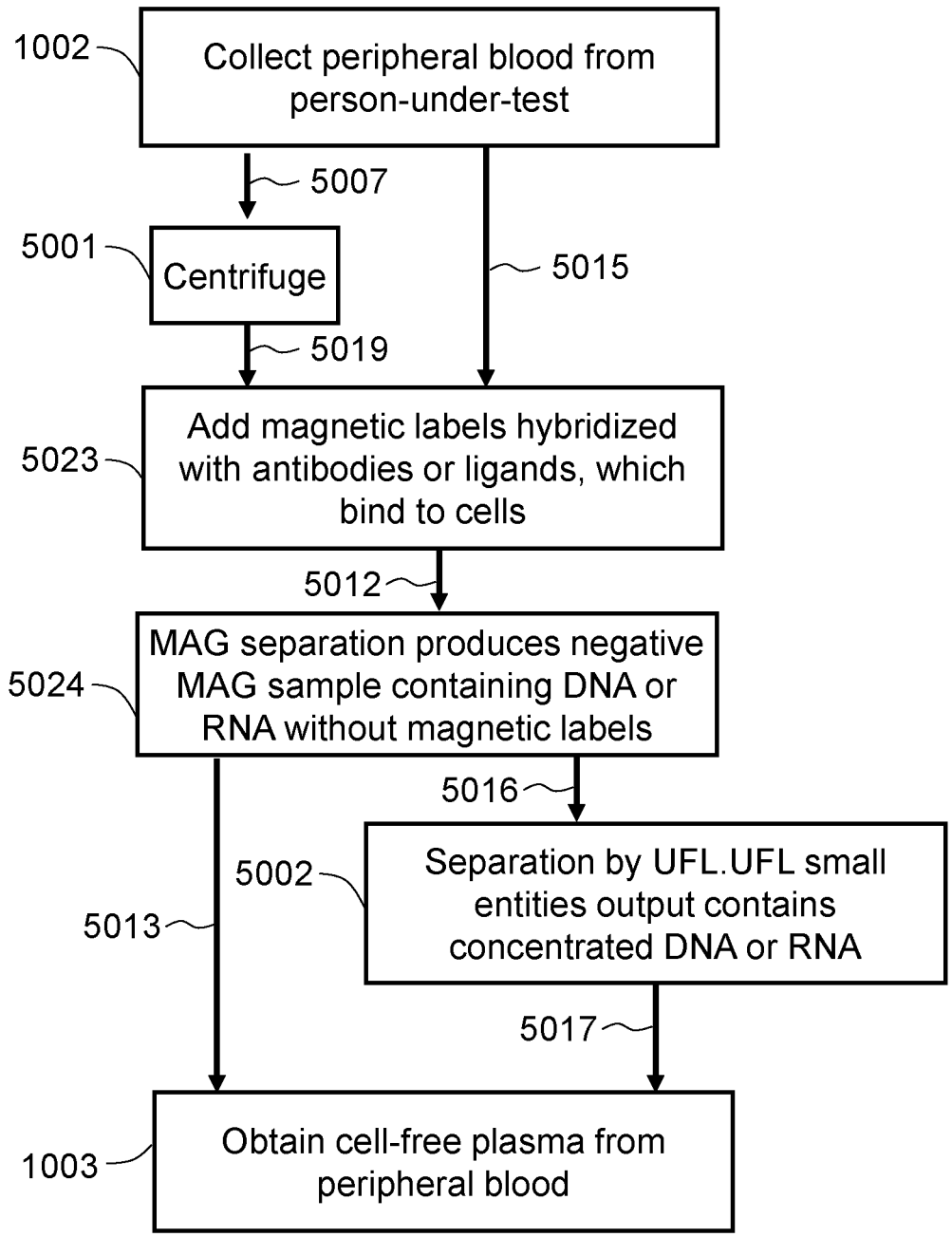
Figure 93:
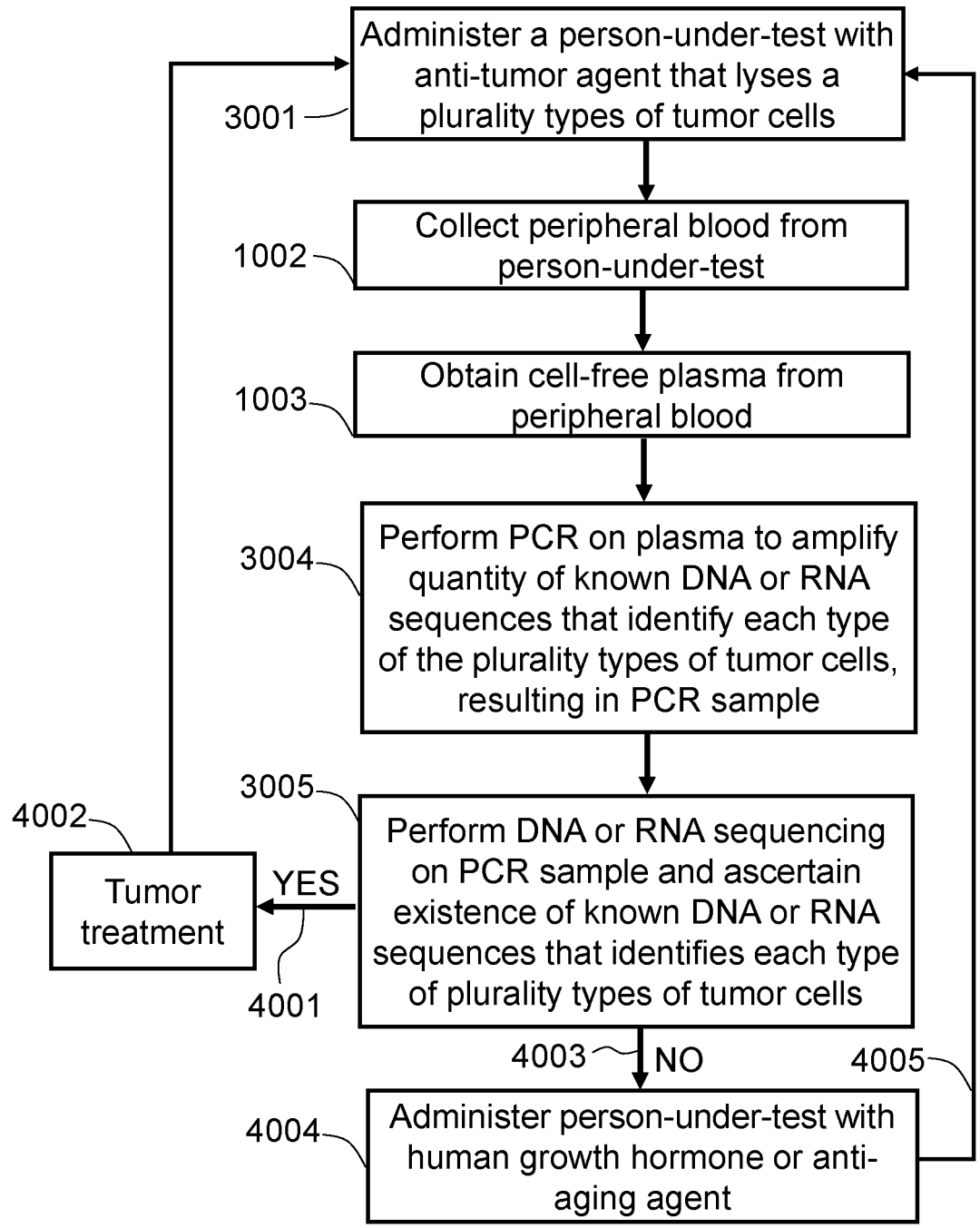

FIG. 86A illustrates first example of cancer treatment.
FIG. 86B illustrates second example of cancer treatment.
FIG. 86C illustrates third example of cancer treatment.
FIG. 87 illustrates first method of tumor detection.
FIG. 88 illustrates second method of tumor detection.
FIG. 89 illustrates third method of tumor detection.
FIG. 90 illustrates embodiment of first process flow to obtain cell-free plasma.
FIG. 91 illustrates embodiment of second process flow to obtain cell-free plasma.
FIG. 92 illustrates embodiment of third process flow to obtain cell-free plasma.
FIG. 93 illustrates method of using tumor detector for anti-aging purpose.

For purposes of clarity and brevity, like elements and components will bear the same designations and numbering throughout the Figures, which are not necessarily drawn to scale.

DETAILED DESCRIPTION OF THE INVENTION

While the current invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Examples of biological entities described hereafter include: cell, bacteria, virus, molecule, particles including RNA and DNA, cell cluster, bacteria cluster, molecule cluster, and particle cluster. Large entities and small entities refer to biological entities within the same fluid having relatively larger physical size and smaller physical size, respectively. In one embodiment, large entities include any of: cells, bacteria, cell cluster, bacteria cluster, particle cluster, entities bound with magnetic labels, and entities bound with optical label. In another embodiment, small entities include any of: molecules, particles, virus, cellular debris, non-bound free magnetic labels, and non-bound free optical labels. In another embodiment, large entities have a physical size larger than 1 micrometer (μm), and small entities have a physical size less than 1 μm. In yet another embodiment, large entities have a physical size larger than 2 μm, and small entities have a physical size less than 500 nanometer (nm). In yet another embodiment, large entities have a physical size larger than 5 μm, and small entities have a physical size less than 2 μm. Biological sample includes: blood, body fluid, tissue extracted from any part of the body, bone marrow, hair, nail, bone, tooth, liquid and solid from bodily discharge, or surface swab from any part of body. Entity liquid, or fluid sample, or liquid sample, or sample solution, includes: biological sample in its original liquid form, biological entities being dissolved or dispersed in a buffer liquid, or biological sample after dissociation from its original biological sample non-liquid form and dispersed in a buffer fluid. Biological entities and biological sample may be obtained from human or animal. Biological entities may also be obtained from plant and environment including air, water and soil. Entity fluid, or fluid sample, or sample may contain various types of magnetic or optical labels, or one or more chemical reagents that may be added during various steps within the embodiments of this invention. Sample flow rate is volume amount of a fluid sample flowing through a cross-section of a channel, or a fluidic part, or a fluidic path, in a unit time, where volume may be in unit of liter (l), milliliter (ml), microliter (μl), or nanoliter (nl), and unit time may be in unit of minute (min), second (s), millisecond (ms), microsecond (μs), or nanosecond (ns). Sample flow speed is the distance that a free molecule or a free entity travels within a liquid sample in a channel, or a fluidic part, or a fluidic path, in a unit time, where distance may be in unit of meter (m), centimeter (cm), millimeter (mm), or micrometer (μm). Separation efficiency is percentage of target entities within a liquid sample that are successfully separated from the liquid sample by a method designed to separate the target entities. Buffer fluid is a fluid base where biological entities may be dissolved into, or dispersed into, without introducing additional biological entities.

Figure 4:
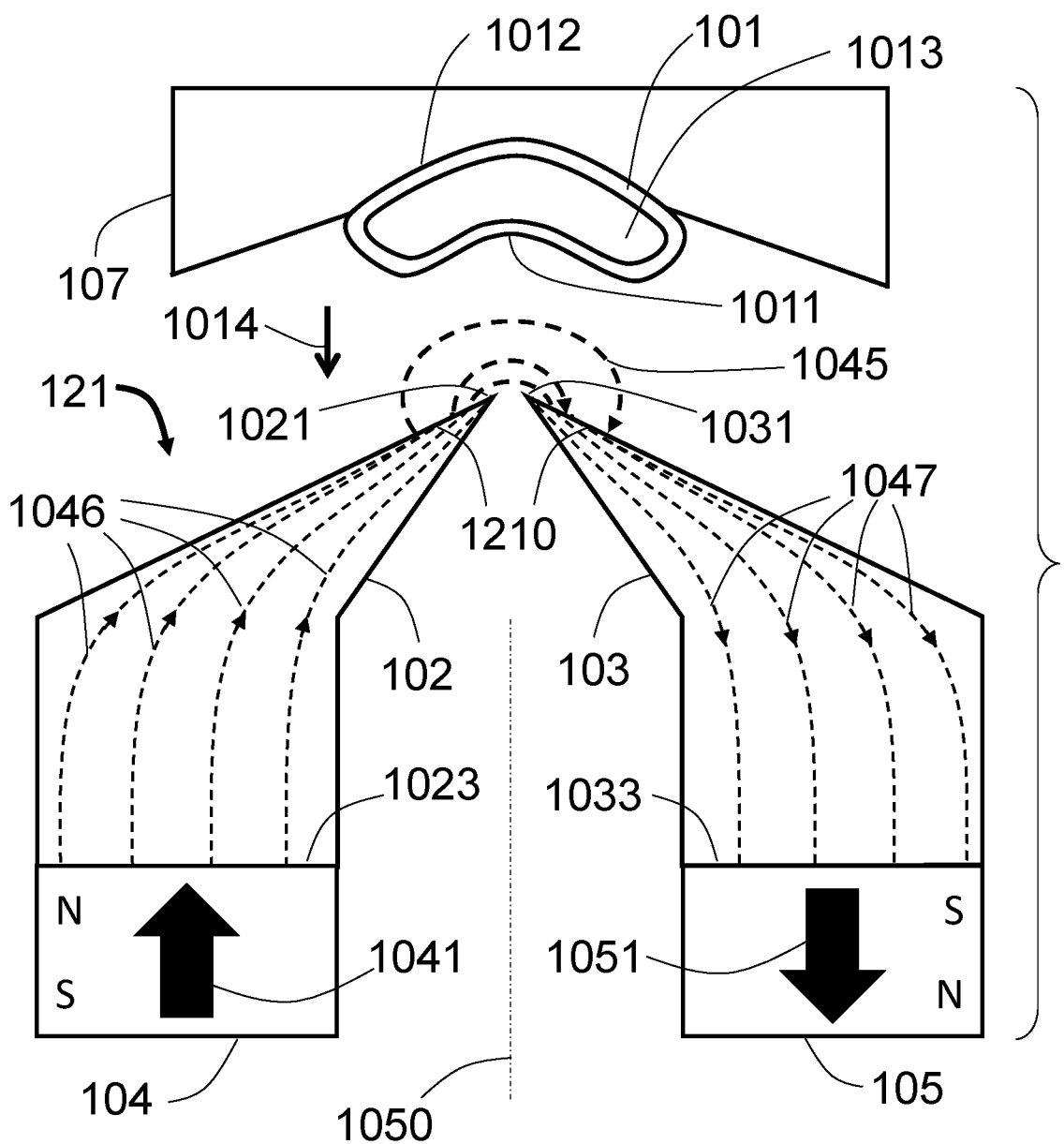
FIG. 4 is a cross-sectional view of the first embodiment of a magnetic separation device ("MAG") with a "C" shape rigid channel.

FIG. 4 shows a cross-sectional view of the first embodiment of a magnetic separation device ("MAG") of the current invention. MAG 121 is composed of two magnetic field producing poles, pole 102 and pole 103. Each of the poles 102 and 103 is composed of soft magnetic material, which may include one or more elements of iron (Fe), cobalt (Co), nickel (Ni), iridium (Ir), manganese (Mn), neodymium (Nd), boron (B), samarium (Sm), aluminum (Al). Pole 102 has a magnetic flux collection end 1023 and a tip end 1021, where shape of the pole 102 is converging from the flux collection end 1023 towards the tip end 1021. In FIG. 4, flux collection end 1023 is a flat surface which is contacting, or in proximity to, the North Pole ("N") surface of a permanent magnet 104. Permanent magnet 104 has a magnetization shown by arrow 1041 in FIG. 4 which points from the South Pole ("S") surface to the N surface of the magnet 104. Magnetization 1041 produces magnetic field in free space, which can be described as flux lines 1046 emitting from N surface and returning to S surface of the magnet 104. Pole 102 flux collection end 1023 being in contact with, or in close proximity to, the N surface of magnet 104 as shown in FIG. 4. Due to the soft magnetic material of pole 102, magnetic flux 1046 from the N surface of magnet 104 is collected by the pole 102 and enters the body of the pole 102 through flux collection end 1023. Due to the converging shape of the pole 102, the collected magnetic flux is mainly channeled within the soft magnetic body of the pole 102 and emitted from the tip end 1021 of pole 102. Said close proximity between flux collection end 1023 and N surface of magnet 104 may be a gap distance in between surface of 1023 and N surface being less than 1 mm. Tip end 1021 may have a much smaller surface area than flux collection end 1023, which makes flux exiting the tip end 1021 having a higher flux density than when flux 1045 is emitted by N surface of magnet 104, i.e. magnetic flux 1045 is concentrated and thus creates a local high magnetic field and high field gradient around the tip end 1021. It is preferred that tip end 1021 of the pole 102 is as small as possible, for example as a convergence point, to produce largest flux concentration for achieving highest magnetic field. However, in practice, due to manufacturing process, tip end 1021 may have a curved or domed shape, which would not affect the general concept of flux concentration by the tip end 1021. Pole 103 is similar to pole 102 in that pole 103 has a larger flux collection end 1033 and a smaller tip end 1031, where flux collection end 1033 is in contact with, or in close proximity to, S surface of permanent magnet 105. It is preferred that pole 103 and magnet 105 are identical to pole 102 and magnet 104, but arranged to mirror pole 102 and magnet 104 around a center line 1050. Magnet 105 magnetization 1051 is opposite to magnetization 1041 of magnet 104. Magnetic flux 1047 collected by flux collection end 1033 from S surface of pole 103 is opposite to that of pole 102, and flux emitted from tip end 1031 of pole 103 is opposite to that of tip end 1021. Thus, between the gap of tip ends 1021 and 1031, emitted flux can form closed loop and further enhance the magnetic field strength and field gradient around the tip ends 1021 and 1031. Dashed lines 1045 represent the flux emitted from tip end 1021 and returned to tip end 1031. Flux lines 1045 closer to tip ends 1021 and 1031 being denser indicates stronger magnetic field and larger field gradient closer to the gap area. As shown in FIG. 4, top section of pole 102 is tilted to the right side, while top section of pole 103 is tilted to the left. This tilted shape diverts the magnetic flux within poles 102 and 103 away from bottom section of the poles and helps make the tip end 1021 of pole 102 and tip end 1031 of pole 103 the closest spaced features of the poles 102 and 103 to achieve high field in gap between tip ends 1021 and 1031 while minimizing flux leakage between lower bodies of poles 102 and 103. In FIG. 4, the tilted top sections of the poles 102 and 103 form a triangle shape, or convex shape, top surface 1210 of the MAG 121, which will be referred to as "MAG wedge" 1210 of MAG 121 hereafter. Permanent magnets 104 and 105 may be composed of any of, but not limited to, Nd, Fe, B, Co, Sm, Al, Ni, Sr, Ba, O, NdFeB, AlNiCo, SmCo, strontium ferrite (SrFeO), barium ferrite (BaFeO), cobalt ferrite (CoFeO).

FIG. 4 embodiment includes a rigid fixed shape channel 101. Channel 101 has a channel wall enclosing a channel space 1013. The fluid sample may flow through channel 101 in the channel space 1013 along the channel 101 length direction that is perpendicular to the cross-section view of FIG. 4. Channel 101 has a top surface 1012 and a bottom surface 1011. Bottom surface 1011 is formed in a shape conforming to the MAG wedge surface 1210, such that when channel 101 is moved in direction 1014 to be in contact with the MAG 121 poles 102 and 103, bottom surface 1011 of channel 101 is in contact with MAG wedge surface 1210 with no or minimal gap in between bottom surface 1011 and MAG wedge surface 1210. Top surface 1012 of channel 101 is preferred to be conformal to bottom surface 1011 to produce a channel space 1013 with a shape that maximizes exposure of fluid sample flowing through channel 101 to the highest magnetic field region of the MAG wedge gap field 1045.

In FIG. 4 embodiment, poles 102 and 103, magnets 104 and 105, and channel 101 extend in the direction perpendicular to the cross-section view of FIG. 4, which will be referred to as "length direction" hereafter. Fluid sample flows in the channel 101 and is contained in channel space 1013 along the length direction. Channel 101 being a rigid and fixed shape channel, the wall thickness of channel 101 at surface 1011 may be thinner than wall thickness at surface 1012, such that channel 101 mechanical robustness is maintained by the thicker wall at surface 1012, and magnetic field effect on fluid sample is enhanced by thinner wall at surface 1011, allowing fluid sample being closer to the MAG wedge 1210 and tip ends 1021 and 1031. Channel 101 may be attached to a non-magnetic channel holder 107 at the top surface 1012. Channel holder 107 may align channel 101 to MAG wedge 1210, move channel 101 to separation position in contact with MAG 121, or lift channel 101 away from MAG 121 after magnetic separation. Channel holder 107 may be composed of any non-magnetic material including, but not limited to, metal, non-metal element, plastic, polymer, ceramic, rubber, silicon, and glass. In FIG. 4, flux collection ends 1023 and 1033 of the soft magnetic poles 102 and 103 may also be referred to as base ends 1023 and 1033.

Permanent magnets described in different embodiments of this invention, for example magnets 104 and 105 of FIG. 4, may each have opposite magnetization direction to that is described in each of the figures and embodiments without affecting the designs, functions and processes of the embodiments.

Figure 1A:
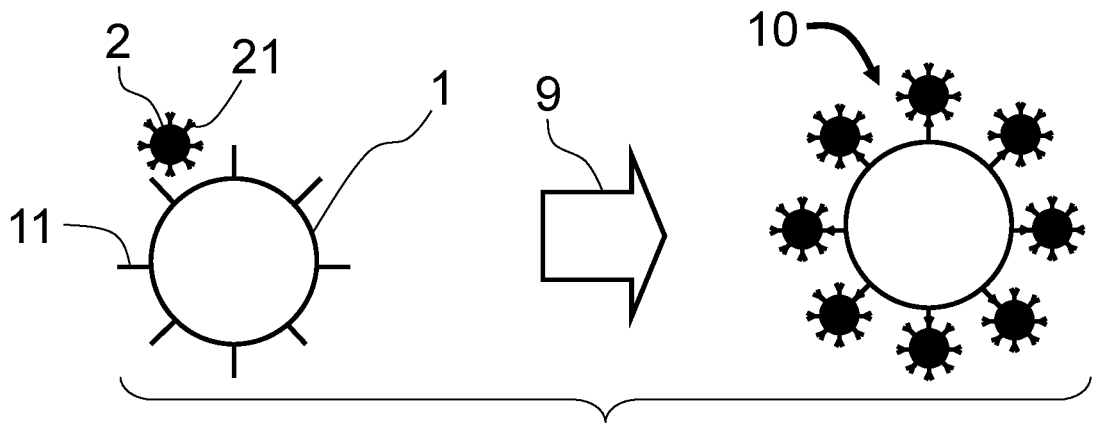
FIG. 1A illustrates superparamagnetic labels (SPLs) binding to a cell.
Figure 1B:
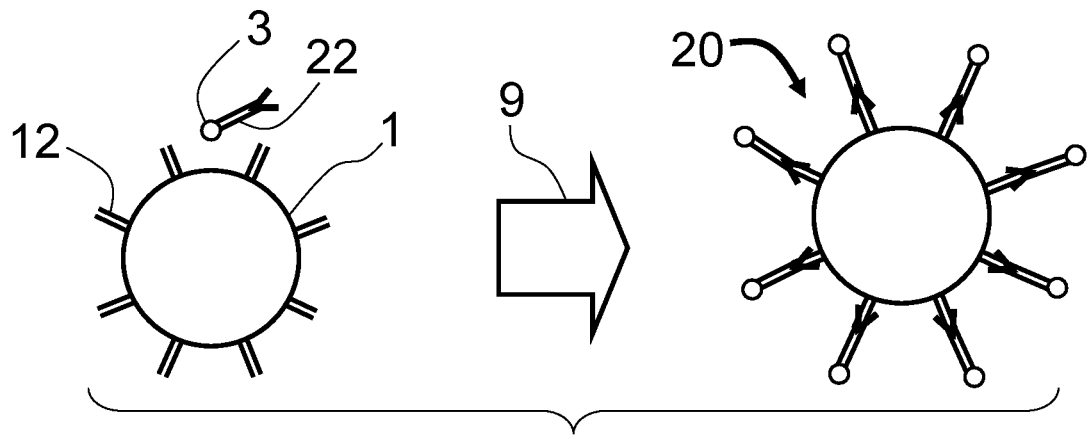
FIG. 1B illustrates optical fluorescent labels (OFLs) binding to a cell.
Figure 1C:
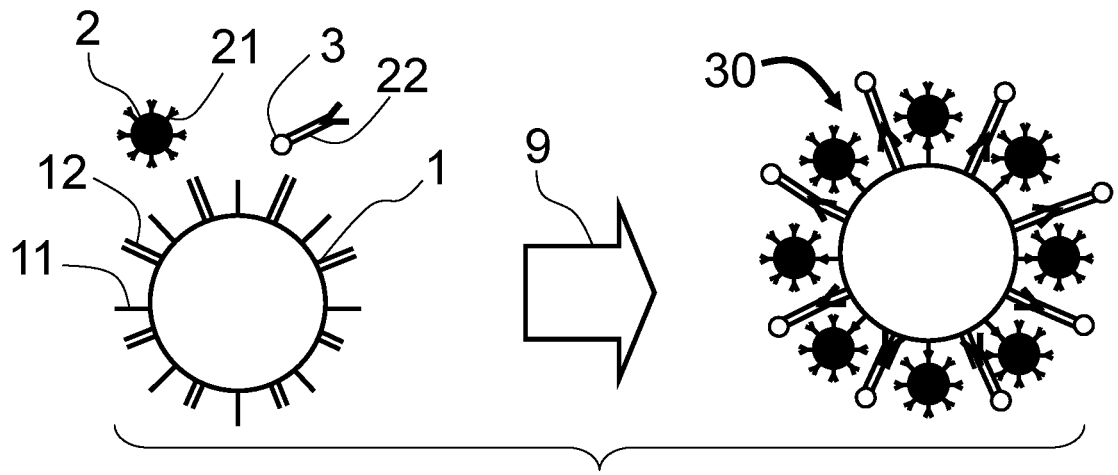
FIG. 1C illustrates SPLs and OFLs binding to a cell.
Figure 2A:
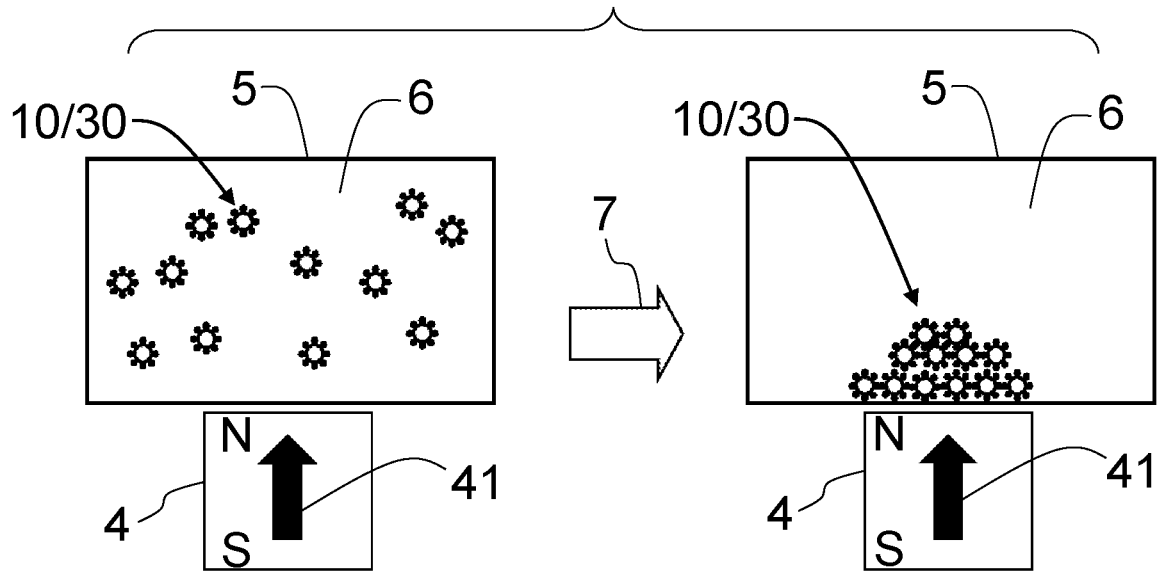
FIG. 2A illustrates cells bound with SPLs being separated by a magnet.
Figure 2B:
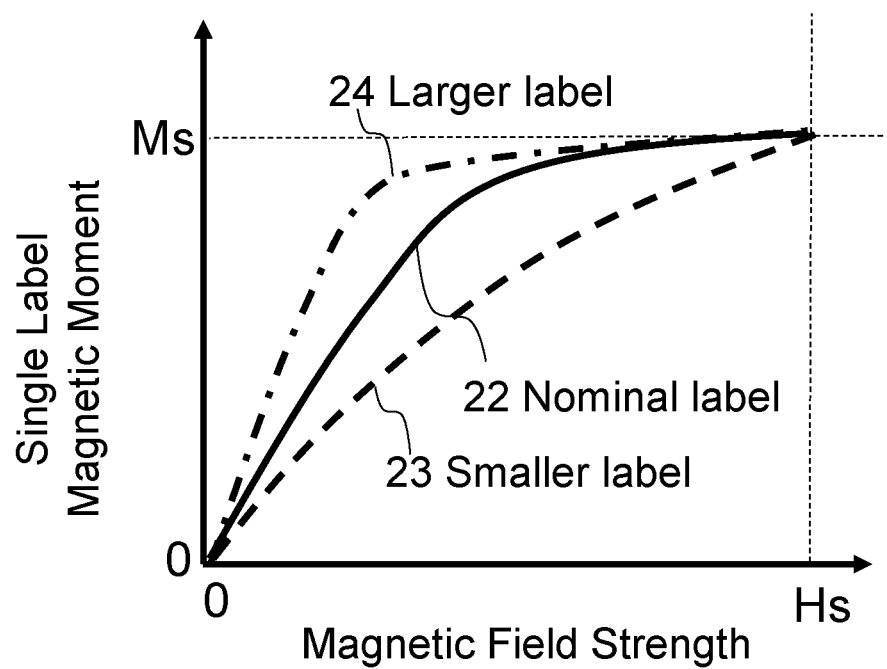
FIG. 2B is a plot of SPL magnetization vs magnetic field strength for different SPL sizes.
Figure 3A:
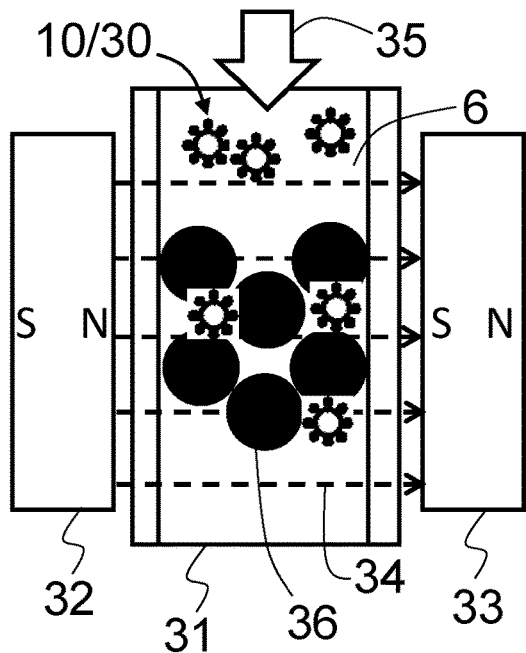
FIG. 3A is a cross-sectional view of a prior art magnetic cell separator.
Figure 3B:
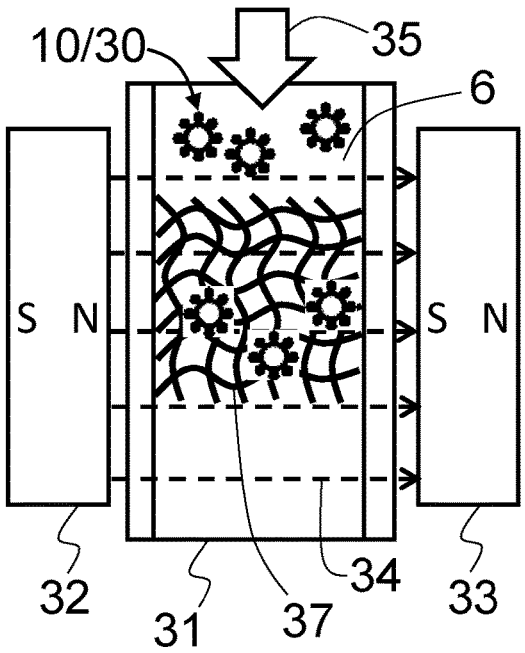
FIG. 3B is a cross-sectional view of a prior art magnetic cell separator.
Figure 3C:
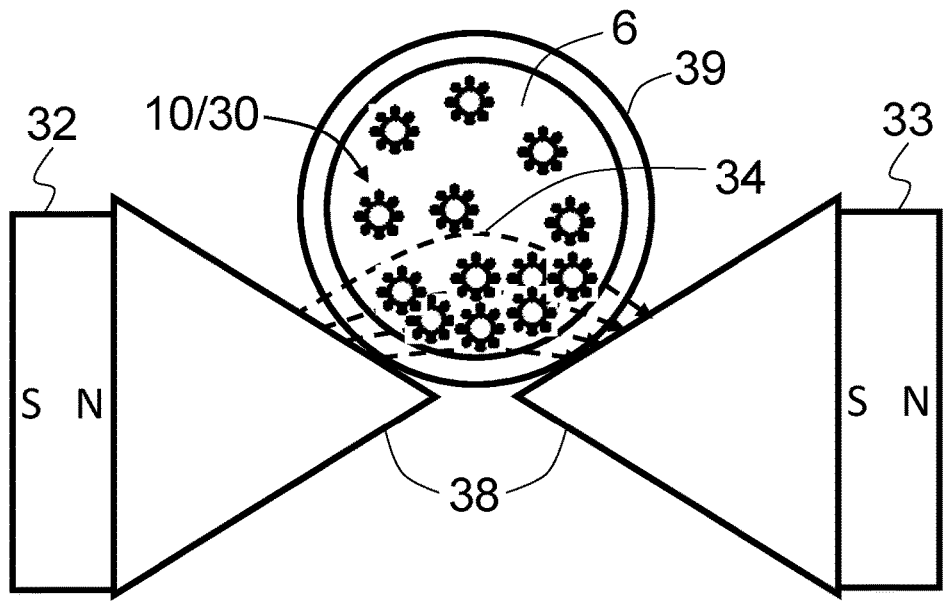
FIG. 3C is a cross-sectional view of a prior art magnetic cell separator.
Figure 5:
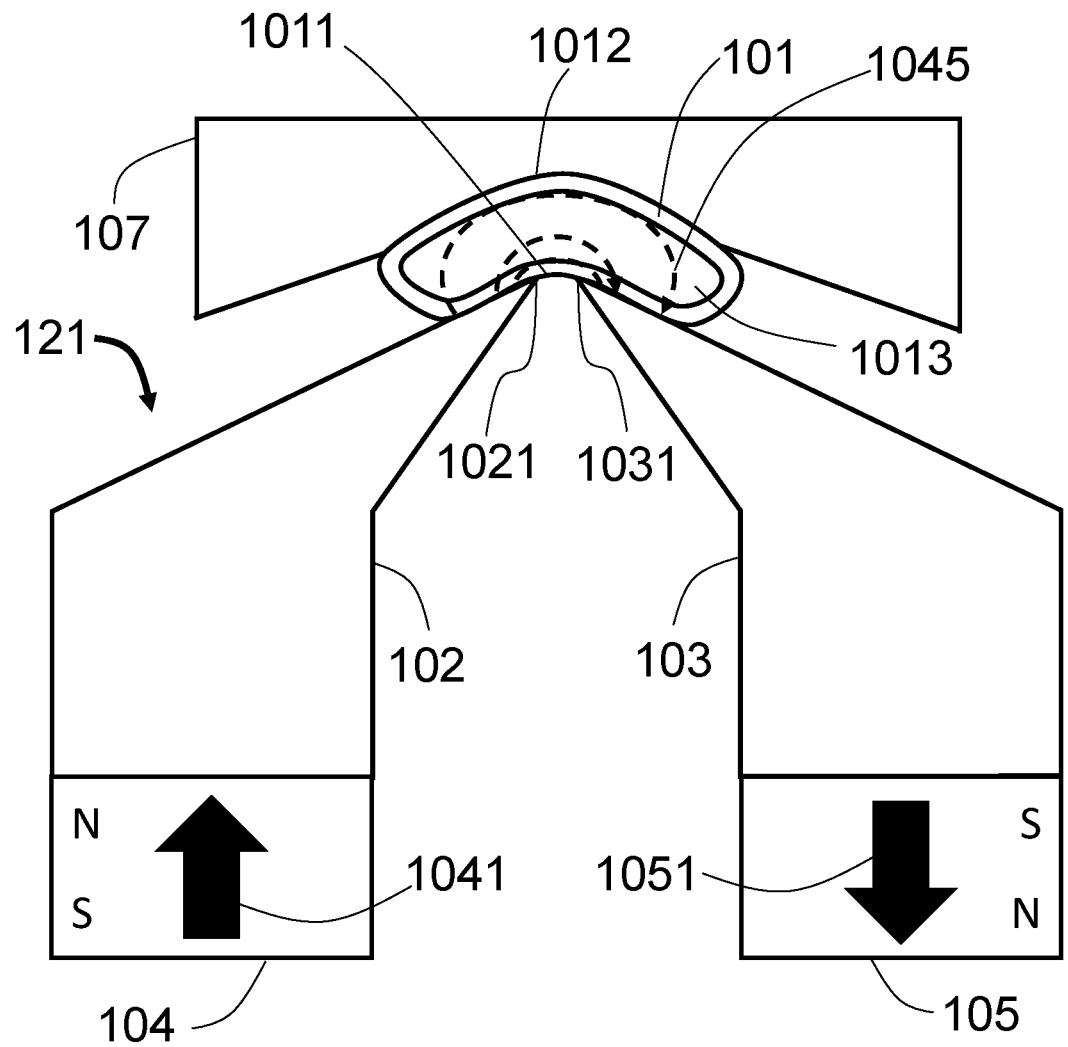
FIG. 5 is a cross-sectional view of the first embodiment of MAG having a "C" shape rigid channel in separation position.

FIG. 5 is the cross-sectional view of FIG. 4 first embodiment of MAG with channel 101 in magnetic separation position. Channel 101 of FIG. 4 moves along direction 1014 and comes into contact with MAG wedge 1210 surface by bottom surface 1011. MAG 121 gap formed by tip ends 1021 and 1031 is brought into contact with, or minimal distance to, wall of channel 101 and the fluid sample flowing in the channel 101. Channel 101 "C" shape matching to the MAG wedge shape helps achieve large cross-sectional area of the channel space 1013 to maintain a high flow rate, and at the same time confines cells 10/30 in the fluid sample flowing in channel 101 to a high field and high gradient region of the MAG 121 gap field as indicated by the field lines 1045. Compared to prior art of FIG. 3A and FIG. 3B, first embodiment MAG 121 does not introduce foreign material into the channel 101 while achieving comparable or higher magnetic field and field gradient on cells 10/30 flowing through the channel 101. Removal of poles 102 and 103 together with magnets 104 and 105 from channel 101 will eliminate field generation source and avoids limitation of prior art domain related cell loss. Compared to prior art of FIG. 3C, MAG wedge of FIG. 5 being in contact with the channel 101 wall brings highest achievable magnetic field and field gradient to the fluid sample in the channel 101 for a more efficient cell 10/30 separation. Channel 101 shape being conformal to MAG wedge shape allows channel 101 to have a large cross-sectional sample flow area, while avoiding the deficiency of prior art that cells 10/30 at top end of a circular channel experiencing much lower magnetic field than at lower end, which ultimately limits sample flow rate. Thus, sample flow rate in channel 101 can be higher than prior art while achieving better magnetic separation efficiency.

Figure 6:
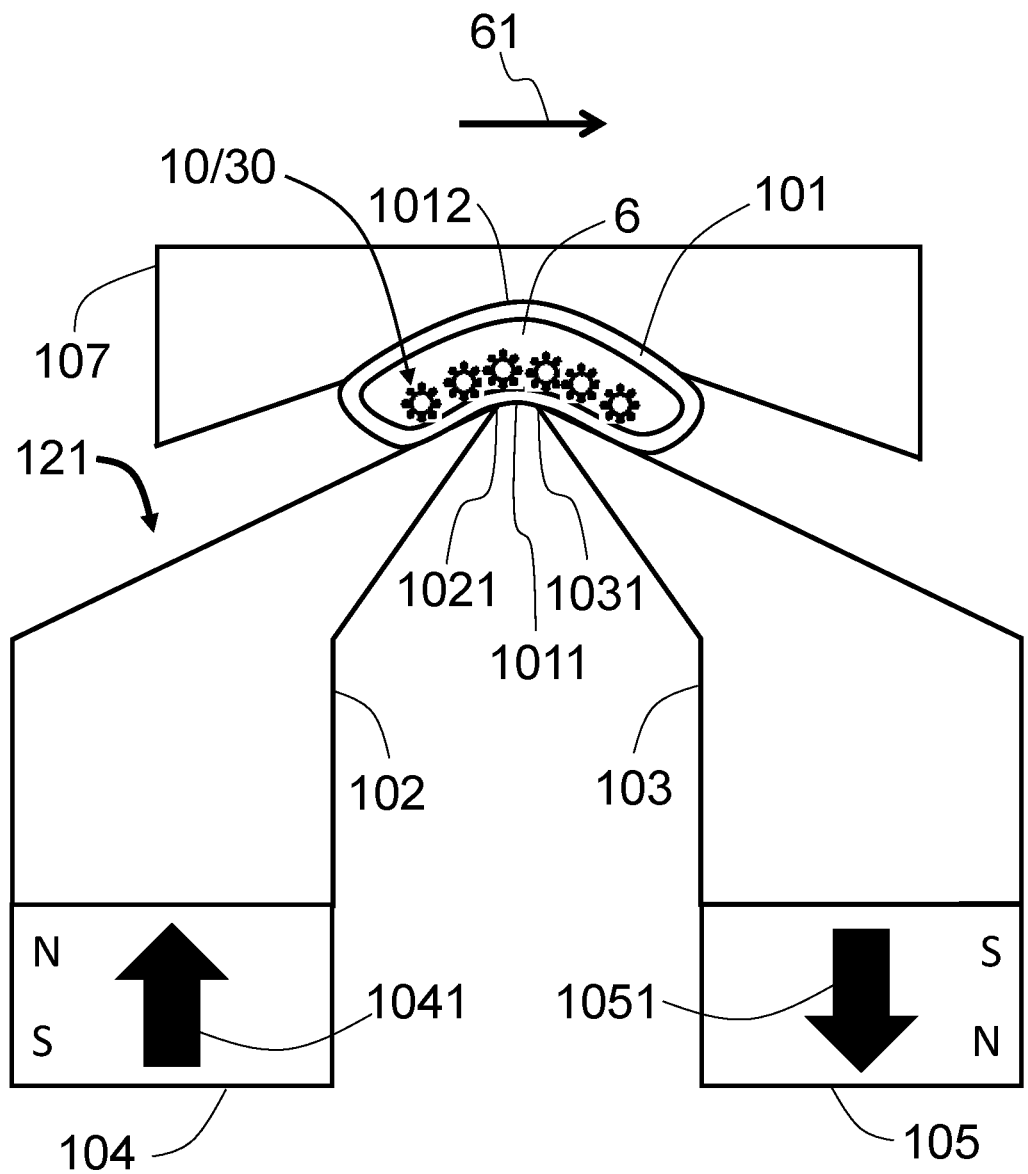
FIG. 6 is a cross-sectional view of the first embodiment of MAG having a "C" shape rigid channel in separation position with cells being separated.

FIG. 6 is same as FIG. 5, except biological entities, or cells 10/30 for simplicity of description, are included to describe magnetic separation by MAG 121 from a fluid sample 6. Fluid sample 6 carrying cells 10/30 is flown through channel 101 along length direction of channel 101 perpendicular to the FIG. 6 cross-sectional view. MAG 121 gap magnetic field magnetizes the SPLs 2 attached to cells 10/30 and field gradient pulls cells 10/30 from the fluid 6 towards the MAG wedge to form conglomerate layer on the 1011 bottom surface of channel 101. Due to MAG 121 design and channel 101 shape, cells 10/30 close to top surface 1012 experience magnetic field not significantly lower than close to bottom surface 1011, and distance for cells 10/30 to travel from top surface 1012 to conglomerate layer on bottom surface 1011 is much shorter than in prior art. These characteristics allow MAG 121 to resolve deficiencies of prior art.

Figure 7:
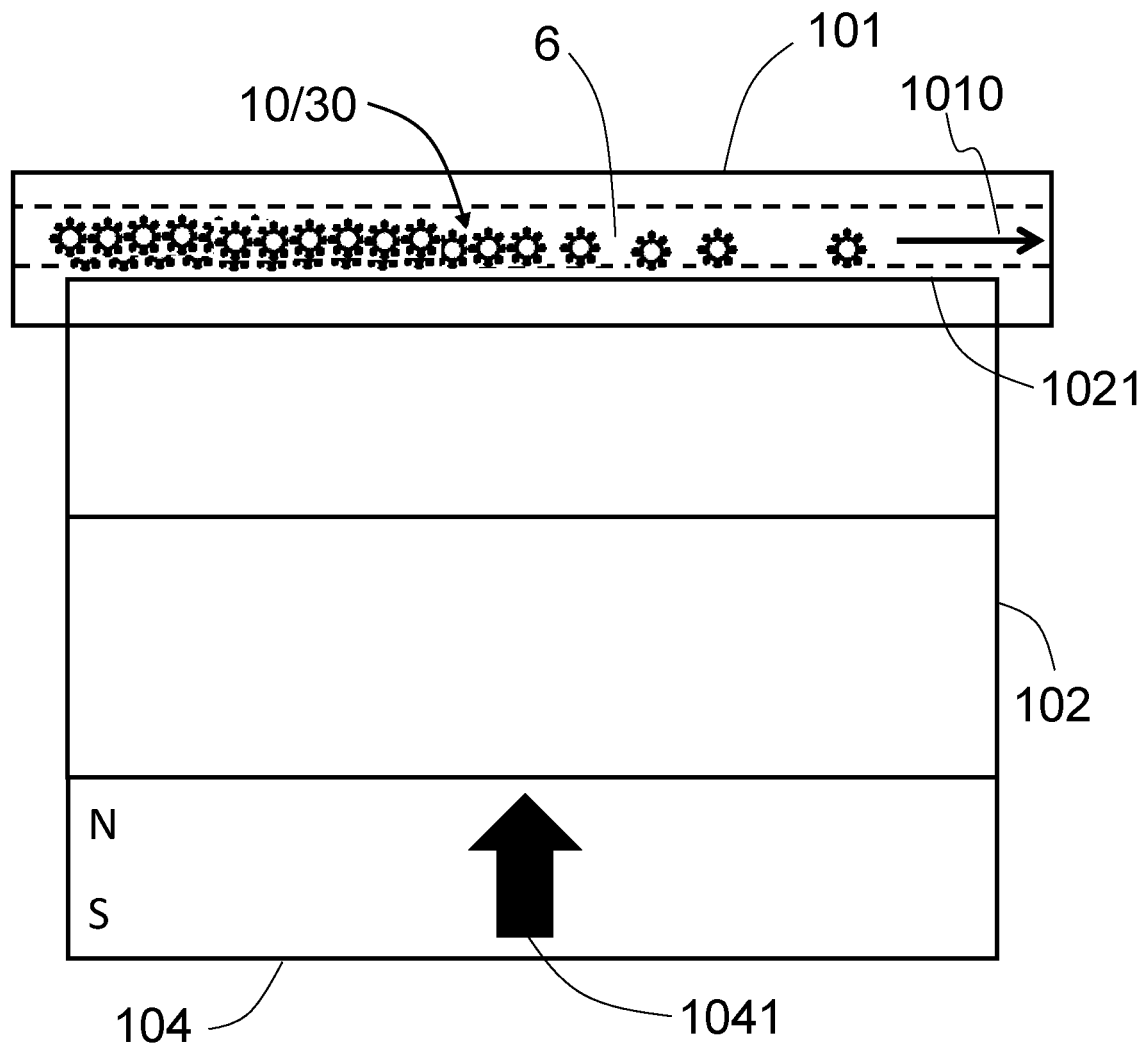
FIG. 7 is a side view of FIG. 6.

FIG. 7 is a side view of FIG. 6 along direction 61 of FIG. 6. Fluid sample 6 carrying cells 10/30 flows from left to right in the channel 101 as indicated by arrow 1010. With the MAG 121 gap field, cells 10/30 are separated from fluid 6 to form conglomerate on the channel wall of bottom surface 1011. FIG. 7 shows that majority of the cells 10/30 are separated from liquid 6 at the earlier section of the channel 101 length, as indicated by the crowded population of cells 10/30. As certain tail population cells 10/30 may have comparatively smaller size SPLs 2 or fewer number of SPLs 2 bound to it surface, time required for such tail population cells to be pulled to bottom surface 1011 is longer than nominal population when fluid 6 flows through channel 101. Thus, population of separated cells 10/30 will show density decrease from inlet towards outlet of channel 101.

Figure 8A:
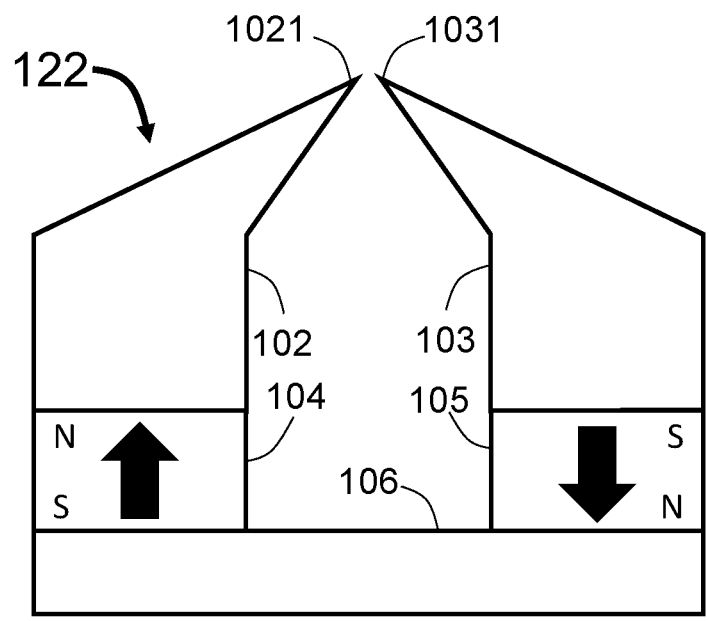
FIG. 8A is a cross-sectional view of the second embodiment of MAG.

FIG. 8A is a cross-sectional view of a second embodiment of MAG of current invention. MAG 122 in FIG. 8A is substantially similar to MAG 121, except a soft magnetic shield 106 is attached to the S surface of magnet 104 and N surface of magnet 105. Magnetic flux from S surface of magnet 104 and N surface of magnet 105 forms closure path within the soft magnetic shield 106. MAG 122, as compared to MAG 121, will have less magnetic flux leakage outside of the MAG 122 structure. The magnetic flux generated by magnets 104 and 105 are mainly confined within the soft magnetic material body of poles 102 and 103, and shield 106. MAG 122 is preferred in applications where magnetic interference from MAG 122 to other surrounding instrument or equipment is desired to be minimized.

Figure 8B:
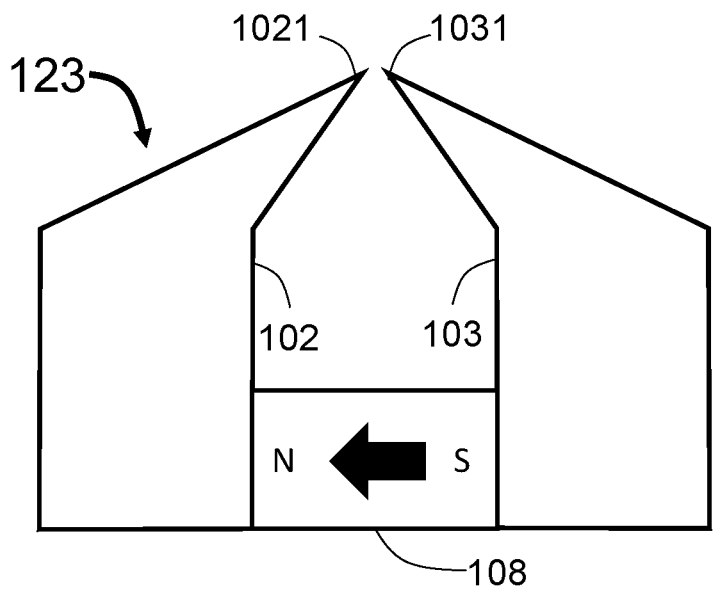
FIG. 8B is a cross-sectional view of the third embodiment of MAG.

FIG. 8B is a cross-sectional view of a third embodiment of MAG of current invention. Compared to MAG 121, MAG 123 of FIG. 8B incorporates only one permanent magnet 108, which is attached to both poles 102 and 103. Flux from N surface of magnet 108 and flux from S surface of magnetic 108 is conducted by poles 102 and 103 to produce MAG 123 gap field by tip ends 1021 and 1031. Compared to MAG 121, magnetic flux generated by magnet 108 is mainly confined within the soft magnetic material body of poles 102 and 103, and MAG 123 is comparatively easier to assemble and produces less magnetic flux leakage.

Figure 9:
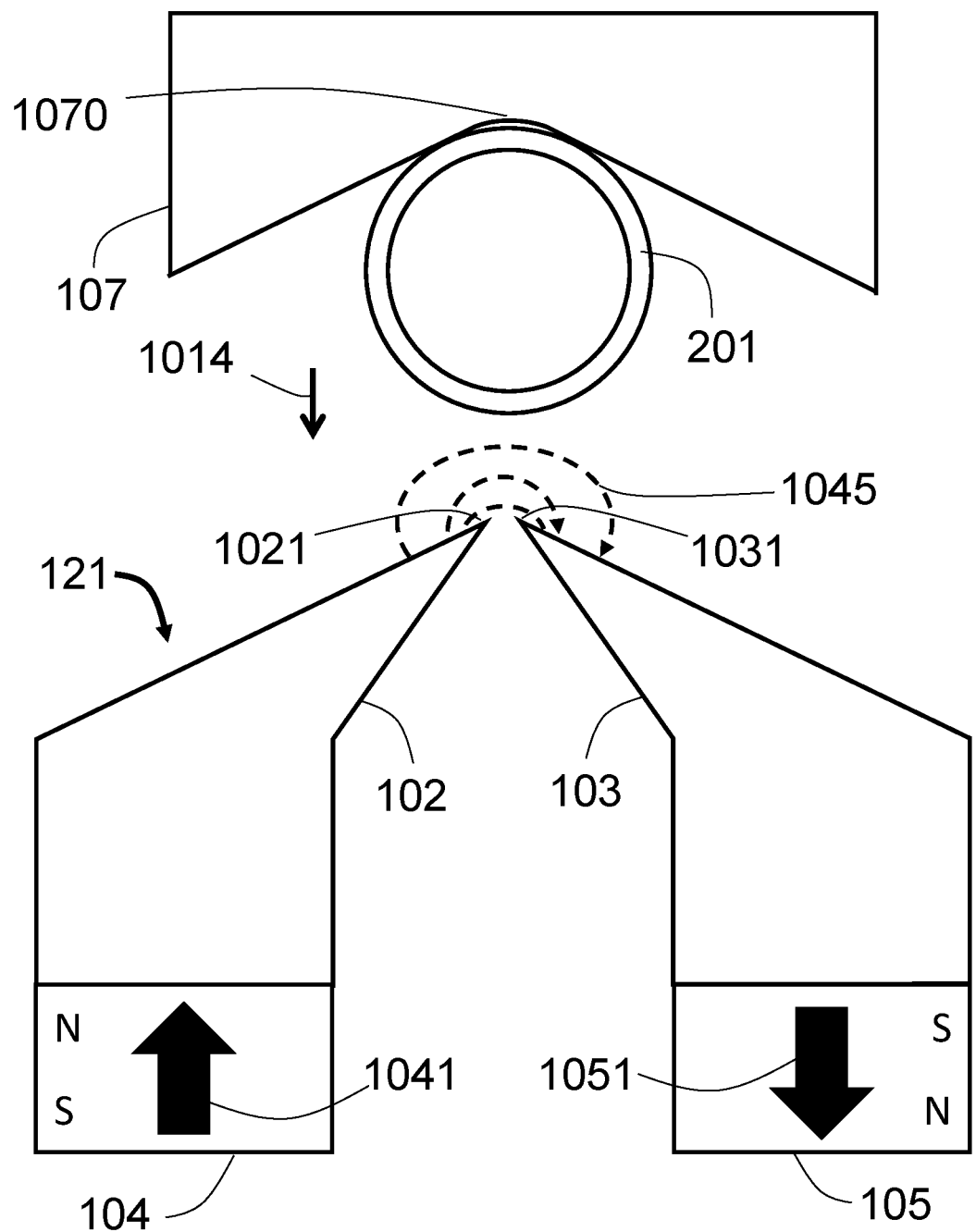
FIG. 9 a cross-sectional view of the first embodiment of MAG with a flexible channel.

FIG. 9 shows a cross-sectional view of the first embodiment MAG 121 being used for magnetic separation in combination with a flexible channel 201. FIG. 9 is similar to FIG. 4, except that the rigid channel 101 is replaced with a flexible channel 201. Flexible channel 201 may assume any shape, including a circular shape tubing form in its non-deformed state, but can be deformed into other shapes by external force. Wall material of channel 201 is deformable and may be composed of any of, but not limited to, silicone, silicone rubber, rubber, PTFE, FEP, PFA, BPT, Vinyl, Polyimide, ADCF, PVC, HDPE, PEEK, LDPE, Polypropylene, polymer, thin metal or fiber mesh coated with polymer layer. Flexible channel 201 is also shown in FIG. 9 to have a channel holder 107 attached to the back of channel 201. Channel holder 107 may be composed of any non-magnetic material including, but not limited to, metal, non-metal element, plastic, polymer, ceramic, rubber, silicon, and glass. Channel 201 may attach to holder 107 through surface bonding, for example by gluing or injection molding, or via mechanical attachment through components 1074 of FIG. 32. Holder 107 has a bottom surface 1070 in contact with the top surface of channel 201, where surface 1070 is preferred to be substantially conformal to the MAG 121 wedge shape. In FIG. 9, holder 107 aligns flexible channel 201 to MAG 121 wedge gap and moves channel 201 towards MAG wedge gap in direction 1014.

Figure 10:
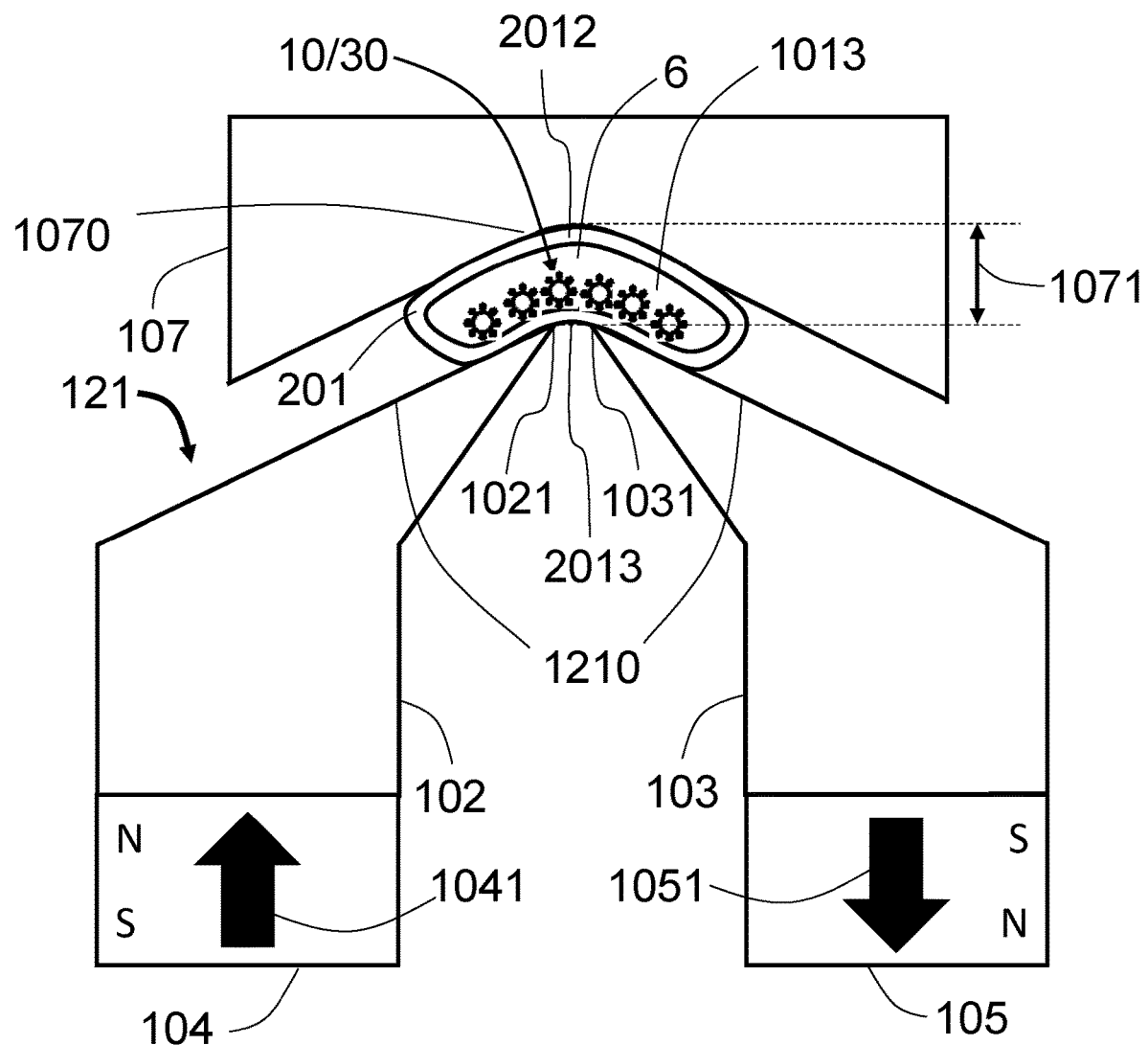
FIG. 10 illustrates the first embodiment of MAG having a flexible channel in separation position with cells being separated.

FIG. 10 illustrates the flexible channel 201 being pushed against the MAG wedge of MAG 121 by the channel holder 107. With pressure exerted by the holder 107 on flexible channel 201 against the MAG wedge of MAG 121, channel 201 is deformed in FIG. 10 with bottom surface 2013 of channel 201 becoming conformal and in surface contact with MAG wedge surface 1210. Meanwhile, as holder 107 bottom surface 1070 may also be conformal to the MAG wedge shape, top surface 2012 of channel may also be molded into a shape that is substantially conformal to the MAG wedge. FIG. 10 depicts the "separation position" of flexible channel 201 relative to the MAG 121 during magnetic separation of cells 10/30 from sample fluid 6. Shape of flexible channel 201 is substantially similar to channel 101 of FIG. 5 and FIG. 6, except such shape of channel 201 at separation position is result of channel 201 self-aligning and self-conforming to MAG wedge without the need of a manufacturing process to achieve shape of channel 101. Additionally, the flow space within channel 201 at separation position may be adjusted to allow for larger or smaller cross-sectional area of the flow space of channel 201, such that optimization of fluid sample 6 flow rate through channel 201 and cells 10/30 magnetic separation efficiency may be optimized. The flow space adjustment may be achieved by changing the vertical distance 1071 from the holder 107 surface 1070 top point in contact with channel 201 top surface 2012, to tip ends 1021 and 1031 or to an imaginary plane where tip ends 1021 and 1031 reside. With a larger 1071 distance, flexible channel 201 is less deformed and a larger flow space is realized, which allows for a slower flow speed at the same fluid flow rate. While with a smaller 1071 distance, flexible channel 201 has a smaller flow space but top edge 2012 is also closer to the MAG wedge gap and tip ends 1021 and 1031, which allows for higher magnetic field and faster separation of cells 10/30. Thus optimization between flow rate and separation efficiency may be achieved by adjusting the distance 1071 for a given combination of MAG 121 design and flexible channel 201. In one embodiment, distance 1071 is more than 0 mm and less than or equal to 1 mm. In another embodiment, distance 1071 is more than 1 mm and less than or equal to 3 mm. In yet another embodiment, distance 1071 is more than 3 mm and less than or equal to 5 mm. In yet another embodiment, distance 1071 is more than 5 mm and less than or equal to 10 mm. In yet another embodiment, distance 1071 is more than 2 times and less than or equal to 3 times of the wall thickness of flexible channel 201. In yet another embodiment, distance 1071 is more than 3 times and less than or equal to 5 times of the wall thickness of flexible channel 201. In yet another embodiment, distance 1071 is more than 5 times and less than or equal to 10 times of the wall thickness of flexible channel 201. Flexible channel 201 at separation position functions similarly to channel 101 in FIG. 6. FIG. 10 also shows that during magnetic separation, cells 10/30 form conglomerate along channel 201 wall of lower surface 2013 directly opposing the MAG wedge surface 1210. Thickness of channel 201 wall at bottom surface 2013 may be thinner than channel 201 wall at top surface 2012.

Figure 11:
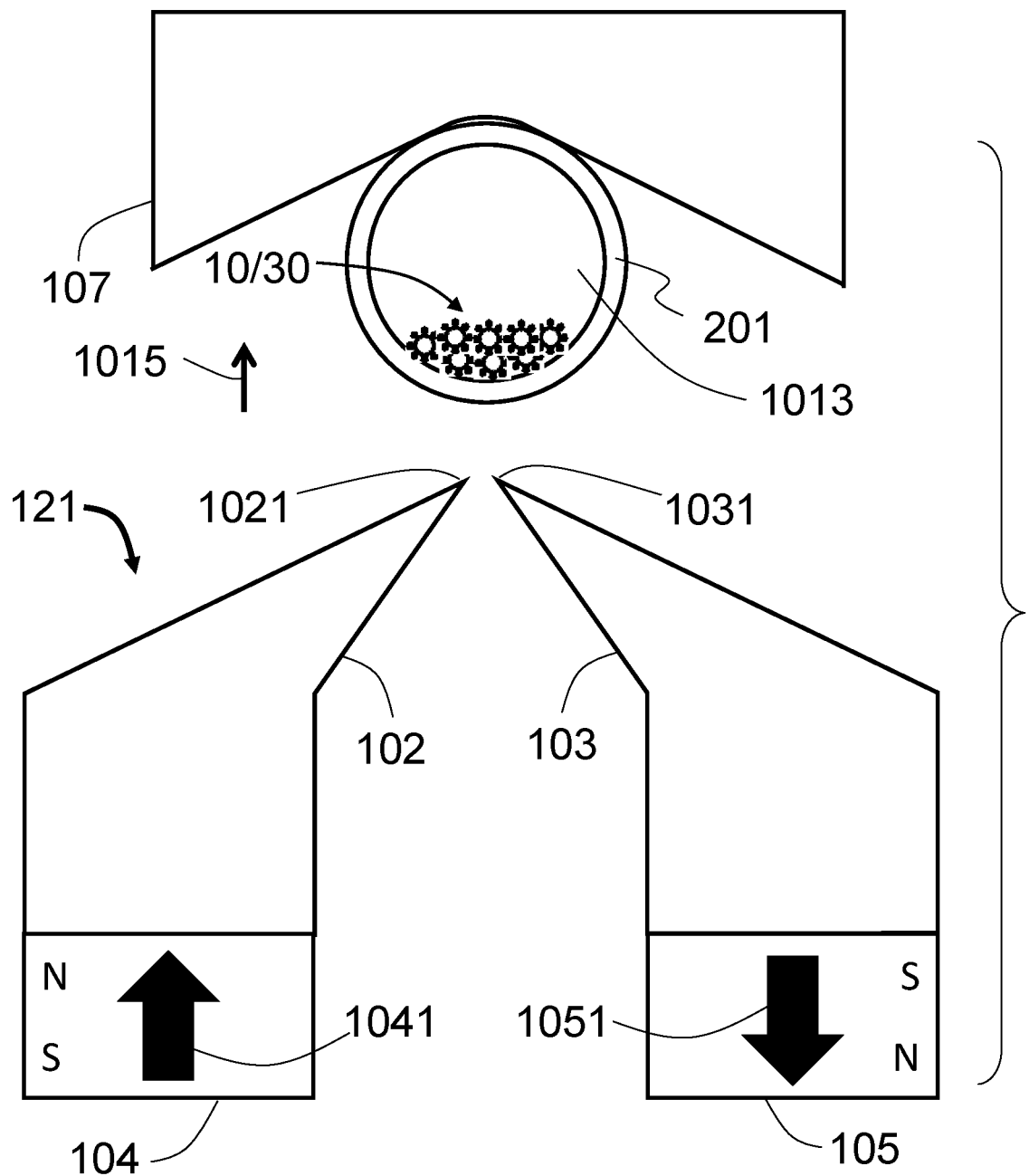
FIG. 11 illustrates the first embodiment of MAG having a flexible channel in lifted position after cell separation.

FIG. 11 illustrates that after magnetic separation is completed in FIG. 10, the channel holder 107 moves away from the MAG 121 in direction 1015, causing the flexible channel 201 to separate from MAG wedge of MAG 121 to "lifted position." Flexible channel 201 may also return to its non-deformed shape, for example circular tubing as shown in FIG. 11. Magnetically separated cells 10/30 in FIG. 10 may retain the conglomerate form at the bottom surface of the flexible channel 201 in lifted position. After FIG. 11 lifted position of flexible channels 201 is reached, dissociation procedures to break up the cells 10/30 in the conglomerate form within the flexible channel 201 may be performed, as described in FIG. 22A through FIG. 30B. Flexible channel 201 returning to non-deformed shape, for example circular tubing of FIG. 11, provides a larger cross-sectional area of the channel space 1013 as shown in FIG. 11 than the separation position shown in FIG. 10. Such larger channel space 1013 may be preferred for easier dissociation of cells 10/30 from the conglomerate form. Additional buffer fluid may be injected into the channel space 1013 of channel 201 in lifted position to assist channel 201 returning to non-deformed shape.

MAG 121 in FIG. 9 through FIG. 11 may be replaced by MAG 122 or MAG 123 without limitation on described methods and processes.

Figure 12:
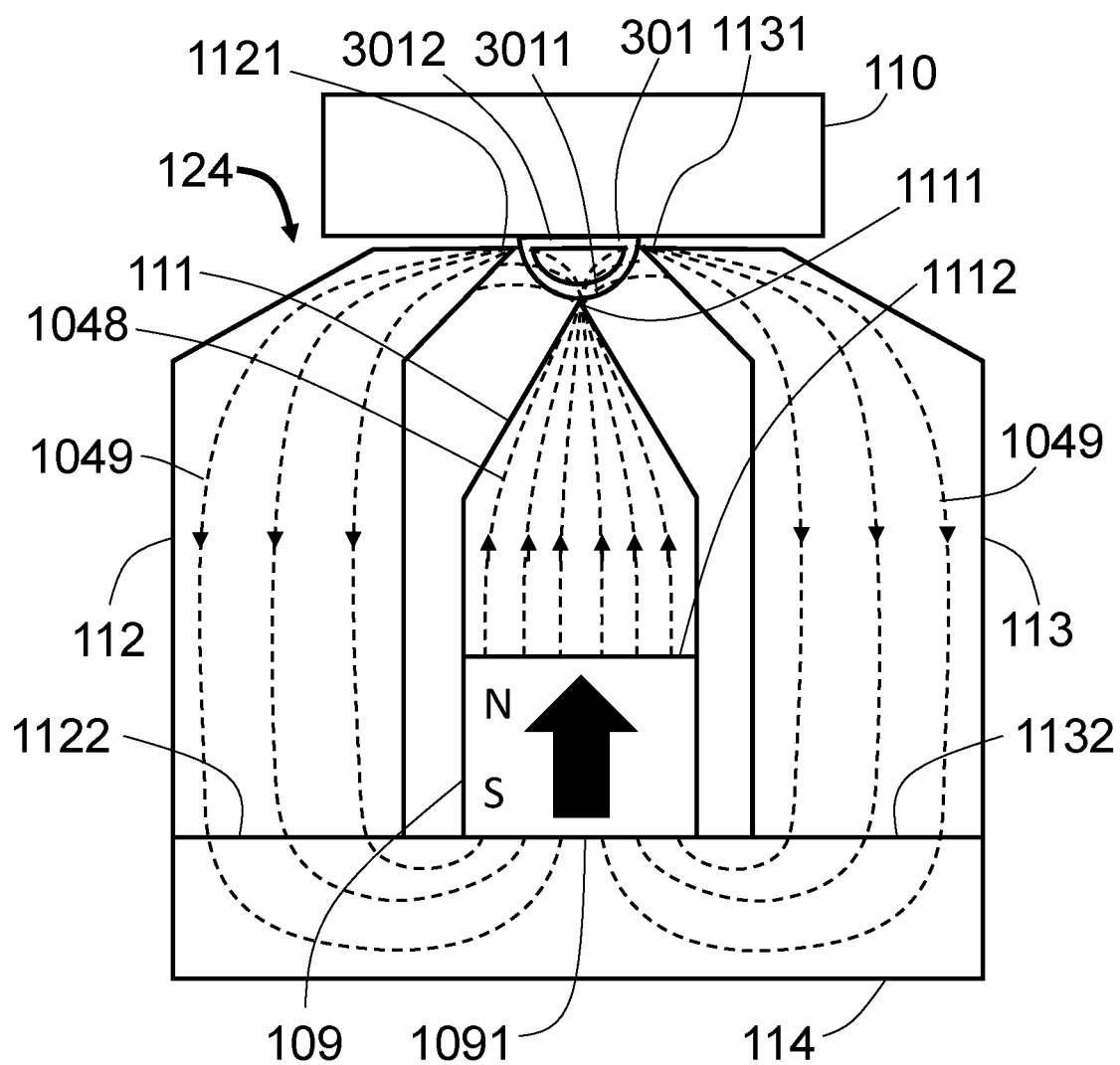
FIG. 12 illustrates cross-sectional view of the fourth embodiment of MAG having a "D" shape rigid channel in separation position.

FIG. 12 illustrates cross-sectional view of the fourth embodiment of MAG 124. MAG 124 has three soft magnetic poles 111, 112 and 113. Center pole 111 is attached to N surface of permanent magnet 109 at a flux collection end 1112, similar to flux collection end 1023 of pole 102 in FIG. 4. Flux 1048 from magnet 109 N surface is conducted by pole 111 soft magnetic body and then emitted from a tip end 1111, which is much smaller in area size than flux collection end 1112 of pole 111 and functions similar to tip end 1021 of FIG. 4 to produce a local high field around tip end 1111 by concentrating the magnetic flux conducted from magnet 109. Side poles 112 and 113 have flux collection ends 1122 and 1132, respectively, which are attached to same top surface of a soft magnetic bottom shield 114. Bottom shield 114 is then attached to S surface of the permanent magnet 109. Thus the magnetic flux 1049 from the S surface of magnet 109 is conducted through the body of bottom shield 114 and divided between poles 112 and 113 and further conducted to the tip ends 1121 and 1131 of poles 112 and 113 respectively. Tip end 1111 is formed in proximity to tip ends 1121 and 1131. In one embodiment, tip end 1111 may recess from an imaginary plane, where tip ends 1121 and 1131 reside, towards magnet 109 by an offset distance between 0 mm and 1 mm. In another embodiment, tip end 1111 may recess from an imaginary plane, where tip ends 1121 and 1131 reside, towards magnet 109 by an offset distance between 1 mm and 5 mm. In yet another embodiment, tip end 1111 may recess from an imaginary plane, where tip ends 1121 and 1131 reside, towards magnet 109 by an offset distance between 5 mm and 10 mm. Tip end 1111 is preferred to be spaced equally to tip ends 1121 and 1131. Top section of pole 112 is tilted to the right side, while top section of pole 113 is tilted to the left, similar to pole 102 and pole 103 of FIG. 4. Such tilting is to increase gap between the main bodies of poles 112 and 113 to main body of pole 111 to reduce flux leakage such that flux concentration around tip ends 1111, 1121 and 1131 is maximized. When flux is emitted from tip ends 1111, 1121 and 1131, flux 1048 conducted by center pole 111 is opposite to the flux 1049 conducted by side poles 112 and 113, and the flux forms closure between tip ends 1111 and 1121 and tip ends 1111 and 1131. Thus, the magnetic flux generated by N and S surface of magnet 109 is conducted within bodies of poles 111, 112, 113 and shield 114 with minimal leakage to outside of MAG 124 structure. Flux density is highest around tip end 1111, with tip ends 1121 and 1131 also producing high flux density, which all indicate high magnetic field and field gradient around tip ends 1111, 1121 and 1131. Compared to MAG 121, 122 and 123, MAG 124 has the advantage of more efficient flux closure within the MAG 124 soft magnetic bodies with less leakage and thus higher flux density around tip end 1111 to produce higher magnetic field and field gradient in channel 301.

Channel 301 is a rigid channel similar to channel 101 of FIG. 4, and has a fixed shape similar to a rotated "D". Channel 301 is shown to be in magnetic separation position in FIG. 12, where tip ends 1111, 1121 and 1131 may all be in contact with the curved bottom surface 3011 of the "D" shape channel 301 to provide highest possible magnetic field and field gradient that MAG 124 can produce in the channel space through which fluid sample flows in channel 301. In another embodiment, tip end 1111 may be in contact with the surface 3011 and tip ends 1121 and 1131 are not contacting surface 3011. Top surface 3012 of channel 301, in one embodiment, may be on the imaginary plane where tip ends 1121 and 1131 reside, and in another embodiment top surface 3012 may be above the imaginary plane by a distance in between 0 mm and 1 mm, and in yet another embodiment top surface 3012 may be above the imaginary plane by a distance in between 1 mm and 5 mm. In one embodiment, channel 301 wall thickness at surface 3012 is thicker than wall thickness at surface 3011. Channel 301 may be attached to a non-magnetic channel holder 110 at the top surface 3012. Channel holder 110 may align channel 301 to MAG gap of MAG 124, move channel 301 to separation position in contact with MAG 124 pole 111 tip end 1111, or lift channel 301 away from MAG 124 after magnetic separation.

Figure 13:
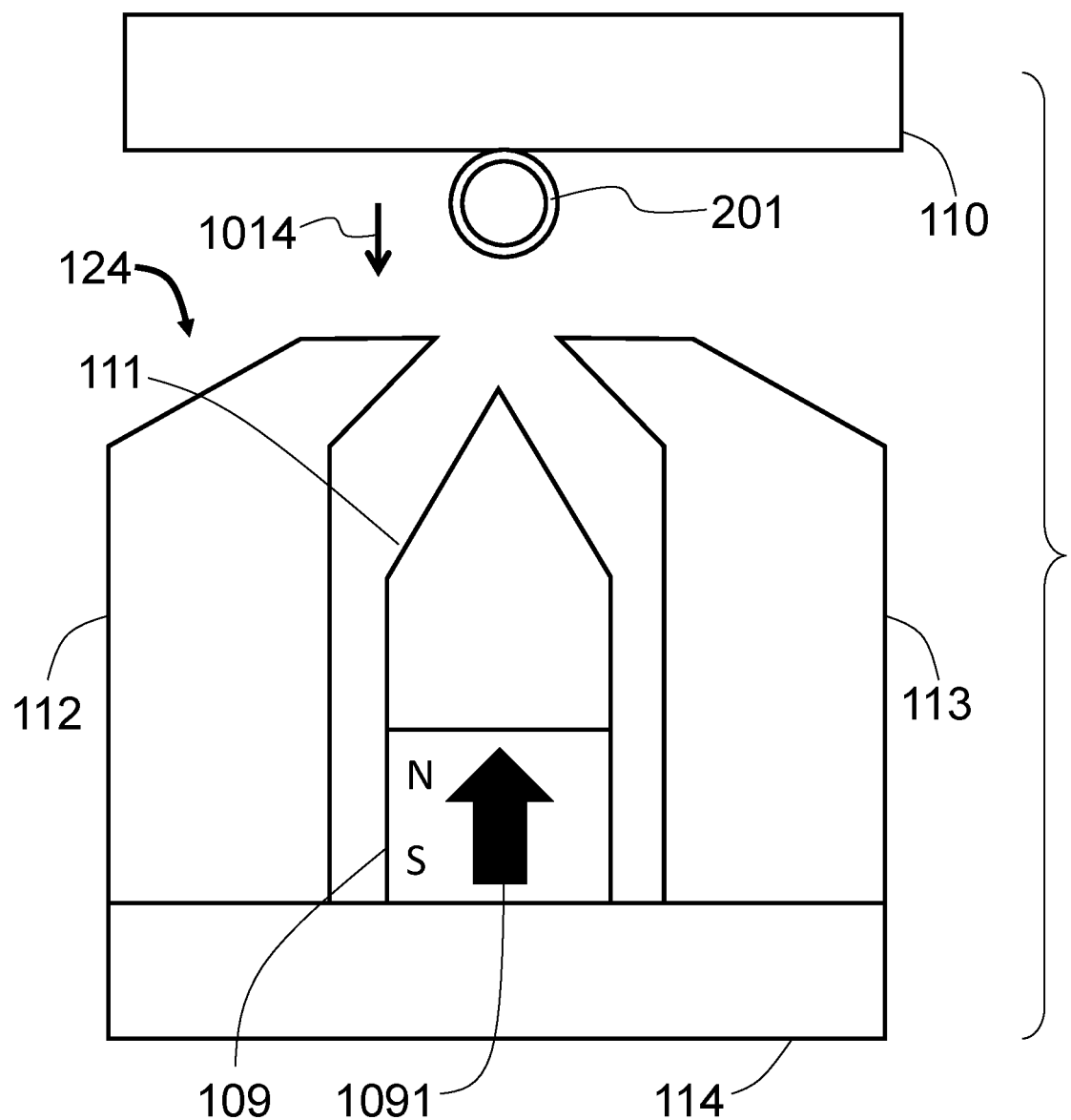
FIG. 13 illustrates cross-sectional view of the fourth embodiment of MAG with a flexible channel.

FIG. 13 shows a cross-sectional view of the fourth embodiment MAG 124 being used for magnetic separation in combination with the flexible channel 201, which is same as in FIG. 9. Channel holder 110 may have a different shape than channel holder 107 of FIG. 9. Before magnetic separation, channel holder 110 is attached to channel 201. Channel holder 110 aligns channel 201 to MAG gap of MAG 124, which is composed of tip ends 1111, 1121 and 1131 as in FIG. 12, and moves channel 201 into the MAG gap of MAG 124 in direction 1014.

Figure 14:
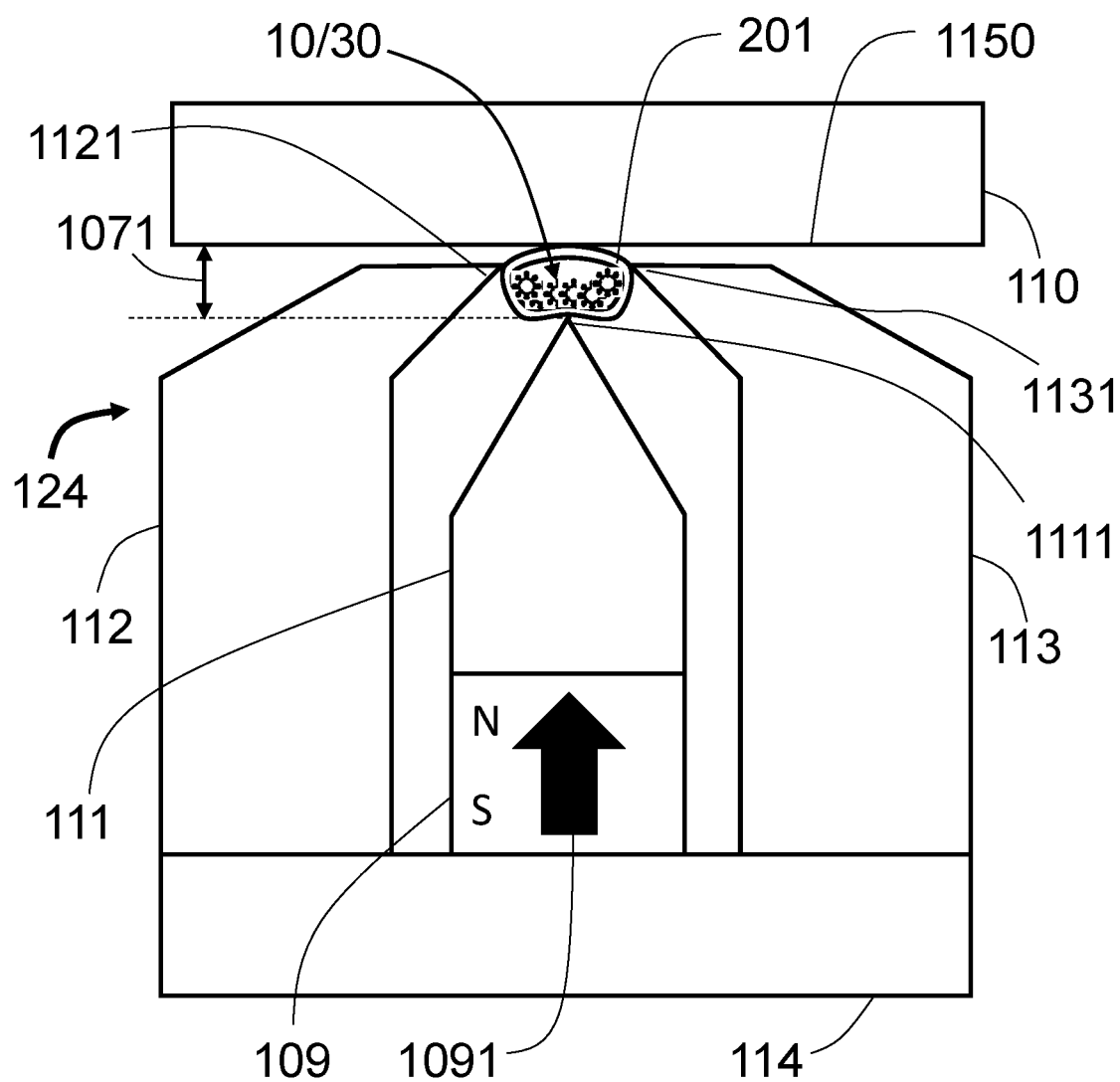
FIG. 14 illustrates cross-sectional view of the fourth embodiment of MAG having a flexible channel in separation position with cells being separated.

FIG. 14 illustrates the flexible channel 201 in separation position in the fourth embodiment MAG 124 with cells 10/30 being separated and forming conglomerate around bottom and side walls of the channel 201 close to the tip ends 1111, 1121 and 1131. In FIG. 14, flexible channel 201 is deformed, similar to FIG. 10, to conform to the MAG gap boundaries, which are mainly defined by the tip ends 1111, 1121 and 1131. Shape of channel 201 may be different from channel 301 in separation position due to flexible channel 201 conforming to the MAG gap boundaries under pressure from holder 110. Shape of channel 201 in FIG. 14 may provide higher liquid sample flow rate with higher separation efficiency than channel 301. Distance 1071 between the lower surface 1150 of holder 110 and tip end 1111 may be adjusted to optimize flow rate in channel 201. Range of distance 1071 is same as 1071 described in FIG. 10.

Figure 15A:
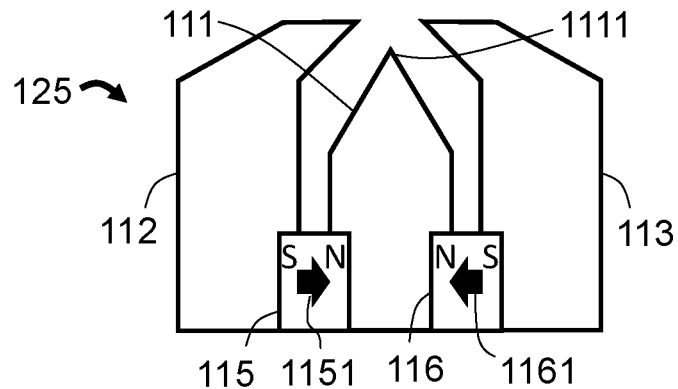
FIG. 15A illustrates cross-sectional view of the fifth embodiment of MAG.

FIG. 15A illustrates cross-sectional view of the fifth embodiment MAG 125. MAG 125 is same as MAG 124, except the magnet 109 and bottom shield 114 of MAG 124 of FIG. 12 are removed in MAG 125. Permanent magnets 115 and 116 with opposing magnetizations 1151 and 1161 are placed in between poles 111 and 112 and between poles 111 and 113, respectively, as shown in FIG. 15A. Magnetizations 1151 and 1161 are horizontal in FIG. 15A, which enables center pole 111 conducting N surface fluxes from both magnets 115 and 116, while side poles 112 and 113 conduct S surface fluxes from magnet 115 and 116, respectively. Compared to MAG 124, MAG 125 may produce higher field around tip ends 1111, 1121 and 1131 due to two magnets 115 and 116 being used. MAG 125 may also be easier to assemble than MAG 124.

Figure 15B:
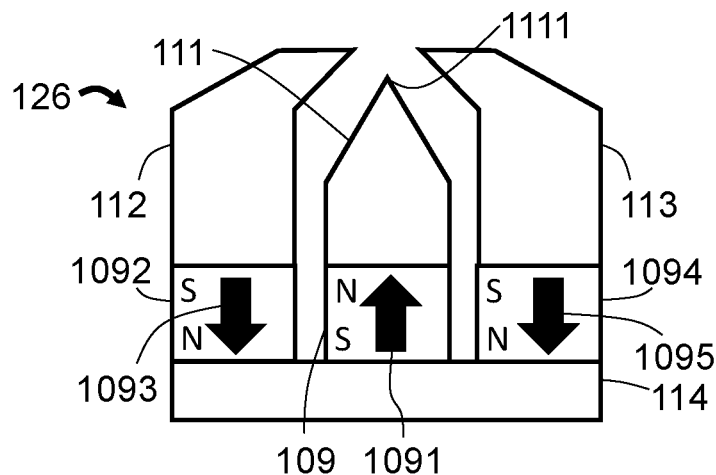
FIG. 15B illustrates cross-sectional view of the sixth embodiment of MAG.

FIG. 15B illustrates cross-sectional view of the sixth embodiment MAG 126. MAG 126 is same as MAG 124, except the side poles 112 and 113 are attached to S surfaces of permanent magnets 1092 and 1094, respectively, with magnetizations 1093 and 1095 being opposite to magnetization 1091 of magnet 109. Bottom shield 114 is attached to both N surfaces of magnets 1092 and 1094 and S surface of magnet 109, thereby forming internal flux closure in shield 114 between magnets 109, 1092 and 1094. Compared to MAG 124, MAG 126 may produce higher field around tip ends 1111, 1121 and 1131 due to three magnets 109, 1092 and 1094 being used in MAG 126.

Figure 15C:
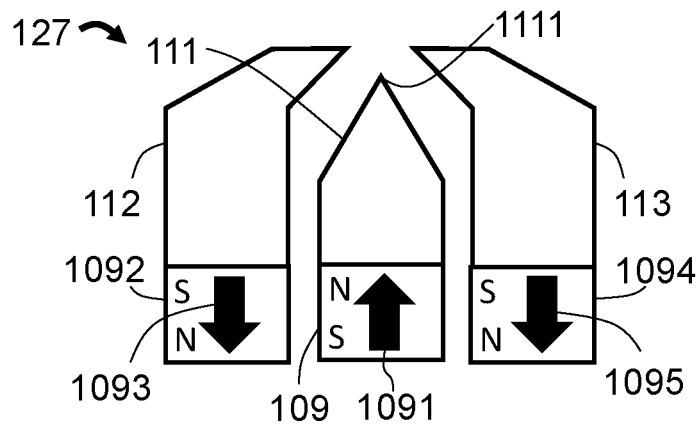
FIG. 15C illustrates cross-sectional view of the seventh embodiment of MAG.

FIG. 15C illustrates cross-sectional view of the seventh embodiment MAG 127. MAG 127 is same as MAG 126 of FIG. 15B, except the bottom shield 114 is removed.

Figure 16:
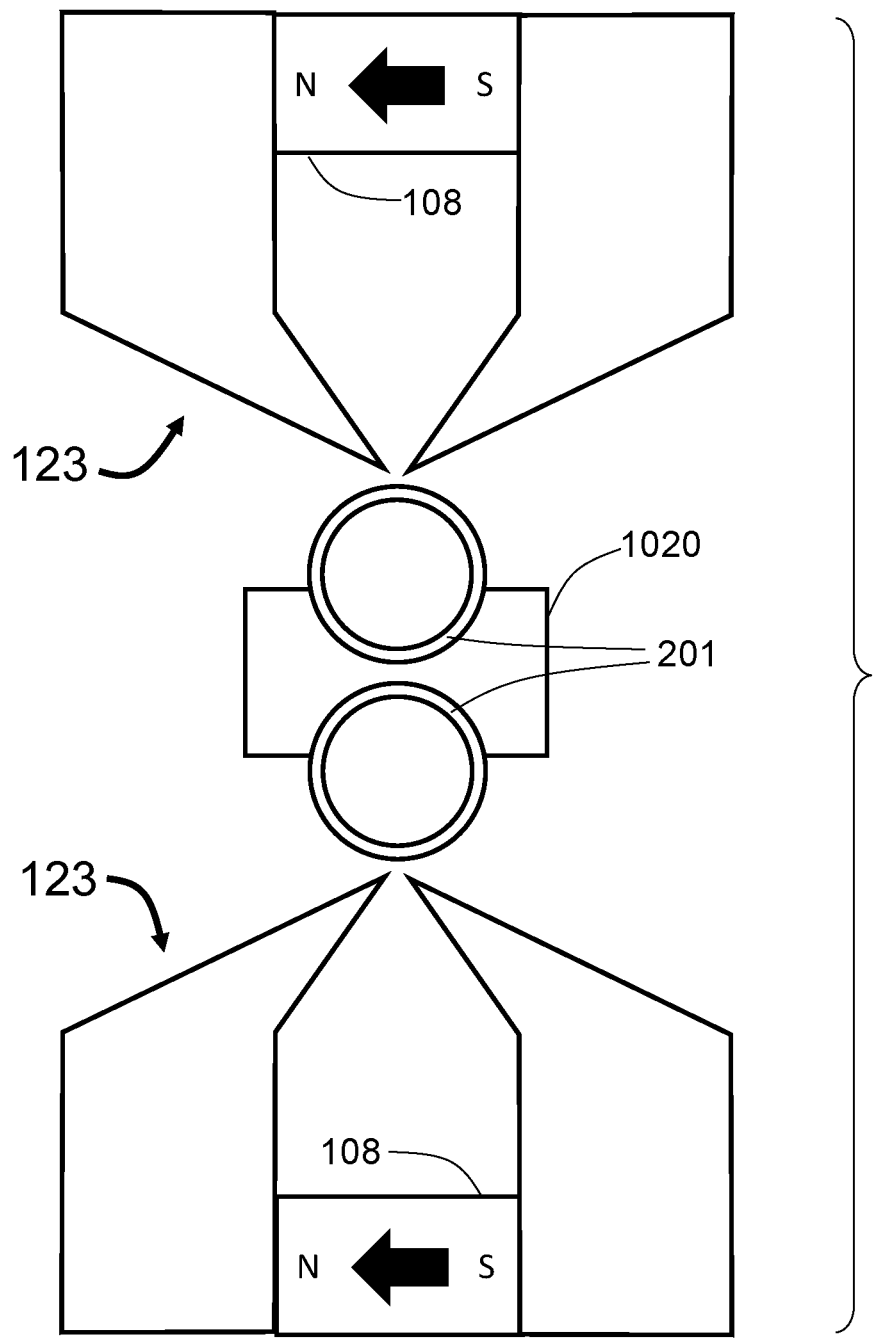
FIG. 16 illustrates cross-sectional view of a pair of third embodiment of MAGs with a pair of flexible channels on a single channel holder.

FIG. 16 illustrates two of the third embodiment MAGs 123 being used for magnetic separation on a pair of flexible channels 201. The pair of flexible channels 201 are fixed on the same channel holder 1020 in FIG. 16. The top MAG 123 and bottom MAG 123 are substantially identical, with top MAG 123 being upside down vertically. MAG wedges of the top and bottom MAGs 123 are substantially aligned with center of top and bottom channels 201. The magnets 108 of both top and bottom MAGs 123 may have same magnetization direction, as the arrows within magnets 108 in FIG. 16 indicate, such that the magnetic fields produced in the top and bottom channels 201 by the top MAG 123 and bottom MAG 123 during magnetic separation have same direction horizontal field component, which limits magnetic flux leakage between top MAG 123 soft magnetic poles and bottom MAG 123 soft magnetic poles.

Figure 17:
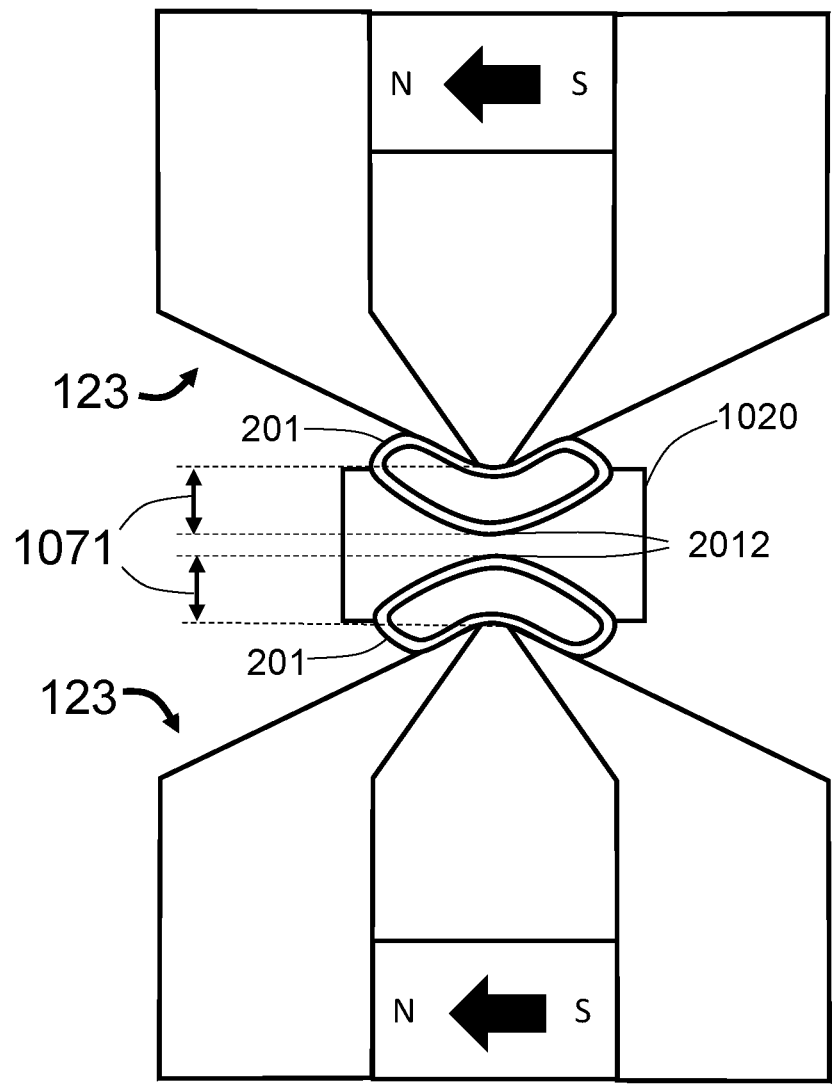
FIG. 17 illustrates cross-sectional view of a pair of third embodiment of MAGs with a pair of flexible channels on a single channel holder in separation position.

FIG. 17 illustrates the two MAGs 123 of FIG. 16 being moved into separation position against the two flexible channels 201, which is same process as in FIG. 10. After reaching FIG. 17 separation position, fluid sample carrying cells 10/30 may flow through the channels 201 in length direction perpendicular to the cross-section view to start magnetic separation of cells 10/30 by top and bottom MAGs 123. Distance 1071 between the holder 1021 surface contacting the channel 201 outer edge 2012 and MAG 123 tip ends 1021 and 1031, or the imaginary plane where tip ends 1021 and 1031 reside, may be adjusted to optimize flow rate in each of the two channels 201. Range of adjustment of distance 1071 is same as 1071 described in FIG. 10.

MAG 123 in FIG. 16 and FIG. 17 may be replaced by MAG 121 or MAG 122, and channel 201 may also be replaced with channel 101.

Figure 18:
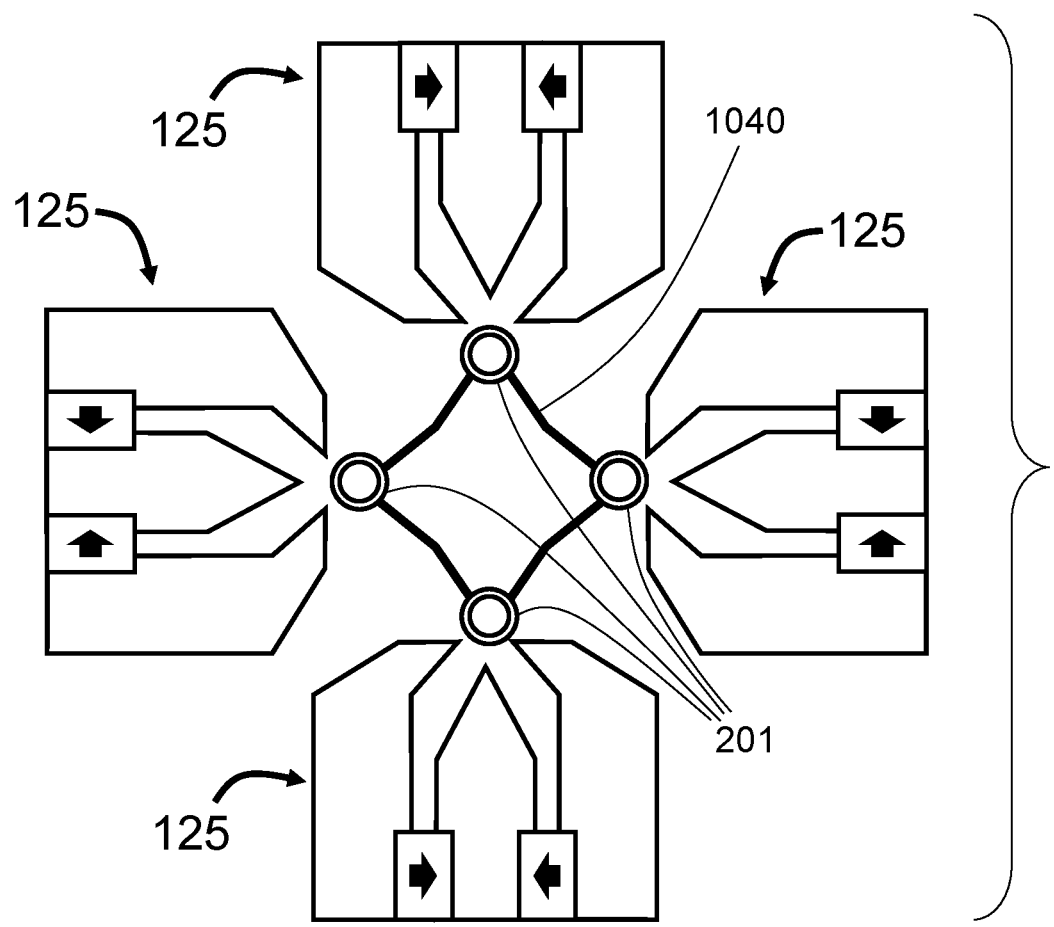
FIG. 18 illustrates cross-sectional view of four of fifth embodiment of MAGs with four flexible channels on a single channel holder.

FIG. 18 illustrates four of the fifth embodiment MAG 125 being used for magnetic separation on four flexible channels 201. The four flexible channels 201 are fixed on the same channel holder 1040 as shown in FIG. 18. The four MAGs 125 are substantially identical. MAG gaps of the four MAGs 125 are substantially aligned with centers of the corresponding flexible channels 201. The permanent magnet arrangement within each MAG 125 should be identical. For example, center pole of each of the four MAGs 125 is attached to N surfaces of both magnets within each respective MAG 125, and side poles of each of the four MAGs 125 are attached to S surfaces of magnets within each MAG 125, as shown in FIG. 18. Thus, neighboring MAGs 125 closest to adjacent side poles have same magnetic polarity, and leakage from side pole to side pole between neighboring MAGs 125 may be minimized or avoided. Additionally, four MAGs used on four channels 201 in FIG. 18 is only shown in FIG. 18 as an example of multiple channel process capability with a circular channel arrangement, where channels are positioned at center of the MAG 125 circular array. Fewer or more MAGs 125 used on corresponding number of channels 201 may be achieved using FIG. 18 type circular arrangement without limitation. FIG. 18 multiple channel circular arrangement with MAG 125 is intrinsically more flexible than MAG 123 shown in FIG. 16, as two pole design of FIG. 16 MAG 123 may lead to magnetic flux leakage through the poles of neighboring MAGs 123 when number of MAGs 123 is more than two.

Figure 19:
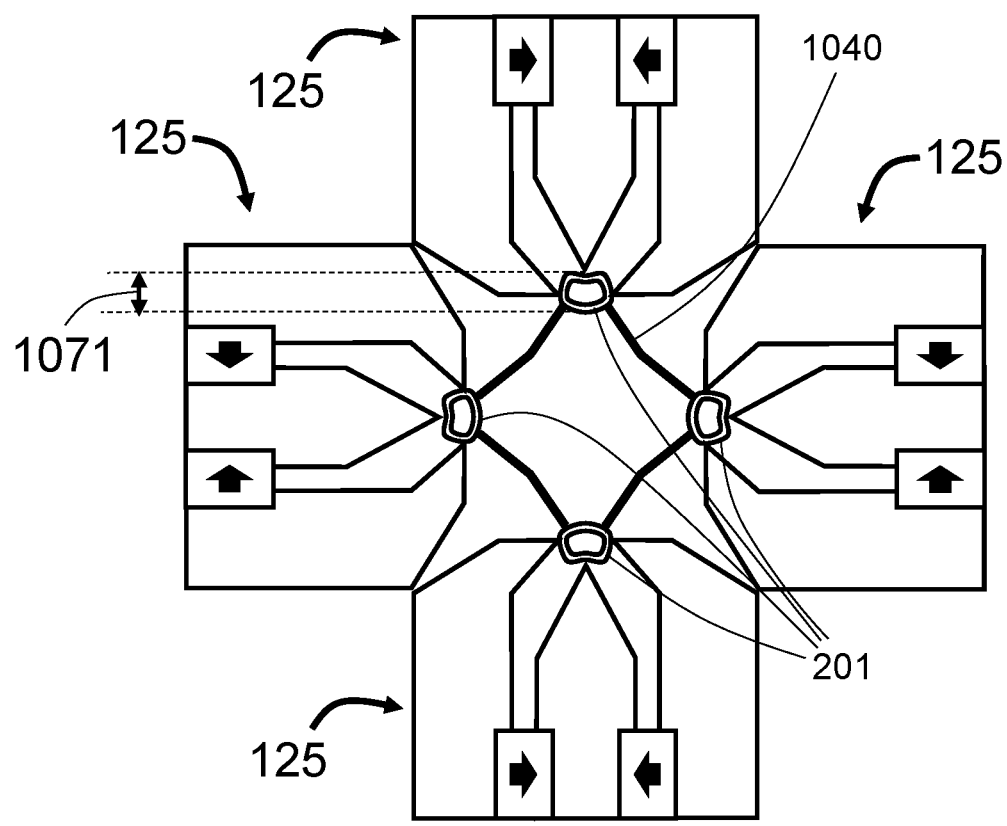
FIG. 19 illustrates cross-sectional view of four of fifth embodiment of MAGs with four flexible channels on a single channel holder in separation position.

FIG. 19 illustrates the four MAGs 125 of FIG. 18 being moved into separation position against the four flexible channels 201, which is same process as in FIG. 14. After reaching FIG. 19 separation position, fluid sample carrying cells 10/30 may flow through the channels 201 in length direction perpendicular to the view of FIG. 19 to start magnetic separation of cells 10/30 by the four MAGs 125. Similar to in FIG. 17, distance 1071 between the holder 1040 surface contacting the channel 201 outer edge 2012 and MAG 125 center pole 111 tip end 1111 for each channel 201 and MAG 125 pair may be adjusted to optimize flow rate in each of the four channels 201. Range of adjustment distance 1071 is same as 1071 described in FIG. 10.

MAG 125 in FIG. 18 and FIG. 19 may be replaced by MAG 124, MAG 126, or MAG 127. The channel 201 may also be replaced by channel 301.

FIG. 20A illustrates the sixth embodiment of MAG 128 with a rotated "D" shape rigid channel 320 in separation position. MAG 128 is similar to MAG 123, except that MAG wedge of MAG 123 is modified from a triangle shape to a flat top in MAG 128. MAG 128 pole 1022 is similar to pole 102 of MAG 123, but with a flat top surface 1042 on pole 1022 instead of a tip end on pole 102. Same flat top 1052 exists on pole 1032, which is similar to pole 103 of MAG 123. Due to the flat top of the MAG wedge in MAG 128, rigid channel 320 may have a flat bottom surface 1062 matching and in contact with the MAG wedge flat surface in separation position, to gain highest magnetic field and field gradient region from MAG 128. Channel 320 may be attached to a non-magnetic channel holder 1102 at the top surface. Channel holder 1102 may align channel 320 to MAG wedge of MAG 128, move channel 320 to separation position in contact with MAG 128 poles 1022 and 1032 tip ends, or lift channel 320 away from MAG 128 after magnetic separation.

FIG. 20B illustrates the sixth embodiment MAG 128 being used on a flexible channel 201, where channel 201 is attached to channel holder 1102. Channel holder 1102 moves channel 201 towards MAG wedge of MAG 128 along direction 1014.

FIG. 20C illustrates the sixth embodiment MAG 128 having the flexible channel 201 of FIG. 20B moved into separation position, with cells 10/30 being separated from a liquid sample to form conglomerate at bottom surface of channel 201, against the top flat surface of the MAG wedge of MAG 128. Channel 201 is forced to form into a rotated "D" shape channel by holder 1102 pushing channel 201 against the flat top of MAG wedge of MAG 128, where channel 201 shape in separation position is similar to channel 320 of FIG. 20A. Distance 1071 between the holder 1102 bottom surface 1062 contacting the channel 201 top edge 2012 and MAG 128 pole surfaces 1042 and 1052 may be adjusted to optimize flow rate in channel 201. Range of adjustment distance 1071 is same as 1071 described in FIG. 10.

Magnet 108 of MAG 128 may be replaced by placement of magnets 104 and 105 as in MAG 121, and by placement of magnets 104 and 105 and bottom shield 106 as in MAG 122.

FIG. 21A illustrates the seventh embodiment MAG 129 with a "V" shape rigid channel 330 in separation position. MAG 129 is different from MAG 123 in pole shape, where pole 1024 and pole 1034 of MAG 129 have flux concentration tip ends 3301 and 3302 that form a "V" shaped notch, instead of the triangle wedge shape of the MAG 123. With the V shape MAG notch of MAG 129, rigid channel 330 is also made into a V shape, with the lower edges 3303 and 3304 making direct contact with the surfaces of the tip ends 3301 and 3302. Additionally, channel 330 may also preferably have a V shape notch recessed into the channel at the top edge 3305 following the V shape of the 3303 and 3304 edges, which helps confine fluid sample in the V shaped channel space 3306 to flow closer to the pole surfaces 3303 and 3004 that provide higher field and field gradient. Channel 330 may be attached to a non-magnetic channel holder 1103 at the top surface 3305. Channel holder 1103 may align channel 330 to MAG notch of MAG 129, move channel 330 to separation position in contact with poles 1024 and 1034 tip end surfaces, or lift channel 330 away from MAG 129 after magnetic separation.

FIG. 21B illustrates the seventh embodiment MAG 129 being used with a flexible channel 201, where channel 201 is attached to channel holder 1103 at the top edge of channel 201. Channel holder 1103 moves channel 201 towards MAG 129 notch along direction 1014. Channel holder 1103 has a triangle shape, where a convergence point of the triangle touches the channel 201 top edge.

FIG. 21C illustrates the seventh embodiment MAG 129 with the flexible channel 201 of FIG. 21B moved into separation position, with cells 10/30 being separated from a liquid sample to form conglomerate on bottom surface of channel 201, against the top surfaces of the MAG notch of tip ends 3301 and 3302 of MAG 129. Channel 201 is forced to form into a "V" shape channel by holder 1103. In FIG. 21C, holder 1103 forces channel 201 against the MAG notch of MAG 129 with the lower convergence point and deforms the top wall of the channel 201 downwards to move closer to the tip ends 3301 and 3302. The same force also causes lower wall of channel 201 to conform to the MAG notch of MAG 129 and to make contact with the tip ends 3301 and 3302 top surfaces 3303 and 3304. Thus, channel 201 shape in FIG. 21C in separation position shows V shape similar to channel 330 of FIG. 21A, which brings cells 10/30 in channel space 3306 closer to high field and high gradient tip ends 3301 and 3302 and tip surfaces 3303 and 3304. Vertical distance 1071 between the holder 1103 bottom convergence point contacting the channel 201 top edge 2012 and MAG 129 tip ends 3301 and 3302, or an imaginary plane where tip ends 3301 and 3302 reside, may be adjusted to optimize flow rate in channel 201. Range of adjustment distance 1071 is same as 1071 described in FIG. 10.

Magnet 108 of MAG 129 may be replaced by placement of magnets 104 and 105 as in MAG 121, and by placement of magnets 104 and 105 and bottom shield 106 as in MAG 122.

Figure 22A:
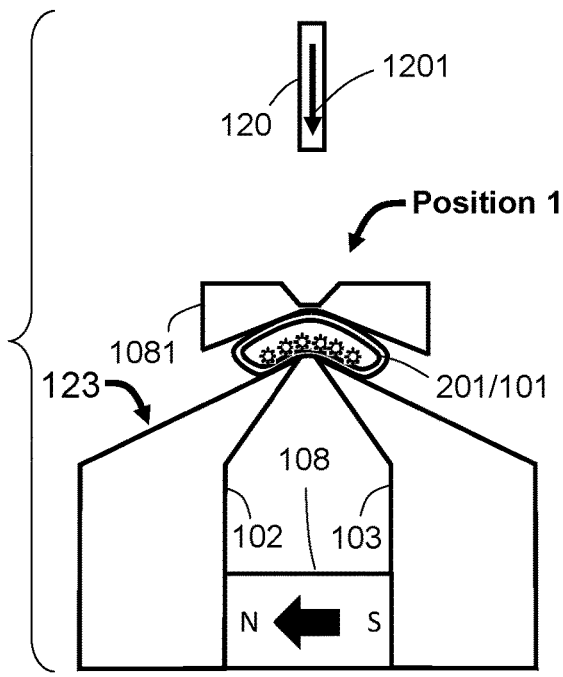
FIG. 22A illustrates the third embodiment of MAG having a flexible channel in separation position with cells being separated, and a demagnetization ("DMAG") magnet positioned over and away from MAG.

From FIG. 22A through FIG. 27D, various methods to demagnetize or dissociate magnetically separated cells 10/30 from conglomerate in MAG channel will be described. For simplicity of description, flexible channel 201 is used. However, channels in FIG. 22A through FIG. 27D may be labeled as "201/101", indicating flexible channel 201 used for description may be replaced with rigid channel 101 without affecting the function and results of the described method. Also for the simplicity of description, MAG 123 is used in FIG. 22A through FIG. 27D, while any other MAG embodiment together with corresponding channel as described in prior figures may be used under same concepts without limitation FIG. 22A is substantially similar to FIG. 10, where channel 201 is at separation position and cells 10/30 have been separated by magnetic field from MAG. In FIG. 22A, MAG 123 is used instead of MAG 121 of FIG. 10. Channel holder 1081 may be different from channel holder 107 of FIG. 10 by having a top surface notch that allows the cells 10/30 demagnetization by dissociation magnetic structure ("DMAG"), which is permanent magnet 120 in FIG. 22A that is able to reach closer to the channel 201/101 to provide sufficient field to demagnetize or dissociate cells 10/30 from the conglomerate in channel 201/101. Such notch is preferred, but may not be required. DMAG magnet 120 is positioned away from MAG 123 of FIG. 22A without affecting magnetic separation of cells 10/30 by MAG 123. DMAG magnet 120 magnetization is labeled in vertical direction 1201, but may also be in horizontal direction without causing functional difference. Channel 201/101 position relative to the MAG 123 and DMAG 120 in FIG. 22A is "Position 1".

Figure 22B:
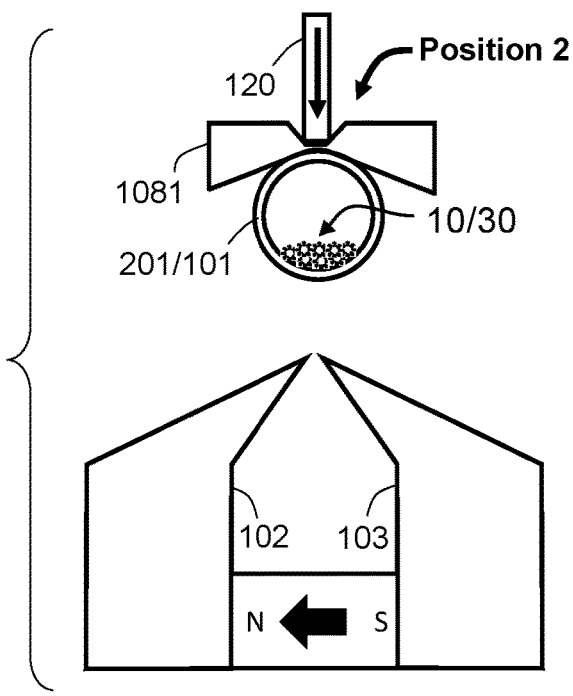
FIG. 22B illustrates the flexible channel of FIG. 22A departing MAG and moving into position where flexible channel holder is in close proximity to, or contacts, the DMAG magnet.

FIG. 22B is similar to FIG. 11, where channel holder 1081 moves channel 201/101 away from MAG 123 and comes into contact with, or is in close proximity to, DMAG magnet 120 at the top surface of holder 1081. The magnet 120 may fit into the notch of holder 1081 to provide highest magnetic field on cells 10/30 conglomerate in channel 201/101. Cells 10/30 form conglomerate after magnetic separation by MAG and do not break free from the conglomerate automatically due to SPLs 2 on cells 10/30 not self-demagnetizing when they are part of a conglomerate. By removing cells 10/30 gradually with magnetic field gradient from magnet 120, for example cells 10/30 with higher magnetic moment SPL 2 that respond to weaker magnetic field from DMAG 120 faster, conglomerate may reach to a critical volume that remaining cells 10/30 in the conglomerate do not see enough magneto-static field from other cells 10/30 and will self-demagnetize into individual cells 10/30 due to the regained superparamagnetic nature of SPL 2. Therefore, to dissociate cells 10/30 from conglomerate, removing certain amount of cells 10/30, or breaking up the conglomerate from a continuous large piece into multiple smaller pieces will help cells 10/30 to achieve self-demagnetization. Channel 201/101 position relative to the MAG 123 and DMAG 120 in FIG. 22B is "Position 2". Channel 201 compared to channel 101 may have an advantage during cells 10/30 dissociation by DMAG magnet 120, as channel 201 provides a larger channel space that allows farther separation between free cells 10/30 and conglomerate, or between broken-up conglomerate pieces, which helps to reduce magneto-static coupling and enhances self-demagnetization speed of SPLs 2 on cells 10/30. For flexible channel 201, before Position 2 or in Position 2, it is preferred to fill the channel 201 with additional buffer fluid to return the channel 201 to circular shape for larger channel space.

Figure 22C:
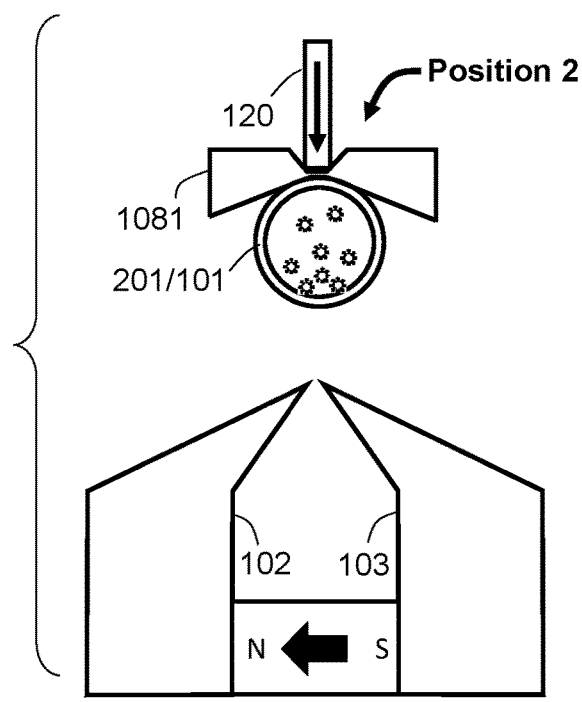
FIG. 22C illustrates the cells in the flexible channel of FIG. 22B being dissociated from conglomerate by the DMAG magnet.

FIG. 22C illustrates the cells 10/30 in the channel 201/101 of FIG. 22B being dissociated from conglomerate by the DMAG magnet 120 in Position 2.

Figure 22D:
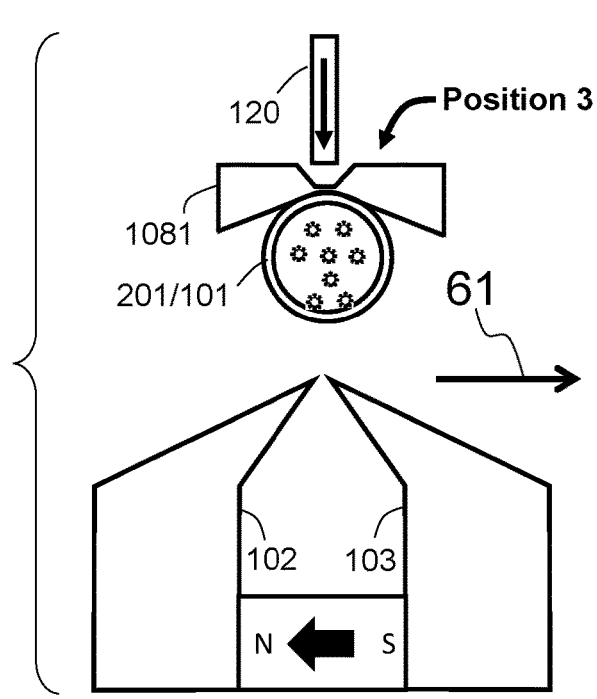
FIG. 22D illustrates the flexible channel of FIG. 22C moving into a low magnetic field position between MAG and DMAG magnet.

FIG. 22D illustrates the channel holder 1081 moving channel 201/101 from FIG. 22C DMAG Position 2 to a position, "Position 3", between MAG 123 and DMAG magnet 120. In Position 3, combined field on the cells 10/30 within channel 201/101 may be the smallest, which may help SPL 2 to self-demagnetize. Channel 201/101 may be kept in Position 3 for extensive time to allow SPL 2 and cells 10/30 to fully self-demagnetize and conglomerate to dissociate.

For an effective break up of conglomerate, mechanical agitations may be added to the conglomerate by the magnetic forces exerted by MAG and DMAG magnets. For example, channel holder 1081 may repeatedly move channel 201/101 between Positions 1 and 2, or Positions 2 and 3, or Positions 1, 2 and 3, such that alternating magnetic forces by MAG and DMAG may move whole or part of the conglomerate in the channel space, thus helping break up the conglomerate into smaller pieces or causing enough cells 10/30 to break free from the conglomerate, which may self-dissociate. After conglomerate is sufficiently dissociated, free cells 10/30 may be flushed out of channel 201/101 in Position 3 or Position 2.

FIG. 23A illustrates that mechanical vibration may be applied to the channel holder 1081 by a motor 130 when channel 201/101 is in Position 2 of FIG. 22B or Position 3 of FIG. 22D. Such vibration may be transferred from holder 1081 through wall of channel 201/101 and into the fluid within the channel 201/101 to cause localized turbulence flow at various locations within the channel 201/101, which may help to mechanically break up the conglomerate into small pieces to assist conglomerate dissociation.

FIG. 23B illustrates that ultrasound vibration by a piezoelectric transducer ("PZT") 131 may be applied to the channel holder 1081. Similar to FIG. 23A, ultrasound vibration may be transferred into the fluid within the channel 201/101 to cause localized high frequency turbulence within the channel 201/101, which may help to mechanically break up the conglomerate into small pieces to assist conglomerate dissociation.

FIG. 23C illustrates that mechanical vibration of FIG. 23A may be applied to the channel 201/101 wall directly by motor 130.

FIG. 23D illustrates ultrasound vibration of FIG. 23B may be applied to the channel 201/101 wall directly by PZT 131.

FIG. 23E is a side view of the channel 201/101 along the direction 61 shown in FIG. 22D. Arrows 1030 represent alternating directions that pulsed fluid flow may be applied to the channel liquid sample to produce a flow jittering in the liquid within the channel 201/101, which may also produce local turbulence flow with fluid in channel 201/101 to help mechanically break up the conglomerate into small pieces to assist conglomerate self-dissociation. FIG. 23E alternating pulsed flow may be combined with FIG. 23A through FIG. 23D vibration methods to apply to channel 201/101 in Position 2 or Position 3 of FIG. 22B through FIG. 22D.

When conglomerate in channel 201/101 is of large size, multiple rounds of cells 10/30 dissociation with FIG. 22B to FIG. 23E methods, and flushing of cells 10/30 out of channel 201/101, may be used. During each flush, a certain part of cells 10/30 may be washed out of channel, making dissociation of remaining cells 10/30 still in the conglomerate in channel 201/101 easier in next round.

Figure 24A:
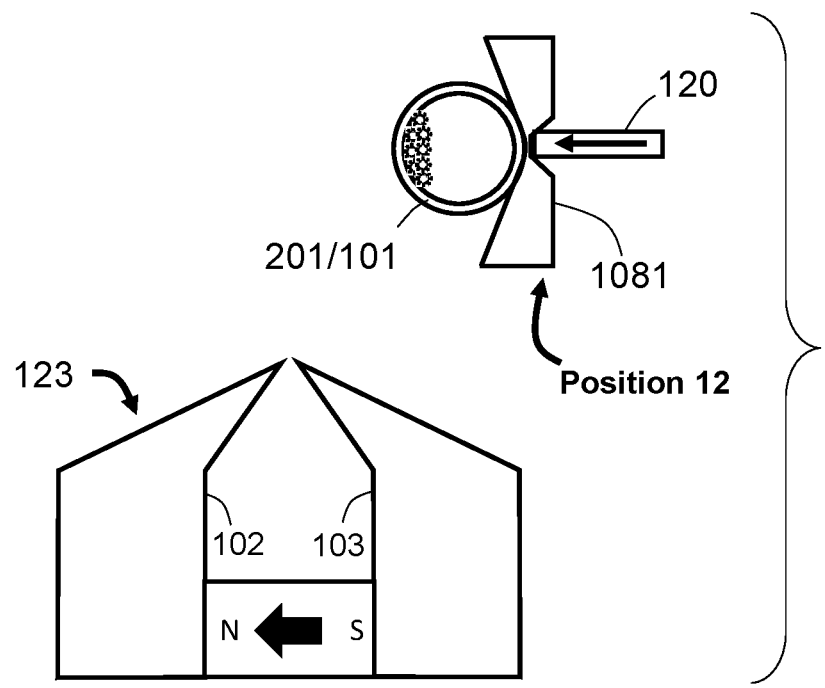
FIG. 24A illustrates the third embodiment of MAG having a flexible channel holder in close proximity to, or in contact with, a DMAG magnet after cells are magnetically separated by MAG, where DMAG magnet is positioned on the side and away from MAG.

FIG. 24A is similar to FIG. 22B, where channel holder 1081 is in contact, or in close proximity to, DMAG magnet 120 after cells 10/30 are magnetically separated by MAG 123. Different from that in FIG. 22B, DMAG magnet 120 of FIG. 24A is positioned on the side of and away from MAG 123, and holder 1081 is also rotated compared to FIG. 22B to fit its top surface notch to the magnet 120. Placement of magnet 120 in FIG. 24A may reduce magnetic field interference between MAG 123 and DMAG magnet 120. Channel 201/101 position relative to the MAG 123 and DMAG 120 in FIG. 24A is "Position 12".

Figure 24B:
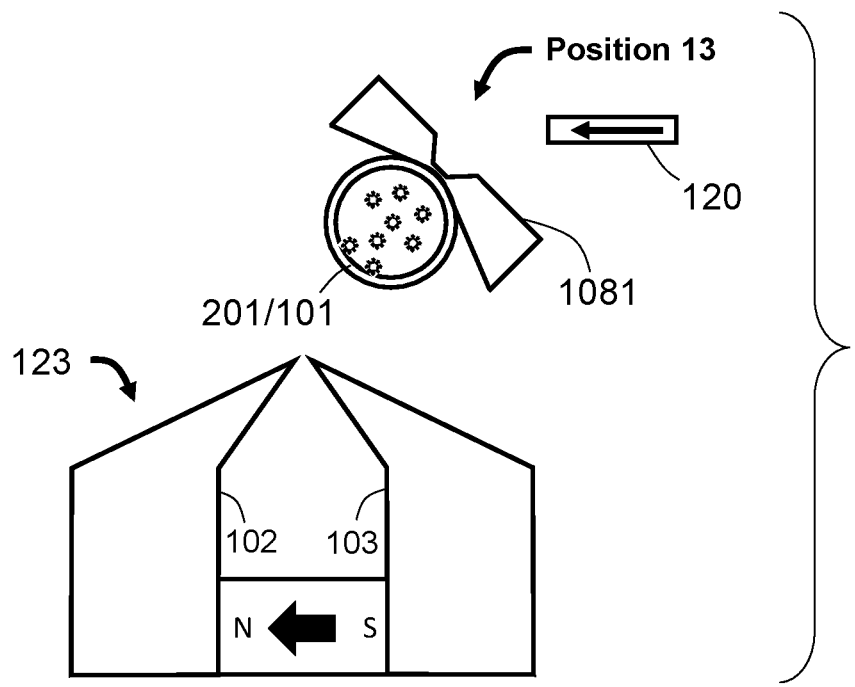
FIG. 24B illustrates the flexible channel of FIG. 24A rotating into a low magnetic field position between MAG and DMAG magnet.

FIG. 24B illustrates that after cells 10/30 are dissociated in Position 12 of FIG. 24A, the channel 201/101 together with channel holder 1081 of FIG. 24A are rotated away from magnet 120 of FIG. 24A into a position between MAG 123 and DMAG magnet 120, where combined magnetic field from MAG 123 and DMAG magnet 120 on channel 201/101 and cells 10/30 therein is lowest, which is similar to Position 3 of FIG. 22D. Channel 201/101 position relative to the MAG 123 and DMAG 120 in FIG. 24B is "Position 13".

Figure 25A:
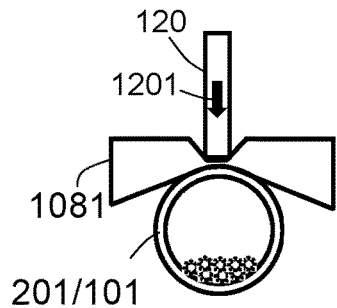
FIG. 25A illustrates a flexible channel holder at demagnetization position, where DMAG magnet is a permanent magnet.

FIG. 25A illustrates DMAG structure that is same as that in FIG. 22B, where DMAG structure includes only permanent magnet 120 with magnetization 1201.

Figure 25B:
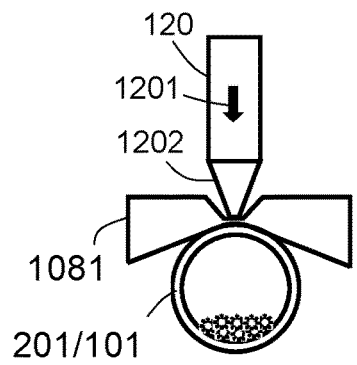
FIG. 25B illustrates a flexible channel holder at demagnetization position, where DMAG magnet is a permanent magnet attached with a soft magnetic pole.

FIG. 25B illustrates DMAG structure that includes permanent magnet 120 and a soft magnetic pole 1202 with convergence shape towards channel 201/101. Soft magnetic pole 1202 convergence shape helps to concentrate magnetic flux from magnet 120 to produce higher field and high field gradient on cells 10/30 in channel 201/101 in Position 2 to more effectively demagnetize and dissociate the conglomerate of cells 10/30.

Figure 25C:
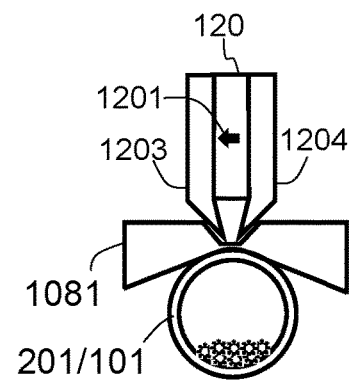
FIG. 25C illustrates a flexible channel holder at demagnetization position, where DMAG magnet is a permanent magnet attached with a pair of soft magnetic poles.

FIG. 25C illustrates DMAG structure that includes permanent magnet 120 and a pair of soft magnetic poles 1203 and 1204. Magnetization 1201 of magnet 120 is in horizontal direction, and each of poles 1203 and 1204 has an convergence shape pointing towards channel 201/101. The convergence ends of poles 1203 and 1204 form a DMAG gap sitting in, or in close proximity to, the channel holder 1081 top surface notch. Flux from magnet 120 is conducted by the poles 1203 and 1204 and concentrated in the DMAG gap to produce high field and high field gradient on cells 10/30 in channel 201/101 in Position 2 to more effectively demagnetize and dissociate the conglomerate of cells 10/30.

Figure 25D:
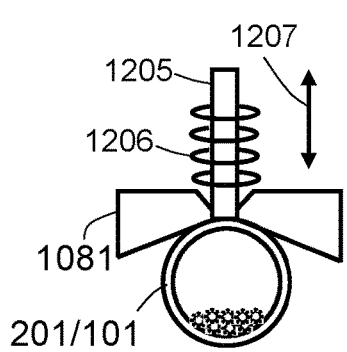
FIG. 25D illustrates a flexible channel holder at demagnetization position, where DMAG magnet is an electromagnet.

FIG. 25D illustrates DMAG structure that includes an electromagnet including a soft magnetic core 1205 and coils 1206, where electric current following in the coils 1206 may produce magnetization in core 1205 in directions of 1207, and core 1205 functions like magnet 120 to product magnetic field on cells 10/30 in channel 201/101 in Position 2 to demagnetize or dissociate the conglomerate of cells 10/30. By changing the electric current amplitude and direction in coils 1206, magnetic field from core 1205 on cells 10/30 may change strength and direction. In one embodiment, DC current is applied to coils 1206. In another embodiment, AC current with alternating polarities is applied to coils 1206. In yet another embodiment, current applied to coils 1206 is programmed to vary in amplitude, or in direction, or in frequency, or in amplitude ramp up or ramp down rate, to more effectively demagnetize and dissociate the conglomerate of cells 10/30.

Figure 25E:
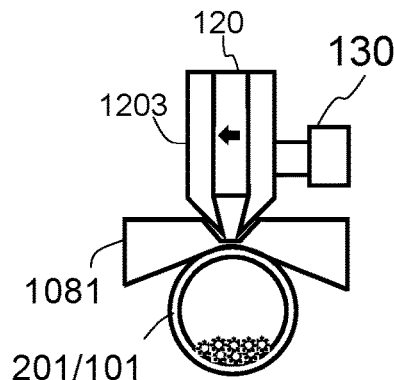
FIG. 25E illustrates flexible channel holder at demagnetization position, where mechanical vibration is applied to DMAG magnet by a motor.

FIG. 25E illustrates that motor 130 shown in FIG. 23A may produce mechanical vibrations on DMAG structure of FIG. 25C. Such vibrations may be transferred from DMAG structure to holder 1081 through DMAG structure to holder 1081 contact, and finally transferred to fluid in channel 201/101, where DMAG structure can be changed to any of DMAG structures described in FIG. 25A through FIG. 25D.

Figure 25F:
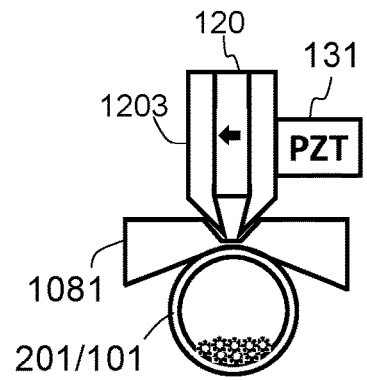
FIG. 25F illustrates flexible channel holder at demagnetization position, where ultrasound vibration is applied to DMAG magnet by a PZT.

FIG. 25F illustrates that PZT 131 shown in FIG. 23B may produce ultrasound vibrations on DMAG structure of FIG. 25C. Such vibrations may be transferred from DMAG structure to holder 1081 through DMAG structure to holder 1081 contact, and finally transferred to fluid in channel 201/101, where DMAG structure can be changed to any of DMAG structures described in FIG. 25A through FIG. 25D.

To achieve demagnetization and dissociation of cells 10/30 from conglomerate in channel 201/101, an alternative method as described in FIG. 26A through FIG. 26D may be used without using a DMAG structure, where the function of DMAG structure is achieved with the same MAG.

FIG. 26A is same as FIG. 22A, where channel 201/101 is in separation position and cells 10/30 are separated by magnetic field of MAG 123 in channel 201/101, except channel holder 1082 may not have the top surface notch as holder 1081. Channel 201/101 position relative to the MAG 123 in FIG. 26A is "Position 21".

FIG. 26B illustrates channel 201/101 of FIG. 26A is lifted from MAG 123 to a lower field position, "Position 22". In Position 22 channel 201/101 may rotate around its center as indicated by arrow 210, preferable by 180 degrees. Such rotation may require channel 201/101 not being permanently fixed to holder 1082

FIG. 26C illustrates channel 201/101 of FIG. 26B after rotation of 180 degrees in Position 22. The cells 10/30 conglomerate formed on inner wall of channel 201/101 rotates together with channel wall to be at the top end of the channel 201/101 relative to MAG 123.

FIG. 26D illustrates that channel 201/101 is moved from Position 22 closer to MAG 123 to a Position 23 in between Position 21 and Position 22, where magnetic field from MAG 123 on cells 10/30 is stronger than Position 22 but weaker than Position 21. Cells 10/30 in conglomerate at top end of channel 201/101 may then be pulled away by MAG 123 field from conglomerate and demagnetization and dissociation of conglomerate may start. The process of FIG. 26B through FIG. 26D may repeat multiple times, where channel 201/101 may return to Position 22 from Position 23 to perform another rotation and then move back to Position 23, until cells 10/30 are sufficiently dissociated in channel 201/101. At end of demagnetization, cells 10/30 may be flushed out of channel 201/101 preferably in Position 22. Mechanical vibrations and flow jittering as described in FIG. 23C through FIG. 23E may be applied to channel 201/101 in Position 22 and Position 23.

FIG. 27A is same as FIG. 26A, where channel 201/101 is in separation position and cells 10/30 are separated by magnetic field of MAG 123. Channel 201/101 position relative to the MAG 123 is "Position 21". Channel 201/101 is attached to holder 1082 in FIG. 27A.

FIG. 27B illustrates channel 201/101 of FIG. 27A being lifted from MAG 123 to lower field Position 22 by holder 1082.

FIG. 27C illustrates that in Position 22, dissociation of cells 10/30 in channel 201/101 may be achieved only through mechanical vibration exerted by motor 130. FIG. 27C shows that motor 130 applies mechanical vibration to holder 1082. Such vibration may be transferred from holder 1082 through wall of channel 201/101 and into the fluid within the channel 201/101 to cause localized turbulence flow at various locations within the channel 201/101, which may help to mechanically break up the conglomerate into small pieces to assist self-dissociation of cells 10/30 conglomerate. Motor 130 may also exert vibration directly on channel 201/101 as shown in FIG. 23C instead of through holder 1082. Alternating direction pulsed fluid flow as described in FIG. 23E may be applied to the channel liquid sample to produce a flow jittering in the liquid within the channel 201/101 at the same time during motor 130 vibration application.

FIG. 27D illustrates that in Position 22, dissociation of cells 10/30 in channel 201/101 may be achieved primarily through ultrasound vibration exerted by PZT 131. FIG. 27D shows that PZT 131 applies ultrasound vibration to holder 1082. The ultrasound vibration may be transferred into the fluid within the channel 201/101 to cause localized high frequency turbulence within the channel 201/101, which may help to mechanically break up the conglomerate into small pieces to assist self-dissociation of cells 10/30 conglomerate. PZT 131 may also exert ultrasound vibration directly on channel 201/101 as shown in FIG. 23D. Alternating direction pulsed fluid flow as described in FIG. 23E may be applied to the channel liquid sample to produce a flow jittering in the liquid within the channel 201/101 at the same time during PZT 131 ultrasound vibration application.

FIG. 28A through FIG. 30B describe embodiments of methods to assist cells 10/30 conglomerate dissociation by mechanical agitations, which may be applied to channel 201/101 in FIG. 27B in Position 22 and applied to channel 201/101 in FIG. 22B through FIG. 22D, FIG. 23A through FIG. 23D, FIG. 24A through FIG. 25F, FIG. 26B through FIG. 26D, FIG. 27B through FIG. 27D.

Figure 28A:
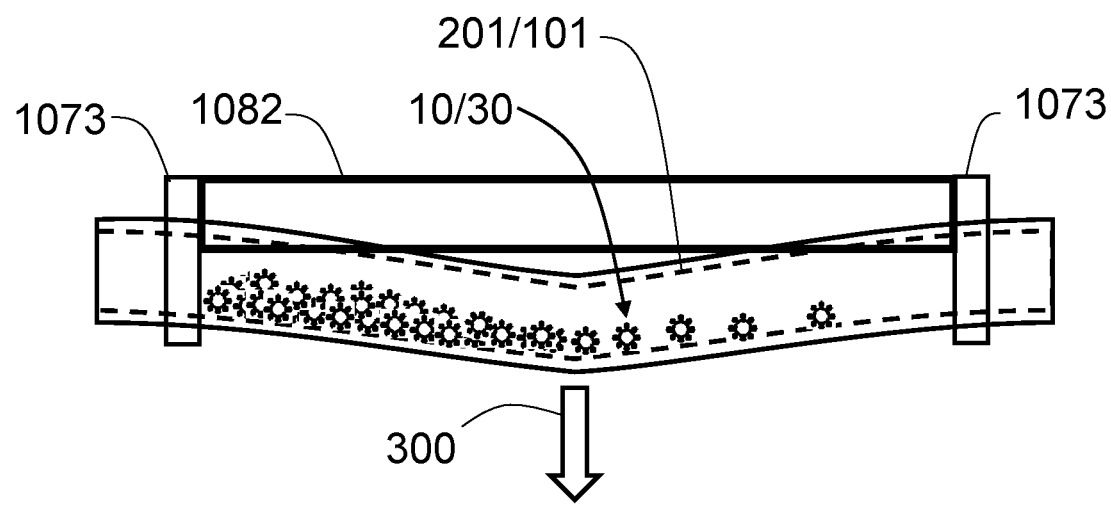
FIG. 28A illustrates a side view of a flexible channel where the flexible channel is mechanically stretched.

FIG. 28A shows a side view of channel 201/101 and holder 1082 along direction 61 of FIG. 27B, where cells 10/30 are magnetically separated by MAG field and form conglomerate on lower side of the channel 201/101 wall. Channel mounts 1073 may be used to attach channel 201/101 to channel holder 1082. Channel mounts 1073 may fix channel 201/101 at sections attached to mounts 1073 as anchors against channel 201/101 deformation, compression or elongation during mechanical agitation process. Channel mounts 1073 may also perform a valve function that closes fluid flow into or out of flexible channel 201 section between two channel mounts 1073 before mechanical agitation process of FIG. 28A, such that fluid enclosed in channel 201 may more efficiently produce localized turbulence within the channel 201. FIG. 28A illustrates that an externally applied force 300 may stretch or deform the channel 201/101 in a direction away from the holder 1082, for example perpendicular to the channel 201/101 length direction. Such deformation or stretch of channel 201/101 builds up elastic energy in the channel 201/101 wall material.

Figure 28B:
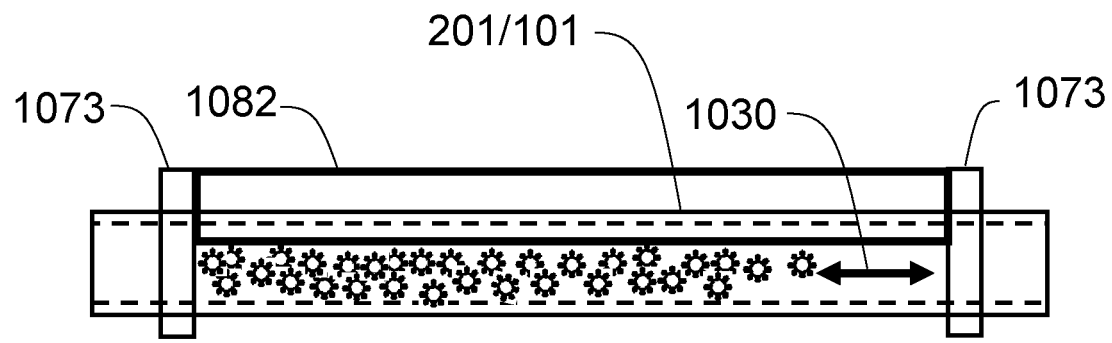
FIG. 28B illustrates cells being dissociated from conglomerate after removal of the external force of FIG. 28A.

FIG. 28B illustrates that when force 300 of FIG. 28A is removed, elastic energy built up in channel 201/101 wall acts to spring back channel 201/101 towards its original non-deformed and non-stretched position. Depending on channel 201/101 wall material property, such spring back may provide a transient turbulence flow at various locations within the channel 201/101, which may help to mechanically break up the cells 10/30 conglomerate into smaller pieces to assist self-dissociation of cells 10/30 conglomerate. After removal of force 300 and spring back of the channel 201/101, alternating flow 1030 may be similarly applied as in FIG. 23E to assist dissociation process of conglomerate of cells 10/30, where valve function of channel mounts 1073 may be turned off to allow fluid flow within channel 201/101.

The deform/stretch and release process of the channel 201/101 as illustrated in FIG. 28A and FIG. 28B may be repeated as many times as needed until conglomerate of cells 10/30 is sufficiently dissociated, which may then be flushed out of channel 201/101 by buffer fluid.

Figure 29A:
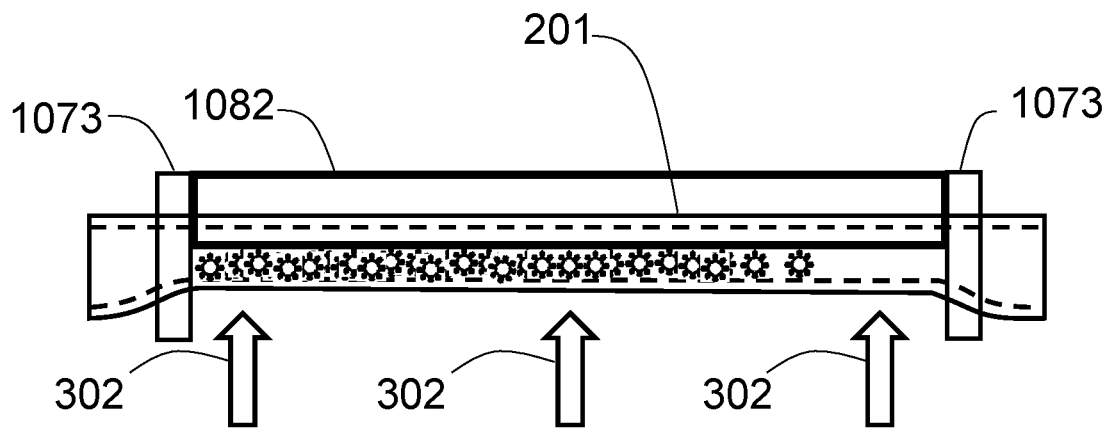
FIG. 29A illustrates a side view of a flexible channel where the flexible channel is mechanically compressed.

FIG. 29A illustrates an alternative method of mechanical agitation from FIG. 28A. Every aspect is same as that in FIG. 28A, except that a compressive force 302 may be applied to compress channel 201 in direction perpendicular to the channel 201 length direction. For example, channel 201 is compressed against channel holder 1082 as shown in FIG. 29A. As liquid within channel 201 has limited compressibility, force 302 may cause channel 201/101 wall to expand in direction perpendicular to the view of FIG. 29A, i.e. in direction perpendicular to both channel length direction and force 302 direction. Such expansion of channel 201/101 wall will again build up elastic energy in the channel 201 wall material.

Figure 29B:
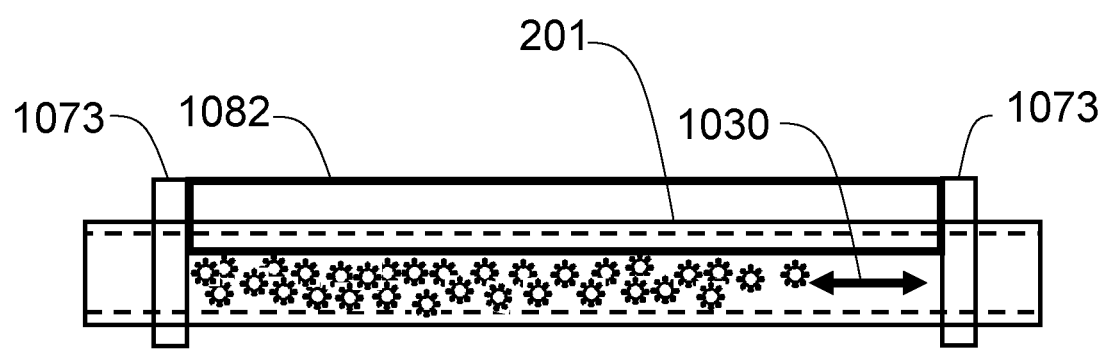
FIG. 29B illustrates cells being dissociated from conglomerate after removal of the external force of FIG. 29A.

FIG. 29B is same as FIG. 28B in every aspect, except that FIG. 29B is after compressive force 302 of FIG. 29A is removed, and elastic energy built up in channel 201 wall acts to spring back channel 201 to its original non-compressed shape. Such spring back may provide a strong transient turbulence flow at various locations within the channel 201, which may help to mechanically break up the cells 10/30 conglomerate into smaller pieces to assist self-dissociation of cells 10/30 conglomerate. After removal of force 302 and spring back of channel shape, alternating flow 1030 may be similarly applied as in FIG. 23E to assist dissociation process of conglomerate of cells 10/30, where valve function of channel mounts 1073 may be turned off.

The compression and release process of the channel 201 as illustrated in FIG. 29A and FIG. 29B may be repeated as many times as needed until conglomerate of cells 10/30 are sufficiently dissociated, which may then be flushed out of channel 201.

Figure 30A:
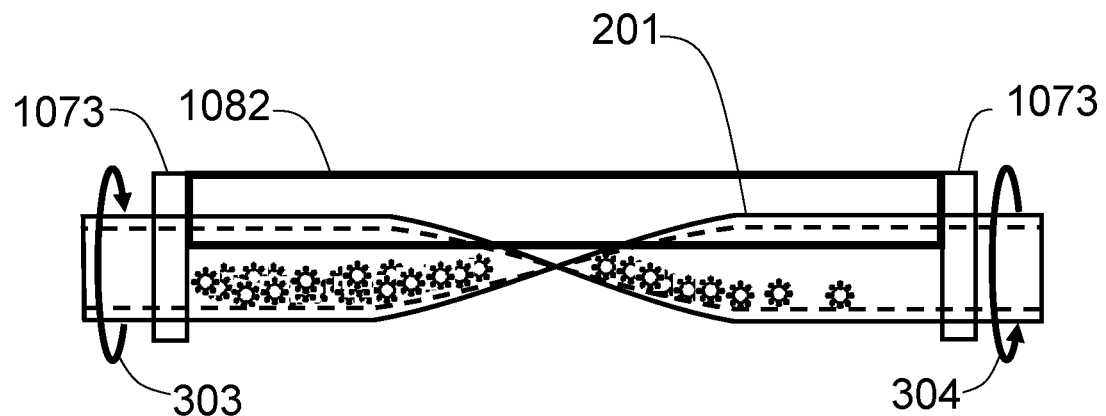
FIG. 30A illustrates a side view of a flexible channel where the flexible channel is mechanically twisted.

FIG. 30A illustrates another alternative method of mechanical agitation. Every aspect is same as in FIG. 28A, except that rotational twisting force 303 or 304 may be applied to channel 201 to twist channel 201 along channel length direction, as shown in FIG. 30A. In one embodiment, only one of rotational force 303 or 304 is applied to one end of channel 201. In another embodiment, both rotational forces 303 and force 304 are applied to difference ends of the channel 201 in opposite rotational directions to cause the channel 201 to twist along channel length direction. Such twist deformation of channel 201 will again build up elastic energy in the channel 201 wall material.

Figure 30B:
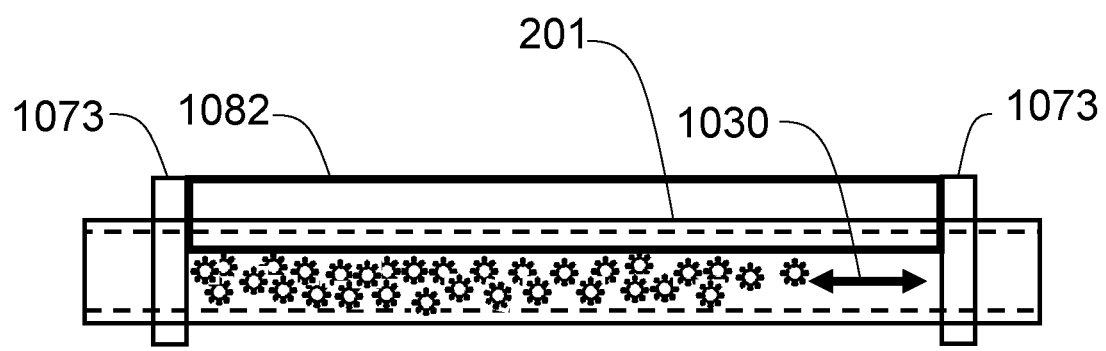
FIG. 30B illustrates cells being dissociated from conglomerate after removal of the external force of FIG. 30A.

FIG. 30B is same as FIG. 28B in every aspect, except that FIG. 30B is after rotational force 303 and force 304 of FIG. 30A are released, and elastic energy built up in channel 201 wall acts to spring back channel 201 towards its original non-twisted shape. Such spring back may provide a strong transient turbulence flow at various locations within the channel 201, which may help mechanically break up the cells 10/30 conglomerate into smaller pieces to assist self-dissociation of cells 10/30 conglomerate. After removal of forces 303 and 304, and spring back of channel 201 shape, alternating flow 1030 may be similarly applied as in FIG. 23E to assist dissociation process of conglomerate of cells 10/30, where valve function of channel mounts 1073 may be turned off.

The twist and release process of the channel 201 as illustrated in FIG. 30A and FIG. 30B may be repeated as many times as needed until conglomerate of cells 10/30 is sufficiently dissociated, which may then be flushed out of channel 201 by buffer fluid.

Mechanical forces 300, 302, 303 and 304 may be applied by mechanical structures that are motorized and able to apply such forces repeatedly to channel 201. Examples may include a flap for providing force 300, a compressor for provide force 302, and twisters for providing forces 303 and 304.

Figure 31:
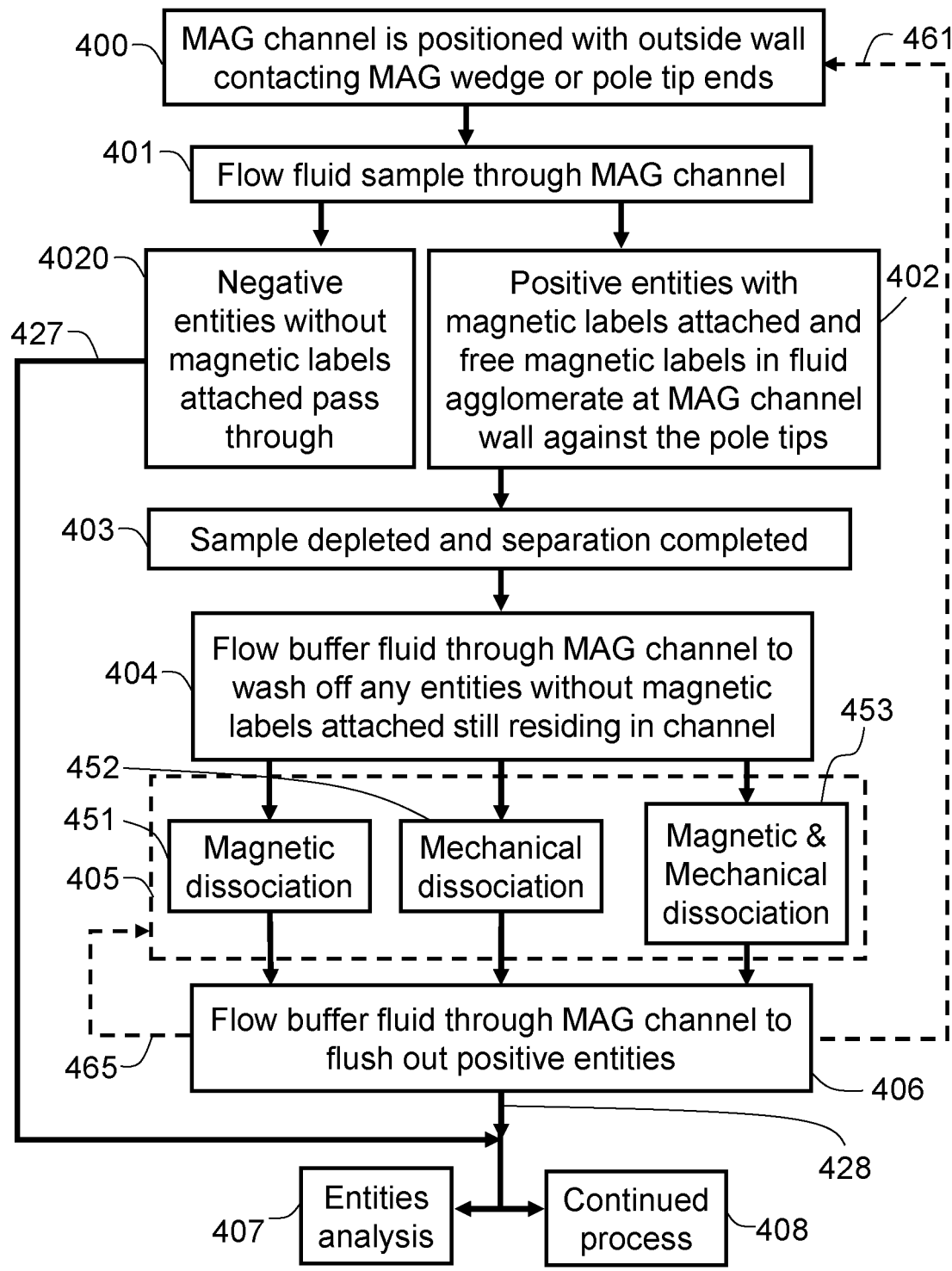
FIG. 31 is a schematic diagram illustrating methods to use MAG to magnetically separate biological entities from fluid solution.

FIG. 31 is a schematic diagram illustrating a method to use MAG to separate biological entities conjugated with magnetic labels, for example cells 10/30, from a fluid solution. MAG channel of FIG. 31 may be any of channels 101, 201, 301, 320, or 330 described in any of the figures accompanied this specification, and MAG of FIG. 31 may be any of the MAG 121, 122, 123, 124, 125, 126, 127, 128, or 129 described with the corresponding channel in any of the said figures. Method of FIG. 31 may include the following steps in sequence. In step 400, MAG channel is positioned with its outside wall contacting MAG wedge surface or pole tip ends, i.e. separation position of Position 1 or Position 21 as in FIG. 5, FIG. 10, FIG. 12, FIG. 14, FIG. 17, FIG. 19, FIG. 20A, FIG. 20C, FIG. 21A, FIG. 21C, FIG. 22A, FIG. 26A, FIG. 27A. In step 401, fluid sample is flowed through the MAG channel in separation position. Then in step 402, positive entities with SPLs 2 attached, for example cells 10/30, and free SPLs 2 within the fluid sample are attracted by the magnetic field of MAG and agglomerate at the MAG channel wall against the MAG wedge or MAG pole tip ends. Meanwhile, in step 402, negative entities without SPLs 2 attached pass through the MAG channel without being attracted. The negative entities may then be processed directly in subsequent procedures as shown by path 427, where subsequent procedures may include entity analysis 407, for example processes included in FIG. 79 through FIG. 81, or negative entities may be passed for continued process 408, for example through a UFL device as shown in FIG. 46A through FIG. 46C, FIG. 50 through FIG. 52, or through repeated MAG process as in FIG. 54A and FIG. 54B. After step 402, in step 403, sample may be depleted at input of the MAG channel and magnetic separation of positive entities may be completed. In step 404, which is an optional step, buffer fluid may be flowed through MAG channel with MAG channel still at separation position to wash off any negative entities without SPLs 2 but may have resided with the conglomerate of positive entities due to non-specific bindings. Then in step 405, MAG channel may be moved away from MAG to dissociation position including Position 2 and Position 22 in FIG. 11, FIG. 22B, FIG. 22D, FIG. 24B, FIG. 26B, FIG. 26D, FIG. 27B, and magnetic dissociation 451, as shown in FIG. 22A through FIG. 26D, or mechanical dissociation 452 as shown in FIG. 27C through FIG. 30B, or magnetic together with mechanical dissociation 453 may be applied to the positive entities in MAG channel. In step 406, buffer fluid may be flowed through MAG channel to flush out dissociated positive entities. If positive entities are not completely dissociated, path 465 shows that repeated dissociation process 405 may be applied to remaining positive entities in MAG channel after prior flush out step, until positive entities are sufficiently dissociated and flushed out of the MAG channel. In the case that fluid sample has a large volume, fluid sample may be separated into multiple sub-volumes. After process of a sub-volume from step 400 to step 406, a next sub-volume may be input into the MAG channel starting from step 400 for continued process as shown by path 461 until completion of the fluid sample of the large volume. After positive entities are collected after step 406, they may be processed in subsequent procedures as shown by path 428, where subsequent procedures may include entity analysis 407 or continued process 408.

Figure 32:
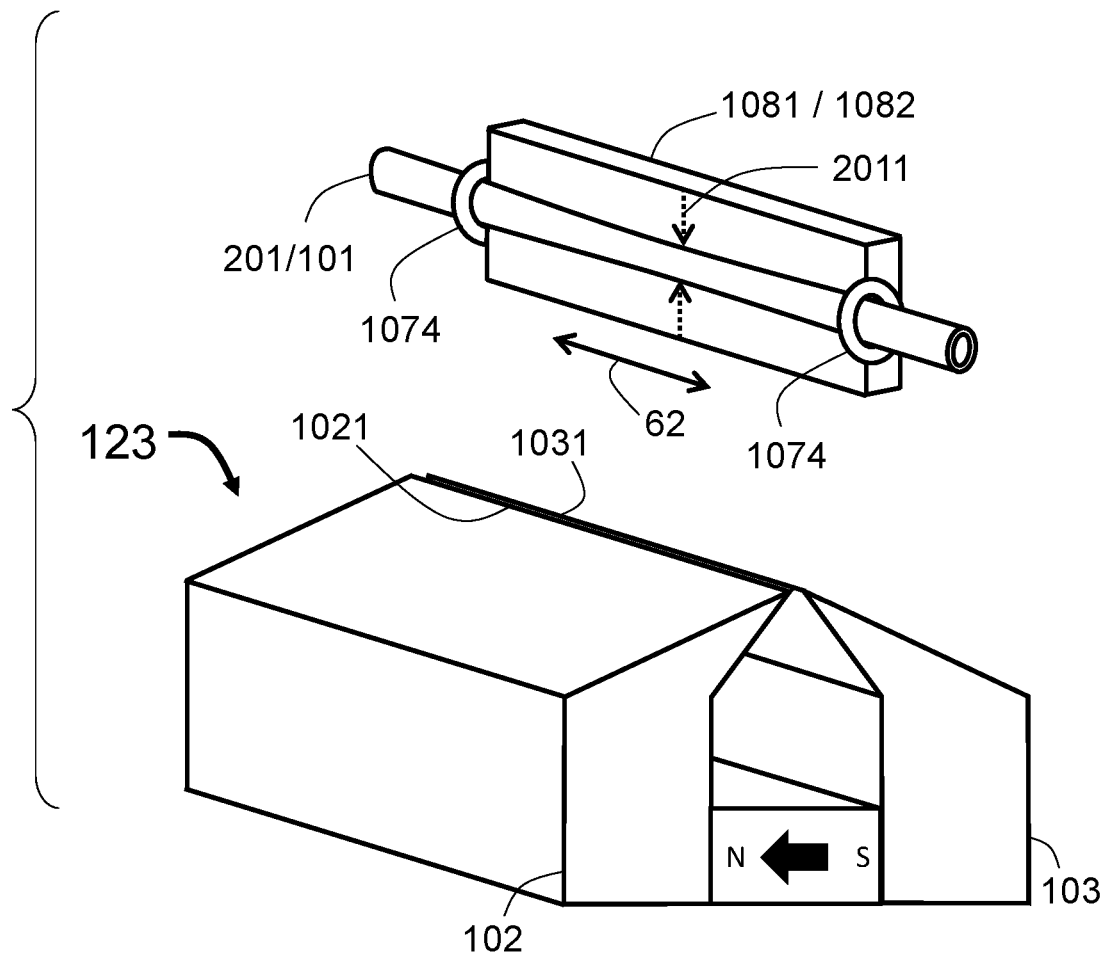
FIG. 32 illustrates a method to align a flexible channel MAG wedge of a MAG device.

FIG. 32 illustrates a method to align channel 201/101 to MAG gap of MAG 123 device. Precise alignment of channel 201/101 to MAG wedge or MAG pole tip ends is important as described in embodiments of this invention. In FIG. 32, side fixtures 1074 may be used to align and position channel 201/101 to designated locations on channel holder 1081 or 1082. The fixtures 1074 may be fitted into a pre-defined slot, notch, clip or other physical features on the sides of the channel holder 1081/1082. In one embodiment, channel 201/101 may be slightly stretched in channel length direction. Thus channel 201/101 may have a reduced width 2011 in between the fixtures 1074. Such stretch helps to guarantee a straight channel which may be then aligned with a straight MAG wedge of MAG 123. After channel 201/101 is attached to holder 1081/1082 by fixtures 1074, holder 1081/1082 may then move channel 201/101 to separation position. Holder 1081/1082 may have a pre-determined physical orientation with respect to MAG 123, for example a hinge, which aligns channel 201/101 to MAG wedge or MAG pole tip ends of MAG 123 precisely. Fixtures 1074 may be the same as channel mounts 1073 in FIG. 28A through FIG. 30B.

FIG. 33A through FIG. 37 illustrate method to utilize peristaltic pumps in embodiments of this invention.

Figure 33A:
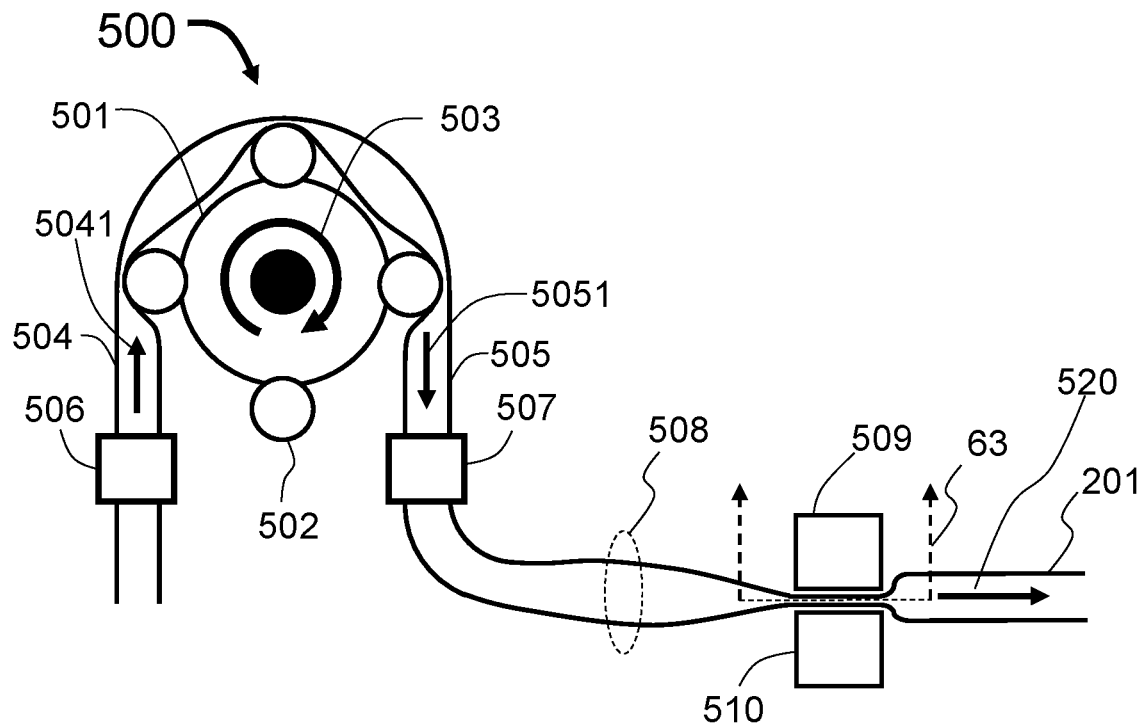
FIG. 33A illustrates a flexible channel attached to the output port of a peristaltic pump, where a flow limiter is attached to the flexible channel to reduce the flow rate pulsation.

FIG. 33A illustrates a typical peristaltic pump 500, which includes a rotor 501, drivers 502 attached to the rotor 501, and pump tubing 504/505, where tubing 504 is fluid incoming section and tubing 505 is fluid outgoing section of the same pump tubing. When rotor 501 rotates in direction 503, drivers 502 will squeeze pump tubing and force fluid to move from incoming section 504 to outgoing section 505 in directions 5041 and 5051, respectively. In the case when rotor rotates reversely to direction 503, fluid moves from outgoing section 505 to incoming section 504 of the pump tubing. Connectors 506 and 507 may be optional connections to incoming fluid line and outgoing fluid line 508, respectively. Advantage for peristaltic pump is the tubing 504/505 may be included as a continuous part of an enclosed fluid line as shown in FIG. 55A through FIG. 60B, which may be made disposable and single use, as well as sterile for clinical purpose. However, due to the spaced drivers 502 along the circumference of the rotor 501, flow rate of fluid output from section 505 has pulsation behavior, where flow rate increases and decreases with the movement of each of the driver 502. Such pulsation is not desired for MAG and UFL fluid driving. FIG. 33A shows output section 505 outputs fluid through connector to channel 508. Channel 508 is preferred to be flexible tubing. Channel 508 may also be a section of channel 201. Flow limiter parts 509 and 510 function together to effectively clamp onto the channel 508 to reduce the fluid flow rate passing through the limiter. With reduced flow rate through the limiter, continued fluid output from pump 500 section 505 into the channel 508 will build up fluid pressure within channel 508. Due to the flexible nature of channel 508, channel 508 may enlarge its width perpendicular to the channel length direction, and forms fluid reservoir within channel 508 with elastic stress built up in channel wall. During pulsation of output flow from pump 500, when 5051 flow rate increases, channel 508 width will increase to build up stress in 508 channel wall and pressure within channel 508. The increased volume of channel 508 absorbs most of the instantaneously incoming flow, while flow rate 520 through limiters 509/510 into channel 201 shows smaller increase. When 5051 flow rate decreases, build-in elastic stress in channel 508 wall and fluid pressure in channel 508 continues to push fluid through the limiters 509/510, and flow rate 520 shows smaller flow rate decrease.

Figure 33B:
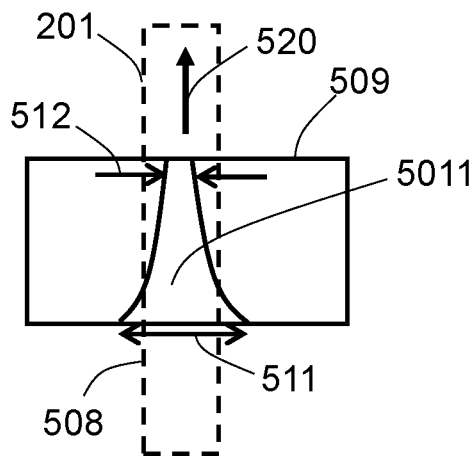
FIG. 33B illustrates a top-down view of the inner structure of a first type flow limiter.

FIG. 33B illustrates top-down view of the inner structure of first type flow limiter 509 along the direction 63. FIG. 33B shows that flow limiter 509 has a shaped trench 5011, which allows fluid to flow through channel 508 when limiters 509 and 510 clamp onto channel 508 as shown in FIG. 33A. Trench 5011 has entrance width 511 to incoming fluid and exit width 512 to channel 201, where width 511 may be larger than width 512. Decreasing trench 5011 width from 511 to 512 reduces the flow rate through the limiters 509/510. Flow limiter 510 may have same top down view and structure as limiter 509 when view in direction opposite to 63.

Figure 33C:
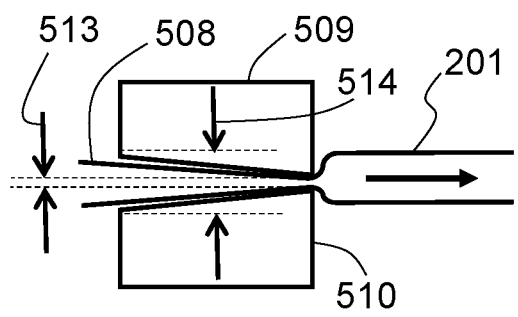
FIG. 33C illustrates a side view of a second type flow limiter.

FIG. 33C illustrates a second type flow limiter in same view as FIG. 33A. After limiters 509 and 510 clamp onto channel 508, flow limiters 509/510 form an effective opening of 514 towards channel 508, and opening of 513 towards channel 201. Opening 513 may be smaller than opening 514, which reduces flow rate through the limiters 509/510.

Figure 34A:
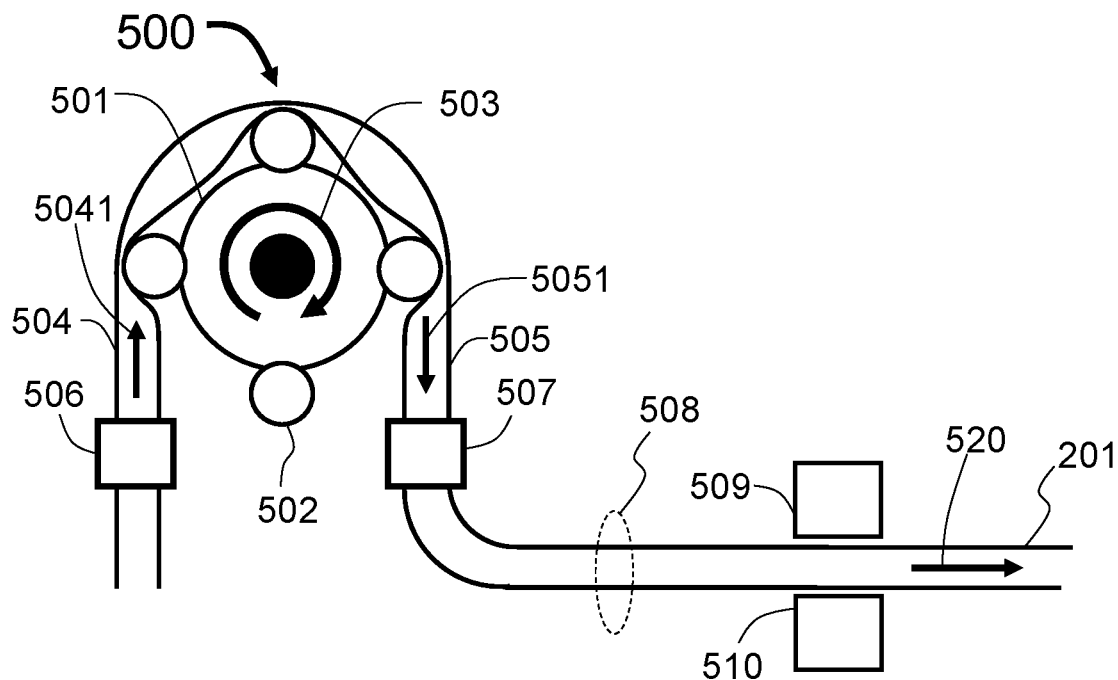
FIG. 34A illustrates FIG. 33A flow limiter being disengaged from the flexible channel.

FIG. 34A is same as FIG. 33A except flow limiters 509/510 are disengaged from the flexible channel 508. Flow from pump 500 through channel 508 and channel 201 is continuous without limiters 509/510 and there is no elastic stress built up in channel 508 wall.

Figure 34B:
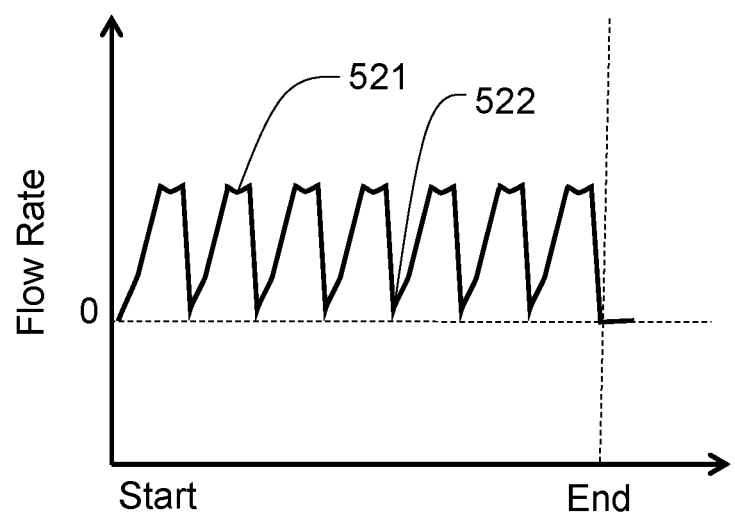
FIG. 34B is a plot illustrating fluid flow rate with large pulsation.

FIG. 34B is a schematic illustration of fluid flow rate 520 corresponding to FIG. 34A situation, which shows large pulsation in flow rate 520. FIG. 34B shows the example 520 flow rate value vs pump 500 operation time from pumping start to pumping end. Value 521 illustrates the high flow rate and value 522 illustrates low flow rate of the pulsation behavior.

Figure 35A:
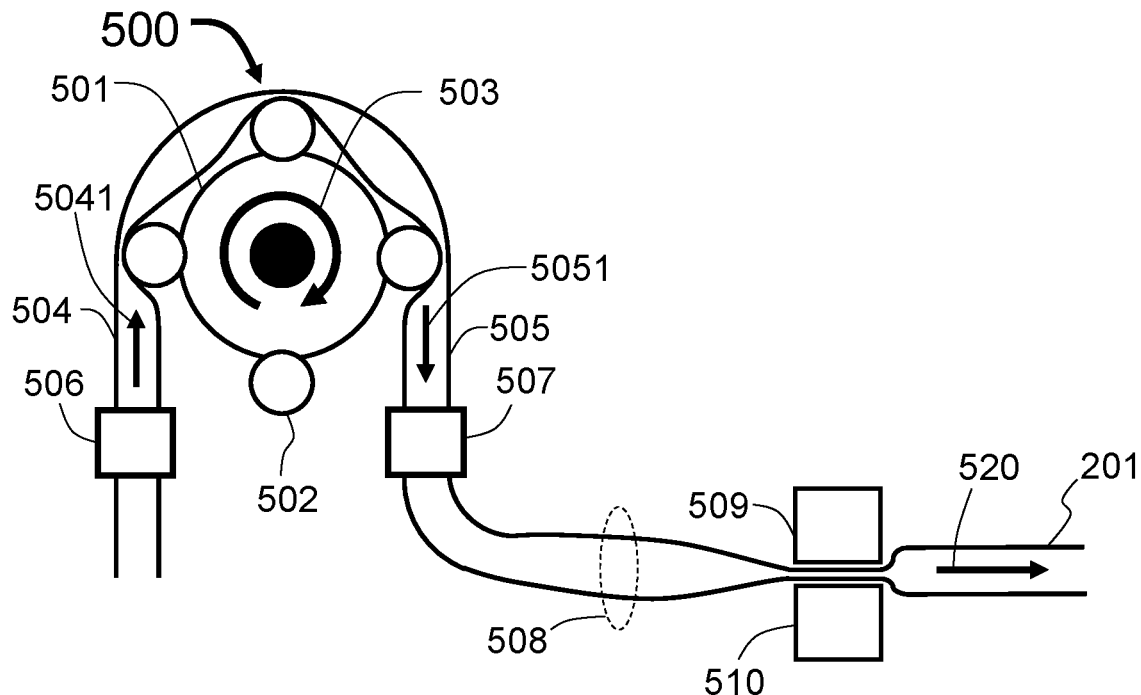
FIG. 35A illustrates FIG. 33A flow limiter being engaged upon the flexible channel.

FIG. 35A is same as FIG. 33A, where flow limiters 509/510 are clamped upon flow channel 508. Flow rate through the flow limiters 509/510 is reduced, and channel 508 has enlarged channel width with elastic stress built up in channel 508 wall.

Figure 35B:
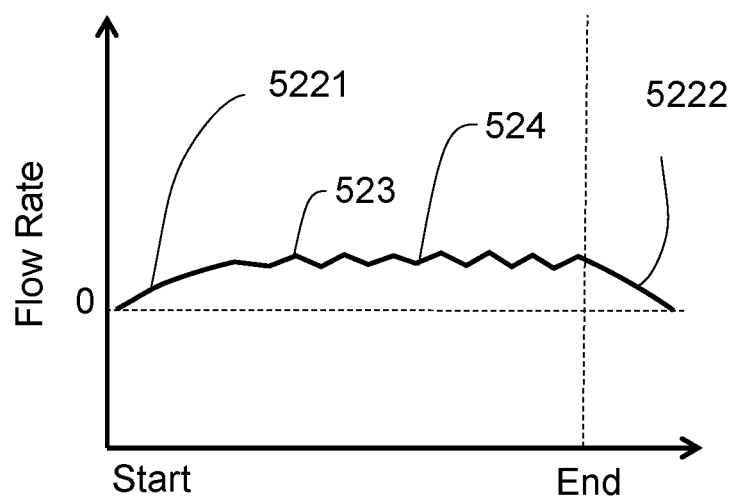
FIG. 35B is a plot illustrating fluid flow rate with reduced pulsation.

FIG. 35B is a schematic illustration of fluid flow rate 520 corresponding to FIG. 35A situation, which shows pulsation reduction in flow rate 520 compared to FIG. 34B. Value 523 corresponds to value 521 of FIG. 34B, and value 524 corresponds to value 522 of FIG. 34B. FIG. 35B illustrates that limiters 509/510 effectively reduce 520 flow rate pulsation. Due to the channel 508 liquid pressure build up at the start of pumping, and channel 508 liquid pressure dissipation at end of pumping, while limiters 509 and 510 are engaged, a flow rate ramp up slope 5221 after pump start and flow rate ramp down slope 5222 after pump end may exist in FIG. 35B.

Figure 36A:
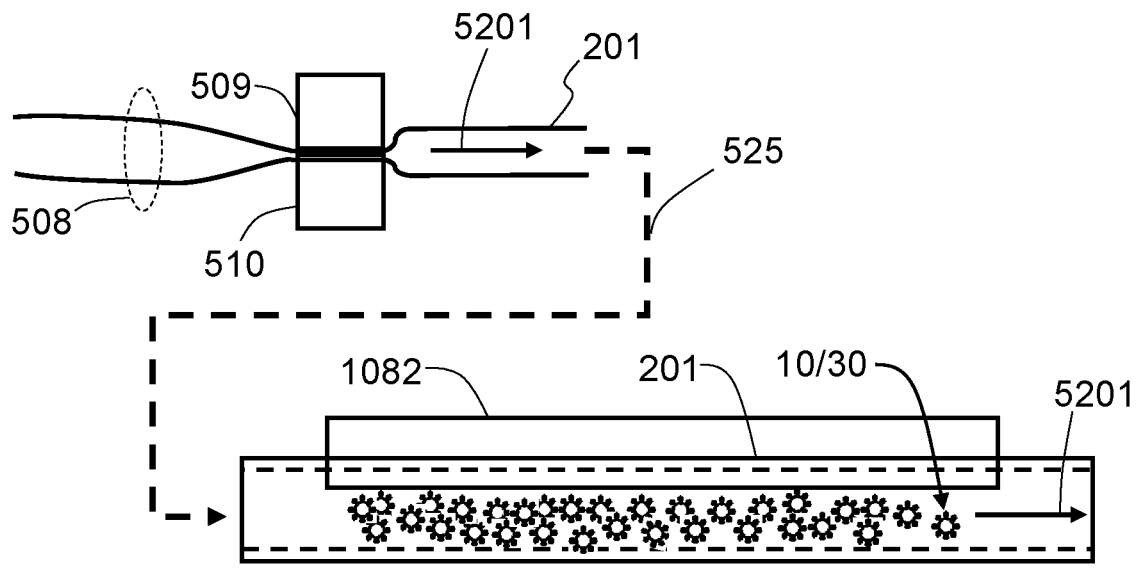
FIG. 36A illustrates FIG. 33A flow limiter causing pressure built up at the fluid incoming end of the flow limiter.
Figure 36B:
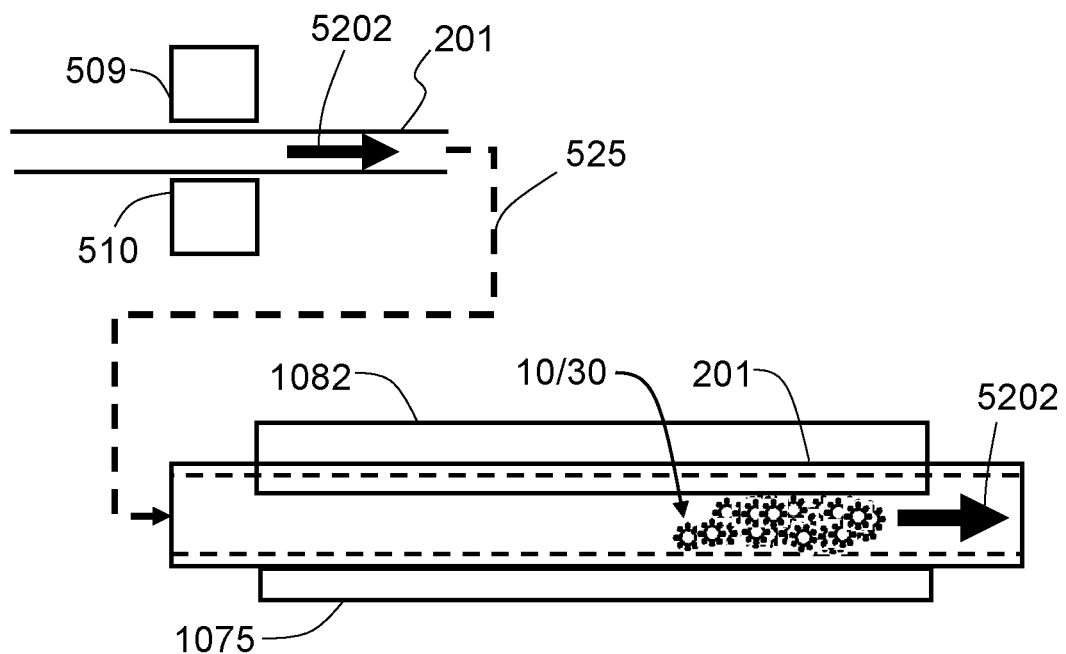
FIG. 36B illustrates FIG. 36A flow limiter being disengaged and causing high speed fluid pulse that pushes the dissociated cells of FIG. 36A out of the channel.

FIG. 36A and FIG. 36B illustrate method to use flow limiters 509/510 to generate instantaneously high flow rate short pulse through channel 201 for flushing out magnetically separated entities, for example dissociated cells 10/30.

FIG. 36A illustrates FIG. 33A and FIG. 35A situation, where flow limiters 509 and 510 are clamped onto the flexible channel 508 while pump 500 pumps fluid into channel 508, where pressure is built up within the flexible channel 508, and elastic stress is built up in wall of channel 508. Line 525 represents a continuous channel 201 from after the limiters 509/510 to channel 201 over MAG structure. Flow rate 5201 represents averaged flow rate of flow rates 523 and 524 of FIG. 35B when flow limiters 509 and 510 are engaged.

FIG. 36B illustrates that flow limiters 509 and 510 are disengaged from the flexible channel 508, similar to FIG. 34A situation, while pump 500 still pumps fluid into channel 508, or immediately after pump 500 stops pumping and before pressure within channel 508 dissipates. At disengagement of limiters 509 and 510, liquid pressure in channel 508 and elastic stress in wall of channel 508 produces an instant high speed fluid pulse flow 5202 into channel 201, which may flush the magnetically separated entities out of the channel 201. Such high speed short pulse flow 5202 may help to achieve complete flush out of cells 10/30 with small volume of fluid that is originally contained in channel 508 of FIG. 36A. FIG. 36B also shows that a rigid cladding structure 1075 may be put into contact with channel 201 to help reducing deformation of flexible channel 201 during the cells 10/30 flush out to maintain the flow speed in channel 201.

Figure 37:
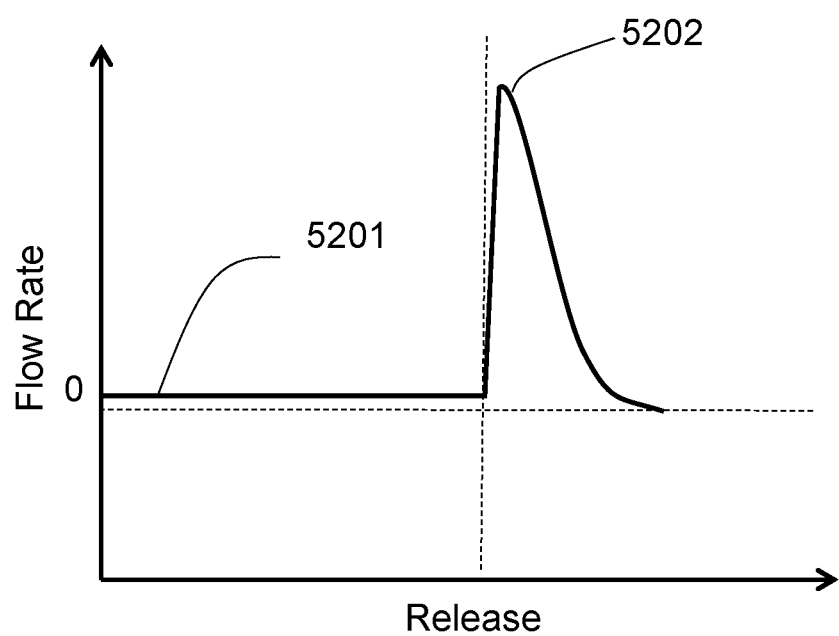
FIG. 37 is a plot illustrating fluid flow rate pulse created by the process of FIG. 36A to FIG. 36B transition where flow limiter is disengaged.

FIG. 37 is a schematic illustration of fluid flow rate pulse created by the flow limiter operation of FIG. 36A to FIG. 36B, where 5201 is the fluid flow rate in channel 201 before limiters 509 and 510 are released, and 5202 is flow rate peak value after limiters 509 and 510 are released.

From FIG. 33A through FIG. 36B, channel 508 is a flexible channel, while channel 201 may be replaced by a rigid channel 101, 301, 320, or 330.

FIG. 38A through FIG. 43 describe various embodiments of micro-fluidic chip ("UFL") and method of use.

FIG. 38A is a top-down view of a first UFL embodiment UFL 600, where micro-fluidic channels are formed as trenches into a substrate material 611. UFL contains an entity fluid 6020 inlet 602, a buffer fluid 6040 inlet 604, a main channel 601, a large entity 6070 outlet 607, and a small entity 6090 outlet 609. Two side channels 603 connect inlet 602 to main channel 601 from the two sides of the main channel 601. Inlet 604 is directly connected to the main channel 601 at the center of the main channel 601. Main channel 601 connects to outlet 607 at the center of the main channel 601, and connects to outlet 609 from two sides of main channel 601 through two side channels 608. Entity fluid 6020 contains both large entities 6070 and small entities 6090. Buffer fluid 6040 is fluid for providing UFL function but without biological entities. Large entity 6070 fluid from outlet 607 contains mainly large entities 6070 and buffer fluid 6040. Small entity 6090 fluid from outlet 609 contains mainly small entities 6090 and fluid of entity fluid 6020 and may contain certain amount of buffer fluid 6040. During operation of UFL 600, buffer fluid 6040 and entity fluid 6020 are simultaneously pumped into outlets 604 and 602, respectively. Buffer fluid 6040 flows along center line of the main channel 601 and entity fluid flows close to the two sides of the main channel as laminar flow. Buffer fluid 6040 carries large entities 6070 to exit outlet 607 and entity fluid carries remaining small entities 6090 to exit outlet 609. Channel 601 is substantially straight and linear along channel length direction from inlet 604 to outlet 607.

FIG. 38B is a cross-sectional view of a portion of the FIG. 38A UFL 600 along direction 64, which includes entity fluid inlet 602, buffer fluid inlet 604, and part of the UFL main channel 601. FIG. 38B illustrates that UFL 600 is composed of two components, substrate 611 and cover 610. Inlets 602 and 604, outlets 607 and 609, channels 601, 603 and 608 are formed in substrate 611 as trenches of same depth 627 and preferably formed in a single step. In one embodiment, depth 627 is between 100 nm and 500 nm. In another embodiment, depth 627 is between 500 nm and 1 µm. In yet another embodiment, depth 627 is between 1 µm and 10 µm. In yet another embodiment, depth 627 is between 10 µm and 100 µm. In yet another embodiment, depth 627 is between 100 µm and 1 mm. Cover 610 contains external access ports to inlets and outlets of UFL 600 to allow entity fluid 6020 and buffer fluid 6040 to enter inlets 602 and 604, and to allow large entity 6070 fluid and small entity 6090 fluid to exit outlets 607 and 609. Inlets 602 and 604, outlets 607 and 609 are shown to be circular shape in FIG. 38A, but may be any other shape, including ellipse, square, rectangle, triangle, polygon, that is suitable for application. Access ports of cover 610 are clearances, i.e. holes, through cover 610 directly over the inlets and outlets 602, 604, 607 and 609. FIG. 38B shows example of access ports 621 and 641 clearances matching to inlets 602 and 604 positions. After manufacture of the UFL 600 substrate 611 with the trenches of inlets, outlets and channels, and cover 610 with the access ports, cover 610 is positioned over the substrate 611 to form enclosed channels 601, 603 and 608. Cover 610 may bond to substrate 611 through any of: (1) surface to surface Van der Waals force; (2) gluing; (3) ultrasound thermal melting when one or both of substrate 611 and cover 610 are made of plastic or polymer material. Access port clearances of cover 610, for example clearances 621 and 641 to inlets and outlets 602, 604, 607 and 609, are preferred to be smaller in size than the corresponding inlets and outlets, which allows for positioning error during cover 610 to substrate 611 alignments without causing function loss of UFL due to misalignment. Injectors 6021 and 6041 then show example of possible external fluid injection to inlets of UFL 600 through cover 610 access port clearances, where the injectors 6021 and 6041 may have a larger nozzles size than the matching access ports 621 and 641 for managing positioning errors between injectors and access ports. FIG. 38B shows that entity fluid 6020 containing large entities 612 and small entities 613, which may be injected by injector 6021, passing through assess port 621 and into inlet 602 and passing into main channel 601 as side laminar flows. Buffer fluid 6040 may be injected by injector 6041, and passes through access port 641 and into inlet 604 and then passes into main channel 601 as center laminar flow.

Substrate 601 may be composed of any of: glass, silicon, alumina-titanium carbide (AlTiC), plastic, polymer, ceramic, or metal, where metal may be composed of any one or any alloy of iron, nickel, chromium, platinum, tungsten, rhenium. In one embodiment, forming of inlets, outlets and channels in substrate 611 includes the steps of: (1) providing a substrate 611 having one substantially flat surface; (2) forming etching mask on top of said flat surface; (3) etching of substrate with a first etching method including: wet etch with fluid chemical, dry etch with chemical gas, plasma enhanced dry etch, sputter etch with ion plasma, and ion beam etch (IBE). Forming of etch mask of step (2), which may be composed of photo resist (PR), may include deposition or spin coating of PR on said flat surface; exposure by optical or ion/electron radiation with patterns of inlets, outlets and channels; development of PR after said exposure, where remaining PR with said patterns serves as etch mask. Etch mask may also be made of a hard mask material that has lower etch rate than the substrate material under the first etching method, and step (2) may include: deposition of a hard mask layer on said flat surface; deposition or spin coating PR layer on hard mask layer; exposure of said PR by optical or ion/electron radiation with patterns of inlets, outlets and channels, development of PR after said optical exposure, where remaining PR with said patterns serves as etch mask for said hard mask; etching hard mask through with a second etch method including any of: wet etch with fluid chemical, dry etch with chemical gas, plasma enhanced dry etch, sputter etch with ion beam; removal of remaining PR layer. Second etch method and first etch method may be different in type, or different in chemistry.

In another embodiment, inlets, outlets and channels in substrate 611 may be formed by thermal press involving the steps of using a heated stencil with physical patterns of the inlets, outlets and channels to melt and deform part of substrate 611 to construct the inlets, outlets and channels, then cooling down substrate 611 and removing the stencil. In thermal press, substrate material is preferred to be plastic or polymer. In yet another embodiment, inlets, outlets and channels in substrate 611 may be formed by imprint, which involves the steps of using a stencil with physical patterns of the inlets, outlets and channels to imprint into a partially or completely melt substrate 611, and then cooling the substrate 611 and finally removing stencil, where cooled substrate retains the patterns of the inlets, outlets and channels transferred from stencil. In imprint, substrate material is preferred to be plastic or polymer. In another embodiment, inlets, outlets and channels are formed in substrate 611 by injection molding, where melted substrate 611 material is injected into a mold cavity that defines substrate 611 body with engraved inlets, outlet and channels. Cover 610 may be composed of a material similar to substrate 611 material. Access ports of cover 610 may be similarly formed in cover 610 as the inlets, outlet and channels being formed in substrate 611 as described above.

FIG. 38C is a schematic diagram illustrating a single fluidic pressure node 615 created between two side walls of the UFL 600 channel 601 of FIG. 38A by ultrasound vibration generated by a PZT 614. FIG. 38C is a cross-section view along direction 65 of FIG. 38A for part of the UFL 600 including main channel 601, substrate 611, cover 610 and PZT transducer 614 attached to the bottom of substrate 611. FIG. 38C shows that after injection of entity fluid 6020 and buffer fluid 6040, entity fluid 6020 containing large entities 612 and small entities 613 mainly flow along the edges of the channel 601 as laminar flow. AC voltage is applied to PZT 614, where frequency (Fp) of AC voltage is preferred to be at a frequency matching to the PZT resonance frequency (Fr). PZT 614 produces ultrasound vibrations in the substrate 611 at frequency Fp. Said ultrasound vibrations transfer to the fluid contained in channel 601. Channel 601 has channel width 625 defined as the normal distance between the two side walls of channel 601. In one embodiment, width 625 is between 100 nm and 1 μm. In another embodiment, width 625 is between 1 μm and 10 μm. In yet another embodiment, width 625 is between 10 μm and 100 μm. In yet another embodiment, width 625 is between 100 μm and 500 μm. In yet another embodiment, width 625 is between 500 μm and 5 mm. When channel width 625 is half wavelength, or an integer multiple of half wavelength, of the ultrasound mode in the fluid within channel 601 at frequency Fp, a standing wave may be present in between the two side walls of channel 601 as indicated by the dashed lines 626. FIG. 38C shows that when channel width 625 is half wavelength of fluid ultrasound mode at frequency Fp, a single fluidic pressure node 615 is formed along the center line of channel 601 in the direction of channel length, which is perpendicular to the view of FIG. 38C. In another embodiment, channel width 625 is an integer multiplied by half wavelength of fluid ultrasound mode at frequency Fp, where integer is larger than 1, and said integer number of fluidic pressure nodes may then be formed across the width 625 with each node being a line along the direction of channel length. Presence of standing wave 626 and pressure node 615 exerts acoustic force, which is shown in FIG. 38D as arrows 628, on entities in the entity fluid laminar flow along the side walls of channel 601 and cause large size entities 6070 to move close to center node 615 during flowing through the channel 601. Said acoustic force 628 has the characteristics of: (1) largest amplitude close to channel 601 side walls with force directions pointing from the side walls towards the node 615; (2) smallest force, or close to zero force, around node 615; (3) being linearly proportional to size of the entities; (4) being a function of the density and compressibility of both the buffer fluid 6040 and the entities. Due to these characteristics, with proper optimization of buffer fluid composition, buffer fluid 6040 laminar flow speed, and entity fluid 6020 laminar flow speed, large entities 612 may be optimized to preferably break the laminar flow barrier to enter the buffer laminar flow due to a larger acoustic force acting on large entities 612, and be concentrated around the center node 615.

FIG. 38D is a schematic diagram illustrating the fluid acoustic wave of FIG. 38C causing larger size entities 612 to move into buffer fluid laminar flow around center of the channel 601. When fluid within the channel 601 exits the channel to outlets 607 and 609, channel 601 center subchannel width 651 of FIG. 38A to outlet 607 may be much smaller than the width 625 of the channel 601, thus only allow large entities 612 at center flow within channel 601 to exit outlet 607 as large entity 6070 fluid. While smaller entities 613 mainly in the close-to-side wall laminar flow exit channel 601 through side channels 608 to exit from outlet 609 as small entity 6090 fluid.

Frequency Fp of PZT 614 vibration in one embodiment is between 100 kHz and 500 Hz, between 500 kHz and 1 MHz in another embodiment, between 1 MHz and 3 MHz in yet another embodiment, between 3 MHz and 10 MHz in yet another embodiment, and between 10 MHz and 100 MHz in yet another embodiment. In FIG. 38C and FIG. 38D, PZT 614 may also be attached to top of cover 610 in FIG. 38C and FIG. 38D, and ultrasound vibrations from PZT 614 is transferred from PZT 614 through cover 610 to fluid within channel 601, or through cover 601 to substrate 611 and then to the fluid within channel 601.

Figure 39:
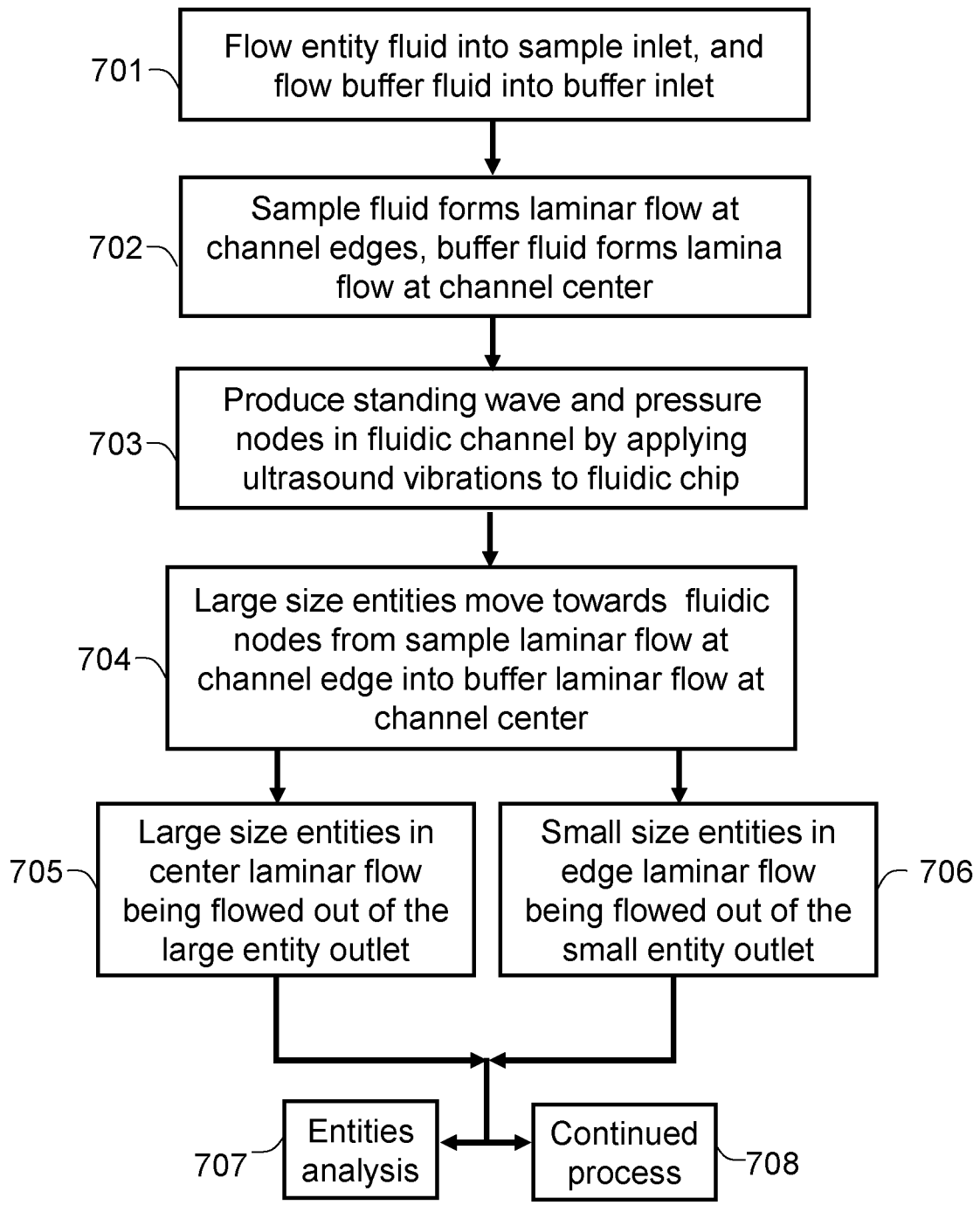
FIG. 39 is a schematic diagram illustrating methods to use UFL to separate biological entities of different sizes.
Figure 40A:
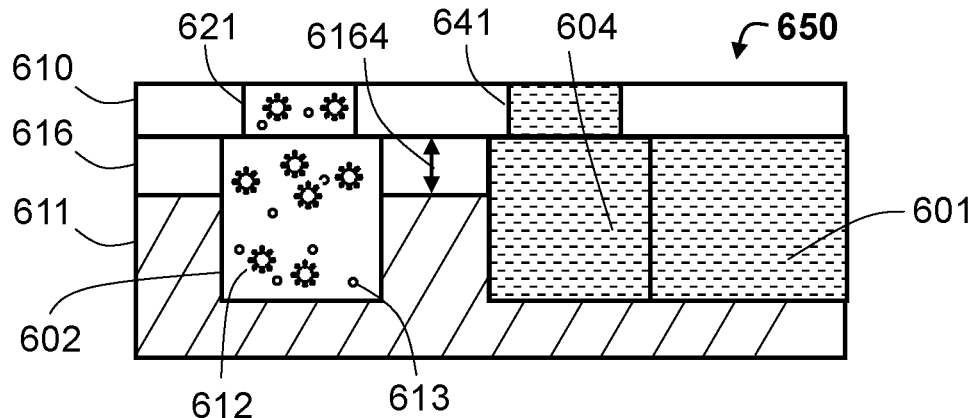
FIG. 40A is a cross-sectional view of a portion of first embodiment UFL which includes a uniformly formed soft magnetic layer.

FIG. 39 is a schematic diagram illustrating methods to use a UFL to separate biological entities of different sizes, where UFL may be UFL 600 from FIG. 38A or FIG. 40A, UFL 620, 630 and 640 from FIG. 41A through FIG. 43. Sequential steps of 701 to 705 and 706 are substantially similar to that described in FIG. 38A, FIG. 38B, FIG. 38C, and FIG. 38D, except steps 703 and 704 refer to possibility of multiple pressure nodes, as shown in FIG. 41B and FIG. 42B. Step 707 entity analysis can be performed on both the large entities 6070 and small entities 6090, and may include processes 903, 904, 905, 906, 5824, 5825, 5826 as described in FIG. 53, FIG. 79, FIG. 80, FIG. 82 and FIG. 83 on corresponding UFL output samples. Examples of continued process 708 include further processing through a MAG device as shown in FIG. 44A through FIG. 45C, FIG. 47 through FIG. 49, or through cascaded UFL process as in FIG. 54C.

FIG. 40A is a cross-sectional view of a portion of a UFL 650 similar to FIG. 38B. UFL 650 is identical to UFL 600 from a top-down view as in FIG. 38A, except that a uniform soft magnetic layer ("SML") 616 is deposited on top the substrate 611 of UFL 650, and patterned together with the substrate 611 to form inlets 602 and 604, outlets 607 and 609, and channels 601, 603 and 608. SML 616 may be composed of at least one element from iron (Fe), cobalt (Co), and nickel (Ni). SML 616 thickness 6164 is between 10 nm and 100 nm in one embodiment, between 100 nm and 1 µm in another embodiment, between 1 µm and 10 µm in yet another embodiment, between 10 µm and 100 µm in yet another embodiment, between 100 µm and 1 mm in yet another embodiment, and between 1 mm and 3 mm in yet another embodiment. Deposition of SML layer 616 on substrate 611 may be accomplished by any of: electroplating, vacuum plating, plasma-vapor-deposition (PVD), atomic layer deposition (ALD), chemical vapor deposition (CVD). Etching of layer 616 together with substrate 611 to form inlets 602 and 604, outlets 607 and 609, and channels 601, 603 and 608 may be accomplished by any of: dry etch, plasma enhanced dry etch, ion plasma etch, and IBE. Layer 616 may be a continuous layer along the channel 601 length direction and forms part of the side walls of the channel 601.

Figure 40B:
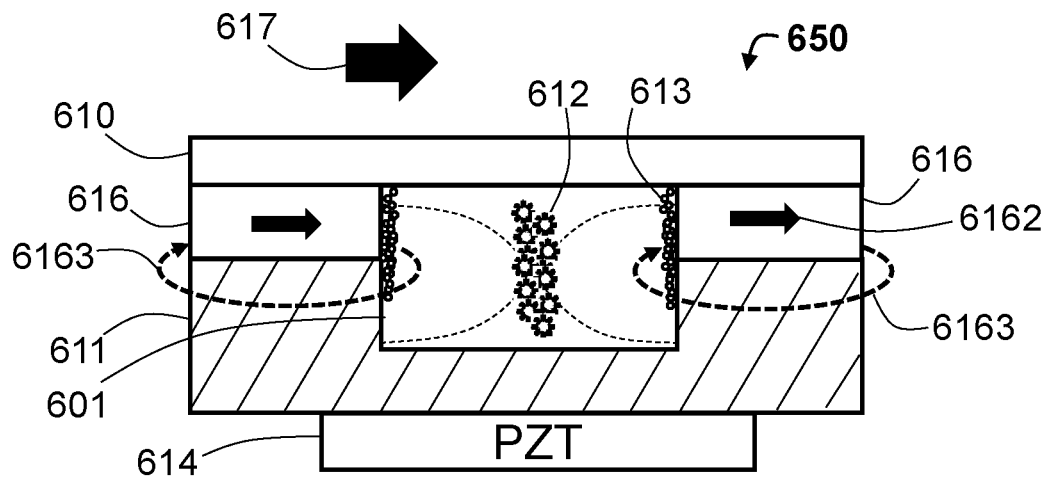
FIG. 40B is a schematic diagram illustrating the fluid acoustic wave and entity separation in UFL of FIG. 40A in the presence of a magnetic field.

FIG. 40B is similar to FIG. 38D and shows a schematic diagram illustrating that the large entities 612 are concentrated by acoustic force 628 to the channel 601 center around the pressure node 615 and small entities 613 mainly remain around the channel 601 side walls. Additionally, a magnetic field 617 is applied in-plane and induces magnetization 6162 in the SML layer 616. For the SML layer 616 located as part of the side walls of the channel 601, magnetization 6162 produces local magnetic field 6163, which has strongest magnetic field strength and field gradient close to the channel 601 side walls. Field 6163 may help maintain magnetic small entities, for example free SPLs 2 that are part of the entity fluid 6020 in positive sample after MAG separation as shown in FIG. 82 and FIG. 83, to stay within the laminar flow close to channel 601 side walls and output from outlet 609 of FIG. 38A.

Figure 40C:
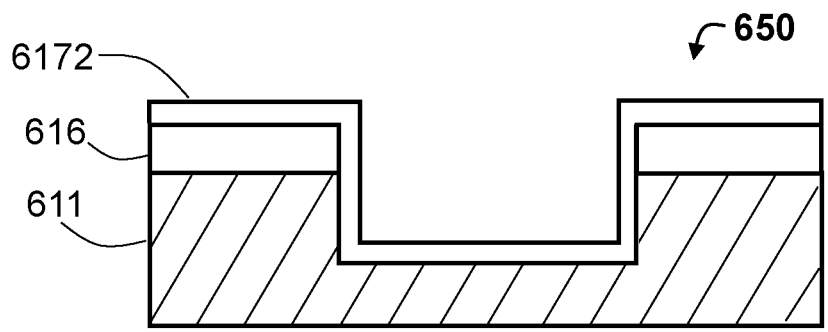
FIG. 40C is a schematic diagram illustrating a protection layer conformably deposited around the UFL surface before attaching cap.

FIG. 40C shows that after etching of SML layer 616 together with substrate 611, and before cover 610 is attached to substrate 611, a passivation layer 6172 may be deposited covering exposed surfaces of SML layer 616 and substrate 611. Layer 6172 may help to isolate fluid reaction with material of SML layer 616. Layer 6172 may be deposited over the etched surfaces of SML 616 and substrate 611, preferably conformably, by vacuum plating, electro-plating, PVD, ALD, CVD, molecular beam deposition (MBE), and diamond like carbon (DLC) deposition. Layer 6172 may be an oxide, or a nitride, or a carbide, of any one or more elements of: Si, Ti, Ta, Fe, Al, W, Zr, Hf, V, Cu, Cr, Zn, Mg, Nb, Mo, Ni, Co, Fe, Ir, Mn, Ru, Pd, and C. Layer 6172 may compose of at least one of: Si, Ti, Ta, Fe, Al, W, Zr, Hf, V, Cu, Cr, Zn, Mg, Nb, Mo, Ni, Co, Fe, Ir, Mn, Ru, Pd, and C. Layer 6172 may be a DLC layer. Thickness of layer 6172 may be between 1 nm and 10 nm in one embodiment, between 10 nm and 100 nm in another embodiment, between 100 nm and 10 µm in another embodiment, and between 10 µm and 100 µm in another embodiment.

Figure 41A:
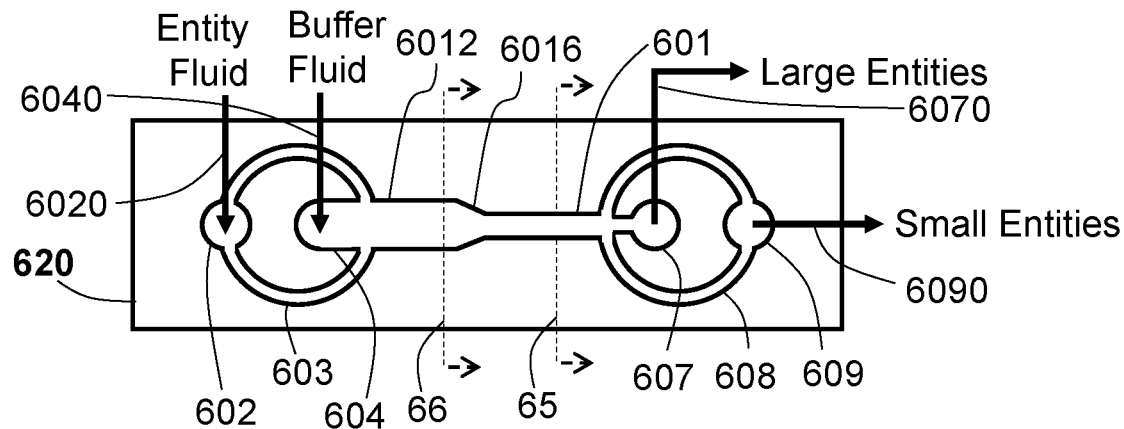
FIG. 41A is a top-down view of a second embodiment UFL including a wide channel and a narrow channel in sequential arrangement.

FIG. 41A is a top-down view of a second UFL embodiment UFL 620, which is same as FIG. 38A, except including a wider section 6012 of the main channel connecting between the inlet 604 and the narrower channel section 601 of FIG. 38A. Slope 6016 represents a transition section 6016 from wider section 6012 to narrow section 601. Channel sections 6012 and 601 are substantially straight and linear along channel length direction. Transition section 6016 may be a section of the main channel, where the main channel includes channel section 6012 connecting through the transition section 6016 to channel section 601. Transition section 6016 functions to funnel fluid flow from wider section 6012 into the narrower section 601. Channel wall of transition section 6016 may intersect straight wall of wider section 6012 at a transition start point. Channel wall of transition section 6016 may intersect straight wall of narrower section 601 at a transition stop point. In one embodiment, the channel shape of the transition section 6016 between transition start point and transition stop point may have a straight slope as shown in FIG. 41A. In another embodiment, the channel shape of the transition section 6016 between transition start point and transition stop point may have a curvature, which may be tangential to one or both of channel wall of wider section 6012 and channel wall of narrower section 601.

Figure 41B:
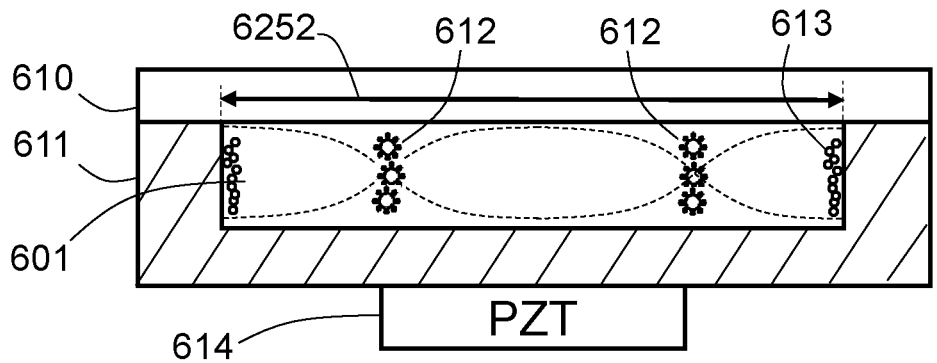
FIG. 41B is a cross-sectional view of second embodiment UFL across wide channel.

FIG. 41B is a cross-sectional view of UFL 620 along direction 66 in FIG. 41A, which is across the wider section 6012. Wider section 6012 has a channel width 6252, which corresponds to the full wavelength of the ultrasound mode in the liquid within channel section 6012 at PZT 614 operating frequency Fp as described in FIG. 38C, and is effectively twice the channel width 625 of channel 601 in FIG. 38C and FIG. 41C. Due to channel width 6252 being equal to the full wavelength of ultrasound mode at Fp, two pressure nodes may exist in channel section 6012. Acoustic force from the ultrasound mode may move and concentrate large entities 612 at each of the two nodes from the channel wall entity laminar flow.

Figure 41C:
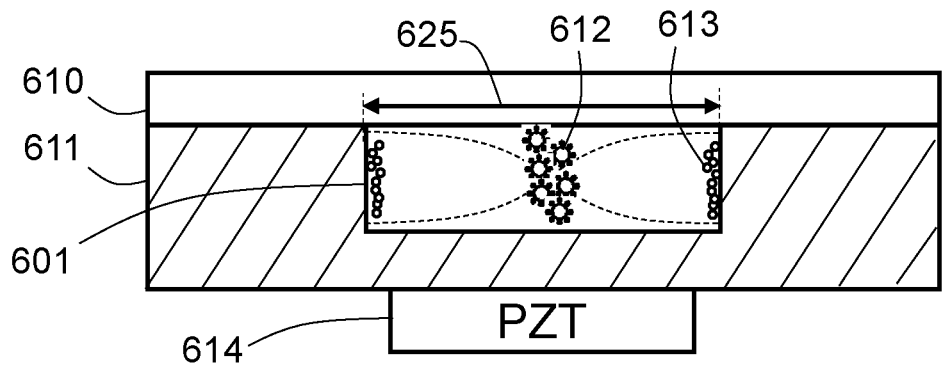
FIG. 41C is a cross-sectional view of second embodiment UFL across narrow channel.

FIG. 41C is a cross-sectional view of UFL 620 along direction 65 in FIG. 41A, which is across the narrower section 601 and is identical to FIG. 38D. After fluid within channel section 6012 flows through the transition 6016 to channel section 601, single pressure node of channel section 601 forces the large entities 612 to concentrate at channel section 601 center, same as in FIG. 41C. Wider section 6012 provides a first stage large entity 612 separation from small entities 613. After transition section 6016, flow speeds of center buffer laminar flow and channel side wall entity laminar flow increase to about twice the speeds of same flows in section 6012 due to the channel width reduction from 6252 to 625. Channel section 601 provides a second stage large entity separation from small entities, together with the increase flow speed in channel section 601. Purity of large entities 612 in 6070 fluid output from outlet 607, as well as purity of small entities 613 in 6090 fluid output from outlet 609, may be enhanced compared to UFL 600 of FIG. 38A.

Figure 42A:
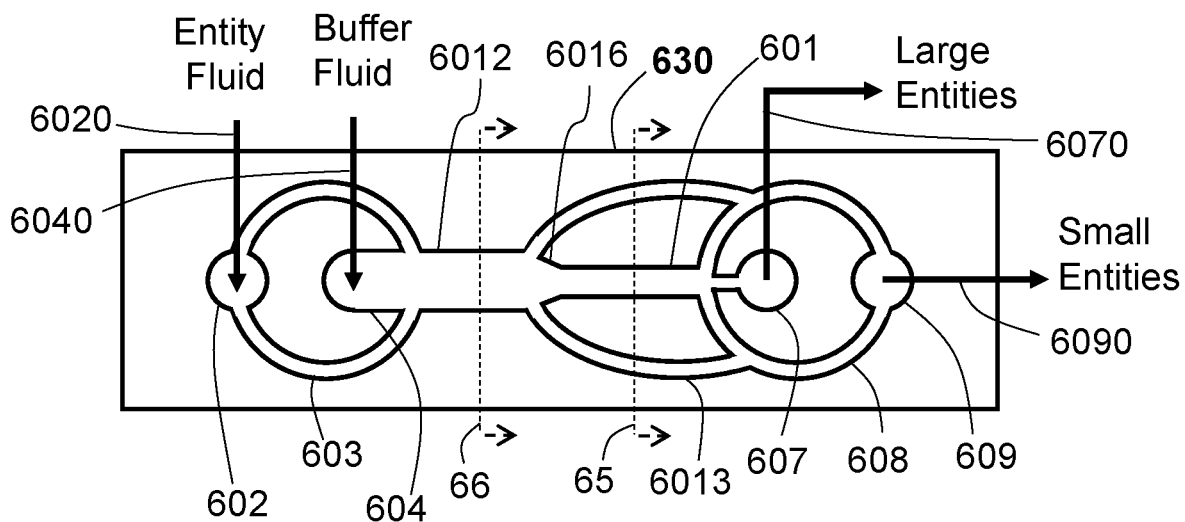
FIG. 42A is a top-down view of a third embodiment UFL including a wide channel and a narrow channel, and side channels from wide channel to narrow channel transition section.
Figure 42B:
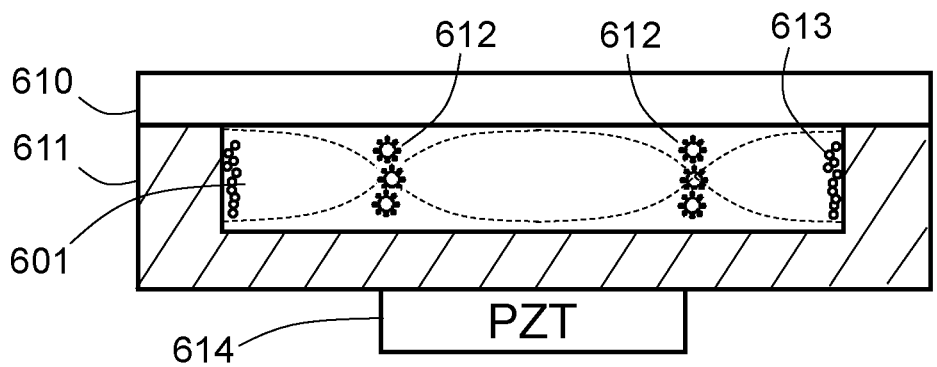
FIG. 42B is a cross-sectional view of third embodiment UFL across wide channel.

FIG. 42A is a top-down view of a third UFL embodiment UFL 630, which is a further enhancement from the UFL 620 of FIG. 41A. Every aspect of FIG. 42A is same as FIG. 41A, except that when compared to UFL 620 of FIG. 41A, UFL 630 of FIG. 43A includes additional side channels 6013 that connect from around the transition section 6016 to side channels 608, or in another embodiment directly to the outlet 609, to divert side wall laminar flow of small entities 613 from wider section, which is also referred to as first stage section 6012 as shown in FIG. 42B, directly to output 6090 without entering narrower section, which is also referred to as second stage section 601. Channel sections 6012 and 601 are substantially straight and linear along channel length direction. In one embodiment, side channels 6013 connect to first stage section 6012 before the transition start point of section 6016 intersects section 6012. In another embodiment, side channels 6013 connect to the transition start point of section 6016 intersecting section 6012. In yet another embodiment, side channels 6013 connect to a point within the transition section 6016 between the transition start point of section 6016 intersecting section 6012 and the transition stop point of section 6016 intersecting section 601. In yet another embodiment, side channels 6013 connect to the transition stop point of section 6016 intersecting section 601. In yet another embodiment, side channels 6013 connect to the second stage section 601 after the transition stop point of section 6016 intersecting section 601.

FIG. 42B is a cross-sectional view of UFL 630 along direction 66 in FIG. 42A, which is across the wider section 6012. FIG. 42B is identical to FIG. 41B.

Figure 42C:
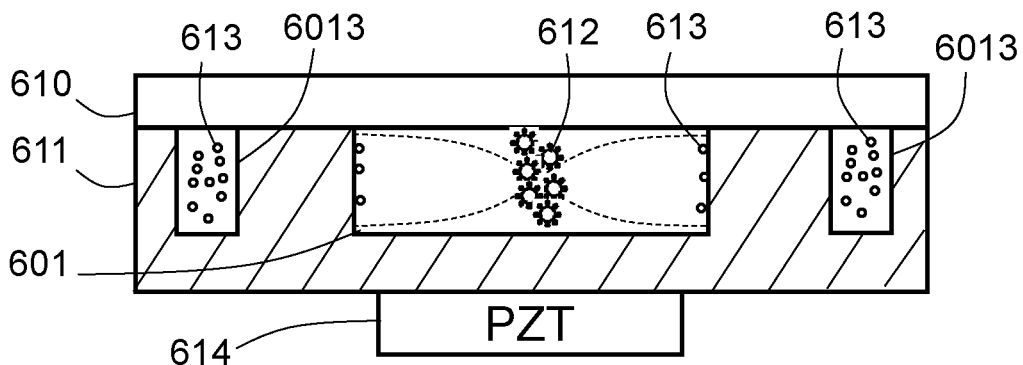
FIG. 42C is a cross-sectional view of third embodiment UFL across narrow channel and side channels.

FIG. 42C is cross-sectional view of UFL 630 along direction 65 in FIG. 42A, which is across the narrower section 601 and side channels 6013. Compared to FIG. 41C, side channels 6013 connecting to around the transition section 6016 of FIG. 42A contain mainly, or purely, small entities 613. While the channel 601 of FIG. 42C includes large entities 612 being separated and concentrated to channel 601 center pressure node similar to FIG. 41C, small entities 613 around section 601 channel walls are reduced in density when compared to FIG. 41C. Due to the pre-channel section 601 small entity diversion by side channels 6013, UFL 630 may have an even higher purity of large entities 612 in fluid output 6070 from outlet 607, as well as higher purity of small entities 613 in fluid output 6090 from outlet 609.

Figure 43:
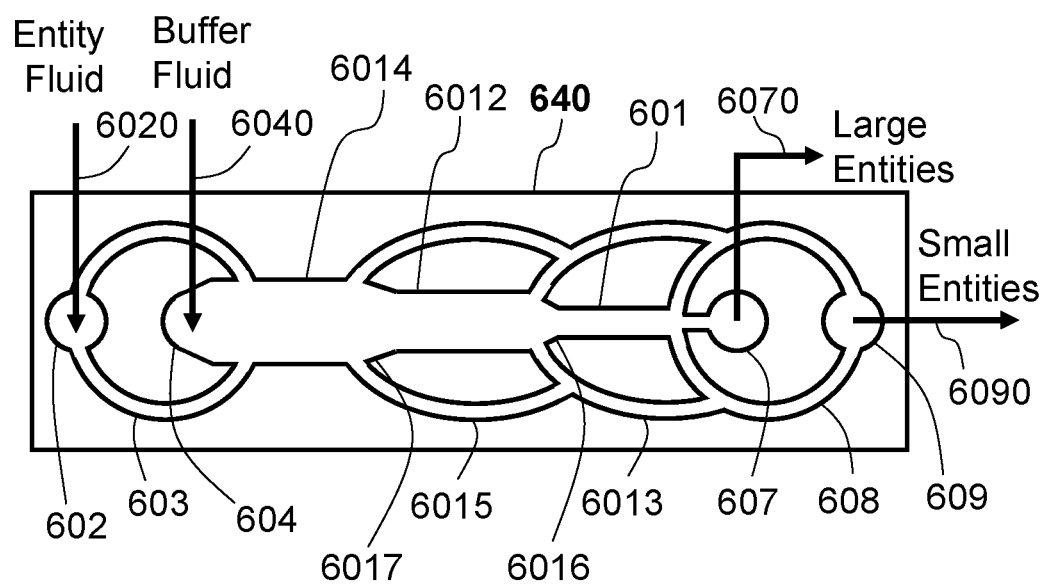
FIG. 43 is a top-down view of a fourth embodiment UFL having three-stage channel width reduction along channel flow direction, and side channels from transition sections.

FIG. 43 is a top-down view of a fourth UFL embodiment UFL 640 having a multiple-stage UFL channel with sequential channel width reduction along the channel flow path. FIG. 43 shows a further enhancement in increasing large entity purity in fluid output 6070 and small entity purity in fluid output 6090. FIG. 43 shows that an additional wider width section 6014 is added between inlet 604 and channel section 6012. Channel width of section 6014 may be three times of the half wavelength of ultrasound mode of the liquid flowing through the UFL 640 channel at PZT frequency Fp, and is one half wavelength wider than channel width 6252 of section 6012. Channel width of section 6014 may also be wider than the channel width 6252 of next stage channel section 6012 by an integer multiplied by the half wavelength, where said integer is larger than one. Channel section 6014 changes to reduced channel width section 6012 through a transition section 6017. Side channels 6015 connect from around the transition section 6017 to side channels 6013, or 608, or directly to outlet 609 to divert small entities 613 from channel side wall laminar flow of section 6014 from entering section 6012, thereby increasing purity of large entity concentration in section 6012. Channel sections 6014, 6012 and 601 are substantially straight and linear along channel length direction.

As a further extension from FIG. 43, a multiple-stage UFL 640 may have multiple channel sections along the UFL 640 channel flow path, where each earlier section of the UFL channel along the channel flow path may have a channel width that is wider than the immediate next section channel width by an integer multiplied by a half wavelength of ultrasound mode in the fluid flow at the PZT frequency Fp, where said integer is equal to or larger than 1. Final channel section before flow exiting the outlets of the UFL 640 is preferred to have a channel width equal to said half wavelength in one embodiment, but may also have a channel width that equals to an integer multiplied by said half wavelength in another embodiment, where integer is larger than one. Side channels connecting to each of the transition areas between adjacent channel sections divert small entities from the earlier channel in the entity laminar flow close to the earlier channel walls towards the outlet 609 to reduce number of small entities entering into immediate next stage channel section.

FIG. 44A through FIG. 65B illustrate various embodiments of method to utilize MAG and UFL devices to separate biological entities from an entity fluid. For simplicity of description UFL 600 of FIG. 38A and MAG 123 with channel 201 are used in the figures for explanation. However, UFL 600 may be replaced with UFL 650, 630, 640 of FIG. 40A, FIG. 41A, FIG. 42A, FIG. 43, while MAG 123 may be replaced with MAG 121, 122, 124, 124,125, 126, 127, 128, 129 and corresponding channel types as described in prior figures without limitation and without sacrifice of performance.

Figure 44A:
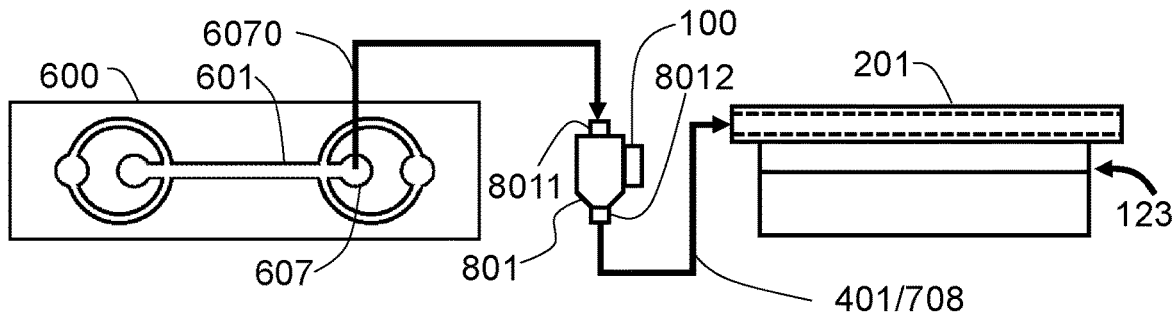
FIG. 44A illustrates first type sample processing method including UFL and MAG, with a first type flow connector connecting the UFL large entity outlet and MAG inlet.

FIG. 44A illustrates first type sample processing method, where biological sample is first passed through UFL 600 and the large entity output 6070 of UFL 600 is then passed through channel 201 adapted to MAG 123, with a first type flow connector 801 connecting the UFL 600 large entity outlet 607 to MAG inlet flow as in step 401 of FIG. 31 or step 708 of FIG. 39. For the in series operation of UFL 600 and MAG 123 devices, optimal flow rate for UFL channel 601 and optimal flow rate for MAG channel 201 may be different. Optimal flow rate for UFL channel 601 acoustic force separation of large and small entities are determined by laminar flow condition, and separation efficiency between large and small entities. Optimal flow rate for MAG 123 separation is determined by the length of channel 201 and magnetic field force on magnetic labels attached to the entities. Direct fluidically coupled flow from UFL 600 outlet 607 to MAG channel 201 inlet will force the flow rate being the same through UFL 600 channel and MAG channel 201, which may incur negative impact on separation efficiency for either one or both of UFL 600 and MAG 123. It is necessary to decouple the fluid flows through UFL 600 and MAG 123 channel 201. Flow connector 801 serves to decouple flow rates of the UFL 600 and MAG 123. Output fluid 6070 is first injected into connector 801 through inlet 8011, and fluid in connector 801 is output through outlet 8012 as flow in steps 401/708 into inlet of channel 201 of MAG 123. Both UFL 600 and MAG 123 channel 201 may operate at their respective optimal flow rates. In one embodiment where MAG 123 channel 201 optimal flow rate is larger than UFL 600 optimal flow rate, MAG 123 extracts fluid 401/708 from connector 801 faster than UFL 600 injects fluid 6070 into the connector 801. A fluid level sensor 100 may be attached to connector 801 to sense fluid level remaining in connector 801. If fluid level drops below a low threshold, sensor 100 may signal MAG 123 to pause flow intake as in steps 401/708 to wait for connector 801 internal liquid level to increase to a higher level before MAG 123 may restart extracting fluid as in steps 401/708 from connector 801. In another embodiment where MAG 123 channel 201 optimal flow rate is smaller than UFL 600 optimal flow rate, MAG 123 extracts fluid as in steps 401/708 from connector 801 slower than UFL 600 injects fluid 6070 into the connector 801. If fluid level increases above a high threshold, sensor 100 may signal UFL 600 to pause flow 6070 output to wait for connector 801 internal liquid level to drop to another lower level before UFL 600 may restart outputting fluid 6070 into connector 801. Flow connector 801 may have the design shown in FIG. 44A, where inlet 8011 is at a higher vertical location than outlet 8012, and flow 6070 enters connector 801 and accumulates at outlet 8012 at inside of 801 due to gravity. Alternatively, liquid sample may be completely processed through UFL 600 first and stored in connector 801. MAG 123 then extracts fluid from connector 801 as input into the MAG 123 channel 201 and completes processing of all liquid sample from connector 801. Connector 801 may be made as part of an enclosed fluidic line, where in the path of flow 6070 from UFL 600 outlet 607 to inlet 8011 of connector 801, to outlet 8012, to flow into inlet of channel 201 as in steps 401/708, fluid sample is not exposed to air, and is sterile.

Figure 44B:
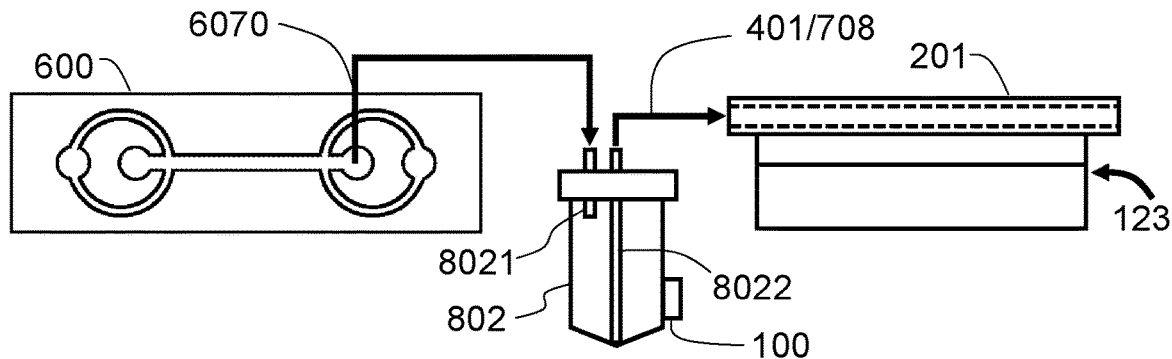
FIG. 44B illustrates first type sample processing method with a second type flow connector connecting the UFL large entity outlet and MAG inlet.

FIG. 44B illustrates first type sample processing method of FIG. 44A using a second type flow connector 802 connecting the UFL 600 large entity outlet 607 to MAG 123 channel 201 inlet. Connector 802 as shown in FIG. 44B takes the form similar to a vial. Flow 6070 enters connector 802 through a short length inlet tube 8021 of connector 802 and drips to bottom of the connector 802 due to gravity. Flow as in steps 401/708 is extracted from the fluid at the bottom of the connector 802 by a long length outlet tube 8022 to input of channel 201. Fluid level sensor 100 may be attached to connector 802 to sense fluid level within connector 802. UFL 600 and MAG 123 may both operate at their respective optimal flow rates, and fluid level sensor 100 may function to pause UFL 600 operation or MAG 123 operation with the same method as described in FIG. 44A. Alternatively, liquid sample may be completely processed through UFL 600 and stored in connector 802. MAG 123 then extracts fluid from connector 802 as input into the MAG 123 channel 201 and completes processing of all liquid sample from connector 802. Connector 802 may be made as part of an enclosed fluidic line similar to connector 801.

Figure 44C:
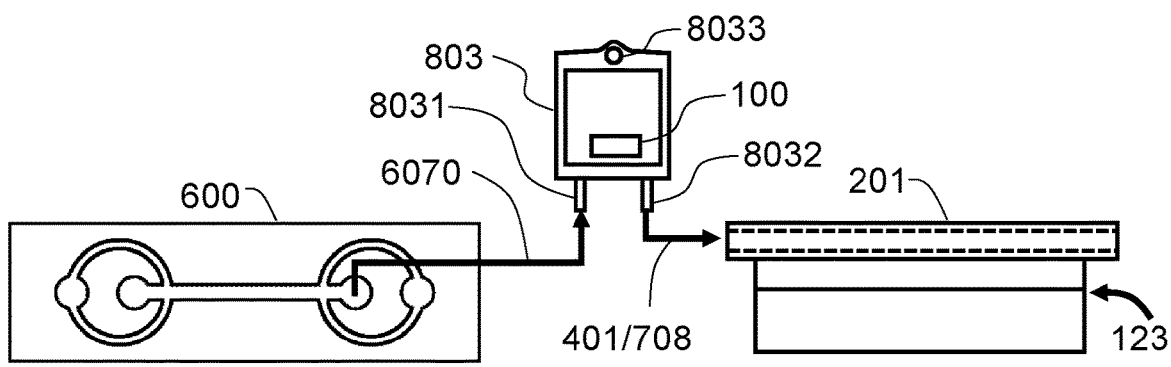
FIG. 44C illustrates first type sample processing method with a third type flow connector connecting the UFL large entity outlet and MAG inlet.

FIG. 44C illustrates first type sample processing method of FIG. 44A using a third type flow connector 803 connecting the UFL 600 large entity outlet 607 to MAG 123 channel 201 inlet. Connector 803 as shown in FIG. 44C takes the form similar to a fluid bag or blood bag. Flow 6070 enters connector 803 through a bottom inlet 8031 and fills connector 803 from bottom of the connector 803 due to gravity. Flow as in steps 401/708 is extracted from the fluid at the bottom of the connector 803 through outlet 8032 to input of channel 201. Fluid level sensor 100 may be attached to connector 803 to sense fluid level within connector 803. UFL 600 and MAG 123 may both operate at their respective optimal flow rates, and fluid level sensor 100 may function to pause UFL 600 operation or MAG 123 operation with the same method as described in FIG. 44A. Alternatively, liquid sample may be completely processed through UFL 600 and stored in connector 803. MAG 123 then extracts fluid from connector 803 as input into the MAG 123 channel 201 and completes processing of all liquid sample from connector 803. Connector 803 may be made as part of an enclosed fluidic line similar to connector 801.

Figure 45A:
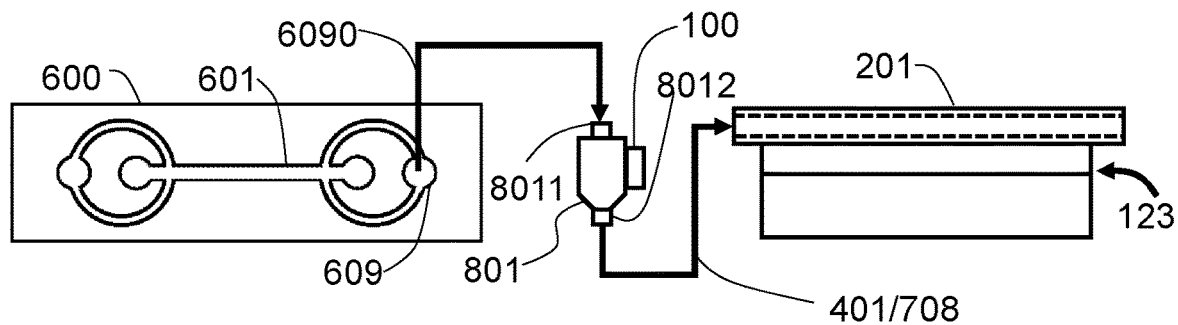
FIG. 45A illustrates second type sample processing method including UFL and MAG, with a first type flow connector connecting the UFL small entity outlet and MAG inlet.

FIG. 45A illustrates second type sample processing method where biological sample is first passed through UFL 600 and the small entity output 6090 of UFL 600 is then passed through MAG 123, with first type flow connector 801 connecting the UFL small entity 6090 outlet 609 to MAG 123 channel 201 inlet. FIG. 45A is identical to FIG. 44A in every aspect except small entity flow 6090 from outlet 609 is injected into the inlet 8011 of connector 801.

Figure 45B:
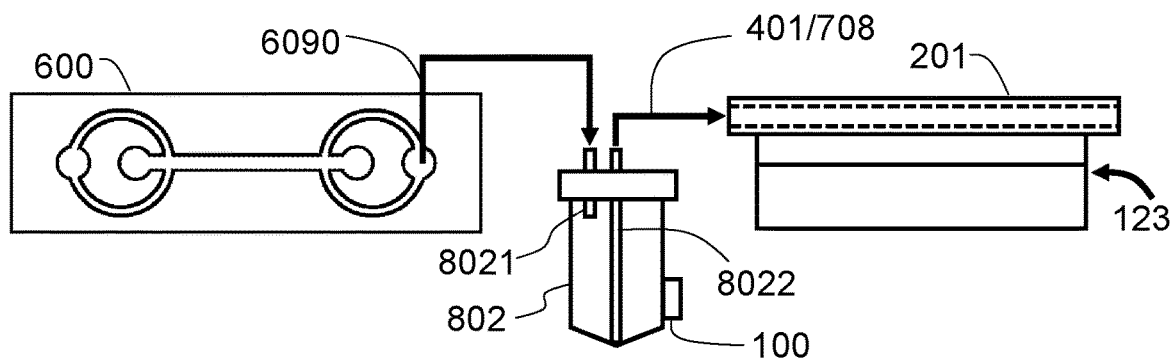
FIG. 45B illustrates second type sample processing method with a second type flow connector connecting the UFL small entity outlet and MAG inlet.

FIG. 45B illustrates second type sample processing method where biological sample is first passed through UFL 600 and the small entity output 6090 of UFL 600 is then passed through MAG 123, with second type flow connector 802 connecting the UFL small entity 6090 outlet 609 to MAG 123 channel 201 inlet. FIG. 45B is identical to FIG. 44B in every aspect except small entity flow 6090 from outlet 609 is injected into the inlet 8021 of connector 802.

Figure 45C:
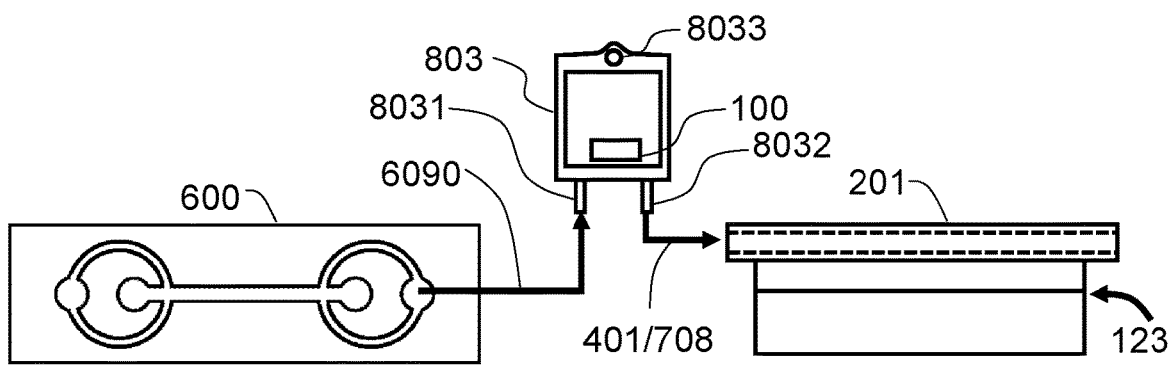
FIG. 45C illustrates second type sample processing method with a third type flow connector connecting the UFL small entity outlet and MAG inlet.

FIG. 45C illustrates second type sample processing method where biological sample is first passed through UFL 600 and the small entity output 6090 of UFL 600 is then passed through MAG 123, with third type flow connector 803 connecting the UFL small entity 6090 outlet 609 to MAG 123 channel 201 inlet. FIG. 45C is identical to FIG. 44C in every aspect except small entity flow 6090 from outlet 609 is injected into the inlet 8031 of connector 803.

Figure 46A:
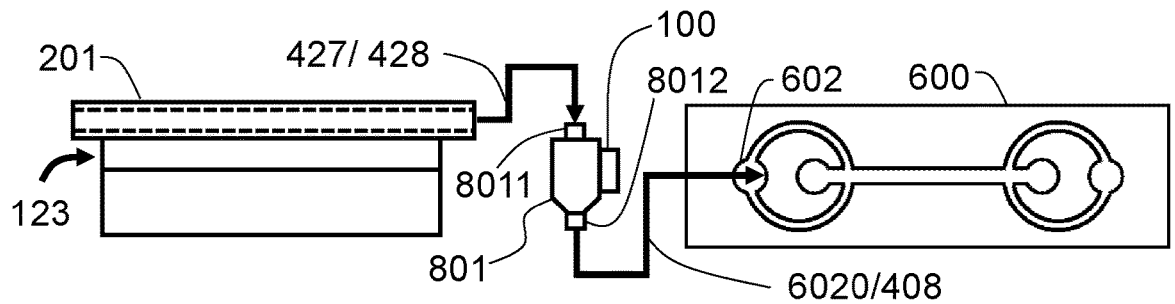
FIG. 46A illustrates third type sample processing method including MAG and UFL, with a first type flow connector connecting the MAG outlet and UFL entity fluid inlet.

FIG. 46A illustrates third type sample processing method where biological sample is first passed through MAG 123 channel 201, and following procedure 427 or 428 of FIG. 31, the output of MAG 123 channel 201 is then passed through UFL 600 as entity fluid 6020 into inlet 602 as in step 408 of FIG. 31, with first type flow connector 801 connecting the MAG 123 channel 201 outlet to UFL 600 entity fluid 6020 inlet 602. In FIG. 46A, output from MAG 123 can be either negative entities that do not have attached SPL 2, or positive entities separated by MAG 123 magnetic field and subsequently dissociated and flushed out of channel 201 as described in FIG. 31. Similar to those in FIG. 44A, MAG 123 and UFL 600 may each operate with their respective optimal flow rate. Fluid level sensor 100 may be attached to connector 801 to sense fluid level remaining in connector 801. Fluid level sensor 100 operates similarly to that in FIG. 44A to sense fluid in connector 801, and depending on the flow rate difference between MAG 123 and UFL 600, may pause MAG 123 or UFL 600 flow to maintain fluid level in connector 801 above a low level or below a high level. Alternatively, liquid sample may be completely processed through MAG 123 first and stored in connector 801. UFL 600 then extracts fluid from connector 801 as input into the inlet 602 and completes processing of all liquid sample from connector 801. Connector 801 may be made as part of an enclosed fluidic line similar to that in FIG. 44A.

Figure 46B:
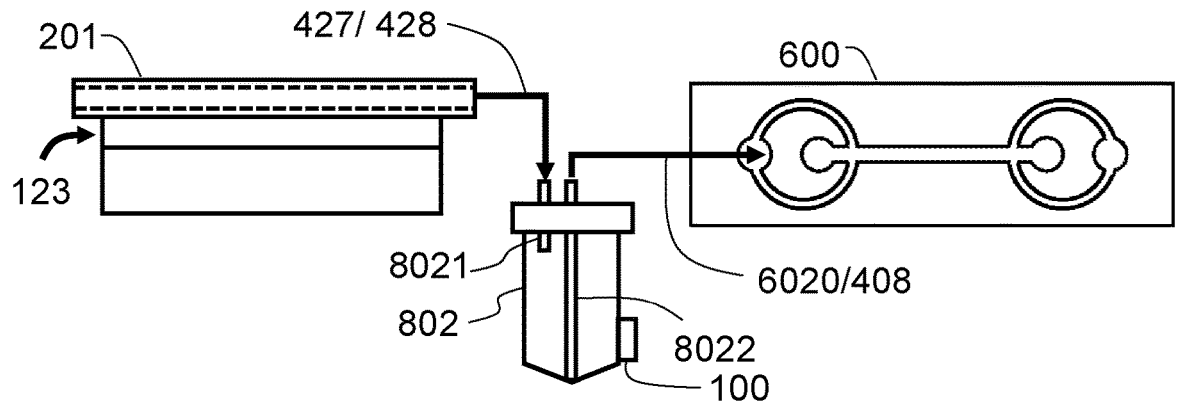
FIG. 46B illustrates third type sample processing method with a second type flow connector connecting the MAG outlet and UFL entity fluid inlet.

FIG. 46B is same as FIG. 46A in every aspect, except replacing connector 801 with connector 802, where operation of connector 802 and attached sensor 100 is same as that described in FIG. 44B.

Figure 46C:
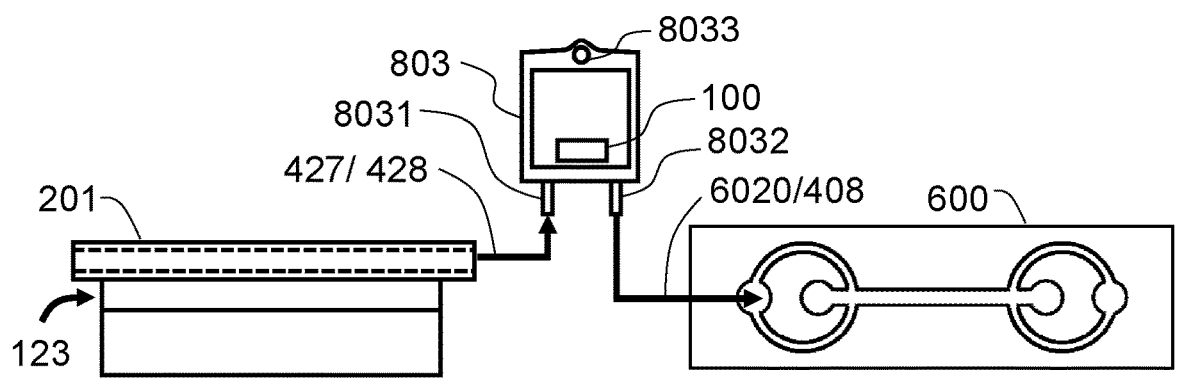
FIG. 46C illustrates third type sample processing method with a third type flow connector connecting the MAG outlet and UFL entity fluid inlet.

FIG. 46C is same as FIG. 46A in every aspect, except replacing connector 801 with connector 803, where operation of connector 803 and attached sensor 100 is same as that described in FIG. 44C.

Figure 47:
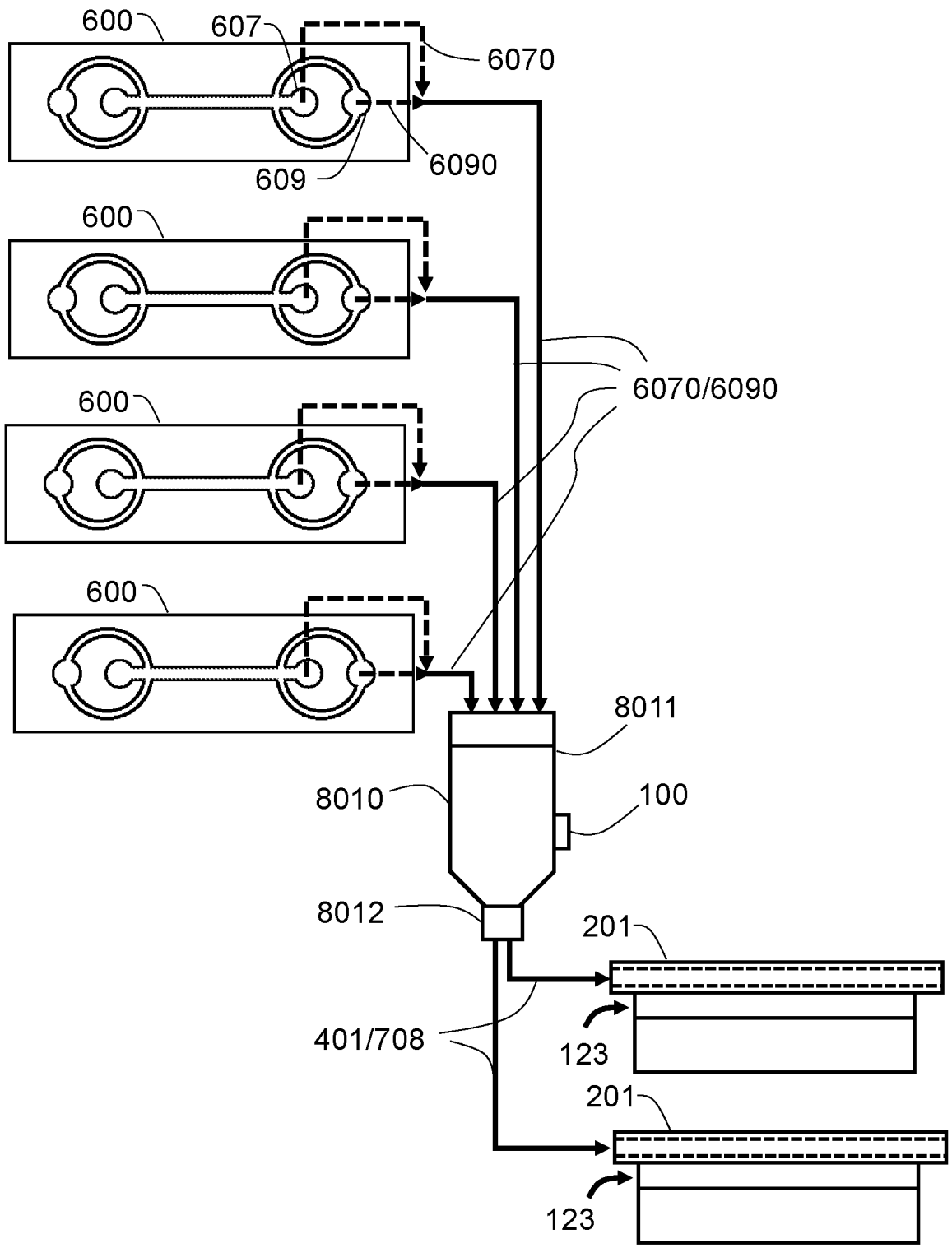
FIG. 47 illustrates fourth type sample processing method including multiple UFLs, a fourth type flow connector, and multiple MAGs.

FIG. 47 illustrates fourth type sample processing method where biological sample is first passed through multiple UFLs 600. Output fluids from the UFLs 600, which can be either large entities 6070 or small entities 6090, are then fed into inlets 8011 of a fourth type flow connector 8010, and from connector 8010 outlets 8012 into the inlets of channels 201 of multiple MAGs 123. FIG. 47 is functionally similar to FIG. 44A and FIG. 45A. Connector 8010 is also functionally same as connector 801, except inlets 8011 of connector 8010 accept multiple fluid outputs from multiple UFLs 600, and outlets 8012 of connector 8010 output to inputs of multiple channels 201 of multiple MAGs 123.

Figure 48:
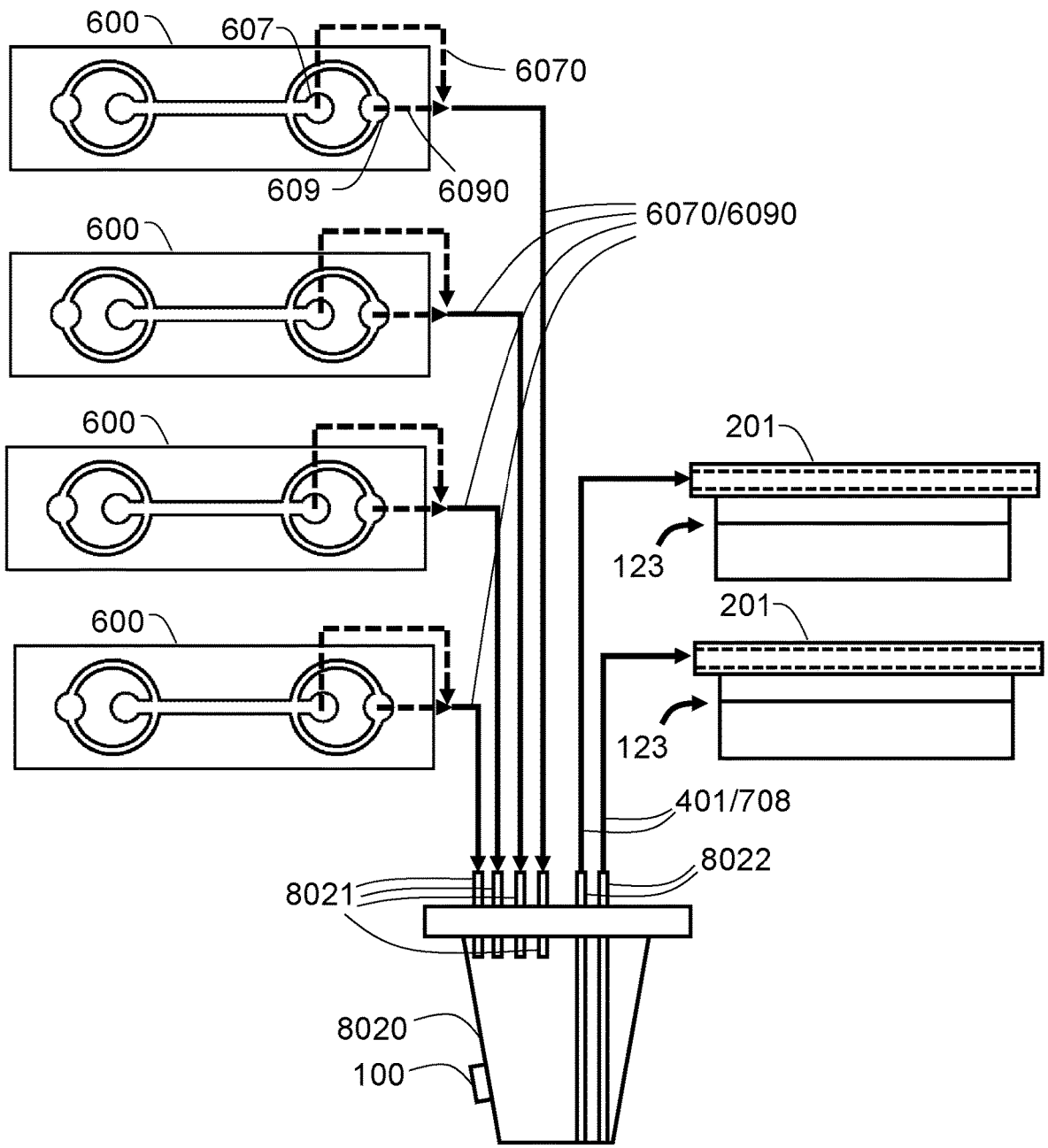
FIG. 48 illustrates fifth type sample processing method including multiple UFLs, a fifth type flow connector, and multiple MAGs.

FIG. 48 illustrates fifth type sample processing method where biological sample is first passed through multiple UFLs 600. Output fluids from the UFLs 600, which can be either large entities 6070 or small entities 6090, are then fed into inlets 8021 of a fifth type flow connector 8020, and from connector 8020 outlets 8022 into the inlets of channels 201 of multiple MAGs 123. FIG. 48 is functionally similar to FIG. 44B and FIG. 45B. Connector 8020 is also functionally same as connector 802, except inlets 8021 of connector 8020 accept multiple fluid outputs from multiple UFLs 600, and outlets 8022 of connector 8020 output to inputs of multiple channels 201 of multiple MAGs 123.

Figure 49:
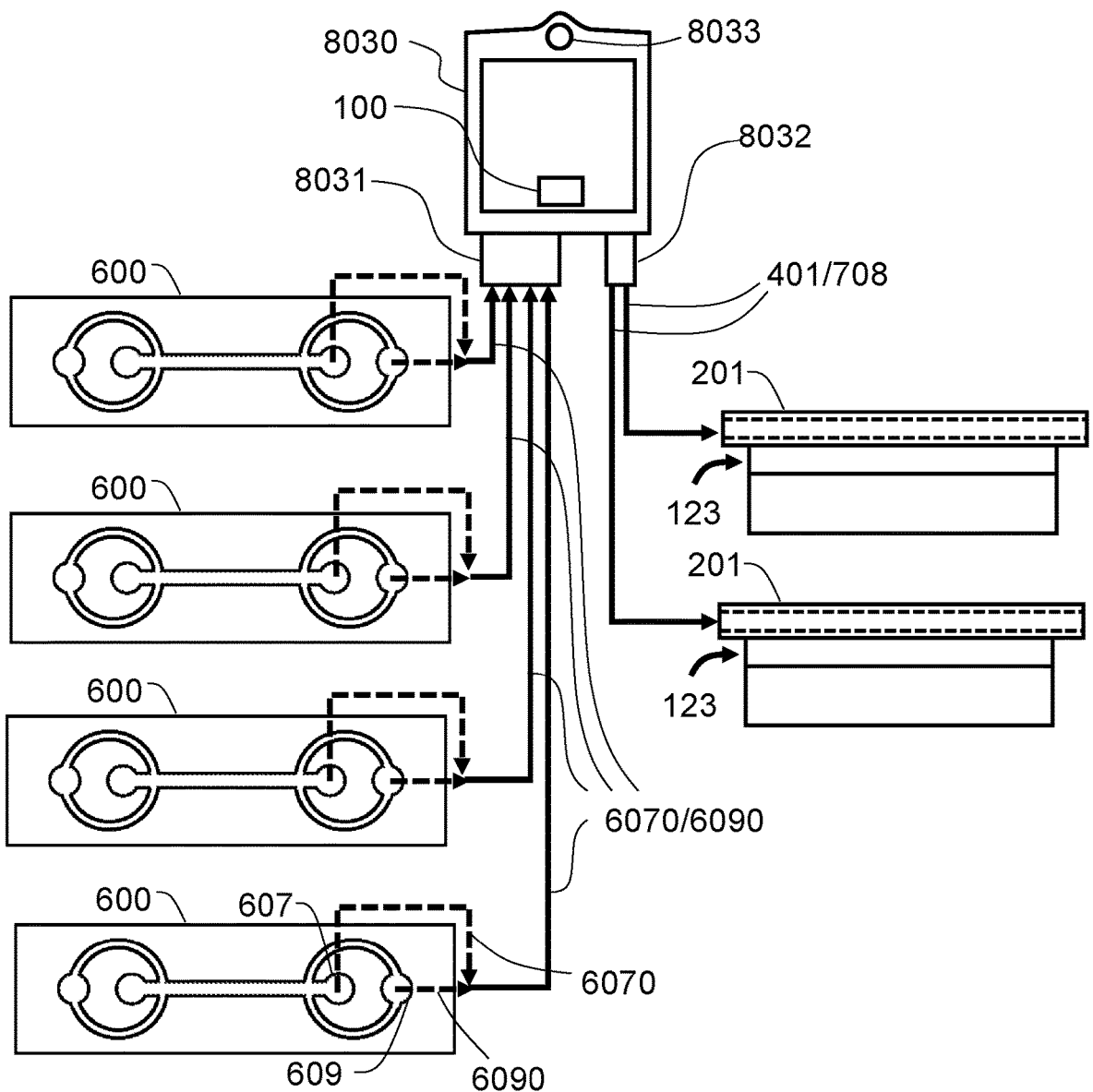
FIG. 49 illustrates fifth type sample processing method including multiple UFLs, a sixth type flow connector, and multiple MAGs.

FIG. 49 illustrates sixth type sample processing method where biological sample is first passed through multiple UFLs 600. Output fluids from the UFLs 600, which can be either large entities 6070 or small entities 6090, are then fed into inlets 8031 of a sixth type flow connector 8030, and from connector 8030 outlets 8032 into the inlets of channels 201 of multiple MAGs 123. FIG. 49 is functionally similar to FIG. 44C and FIG. 45C. Connector 8030 is also functionally same as connector 803, except inlets 8031 of connector 8030 accept multiple fluid outputs from multiple UFLs 600, and outlets 8032 of connector 8030 output to inputs of multiple channels 201 of multiple MAGs 123.

In each of FIG. 47, FIG. 48, and FIG. 49, in one embodiment, same biological sample is divided and processed simultaneously through multiple UFLs 600. In another embodiment, each of the UFLs 600 processes a different biological sample. Output from each UFL 600, either large entity 6070 fluid from outlet 607 or small entity fluid from outlet 609, shown as dashed lines in FIG. 47, FIG. 48 and FIG. 49, may be individually input into the inlet 8011 of connector 8010 of FIG. 47, or into inlet 8021 of connector 8020 of FIG. 48, or into inlet 8031 of connector 8030 of FIG. 49, as shown by solid lines 6070/6090 in each of FIG. 47, FIG. 48 and FIG. 49. From outlet 8012, 8022, 8032 of FIG. 47, FIG. 48 and FIG. 49, respectively, following step 401 or 708, each of the MAGs 123 of FIG. 47, FIG. 48, or FIG. 49 may extract fluid sample from corresponding connector 8010, 8020, and 8030 into its corresponding channel 201. Each of the UFLs 600 and each of the MAGs 123 of FIG. 47, FIG. 48, or FIG. 49 may operate at its own respective optimal sample flow rate, which may be different between different UFLs 600 and different between different MAGs 123 within same figure. Due to the existence of the connector 8010, 8020, and 8030, flow rate interferences between the different UFLs 600 and MAGs 123 within each of FIG. 47, FIG. 48 and FIG. 49 are minimized or eliminated. Fluid level sensor 100 may be attached to buffers 8010, 8020, and 8030 to sense fluid level remaining in each of the flow connectors 8010, 8020, and 8030. Fluid level sensor 100 operates similarly to that in FIG. 44A through FIG. 44C in sensing fluid in flow connectors 8010, 8020, and 8030, and depending on the flow rate difference between MAGs 123 and UFLs 600 of each figure, may pause operation of one or more MAGs 123, or may pause operation of one or more UFLs 600 of each figure to maintain fluid level in corresponding connector 8010, 8020, or 8030 to be above a low level threshold or below a high level threshold. Alternatively, liquid sample may be completely processed through all UFLs 600 first and stored in corresponding connector 8010, 8020, or 8030 of each FIG. 47, FIG. 48 and FIG. 49. MAGs 123 then extract fluid from corresponding connector 8010, 8020, or 8030 of each figure and complete processing of all liquid sample from each corresponding connector 8010, 8020, or 8030. Connectors 8010, 8020, and 8030 may each be made as part of a set of enclosed fluidic lines, which may include UFLs 600, channels 201 and connections from UFLs 600 to each connector 8010, 8020, 8030 and from each connector 8010, 8020, or 8030 to channels 201, similar to that described in FIG. 44A through FIG. 44C.

Figure 50:
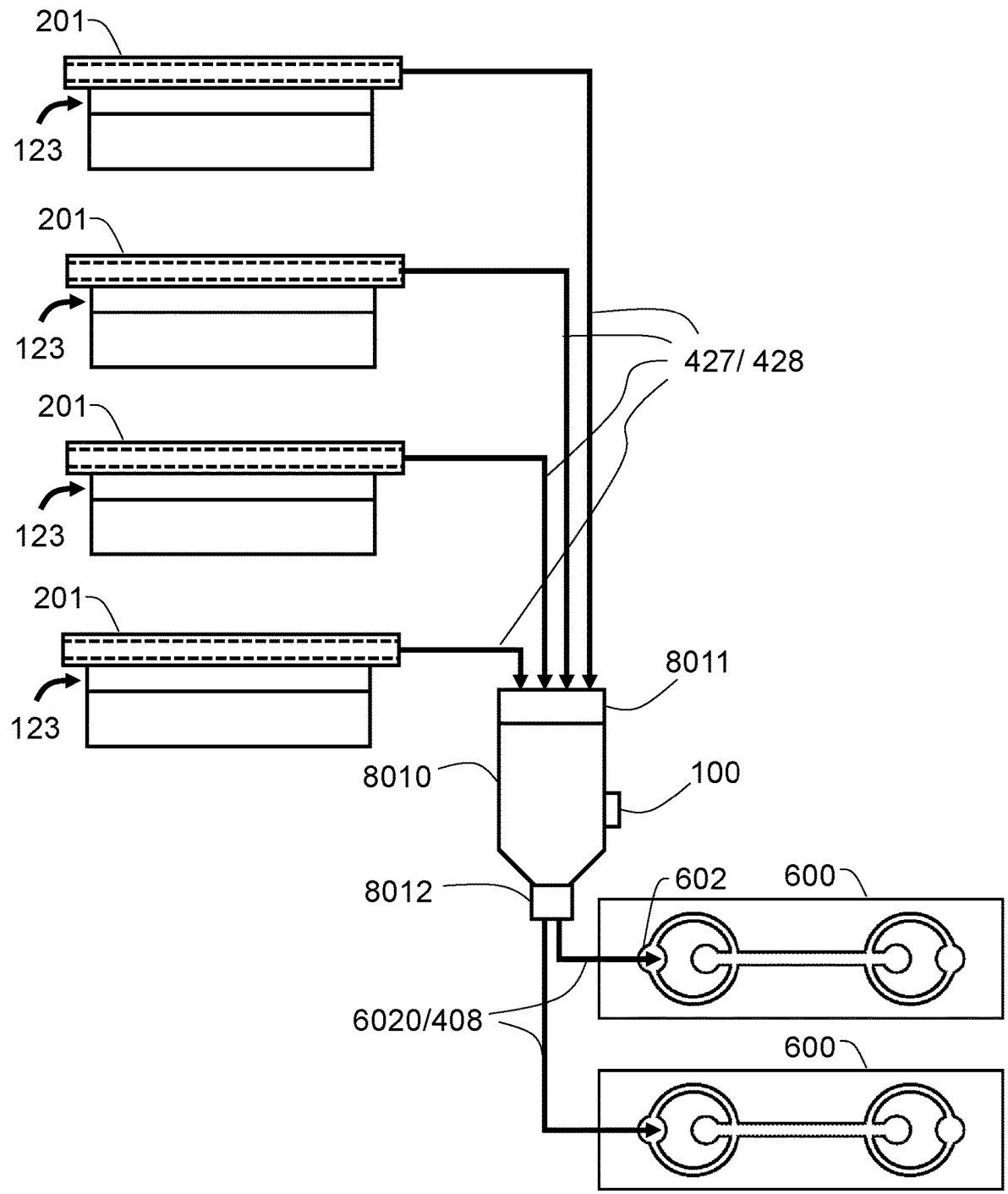
FIG. 50 illustrates seventh type sample processing method including multiple MAGs, a fourth type flow connector, and multiple UFLs.

FIG. 50 illustrates seventh type sample processing method where biological sample is first passed through multiple MAGs 123. Output fluids from the MAGs 123 channels 201 are then fed into inlets 8011 of flow connector 8010 of FIG. 47, and from flow connector 8010 outlets 8012 into the entity fluid inlets 602 of multiple UFLs 600.

Figure 51:
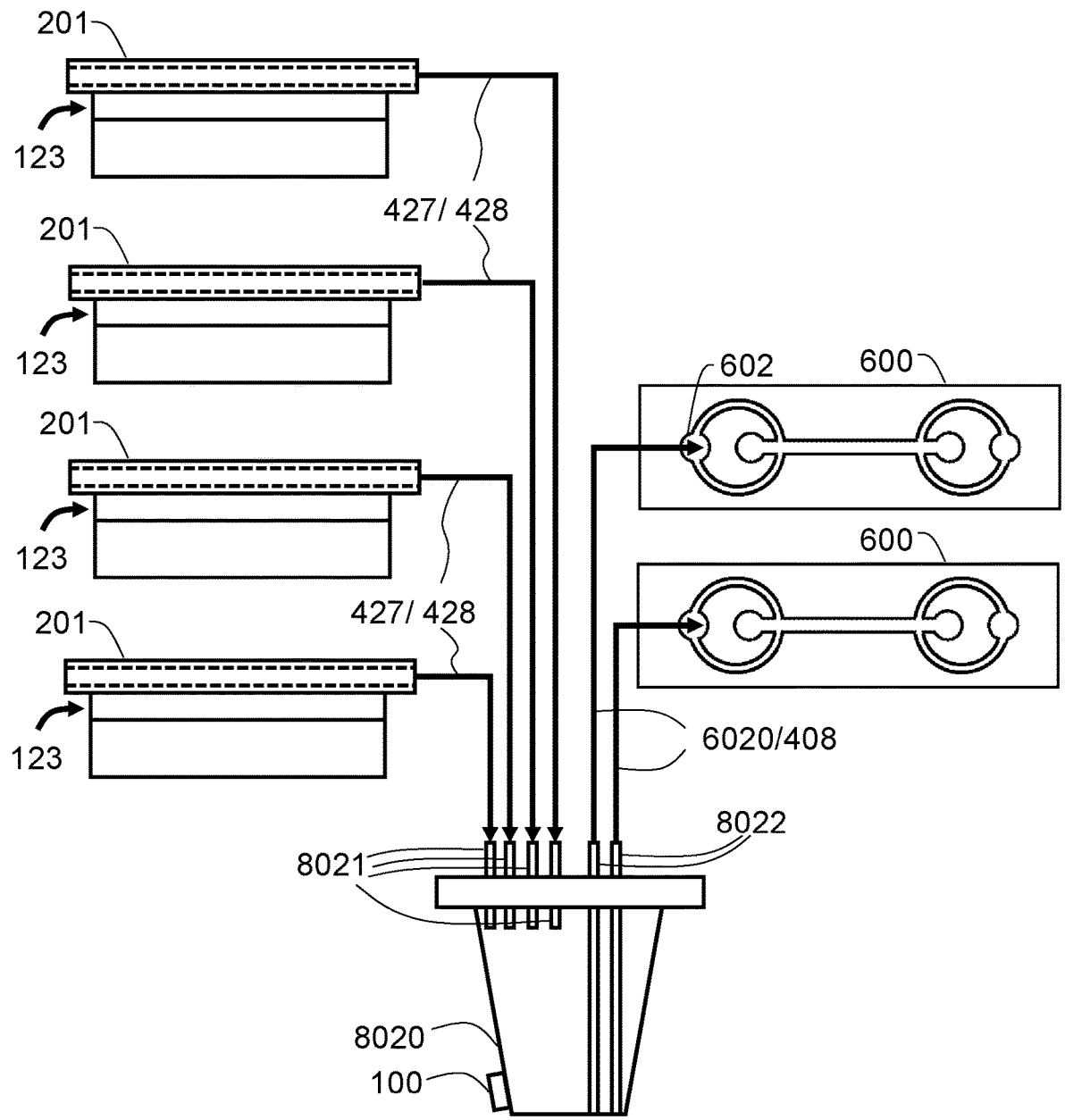
FIG. 51 illustrates eighth type sample processing method including multiple MAGs, a fifth type flow connector, and multiple UFLs.

FIG. 51 illustrates eighth type sample processing method where biological sample is first passed through multiple MAGs 123. Output fluids from the MAGs 123 channels 201 are then fed into inlets 8021 of flow connector 8020 of FIG. 48, and from flow connector 8020 outlets 8022 into the entity fluid inlets 602 of multiple UFLs 600.

Figure 52:
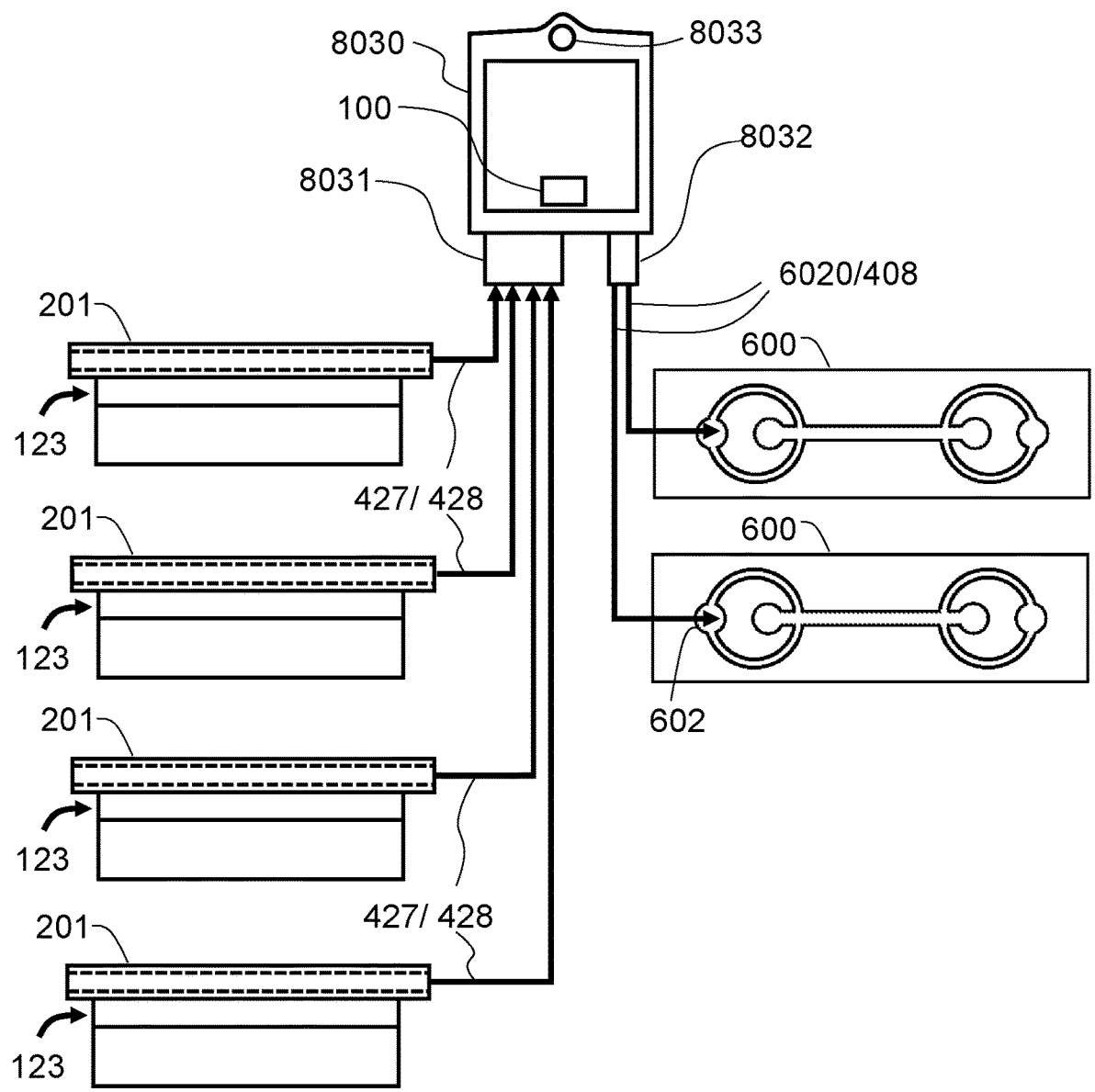
FIG. 52 illustrates ninth type sample processing method including multiple MAGs, a sixth type flow connector, and multiple UFLs.

FIG. 52 illustrates ninth type sample processing method where biological sample is first passed through multiple MAGs 123. Output fluids from the MAGs 123 channels 201 are then fed into inlets 8031 of flow connector 8030 of FIG. 49, and from flow connector 8030 outlets 8032 into the entity fluid inlets 602 of multiple UFLs 600.

In each of FIG. 50, FIG. 51, and FIG. 52, in one embodiment, same biological sample is divided and processed simultaneously through multiple MAGs 123. In another embodiment, each of the MAGs 123 processes a different biological sample. Output from each MAG 123, either negative entities following procedure 427, or positive entities following procedure 428, may be individually input into the inlet 8011 of connector 8010 of FIG. 50, or into inlet 8021 of connector 8020 of FIG. 51, or into inlet 8031 of connector 8030 of FIG. 52, as shown by solid lines 427/428 in each of FIG. 50, FIG. 51 and FIG. 52. From outlets 8012, 8022, 8032 of FIG. 50, FIG. 51 and FIG. 52, respectively, following step 408, each of the UFLs 600 of FIG. 50, FIG. 51, or FIG. 52 may extract fluid sample as entity fluid 6020 from corresponding connector 8010, 8020, and 8030 into its corresponding entity inlet 602. Each of the UFLs 600 and each of the MAGs 123 of FIG. 50, FIG. 51, or FIG. 52 may operate at its own respective optimal sample flow rate, which may be different between different UFLs 600 and different between different MAGs 123 within same figure. Due to the existence of the connectors 8010, 8020, and 8030, flow rate interferences between the different UFLs 600 and MAGs 123 within each of FIG. 50, FIG. 51 and FIG. 52 are minimized or eliminated. Fluid level sensor 100 may be attached to flow connectors 8010, 8020, and 8030 to sense fluid level remaining in each of the flow connectors. Fluid level sensor 100 operates similarly to that in FIG. 46A through FIG. 47C in sensing fluid in flow connectors 8010, 8020, and 8030, and depending on the flow rate difference between MAGs 123 and UFLs 600 of each figure, may pause operation of one or more MAGs 123, or may pause operation of one or more UFLs 600 of each figure to maintain fluid level in corresponding connector 8010, 8020, or 8030 to be above a low level threshold or below a high level threshold. Alternatively, liquid sample may be completely processed through all MAGs 123 first and stored in corresponding connector 8010, 8020, or 8030 of each of FIG. 50, FIG. 51 and FIG. 52. UFLs 600 then extract fluid from corresponding connector 8010, 8020, or 8030 of each figure and complete processing of all liquid sample from each corresponding connector 8010, 8020, or 8030. Flow connectors 8010, 8020, and 8030 may each be made as part of a set of enclosed fluidic lines, which may include UFLs 600, channels 201 and connections from channels 201 to each connector 8010, 8020, 8030 and from each connector 8010, 8020, or 8030 to UFLs 600, similar to that described in FIG. 46A through FIG. 46C.

Figure 53:
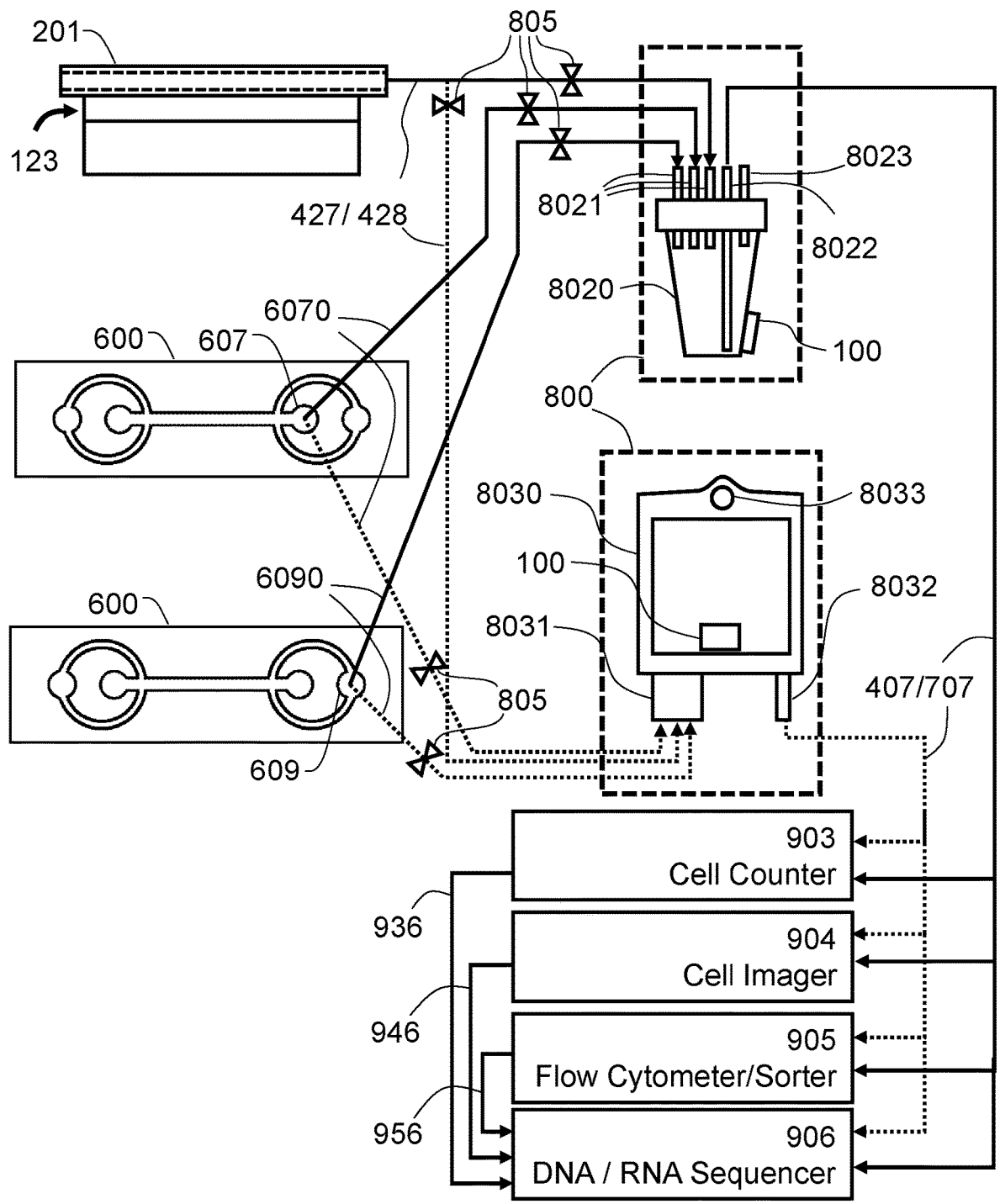
FIG. 53 illustrates tenth type sample processing method including one or more of UFLs and MAGs, a fifth or a sixth type flow connector, and different type of cell processing devices.

FIG. 53 illustrates tenth type sample processing method where biological sample after being passed through one or more of UFLs 600 or MAGs 123, output fluids from the UFLs 600 and MAGs 123 are fed into inlets of a flow connector 8020 or a flow connector 8030, and from the flow connectors 8020 and 8030 outlets into different types of cell processing devices. FIG. 53 shows example of liquid sample output from MAG 123 channel 201, including negative entities following procedure 427 and positive entities following procedure 428, may be injected to inlet 8021 of connector 8020 or inlet 8031 of connector 8030 similar to that in FIG. 51 and FIG. 52. Alternatively, UFL 600 large entity output 6070 from outlet 607 or small entity output 6090 from outlet 609 may be also injected into inlet 8021 of connector 8020 or inlet 8031 of connector 8030 similar to that in FIG. 48 and FIG. 49. After sample fluid is completely processed through UFL 600 or MAG 123, and injected into, and stored within, connector 8020 or connector 8030, entity analysis as in step 407 of FIG. 31 and step 707 of FIG. 39 may be performed by sending sample fluid containing entities from connector 8020 or connector 8030 to any of: cell counter 903, cell imager 904, flow cytometer or sorter 905, and DNA or RNA sequencer 906. Entities may be further sent to DNA or RNA sequencer 906 after cell counter 903 as indicated by flow 936, or after cell imager 904 as indicated by flow 946, or after flow cytometer or sorter 905 as indicated by flow 956. For sending the sample fluid from outlet 8022 of connector 8020, or from outlet 8032 of connector 8030, pressurized chamber 800 may be used to contain the connector 8020 or connector 8030 inside, and force sample fluid out of connector 8020 or connector 8030 in a steady and continuous flow stream. Chamber 800 may be a chamber filled with pressurized air inside. Connector 8020 of vial type may have an additional air port 8023 open to chamber 800 internal pressurized air to help pushing sample fluid out of connector 8020. While connector 8030 may be in a flexible blood bag form, which when under pressured air of chamber 800, will automatically deflate and force sample liquid out through outlet 8032. To avoid back flow into UFL 600 or MAG 123 channel 201, shut off valves 805 may be implemented on output lines from MAG 123 channel 201 and UFL 600 to connector 8020 or connector 8030.

Figure 54A:
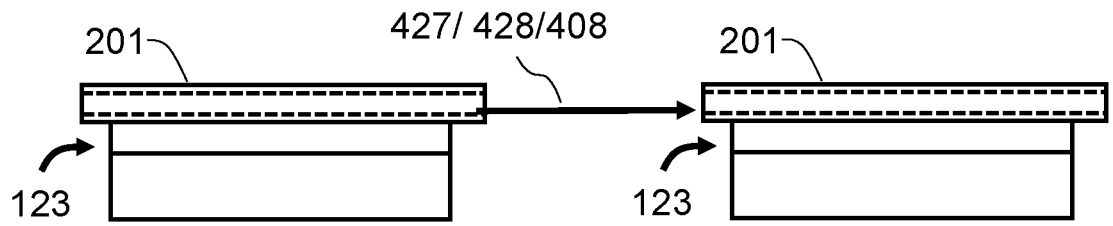
FIG. 54A illustrates eleventh type sample processing method including a multi-stage MAG process.

FIG. 54A illustrates eleventh type sample processing method where biological sample after being passed through a first MAG 123 channel 201 during a magnetic separation may output negative entity fluid following procedure 427, or positive entity fluid following procedure 428, into inlet of a second MAG 123 channel 201 input as in step 408 of a continued process. FIG. 54A illustrates a multi-stage MAG process.

Figure 54B:
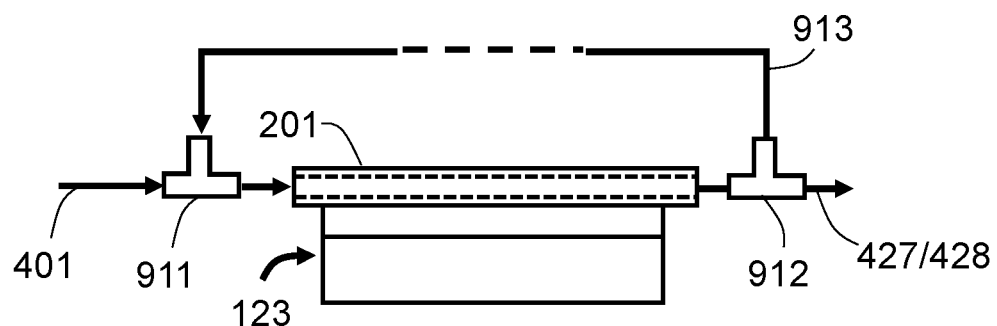
FIG. 54B illustrates twelfth type sample processing method including a multi-cycle MAG process.

FIG. 54B illustrates twelfth type sample processing method where after biological sample being passed through MAG 123 for magnetic separation, output fluid from MAG 123 channel 201, containing either negative entities or position entities, may be diverted through a T-connector 912 into flow 913. Flow 913 may then be re-input back into the input of the channel 201 of MAG 123 for another round of magnetic separation through T-connector 911. T-connector 911 allows initial fluid sample input as in step 401 and recycled flow 913 input to channel 201. T-connector 912 allows output from channel 201 into recycled flow 913 or output from MAG 123 as described in procedures 427 and 428. In one embodiment, recycled flow 913 contains negative entities. Repeated magnetic separation in FIG. 54B helps to achieve complete depletion of all magnetic entities in the negative entity flow before continuing to 427/428 procedure. In another embodiment, recycled flow 913 contains positive entities after dissociation. Repeated process as shown in FIG. 54B helps to increase purity in positive magnetic entities to allow wash off of non-magnetic entities that may be in the conglomerate by non-specific bindings. FIG. 54B illustrates the use of the same MAG 123 for a multi-cycle MAG process.

Figure 54C:
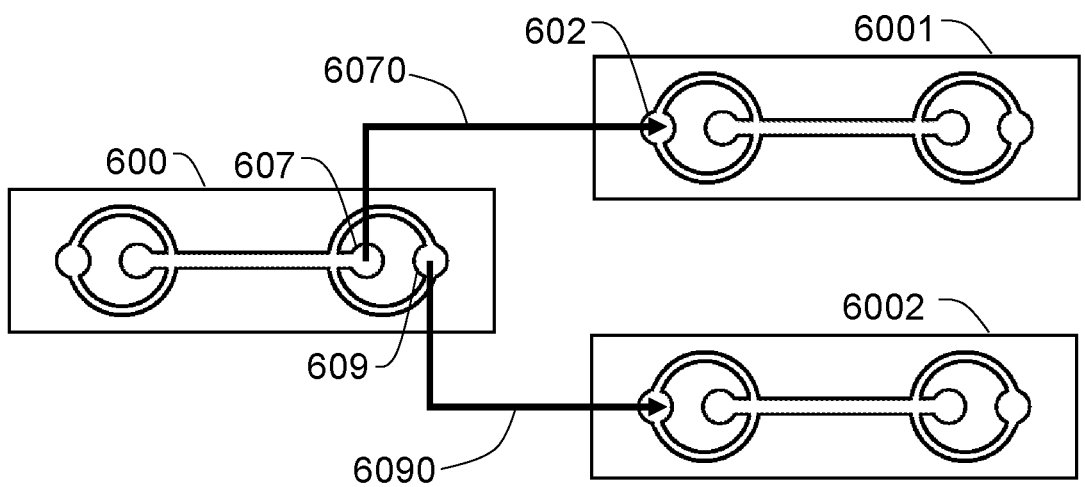
FIG. 54C illustrates thirteenth type sample processing method including a multi-stage UFL process.

FIG. 54C illustrates thirteenth type sample processing method where biological sample after being passed through a first UFL 600, output fluids from first UFL 600, for example large entity fluid 6070 from outlet 607 or small entity fluid 6090 from outlet 609, may be passed into entity fluid inlets 602 of one or more subsequent UFLs 600 as a multi-stage UFL process.

Figure 55A:
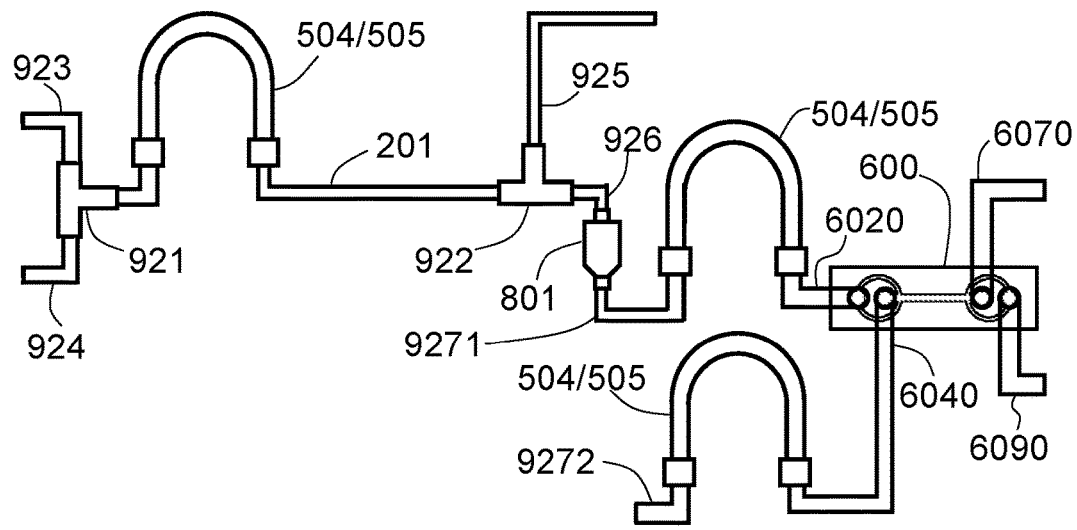
FIG. 55A illustrates first example of closed and disposable fluidic lines for third type sample processing method.

FIG. 55A illustrates first embodiment of closed and disposable fluidic lines for third type sample processing method shown in FIG. 46A, where connector 801 may be replaced with connector 802 or connector 803 without limitation. Input line 923 may connect to a sample liquid container. Input line 924 may connect to a MAG buffer container. Input line 923 and input line 924 are connected through a T-connector 921 to the inlet of the first pump tubing 504/505 that may be mounted onto a peristaltic pump. First pump tubing 504/505 outlet connects to channel 201 which may be used as part of MAG 123. Output of channel 201 connects to T-connector 922, which connects to output line 925 and output line 926. Output line 925 may connect to an MAG output sample container and output line 926 connects to inlet of connector 801. In one embodiment, output line 925 may output negative entities to said MAG output sample container, and output line 926 may output positive entities to connector 801. In another embodiment, output line 925 may output positive entities to said MAG output sample container, and output line 926 may output negative entities to connector 801. Connector 801 outlet connects to input line 9271 of a second pump tubing 504/505. Said second pump tubing 504/505 outlet then connects to UFL 600 sample input line 6020. Input line 9272 may connect to UFL buffer container and connects to inlet of a third pump tubing 504/505. Said third pump tubing 504/505 outlet then connects to UFL 600 buffer input line 6040. UFL 600 large entity 6070 output line may connect to a large entity sample container. UFL 600 small entity 6090 output line may connect to a small entity sample container. FIG. 55A illustrates that besides the input and output lines 923, 924, 925, 9272, 6070, and 6090 that connect to external containers and entire fluid path from sample liquid input to line 923 and from sample output to lines 925, 6070, 6090, all pumps, MAG 123 and other fluidic line components will be externally attached to the lines of FIG. 55A. Thus, lines of FIG. 55A are internally enclosed, suitable for single use disposable purpose and sterile applications.

Figure 55B:
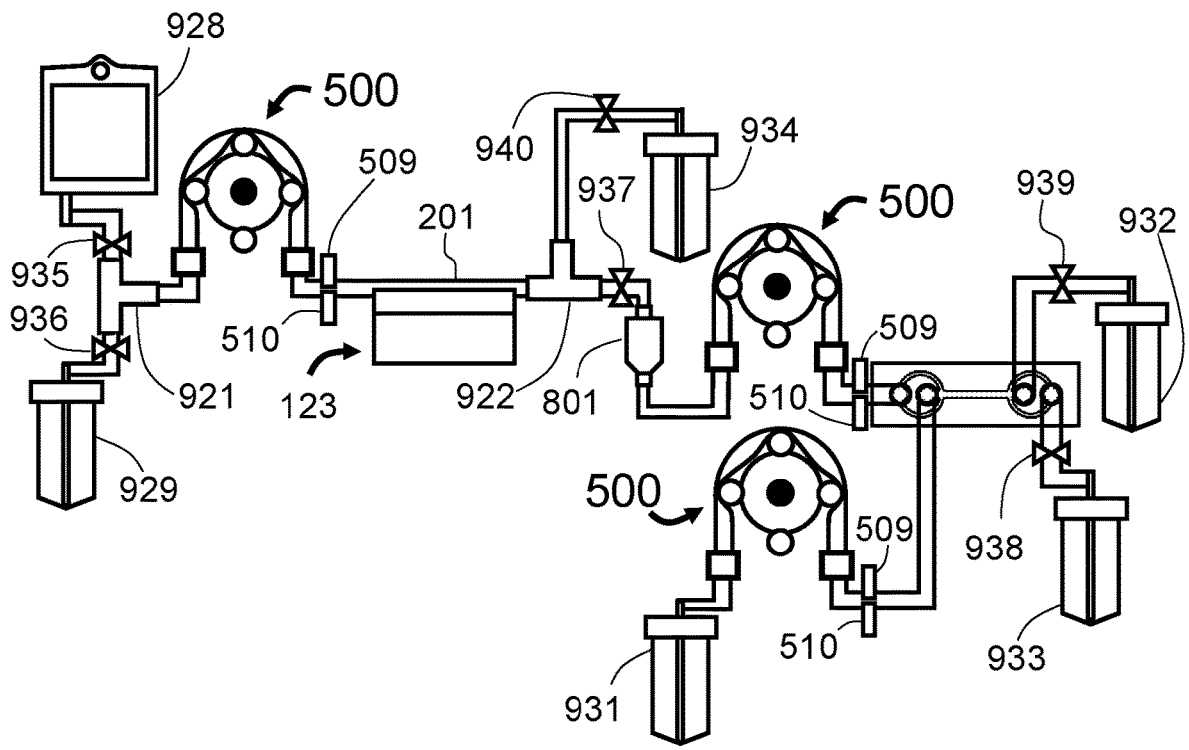
FIG. 55B illustrates fluidic lines of FIG. 55A being connected to, or attached with, various fluidic devices to realize third type sample processing method.

FIG. 55B illustrates fluidic lines of FIG. 55A being connected to, or attached with, various fluidic components. Input line 923 connects to a liquid sample container 928 in blood bag form. Input line 924 connects to buffer container 929. Valves 935 and 936 are attached to lines 923 and 924 to control either sample liquid from bag 928 or buffer from container 929 flowed through T-connector 921 into first pump tubing 504/505. First, second and third pump tubings 504/505 are each installed onto a peristaltic pump 500. Three pumps 500 operate to pump either sample fluid or buffer fluid into MAG 123 and UFL 600. A flow limiter 509/510 may be attached to the output line from each pump 500, including lines 201, 6020, 6040 to reduce flow rate pulsation from the pumps 500. Channel line 201 is mounted onto MAG 123. Output line 925 connects to MAG output sample container 934. Valve 940 is attached to line 925 and valve 937 is attached to line 926, which control negative entities or positive entities from MAG 123 going into either container 934 or the connector 801 through the T-connector 922. Valves 940 and 937 may both shut down the flow in lines 925 and 926 during demagnetization/dissociation process of MAG 123. Input line 9272 may connect to UFL buffer container 931. UFL output line 6070 connects to large entity container 932 and output line 6090 connects to small entity container 933. Adjustable valves 939 and 938 may be attached to the lines 6070 and 6090 to adjust the flow rate within each of lines 6070 and 6090, which in turn controls the laminar flow speed in UFL channel for channel center buffer flow and channel edge entity sample flow.

Figure 56A:
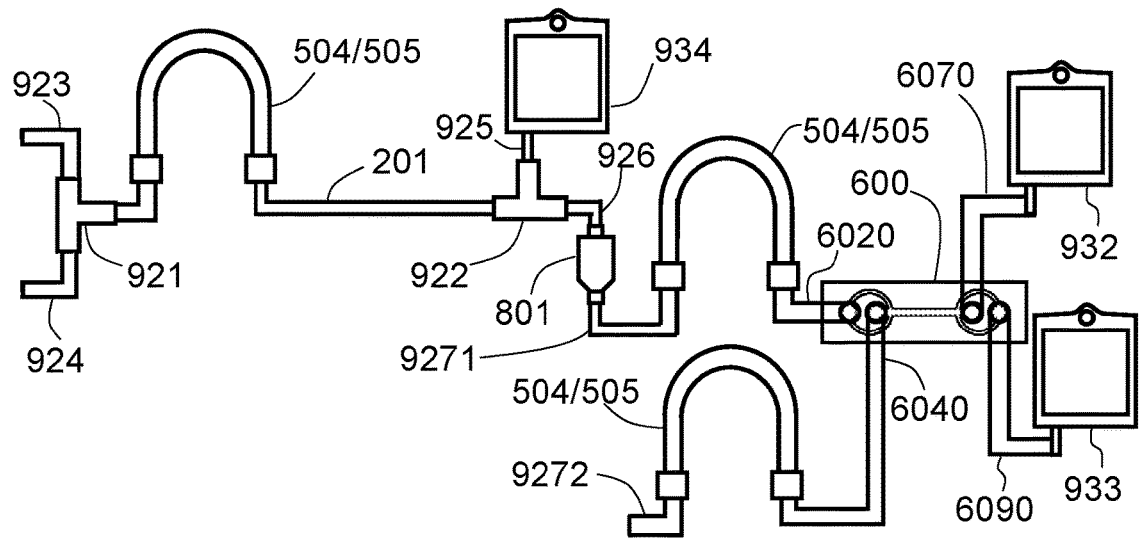
FIG. 56A illustrates second example of closed and disposable fluidic lines for third type sample processing method.

FIG. 56A illustrates second embodiment of closed and disposable fluidic lines for third type sample processing method shown in FIG. 46A. FIG. 56A is identical to FIG. 55A, except the output line 925 is connected to a MAG sample container 934, UFL output line 6070 is connected to a large entity container 932, and UFL output line 6090 is attached to a small entity container 933. FIG. 56A illustrates that containers 934, 932, 933 are in the form of blood bags. Bags 932, 933, 934 as part of the enclosed lines of FIG. 56A may be disposable and made sterile, and may also be separated from the lines after separation process in steps 407 and 408 of FIG. 31, or steps 707 and 708 of FIG. 39.

Figure 56B:
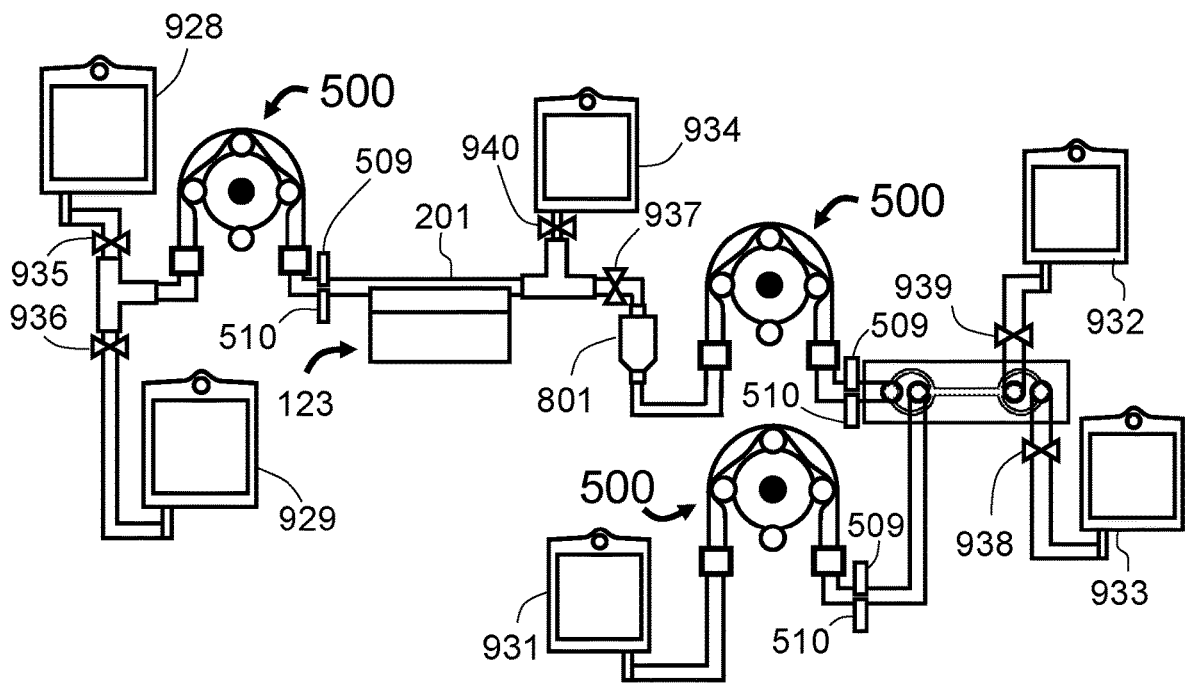
FIG. 56B illustrates fluidic lines of FIG. 56A being connected to, or attached with, various fluidic devices to realize third type sample processing method.

FIG. 56B describes the process of connecting sample container 928, buffer container 929, buffer container 931 to the lines 923, 924 and 9272, respectively, same as in FIG. 55B. Containers 928, 929, 931 are in blood bag form. Also same as described in FIG. 55B, three pump tubings 504/505 are installed on the three peristaltic pumps 500, valves 935, 936, 940, 937, 939, 938, are each attached to the corresponding line, and flow limiter 509/510 may be attached to output line of each pump 500, same as in FIG. 55B.

Figure 57A:
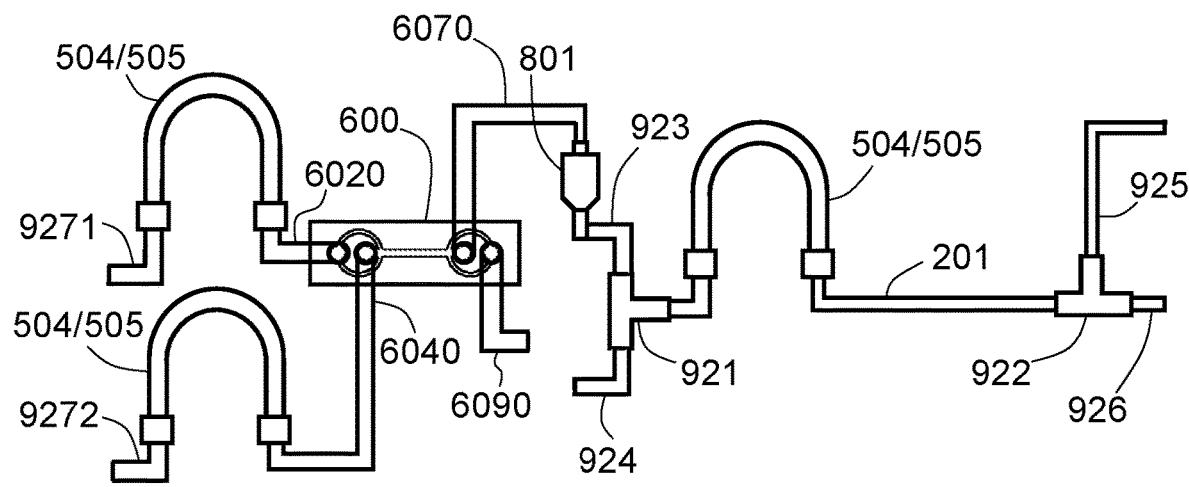
FIG. 57A illustrates example of closed and disposable fluidic lines for first type sample processing method.

FIG. 57A illustrates embodiment of closed and disposable fluidic lines for first type sample processing method shown in FIG. 44A, where connector 801 may be replaced with connector 802 or connector 803 without limitation. Input line 9271 may connect to a UFL sample liquid container, and also connects to inlet of a first pump tubing 504/505, which further connect to entity input line 6020 of UFL 600. Input line 9272 may connect to a UFL buffer container, and also connects to inlet of a second pump tubing 504/505, which further connect to buffer input line 6040 of UFL 600. UFL 600 large entity output line 6070 connects to inlet of connector 801. UFL 600 small entity output line 6090 may connect to a small entity container. Outlet of connector 801 connects to MAG sample input line 923. MAG buffer input line 924 may connect to a MAG buffer container. Input lines 923 and 924 are connected through a T-connector 921 to the inlet of the third pump tubing 504/505. Third pump tubing 504/505 outlet connects to channel 201, which may be used as part of MAG 123. Output of channel 201 connects to T-connector 922, which connects to output line 925 and output line 926. Output lines 925 and 926 may each connect to an MAG output sample container. In one embodiment, output line 925 may output negative entities to a first MAG output sample container, and output line 926 may output positive entities to a second MAG output sample container. FIG. 57A illustrates that besides the input and output lines 9271, 9272, 924, 6090, 925, and 926 that connect to external containers and entire fluid path from UFL sample and UFL buffer to input lines 9271 and 9272 and from sample output to lines 6090, 925 and 926, all pumps, MAG 123 and other fluidic line components will be externally attached to the lines of FIG. 57A. Thus, lines of FIG. 57A are internally enclosed, suitable for single use disposable purpose and sterile applications.

Figure 57B:
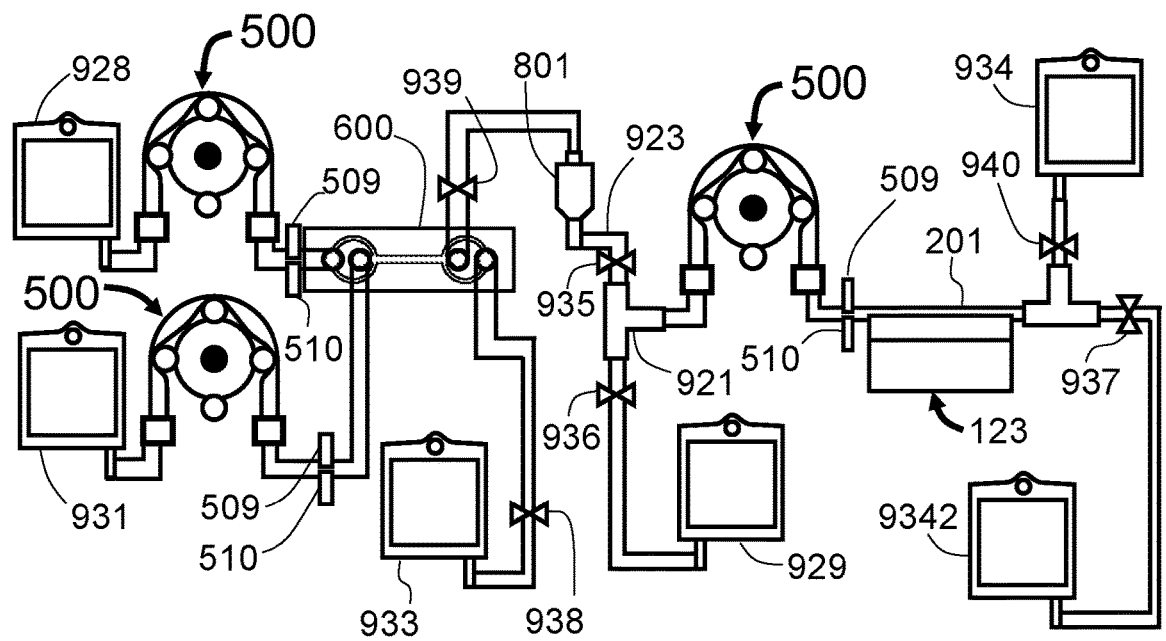
FIG. 57B illustrates fluidic lines of FIG. 57A being connected to, or attached with, various fluidic devices to realize first type sample processing method.

FIG. 57B illustrates fluidic lines of FIG. 57A being connected to, or attached with, various fluidic components. First, second and third pump tubings 504/505 are each installed onto a peristaltic pump 500. Three pumps 500 operate to pump either sample fluid or buffer fluid into MAG 123 and UFL 600. A flow limiter 509/510 may be attached to the output line from each pump 500, including lines 201, 6020, 6040, to reduce flow rate pulsation from the pump 500. Input line 9271 connects to a liquid sample container 928 in blood bag form. Input line 9272 connects to UFL buffer container 931 also in blood bag form. UFL output line 6090 connects to small entity container 933 in blood bag form. Adjustable valves 939 and 938 may be attached to the lines 6070 and 6090 to adjust the flow rate within each of lines 6070 and 6090, which in turn controls the laminar flow speed in UFL 600 channel for channel center buffer flow and channel edge entity sample flow. Input line 924 connects to MAG buffer container 929. Valves 935 and 936 are attached to lines 923 and 924 to control either sample liquid from connector 801 or buffer fluid from container 929 flowed through T-connector 921 into third pump tubing 504/505.

Channel line 201 is mounted onto MAG 123. Output line 925 connects to first MAG output sample container 934. Output line 926 connects to second MAG output sample container 9342. Valve 940 is attached to line 925 and valve 937 is attached to line 926, which control negative entities and positive entities from MAG 123 going into either container 934 or container 9342 through the T-connector 922. Valves 940 and 937 may both shut down the flow in lines 925 and 926 during demagnetization/dissociation process of MAG 123.

Figure 58A:
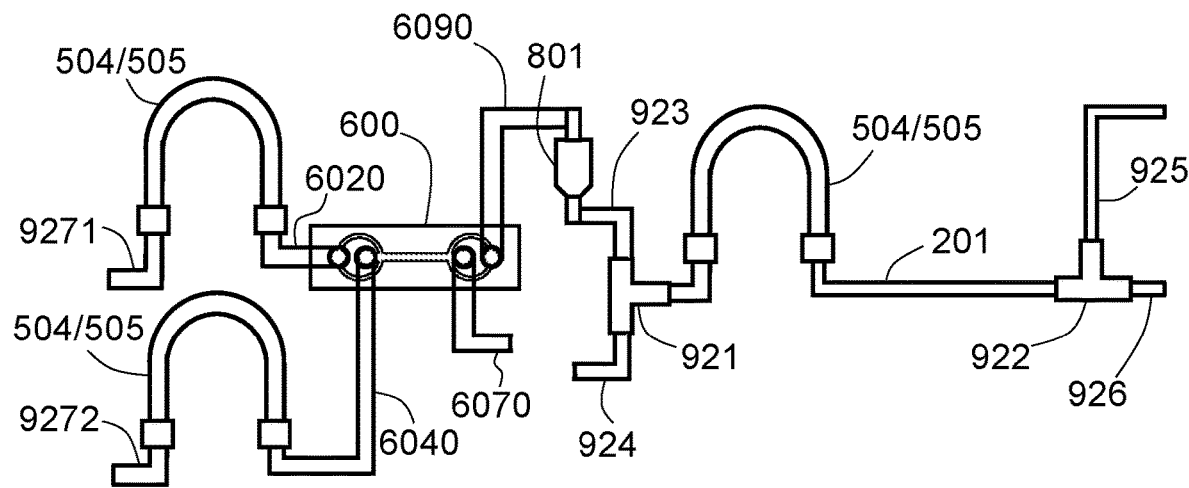
FIG. 58A illustrates example of closed and disposable fluidic lines for second type sample processing method.

FIG. 58A illustrates embodiment of closed and disposable fluidic lines for second type sample processing method shown in FIG. 45A. FIG. 58A is identical to FIG. 57A in every aspect, except the UFL 600 small entity output line 6090 connects to the inlet of the connector 801 instead of the output line 6070 as in FIG. 57A. Large entity output line 6070 of FIG. 58A may connect to a large entity container.

Figure 58B:
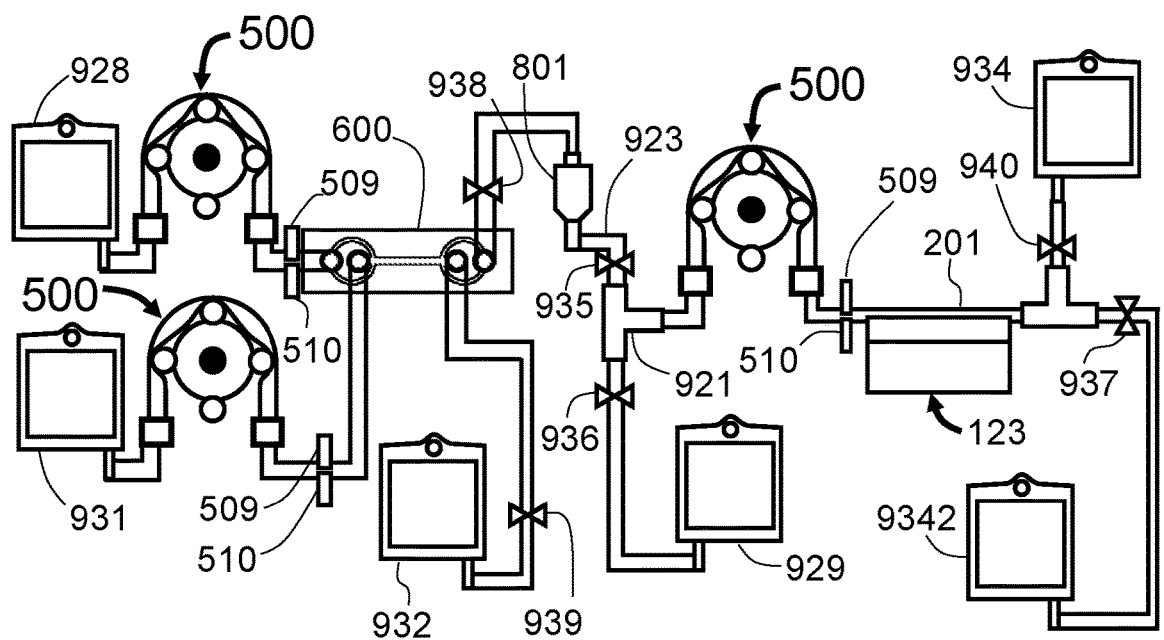
FIG. 58B illustrates fluidic lines of FIG. 58A being connected to, or attached with, various fluidic devices to realize second type sample processing method.

FIG. 58B illustrates fluidic lines of FIG. 58A being connected to, or attached with, various fluidic components. FIG. 58B is identical to FIG. 57B in every aspect, except the UFL 600 small entity output line 6090 connects to the inlet of the connector 801 instead of the output line 6070 as shown in FIG. 57B. Large entity output line 6070 of FIG. 58B connects to a large entity container 932 in blood bag form.

Figure 59A:
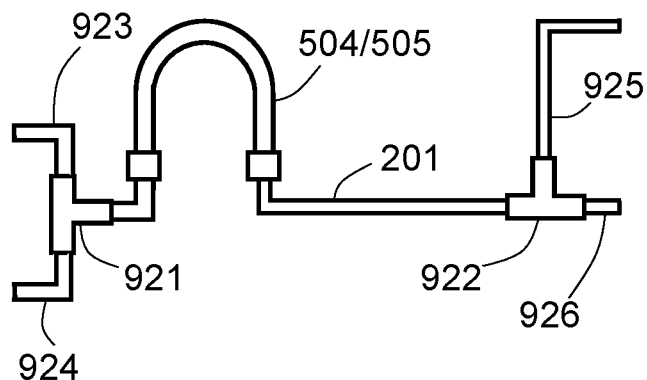
FIG. 59A illustrates example of closed and disposable fluidic lines for sample processing through a single MAG.

FIG. 59A illustrates embodiment of closed and disposable fluidic lines for sample processing through a single MAG. Input line 923 may connect to a sample liquid container. Input line 924 may connect to a MAG buffer container. Input line 923 and input line 924 are connected through a T-connector 921 to the inlet of the pump tubing 504/505 that may be mounted onto a peristaltic pump. Pump tubing 504/505 outlet connects to channel 201 which may be used as part of MAG 123. Output of channel 201 connects to T-connector 922, which connects to output line 925 and output line 926. Output lines 925 and 926 may each connect to an MAG output sample container.

Figure 59B:
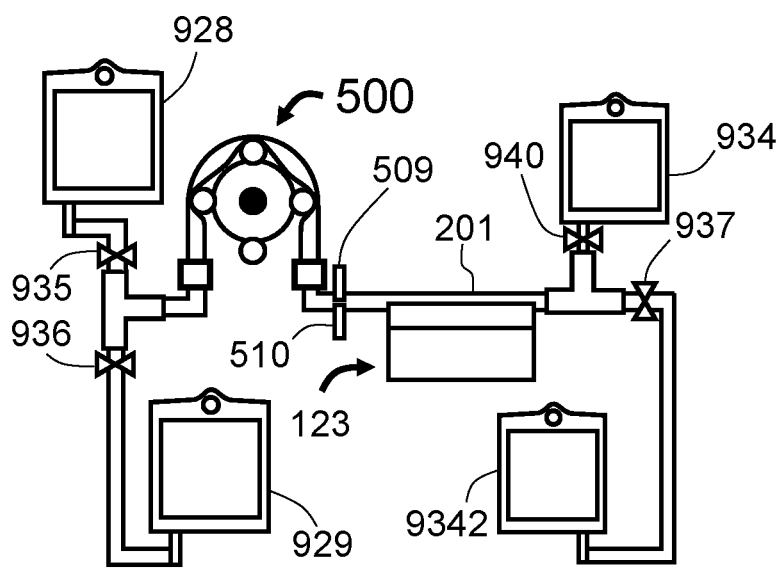

FIG. 59B illustrates fluidic lines of FIG. 59A being connected to, or attached with, various fluidic components. Input line 923 connects to a liquid sample container 928. Input line 924 connects to buffer container 929. Valves 935 and 936 are attached to lines 923 and 924 to control either sample liquid from bag 928 or buffer from container 929 flowed through T-connector 921 into first tubing 504/505. Pump tubing 504/505 is installed into a peristaltic pump 500. Pump 500 operates to pump either sample fluid or buffer fluid into MAG 123. A flow limiter 509/510 may be attached to the output line 201 from pump 500 to reduce flow rate pulsation from the pump 500. Channel line 201 is mounted onto MAG 123. Output line 925 connects to MAG output sample container 934. Output line 926 connects to MAG output sample container 9342. Valve 940 is attached to line 925 and valve 937 is attached to line 926, which control negative entities and positive entities from MAG 123 going into either container 934 or container 9342. Valves 940 and 937 may both shut down the flow in lines 925 and 926 during demagnetization/dissociation process of MAG 123. FIG. 59B shows containers 928, 929, 934 and 9342 may be in the form of blood bags, but they may also be in other physical forms of vial or bottles.

FIG. 60A illustrates embodiment of closed and disposable fluidic lines for sample processing through a single UFL 600. Input line 9271 may connect to a UFL sample liquid container, and also connects to inlet of a first pump tubing 504/505, which further connects to entity input line 6020 of UFL 600. Input line 9272 may connect to a UFL buffer container, and also connects to inlet of a second pump tubing 504/505, which further connects to buffer input line 6040 of UFL 600. UFL 600 large entity output line 6070 may connect to a large entity container. UFL 600 small entity output line 6090 may connect to a small entity container.

FIG. 60B illustrates fluidic lines of FIG. 60A being connected to, or attached with, various fluidic components. First and second pump tubings 504/505 are each installed into a peristaltic pump 500. The two pumps 500 operate to pump sample fluid and buffer fluid into UFL 600. A flow limiter 509/510 may be attached to the output line from each pump 500, including lines 6020 and 6040, to reduce flow rate pulsation from the pump 500. Input line 9271 connects to a liquid sample container 928. Input line 9272 connects to UFL buffer container 931. UFL output line 6070 connects to large entity container 932. UFL output line 6090 connects to small entity container 933. Adjustable valves 939 and 938 may be attached to the lines 6070 and 6090 to adjust the flow rate within each of lines 6070 and 6090, which in turn controls the laminar flow speed in UFL 600 channel for channel center buffer flow and channel edge entity sample flow. FIG. 60B shows containers 928, 931, 932 and 933 may be in the form of blood bags, but they may also be in other physical forms of vial or bottles without limitation.

Figure 61A:
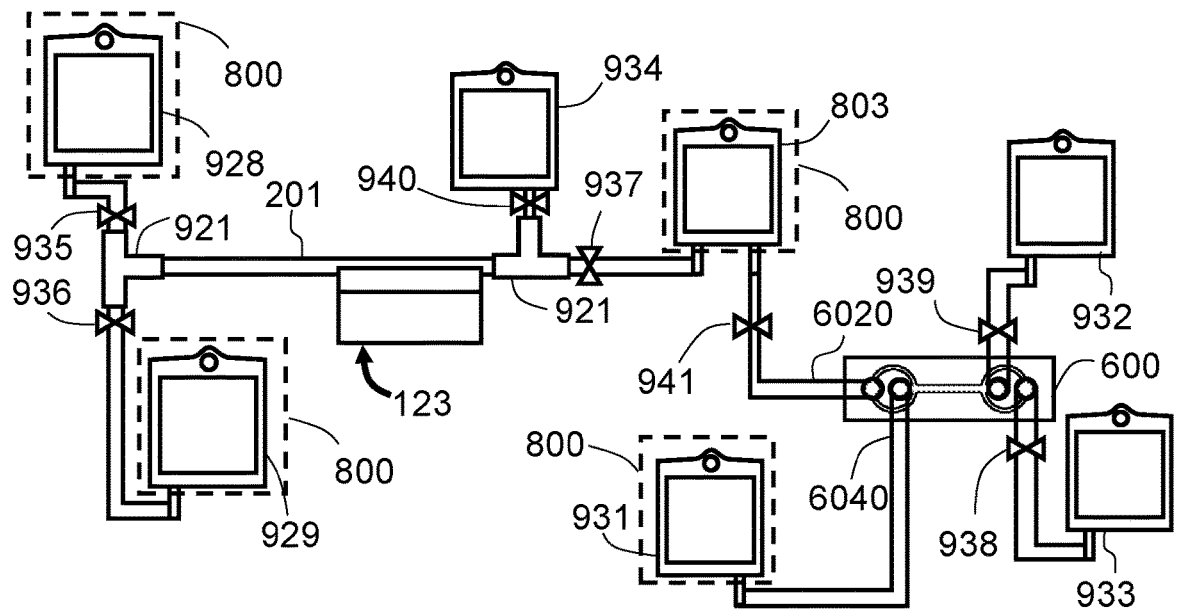

FIG. 61A illustrates replacement of peristaltic pumps of FIG. 56B with pressurized chambers 800 on input sample bags to drive fluid through fluidic lines. In FIG. 61A, pumps 500, pump tubings 504/505, and flow limiters 509/510 of FIG. 56B are removed. Channel 201 is connected directly to T-connector 921. Connector 801 is replaced with connector 803 bag. UFL entity liquid line 6020 is connected to connector 803. Sample liquid bag 928, MAG buffer bag 929, connector 803 bag and UFL buffer bag 931 are each enclosed in a pressure chamber 800. Pressure chamber 800 may operate by increasing pressure of chamber medium, for example air or other fluid, where the bags enclosed in chambers are submerged in the chamber medium. With increase in chamber medium pressure, liquid contained in the bags may be forced out of the bags and into the fluid lines. FIG. 61A operation may need separate MAG 123 and UFL 600 operations. At first stage, valve 941 attached to line 6020 closes. Pressure in chambers 800 enclosing bags 803 and 931 is released. Pressures in chambers 800 enclosing bags 928 and 929 are increased to force sample fluid or buffer fluid into channel 201 to start MAG 123 separation. After MAG 123 separation and sample fluid in bag 928 is depleted, bag 934 and connector 803 are each filled with output samples from MAG 123 after MAG separation. Then, at second stage, valve 937 is closed and valve 941 is opened. Chambers 800 around connector 803 and bag 931 increase pressure to force connector 803 sample and buffer fluid in 931 to flow into the UFL 600 to start UFL separation. After sample in connector 803 is depleted, and UFL 600 separation is finished, bags 932 and 933 contain large and small entities from UFL output. Connector 803 maybe replaced by connector 8020 of FIG. 52 which has an air port 8023.

Figure 61B:
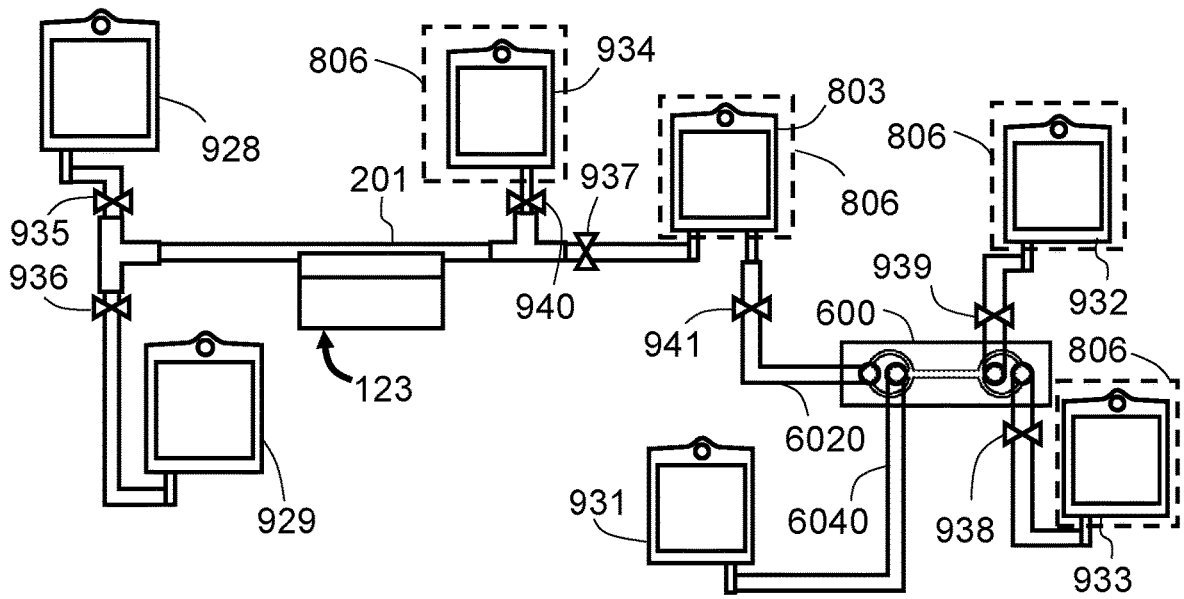

FIG. 61B illustrates replacement of peristaltic pumps of FIG. 56B with vacuum chambers 806 on output sample bags to drive fluid through fluidic lines. FIG. 61B is same as FIG. 61A, except pressure chambers 800 are removed. Bag 934, 932, 933, and connector 803 are each enclosed in a vacuum chamber 806. Vacuum chamber 806 may operate by increasing vacuum level within each chamber 806, where fluid from the fluid lines connected to the bags is forced into the bags enclosed in chambers due to fluid line pressure being larger than the vacuum pressure. FIG. 61B operation may also need separate MAG 123 and UFL 600 operations. At first stage, valve 941 attached to line 6020 closes. Vacuum in chambers 806 enclosing bags 932 and 933 is released. Vacuum in chambers 806 enclosing bags 934 and 803 are increased to force sample fluid or buffer fluid into channel 201 to start MAG 123 separation. After MAG 123 separation and sample fluid in bag 928 is depleted, bag 934 and connector 803 are each filled with output samples from MAG 123 after MAG separation. Then, at second stage, valve 937 is closed and valve 941 is opened. Vacuum in chamber 806 around connector 803 is released. Vacuums in chambers 806 enclosing bags 932 and 933 are increased to force connector 803 sample and buffer fluid in container 931 to flow into the UFL 600 to start UFL separation. After sample in connector 803 is depleted, and UFL 600 separation is finished, bags 932 and 933 contain large and small entities from UFL output. Connector 803 maybe replaced by connector 8020 of FIG. 52 which has an air port 8023.

Figure 62A:
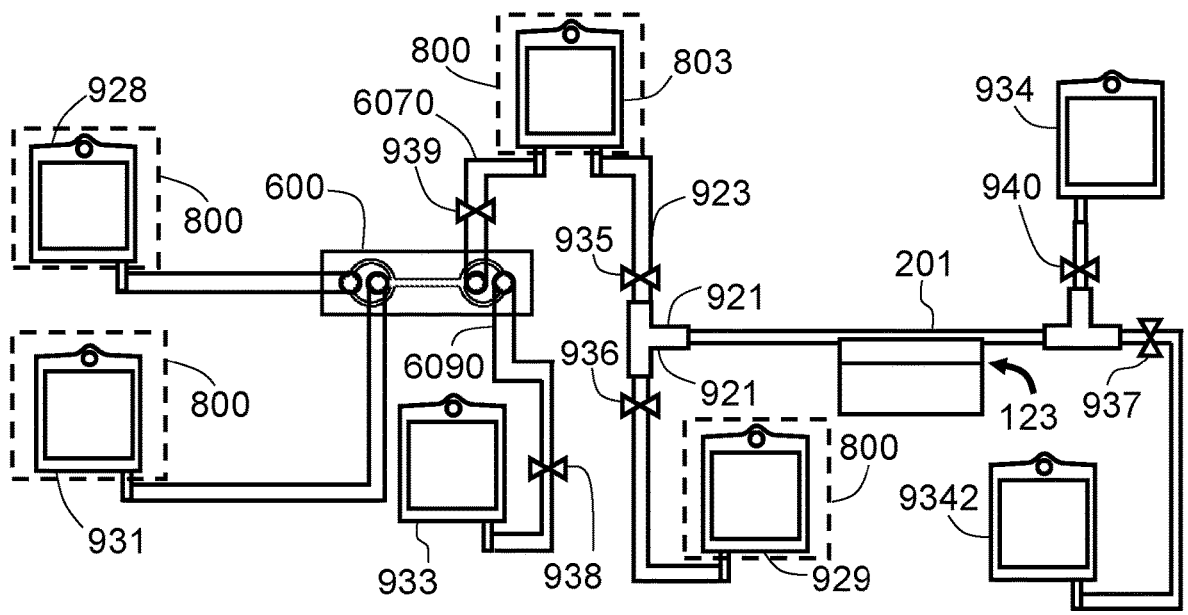

FIG. 62A illustrates replacement of peristaltic pumps of FIG. 57B with pressurized chambers 800 on input sample bags to drive fluid through fluidic lines. In FIG. 62A, pumps 500, pump tubings 504/505, and flow limiters 509/510 of FIG. 57B are removed. Channel 201 is connected directly to T-connector 921. Connector 801 is replaced with connector 803 bag. MAG sample line 923 is connected to connector 803. Sample liquid bag 928, MAG buffer bag 929, connector 803 bag and UFL buffer bag 931 are each enclosed in a pressure chamber 800. FIG. 62A may separate UFL 600 and MAG 123 operations. At first stage, valve 935 attached to line 923 closes. Pressure in chamber 800 enclosing bag 803 is released. Pressures in chambers 800 enclosing bags 928 and 931 are increased to force sample fluid and UFL buffer fluid into UFL 600 inlets to start UFL 600 separation. After UFL 600 separation and sample fluid in bag 928 is depleted, bag 933 contains small entity fluid and connector 803 contains large entity fluid from UFL 600 separation. Then, at second stage, valve 939 is closed and valve 935 is opened. Chambers 800 around connector 803 and bag 929 increase in pressure to force connector 803 large entity fluid sample or MAG buffer fluid in bag 929 to flow into channel 201 of MAG 123 to start MAG 123 separation. After sample in connector 803 is depleted, and MAG 123 separation is finished, bags 934 and 9342 contain positive sample and negative sample from MAG 123 channel 201 output. Connector 803 maybe replaced by connector 8020 of FIG. 52.

Figure 62B:
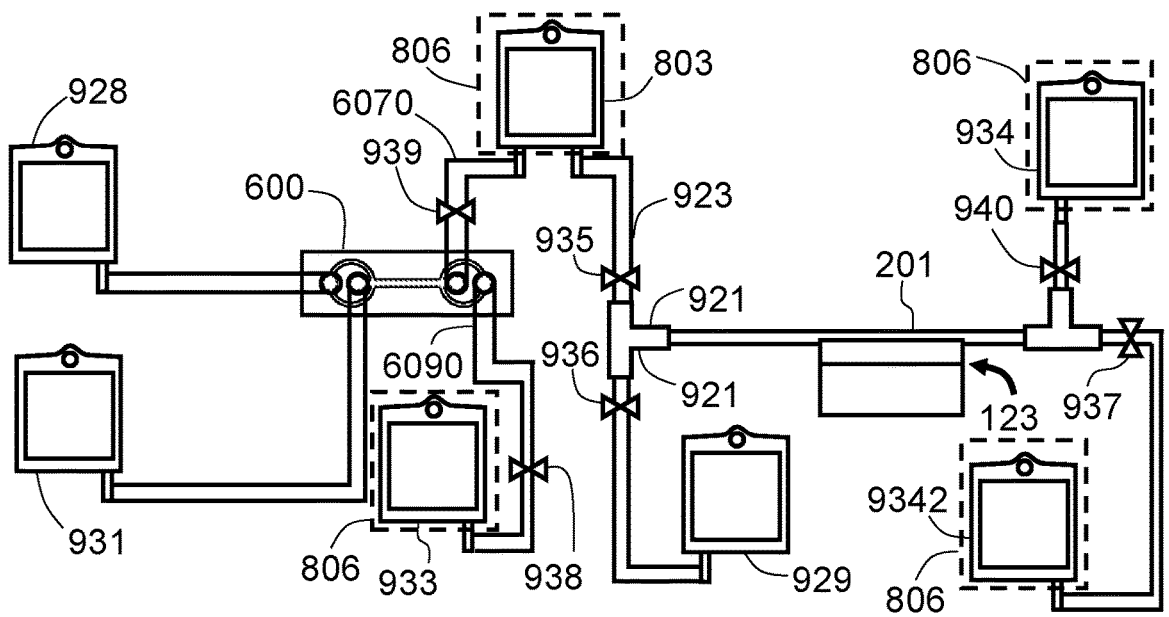

FIG. 62B illustrates replacement of peristaltic pumps of FIG. 57B with vacuum chambers 806 on output sample bags to drive fluid through fluidic lines. FIG. 62B is same as FIG. 62A, except pressure chambers 800 are removed. Bag 934, 9342, 933, and connector 803 are each enclosed in a vacuum chamber 806. FIG. 62B operation may separate MAG 123 and UFL 600 operations. At first stage, valve 935 attached to line 923 closes. Vacuum in chambers 806 enclosing bags 933 and 803 are increased to force sample fluid and UFL buffer fluid into inlets of UFL 600 to start UFL 600 separation. After UFL 600 separation and sample fluid in bag 928 is depleted, bag 933 contains small entity fluid and connector 803 contains large entity fluid from UFL 600 separation. Then, at second stage, valves 938 and 939 are closed and valve 923 is opened. Vacuum in chamber 806 around connector 803 is released. Vacuums in chambers 806 enclosing bags 934 and 9342 are increased to force connector 803 large entity sample or MAG buffer fluid in bag 929 to flow into channel 201 of MAG 123 to start MAG 123 separation. After sample in connector 803 is depleted, and MAG 123 separation is finished, bags 934 and 9342 contain positive sample and negative sample from MAG 123 channel 201 output. Connector 803 maybe replaced by connector 8020 of FIG. 52.

Figure 63A:
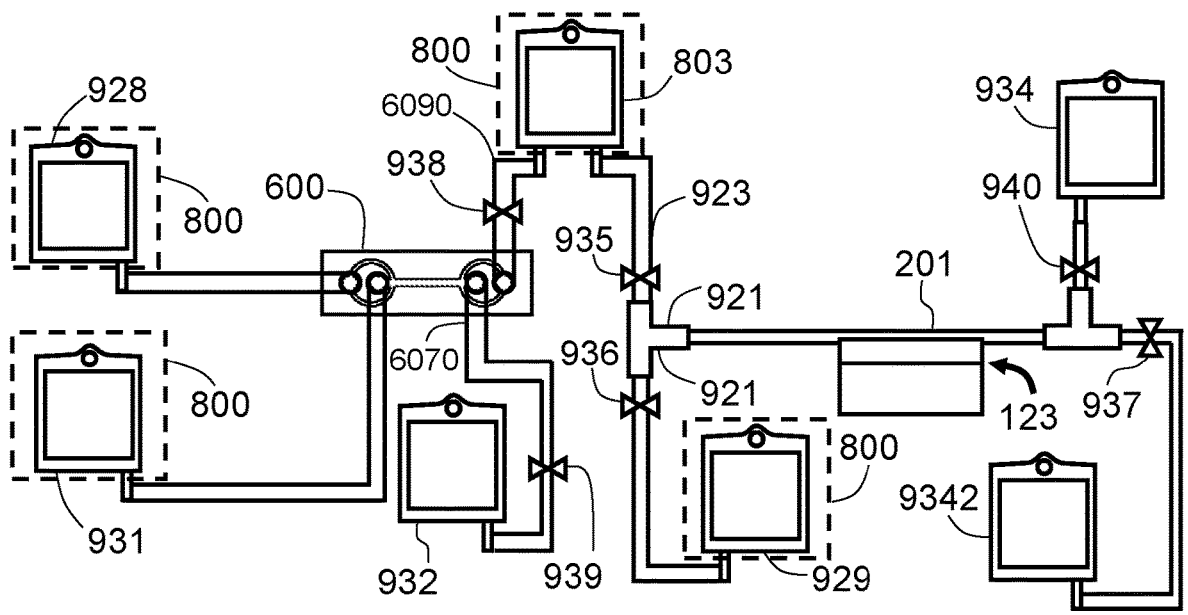

FIG. 63A illustrates replacement of peristaltic pumps of FIG. 58B with pressurized chambers 800 on input sample bags to drive fluid through fluidic lines. FIG. 63A is identical to FIG. 62A in fluid line layout and in operation of UFL 600 and MAG 123 with chambers 800, except that the UFL large entity output 6070 connects to large entity container 932 in blood bag form, and small entity output 6090 connects to connector 803.

Figure 63B:
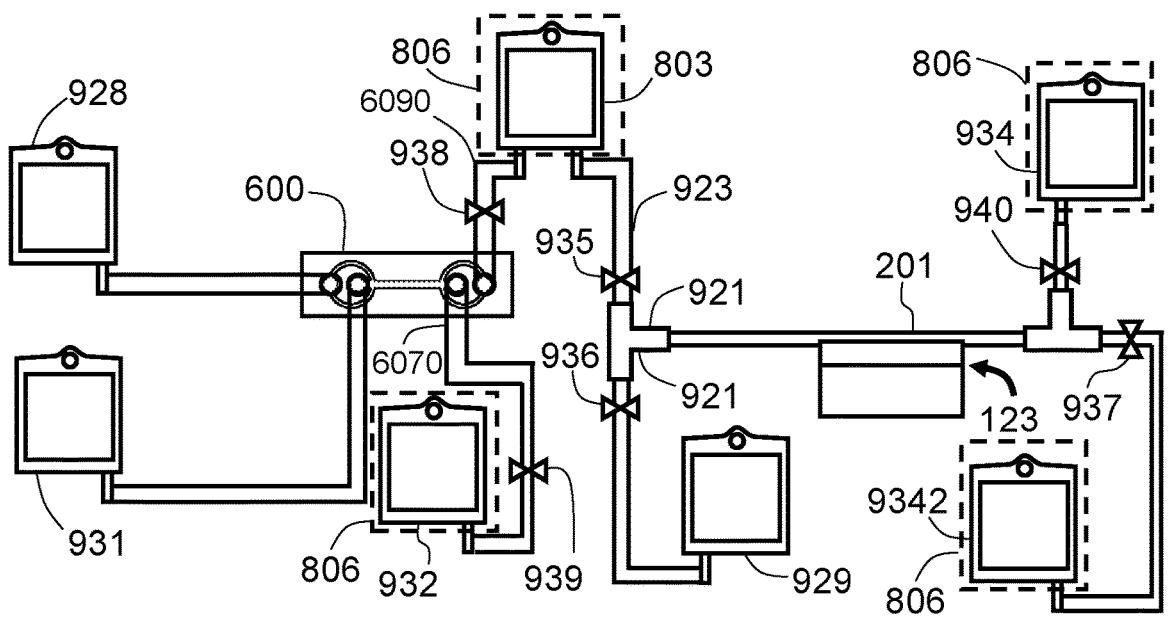

FIG. 63B illustrates replacement of peristaltic pumps of FIG. 58B with vacuum chambers 806 on output sample bags to drive fluid through fluidic lines. FIG. 63B is identical to FIG. 62B in fluid line layout and in operation of UFL 600 and MAG 123 with chambers 806, except that the UFL large entity output 6070 connects to large entity container 932 in blood bag form with large entity container 932 enclosed in vacuum chamber 806 replacing container 933 of FIG. 62B, and small entity output 6090 connects to connector 803.

Figure 64A:
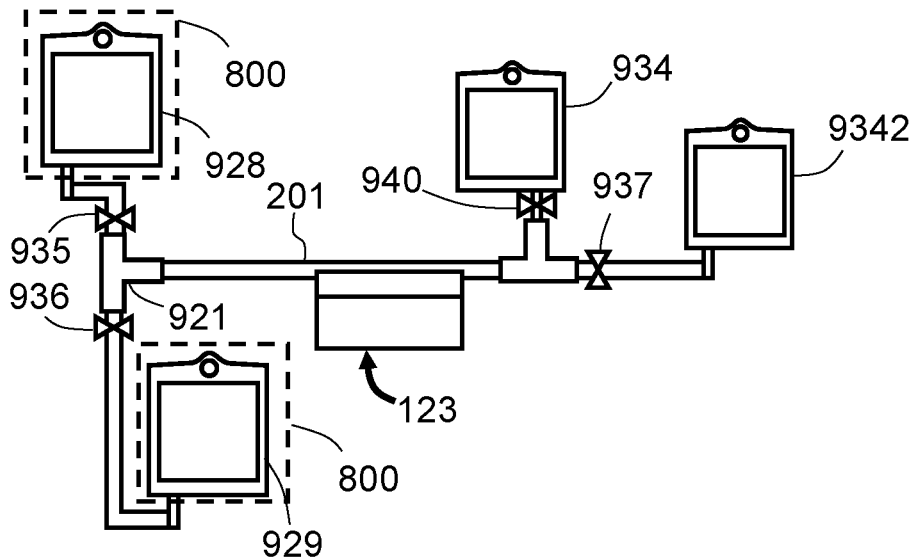

FIG. 64A illustrates replacement of peristaltic pumps of FIG. 59B with pressurized chambers 800 on input sample bags 928 and 929 to drive fluid through channel 201 of MAG 123. In FIG. 64A, pump 500, pump tubing 504/505, and flow limiter 509/510 of FIG. 59B are removed. Channel 201 is connected directly to T-connector 921. Sample liquid bag 928 and MAG buffer bag 929 are each enclosed in a pressure chamber 800. Pressures in chambers 800 enclosing bags 928 and 929 are increased to force sample fluid or buffer fluid into channel 201 to start MAG 123 separation. After MAG 123 separation and sample fluid in bag 928 is depleted, bag 934 and bag 9342 are each filled with either negative entities or positive entities from MAG 123 after MAG separation.

Figure 64B:
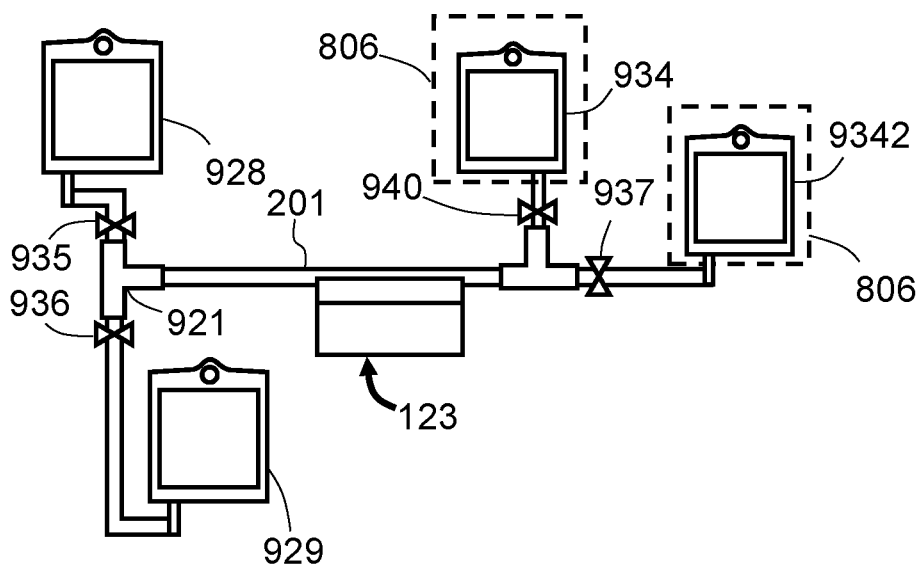

FIG. 64B illustrates replacement of peristaltic pumps of FIG. 59B with vacuum chambers 806 on output sample bags 934 and 9342 to drive fluid through channel 201 of MAG 123. FIG. 64B is same as FIG. 64A, except pressure chambers 800 are removed. Output sample bags 934 and 9342 are each enclosed in a vacuum chamber 806. Vacuums in chambers 806 enclosing bags 934 and 9342 are increased to force entity sample from bag 928 or MAG buffer fluid from bag 929 to flow into channel 201 of MAG 123 to start MAG 123 separation. After sample in bag 928 is depleted, and MAG 123 separation is finished, bags 934 and 9342 contain positive sample and negative sample from MAG 123 channel 201 output.

FIG. 65A illustrates replacement of peristaltic pumps of FIG. 60B with pressurized chambers 800 on sample liquid bag 928 and UFL buffer bag 931 to drive fluid through UFL 600. In FIG. 65A, pump 500, pump tubing 504/505, and flow limiter 509/510 of FIG. 60B are removed. Sample liquid bag 928 and UFL buffer bag 931 are each enclosed in a pressure chamber 800. Pressures in chambers 800 enclosing bags 928 and 931 are increased to force sample fluid and UFL buffer fluid into UFL 600 inlets to start UFL 600 separation. After UFL 600 separation, sample fluid in bag 928 is depleted, bag 932 contains large entity fluid and bag 933 contains small entity fluid.

FIG. 65B illustrates replacement of peristaltic pumps of FIG. 60B with vacuum chambers 906 on output sample bags 932 and 933 to drive fluid through UFL 600. FIG. 65B is same as FIG. 65A, except pressure chambers 800 are removed. Output sample bags 932 and 933 are each enclosed in a vacuum chamber 806. Vacuums in chambers 806 enclosing bags 932 and 933 are increased to force sample liquid from bag 928 and UFL buffer fluid from bag 931 to flow through UFL 600 to start UFL separation. After sample in bag 928 is depleted, and UFL 600 separation is finished, bag 932 contains large entity fluid and bag 933 contains small entity fluid.

Structures, components, and methods as described from FIG. 55A through FIG. 65B on enclosed fluidic lines including one UFL 600 and one MAG 123, may be applied to FIG. 47 through FIG. 52 without limitation, where enclosed fluidic lines including multiple MAGs 123 and multiple UFLs 600 may be achieved by replicating the components on single UFL 600 and single MAG 123 from FIG. 55A through FIG. 65B on each of the UFLs 600 and MAGs 123 of FIG. 47 through FIG. 52.

FIG. 66 through FIG. 88 illustrate embodiments of process flows to utilize MAG and UFL devices to separate biological entities from various biological samples. For simplicity of description, terms UFL and MAG are used in these figures for explanation. However, UFL may be any of UFL 600, 650, 620, 630, 640 of FIG. 40A, FIG. 41A, FIG. 42A, FIG. 43, while MAG may be any of MAG 121, 122, 123, 124, 124,125, 126, 127, 128, 129 with corresponding channel types as described in prior figures without limitation and without sacrifice of performance. If a component, or a structure, in FIG. 66 through FIG. 88 shares same name with another component or structure in prior figures, it then means the same component, or same structure as that in prior figures.

FIG. 66 illustrates embodiment of a first process flow to separate biological entities from peripheral blood using UFL and MAG. In step 5801, peripheral blood sample is collected from a patient or person under test. In step 5802, red blood cell lysing may be performed on said peripheral blood sample, where step 5802 in another embodiment may be skipped. In step 5803, said blood sample from step 5802, or directly from step 5801, is injected into UFL entity fluid inlet 602, while UFL buffer fluid is injected into outlet 604. In step 5804, frequency and vibration strength of PZT attached to UFL are set to produce a standing wave and pressure nodes in UFL fluid. In step 5805, UFL outlet 607 outputs target sample that contains large size entities or cells. In step 5806, magnetic labels hybridized with antibodies or ligands, which specifically bind to surface antigens or receptors on target cells or entities, are added into target sample from step 5805. In step 5807, target sample from step 5806 is incubated to form magnetic labels binding to target cells or entities. In step 5808, target sample from step 5807 is flowed through MAG channel at magnetic separation positon, where during step 5808, negative MAG sample may be forwarded as in step 5815 to be collected in step 5813. In step 5809, target cells or entities bound with magnetic label are separated by MAG within the MAG channel; in step 5810, after step 5809, buffer fluid may be flowed through MAG channel to wash out residual non-target entities without magnetic labels. The washed out fluid may be forwarded as in step 5816 to be collected as negative MAG sample in step 5813. Step 5810 may be skipped in another embodiment. In step 5811, after step 5810 or directly after step 5809, separated entity conglomerate in MAG channel may be dissociated into isolated cells or entities. In step 5812, buffer fluid is flowed through MAG channel to wash out dissociated cells and entities in MAG channel, which, as shown by path 5817, may be collected as positive MAG sample in step 5814.

Peripheral blood sample of FIG. 66 may also be other body fluids, including but not limited to: saliva, tear, mucus, urine, secretion from various organs of body.

FIG. 67 illustrates an embodiment of second process flow to separate biological entities from peripheral blood using MAG. Every other aspect of FIG. 67 is same as FIG. 66, except step 5803, step 5804, and step 5805 of FIG. 66 are removed between step 5802 and step 5806 in FIG. 67. While in FIG. 67, blood sample from step 5802, or blood sample directly from step 5801, is centrifuged in step 6201 to extract target sample containing white blood cells. Target sample form step 6201 is then sent to step 5806. From step 5806, process flow in FIG. 67 is same as that in FIG. 66.

FIG. 68 illustrates an embodiment of third process flow to separate biological entities from peripheral blood using MAG. Every other aspect of FIG. 68 is same as FIG. 66, except step 5803, step 5804, and step 5805 of FIG. 66 are removed between step 5802 and step 5806 in FIG. 68. In FIG. 68, peripheral blood sample collected from patient or person under test in step 6301, which is same as step 5801 of FIG. 66, is regarded as target sample. Target sample from step 5802 after red blood cell lysing, which is after step 6301, or directly from step 6301, is then sent to step 5806. From step 5806, process flow in FIG. 68 is same as that in FIG. 66.

FIG. 69 illustrates an embodiment of fourth process flow to separate biological entities from peripheral blood using MAG. Every other aspect of FIG. 69 is same as FIG. 66, except step 5801, step 5802, step 5803, step 5804, and step 5805 of FIG. 66 are removed before step 5806 in FIG. 69. In FIG. 69, target sample is collected after apheresis of peripheral blood sample collected from patient or person under test. Target sample from step 6401 is then sent to step 5806. From step 5806, process flow in FIG. 69 is same as that in FIG. 66.

FIG. 70 illustrates an embodiment of fifth process flow to separate biological entities from tissue sample using UFL and MAG. Every other aspect of FIG. 70 is same as FIG. 66, except step 5801, step 5802, and step 5803 are removed before step 5804 in FIG. 70. In FIG. 70, tissue sample is collected in step 6501. In step 6502, tissue sample from step 6501 is dissociated in a fluid base. In step 6503, dissociated tissue fluid of step 6502 is injected into UFL channel through inlet 602 and UFL buffer fluid is injected through inlet 604. From step 5804, process flow in FIG. 70 is same as that in FIG. 66. Tissue sample of FIG. 70 may include any of: human body tissue aspirate, human organ tissue aspirate, bone marrow, animal body or organ tissue aspirate. Target cells or entities of FIG. 70 may be rare disease cells, for example cancer cells, or micro-organisms, for example bacteria.

FIG. 71 illustrates an embodiment of sixth process flow to separate biological entities from tissue sample using MAG. Every other aspect of FIG. 71 is same as FIG. 70, except step 6503, step 5804, and step 5805 are removed before step 5806 in FIG. 71. In FIG. 71, tissue sample from step 6501 is dissociated in a fluid base in step 6502 to form target sample, and process continues to step 5806. From step 5806, process flow in FIG. 71 is same as that in FIG. 70.

FIG. 72 illustrates an embodiment of seventh process flow to separate biological entities from surface swab sample using UFL and MAG. Every other aspect of FIG. 72 is same as FIG. 66, except step 5801, step 5802, and step 5803 are removed before step 5804 in FIG. 72. In FIG. 72, surface entities are collected in step 6701 by swab. In step 6702, surface entities collected on swab are dissolved in a fluid base. In step 6703, fluid base with dissolved surface entities from step 6702 is injected into UFL channel through inlet 602 and UFL buffer fluid is injected through inlet 604. From step 5804, process flow in FIG. 72 is same as that in FIG. 66.

Surface entities of FIG. 72 may be collected by swab from subjects including any of: human body, saliva, body fluid, human body discharge, animal, plant, soil, air, water, and merchandise. Target cells or entities of FIG. 72 may include cells from human body, or animal body, or plant, or include micro-organisms, for example bacteria, mold, or spores.

FIG. 73 illustrates an embodiment of eighth process flow to separate biological entities from surface swab sample using MAG. Every other aspect of FIG. 73 is same as FIG. 72, except step 6703, step 5804, and step 5805 are removed before step 5806 in FIG. 73. In FIG. 73, surface entities collected on swab in step 6701 are dissolved in a fluid base in step 6702 to form target sample, and process continues to step 5806. From step 5806, process flow in FIG. 73 is same as that in FIG. 72.

FIG. 74 illustrates an embodiment of ninth process flow to separate biological entities from solid sample using UFL and MAG. Every other aspect of FIG. 74 is same as FIG. 66, except step 5801, step 5802, and step 5803 are removed before step 5804 in FIG. 74. In FIG. 74, solid sample is collected in step 6901. In step 6902, solid sample from step 6901 is dissociated in a fluid base. In step 6903, dissociated solid sample fluid of step 6902 is injected into UFL channel through inlet 602 and UFL buffer fluid is injected through inlet 604. From step 5804, process flow in FIG. 74 is same as that in FIG. 66. Solid sample of FIG. 74 may include any of: solid biological products or waste generated by human, animal, or plant, powder, and soil. Target cells or entities of FIG. 74 may include cells from human body, or animal body, or plant, or include micro-organisms, for example bacteria, mold, or spores.

FIG. 75 illustrates an embodiment of tenth process flow to separate biological entities from solid sample using MAG. Every other aspect of FIG. 75 is same as FIG. 74, except step 6903, step 5804, and step 5805 are removed before step 5806 in FIG. 75. In FIG. 75, solid sample from step 6901 is dissociated in a fluid base in step 6902 to form target sample, and target sample is continuously processed in step 5806. From step 5806, process flow in FIG. 75 is same as that in FIG. 74.

FIG. 76A illustrates addition of both magnetic and fluorescent labels into fluid samples for specific binding to target cells or entities. FIG. 76A shows that step 5806 of FIG. 66 through FIG. 75 may be modified to become step 58061, where in addition to magnetic labels, fluorescent labels hybridized with antibodies or ligands, which specifically bind to surface antigens or receptors on target cells or entities, may also be added in target sample from step 5805.

FIG. 76B then illustrates that incubation step 5807 of FIG. 66 through FIG. 75 may also be modified to become step 58071, which includes incubation of both magnetic and fluorescent labels at the same time to form specific binding to target cells or entities. Binding sites of magnetic labels and fluorescent labels on same target cells or entities may be different.

Steps 5806 and step 58061 may be realized in a flow connector including any one of 801, 802, 803, 8010, 8020, 8030 of prior figures, where flow connector may contain pre-filled hybridized magnetic labels and fluorescent labels in liquid solution, or in dry powder form. Step 5807 and step 58071 may also occur in said flow connector, where said flow connector may also be located in a temperature control chamber to control incubation speed and quality. In another embodiment, said flow connector may have attached or embedded temperature control circuit to control incubation in flow connector.

FIG. 77A illustrates process of removing non-bound free magnetic labels from sample fluid by UFL before magnetic separation by MAG. FIG. 77A shows that for each of FIG. 66 through FIG. 75, step 5818 and step 5819 may be added between step 5807 and step 5808. After target sample is incubated in step 5807, in step 5818, target sample may be injected into second UFL through inlet 602, and buffer fluid may be injected into second UFL through inlet 604. In step 5819, second UFL outputs target sample containing large entities from outlet 607, and non-bound free magnetic labels are output from second UFL outlet 609. Then in step 5808, target sample containing large entities from second UFL outlet 607 is passed through MAG channel for magnetic separation. Target sample in step 5819 may contain cells 10/30 or entities bound with magnetic labels. Second UFL having an attached PZT that operates with a specified ultrasound vibration amplitude and frequency to create a standing wave in second UFL channel fluid is assumed in step 5819.

FIG. 77B illustrates process of removing non-bound free magnetic labels from sample fluid by UFL after magnetic separation by MAG. FIG. 77B shows that for each of FIG. 66 through FIG. 75, step 5820 and step 5821 may be added between step 5812 and step 5814, replacing path 5817. After magnetic conglomerate within MAG channel is dissociated and the positive MAG sample entities from MAG channel are flushed out as in step 5812, flushed out positive MAG sample may be injected into third UFL through inlet 602, and buffer fluid may be injected into third UFL through inlet 604. In step 5821, third UFL outputs positive MAG sample containing large entities from outlet 607, and non-bound free magnetic labels are output from third UFL outlet 609. Then in step 5814, positive MAG sample with reduced or depleted free magnetic labels may be collected. Third UFL having an attached PZT that operates with a specified ultrasound vibration amplitude and frequency to create a standing wave in third UFL channel fluid is assumed in step 5821.

FIG. 78A illustrates process of removing non-bound free magnetic labels and free fluorescent labels from sample fluid by UFL before magnetic separation by MAG. FIG. 78A is similar to FIG. 77A, with step 5807 of FIG. 77A being replaced by step 58071 of FIG. 76B, and step 5819 being replaced by step 58191. After adding magnetic labels and fluorescent labels into target sample as in step 58061 of FIG. 76A, target sample is incubated in step 58071, same as in FIG. 76B, to form magnetic label and fluorescent label binding to target cells or entities. In step 5818, target sample may be injected into second UFL through inlet 602, and buffer fluid may be injected into second UFL through inlet 604. In step 58191, second UFL outputs target sample containing large entities from outlet 607, and non-bound free magnetic labels and free fluorescent labels are output from second UFL outlet 609. Then in step 5808, target sample containing large entities from second UFL outlet 607 is flown through MAG channel for magnetic separation. Target sample in step 58191 may contain cells 30 or entities bound with magnetic and fluorescent labels. Second UFL having an attached PZT that operates with a specified ultrasound vibration amplitude and frequency to create a standing wave in second UFL channel fluid is assumed in step 58191.

FIG. 78B illustrates process of removing non-bound free magnetic labels and free fluorescent labels from sample fluid by UFL after magnetic separation by MAG. FIG. 78B is similar to FIG. 77B, with step 5821 of FIG. 77A being replaced by step 58211. Separated entities in step 5812 and step 5820 of FIG. 78B may contain: cells 30 or entities bound with magnetic and fluorescent labels, non-bound free magnetic labels, and small amount of non-bound free fluorescent labels due to non-specific binding to conglomerate in MAG channel during magnetic separation. In step 58212, third UFL outputs positive MAG sample containing large entities from outlet 607, and non-bound free magnetic and free optical labels are output from third UFL outlet 609. Then in step 5814, positive MAG sample with reduced or depleted free magnetic labels and free fluorescent labels may be collected. Third UFL having an attached PZT that operates with a specified ultrasound vibration amplitude and frequency to create a standing wave in third UFL channel fluid is assumed in step 58212.

FIG. 79 illustrates continued process of negative MAG sample after MAG separation, as in step 408 of FIG. 31, through UFL to remove small entities and passing of large entities into various cell processing devices and procedures. Step 5813 is same as that in FIG. 66 through FIG. 75, where negative MAG sample is collected during MAG separation of a target sample. In step 5822, negative MAG sample of step 5813 is injected into fourth UFL inlet 602, and UFL buffer is injected into inlet 604 of fourth UFL. In step 5823, fourth UFL outputs negative MAG sample containing large entities from outlet 607, and small size entities are removed from large entities and output from fourth UFL outlet 609, and a PZT that attaches to fourth UFL and operates with a specified ultrasound vibration amplitude and frequency to create a standing wave in fourth UFL is assumed to be used. Finally, negative MAG sample containing large entities from outlet 607 of fourth UFL may be sent to be analyzed by any of: cell counter 903, cell imager 904, flow cytometer or sorter 905, DNA/RNA sequencer 906. Alternatively, output from cell counter 903, or output from cell imager 904, or output from flow cytometer or sorter 905, may be further sent to be processed by DNA/RNA sequencer 906 as indicated respectively by paths 936, 946, and 956. Negative MAG sample containing large entities from outlet 607 of fourth UFL in step 5823 may also be sent into the process of cell genetic modification and cell expansion 5824. Prior to DNA/RNA sequencing in DNA/RNA sequencer 906, a polymerase chain reaction (PCR) procedure on DNA/RNA sample obtained from cell lysing of large size entities from outlet 607 of fourth UFL from step 5823 may be performed, where PCR may be targeting one or more target DNA/RNA sequences and amplifies the number of target DNA/RNA sequences in the DNA/RNA sample.

FIG. 80 illustrates continued process of negative MAG sample after MAG separation, as in step 408 of FIG. 31, through UFL to retrieve small entities and passing of small entities into various molecule or small entity processing devices. After step 5813 of FIG. 66 through FIG. 75, where negative MAG sample is collected during MAG separation of a target sample, in step 5822, negative MAG sample of step 5813 is injected into fourth UFL inlet 602, and UFL buffer is injected into inlet 604 of fourth UFL. In step 5825, fourth UFL outputs negative MAG sample containing large entities from outlet 607, and small size entities including DNA, RNA, molecules, and other small particles are output from fourth UFL outlet 609, and a PZT that attaches to fourth UFL and operates with a specified ultrasound vibration amplitude and frequency to create a standing wave in fourth UFL is assumed to be used. Finally, small size entities from outlet 609 of fourth UFL may be sent to be analyzed by any of: particle counter 5835, particle imager 5836, flow cytometer or sorter 905, DNA/RNA sequencer 906. Alternatively, output from particle counter 5835, or output from particle imager 5836, or output from flow cytometer or sorter 905, may be further sent to be processed by DNA/

RNA sequencer 906 as indicated respectively by paths 5827, 5828, and 956. DNA/RNA sequencer 906 may contain a PCR step on small size entities from outlet 609 of fourth UFL from step 5825 prior to DNA/RNA sequencing, where PCR may target one or more particular DNA/RNA sequences to amplify their quantity.

FIG. 81 illustrates entity analysis of negative MAG sample after MAG separation, as in step 407 of FIG. 31, using various analyzing devices. After step 5813 of FIG. 66 through FIG. 75, where negative MAG sample is collected during MAG separation of a target sample, collected negative MAG sample may be sent to be analyzed by any of: cell counter 903, cell imager 904, flow cytometer or sorter 905, particle counter 5835, particle imager 5836, DNA/RNA sequencer 906. Alternatively, output from cell counter 903, or output from cell imager 904, or output from flow cytometer or sorter 905, or output from particle counter 5835, or output from particle imager 5836, may be further sent to be processed by DNA/RNA sequencer 906 as indicated respectively by paths 936, 946, 956, 5827, and 5828. Negative MAG sample may also be sent into the process of cell genetic modification and cell expansion 5824. DNA/RNA sequencer 906 may contain a PCR step on: (1) DNA/RNA obtained after cell lysing of cells contained within negative MAG sample; and (2) DNA/RNA/molecules contained within negative MAG sample. Prior to DNA/RNA sequencing, PCR may target one or more particular DNA/RNA sequences to amplify their quantity.

FIG. 82 illustrates continued process of positive MAG sample after MAG separation, as in step 408 of FIG. 31, through UFL to remove small entities and passing of large entities into various cell processing devices and procedures. Step 5814 is same as that in FIG. 66 through FIG. 75, where positive MAG sample is collected after MAG separation of a target sample. In step 5829, positive MAG sample of step 5814 is injected into fifth UFL inlet 602, and UFL buffer is injected into inlet 604 of fifth UFL. In step 5830, fifth UFL outputs positive MAG sample containing large entities from outlet 607, and small size entities are removed from large entities and output from fifth UFL outlet 609, and a PZT that attaches to fourth UFL and operates with a specified ultrasound vibration amplitude and frequency to create a standing wave in fifth UFL is assumed to be used. Finally, positive MAG sample containing large entities from outlet 607 of fifth UFL may be sent to be analyzed by any of: cell counter 903, cell imager 904, flow cytometer or sorter 905, DNA/RNA sequencer 906. Alternatively, output from cell counter 903, or output from cell imager 904, or output from flow cytometer or sorter 905, may be further sent to be processed by DNA/RNA sequencer 906 as indicated respectively by paths 936, 946, and 956. Positive MAG sample containing large entities from outlet 607 of fifth UFL in step 5830 may also be sent into the process of cell genetic modification and cell expansion 5824. DNA/RNA sequencer 906 may contain a PCR step on DNA/RNA obtained after cell lysing of large size entities from outlet 607 of fifth UFL from step 5830 prior to DNA/RNA sequencing, where PCR may target one or more particular DNA/RNA sequences to amplify their quantity.

FIG. 83 illustrates continued process of positive MAG sample after MAG separation, as in step 408 of FIG. 31, through UFL to retrieve small entities and passing of small entities into various molecule or small entity processing devices. After step 5814 of FIG. 66 through FIG. 75, where positive MAG sample is collected after MAG separation of a target sample, in step 5829, positive MAG sample of step 5814 is injected into fifth UFL inlet 602, and UFL buffer is injected into inlet 604 of fifth UFL. In step 5831, fifth UFL outputs positive MAG sample containing large entities from outlet 607, and small size entities including DNA, RNA, molecules, and other small particles bound by magnetic labels are output from fifth UFL outlet 609, and a PZT that attaches to fifth UFL and operates with a specified ultrasound vibration amplitude and frequency to create a standing wave in fifth UFL is assumed to be used. Finally, small size entities from outlet 609 of fifth UFL may be sent to any of: particle counter 5835, particle imager 5836, flow cytometer or sorter 905, DNA/RNA sequencer 906. Alternatively, output from particle counter 5835, or output from particle imager 5836, or output from flow cytometer or sorter 905, may be further sent to be processed by DNA/RNA sequencer 906 as indicated respectively by paths 5827, 5828, and 956. DNA/RNA sequencer 906 may contain a PCR step on small size entities from outlet 609 of fifth UFL from step 5831 prior to DNA/RNA sequencing, where PCR may target one or more particular DNA/RNA sequences to amplify their quantity.

FIG. 84 illustrates entity analysis of positive MAG sample after MAG separation, as in step 407 of FIG. 31, using various analyzing devices. After step 5814 of FIG. 66 through FIG. 75, where positive MAG sample is collected after MAG separation of a target sample, collected positive MAG sample may be sent to be analyzed by any of: cell counter 903, cell imager 904, flow cytometer or sorter 905, particle counter 5835, particle imager 5836, DNA/RNA sequencer 906. Alternatively, output from cell counter 903, or output from cell imager 904, or output from flow cytometer or sorter 905, or output from particle counter 5835, or output from particle imager 5836, may be further sent to be processed by DNA/RNA sequencer 906 as indicated respectively by paths 936, 946, 956, 5827, and 5828. Positive MAG sample may also be sent into the process of cell genetic modification and cell expansion 5824. DNA/RNA sequencer 906 may contain a PCR step on: (1) DNA/RNA obtained after cell lysing of cells contained within positive MAG sample; and (2) DNA/RNA/molecules contained within positive MAG sample, prior to DNA/RNA sequencing, where PCR may target one or more particular DNA/RNA sequences to amplify their quantity.

FIG. 85A illustrates addition of fluorescent labels to specifically bind to target entities within negative MAG sample immediately after negative MAG sample collection. FIG. 85A shows that in step 58131, immediately after step 5813, where negative MAG sample is collected during MAG separation, fluorescent labels, which are hybridized with antibodies or ligands and specifically bind to surface antigens or receptors on target cells or entities, are added into the negative MAG sample, and then negative MAG sample is incubated to form fluorescent labels bound to target cells or entities. Step 58131 may be inserted between step 5813 and step 5822 in FIG. 79 and FIG. 80, or inserted immediately after step 5813 and before devices or processes 903, 904, 905, 906, 5824, 5825, and 5826 in FIG. 81.

FIG. 85B illustrates addition of fluorescent labels to specifically bind to target entities within positive MAG sample immediately after positive MAG sample collection. FIG. 85B shows that in step 58141, immediately after step 5814, where positive MAG sample is collected after MAG separation, fluorescent labels, which are hybridized with antibodies or ligands and specifically bind to surface antigens or receptors on target cells or entities, are added into the positive MAG sample, and then positive MAG sample is incubated to form fluorescent labels bound to target cells or entities. Step 58141 may be inserted between step 5814 and step 5829 in FIG. 82 and FIG. 83, or inserted immediately after step 5814 and before devices or processes 903, 904, 905, 906, 5824, 5825, and 5826 in FIG. 84.

FIG. 86A through FIG. 93 describe methods to achieve pre-symptom early stage tumor detection, especially in asymptomatic tumor patients who are in very early stage, or have not been diagnosed with tumor, or are showing no symptom, or have tumor that is in such infancy or early stage that may not be detected or located by conventional methods, including imaging or blood test. In the description, terms of "cancer" and "tumor" may be used interchangeably and have same meaning.

Malignant tumor, or cancer, is a disease that results from genetic mutation of normal body cells, which become astray from original cell functions, multiply fast, and evade normal cell life cycle of programmed cell death by human immune system. To increase the survival chance of a patient carrying cancer, it is imperative to identify and locate the cancer at the earliest stage possible. In state-of-art medicine practiced today, tumors are still found or identified either after physical identification by imaging methods including ultrasound, X-ray, computerized tomography (CT), magnetic resonance imaging (MRI), or in most cases after patient showing symptoms due to cancer growth. For cancer to be identified by imaging methods or by patient showing symptoms, cancer growth is typically already underway, and in most cases well developed with cancer cells in the body already growing in significant numbers. For certain cancers, for example pancreatic cancer which is typically asymptomatic even in late stages, detection by conventional method would usually be too late to provide meaningful medical intervention. It is desirable, and imperative, to have a cancer detection method that is able to detect occurrence of a cancer, with location of origination, at its infancy stage, where such detection is preferred before cancer's significant growth, and before any statistical possibility of cancer's spreading from a local growth to other parts of body. This detection method is desirable to be administered to a person-under-test through conventional clinical means, for example typical peripheral blood collection and blood test. By achieving pre-symptom early stage cancer detection and knowing with confidence of cancer type and location, medical intervention may provide most effectiveness in removal of cancer cells, significantly increase survival rate, and eventually cure cancer, and at the same time significantly reduces financial and social burden of cancer treatment.

FIG. 86A illustrates first example of cancer treatment. Cancer cell 2002 exhibits surface antigen, ligand or surface marker 2004, which can be used to identity and kill cancer cell 2002 in human body by an immune cell 2001 with a surface anti-body, or receptor 2003 that specifically binds to surface marker 2004, as shown by bond 2034. Immune cell 2001 may be extracted from the person-under-test (PUT), or from a donor person. Immune cell 2001 may be genetically modified after being collected from the PUT or donor to express surface receptor 2003. Immune cell 2001 with antibody 2003 may be expanded or cultivated in ex vivo environment. Immune cell 2001 may be engineered to suppress, or evade, immune system response of the PUT if immune cell is collected from donor. In practice, immune cells 2001 with antibody 2003 may be administered to PUT with blood infusion, where immune cells 2001 will then find and bind to cancer cells 2002 in vivo through antibody-antigen bond 2034 between antibody 2003 and marker 004 and kill the cancer cells 2002. For example, cell 2001 may be a type of ex vivo engineered chimeric antigen receptor T cell (CAR-T) with receptor 2003 being chimeric antigen receptor (CAR) that targets cancer cell 2002 which has a surface marker 2004. Receptor 2003 may be any of, but not limited to, CD19, CD20, CD22, CD30, ROR1, κ light chain, CD123, CD33, CD133, CD138, and B-cell maturation antigen.

FIG. 86B illustrates second example of cancer treatment. In PUT, the person's internal immune cell 2007, for example a T cell, functions to identify cells which need to be terminated as a normal cell life cycle. For a normal cell, immune cell 2007 forms receptor 2051 to antigen 2052 bond, which enables immune cell 2007 to terminate a normal cell at end of life cycle of the normal cell. Receptor 2501 may include T-cell receptor (TCR), CD 28. However, cancer cell 2002 evades such programmed death from immune cell 2007 by forming another ligand 2054 to receptor 2053 bond with immune cell 2007, which effectively disables the receptor 2051 to antigen 2052 bond that functions to terminate the cancer cell 2002. For example, ligand 2054 and receptor 2053 may be PD-L1 and PD-1, respectively. In FIG. 86B method, antibody 2056 or antigen 2055 may be administered to PUT, such that antibody 2056 may bind to ligand 2054 and antigen 2055 may bind to receptor 2053 in vivo of PUT body, causing effective disconnection of receptor 2053 to ligand 2054 bond, and making termination of the cancer cell 2002 by the immune cell 2007 possible through receptor 2051 to antigen 2052 bond.

FIG. 86C illustrates third example of cancer treatment. In FIG. 86C method, part of immune system cells, for example dendritic cell 2008, may be inserted with cancer cell 2002 RNA or antigen ex vivo, so that cell 2008 may express cancer 2008 surface antigen 2004. When dendritic cell 2008 with surface antigen 2004 is injected into PUT as in path 2009, immune cell 2007 of PUT, for example T cell, may be trained or directed as in path 2010 by the dendritic cell 2008 to recognize the expressed cancer antigen 2004 with expressing corresponding receptor 2003 on immune cell 2007. Immune cell 2007 then is able to recognize cancer cell 2002 in PUT with receptor 2003 to antigen 2004 binding 2034, and subsequently terminate cancer cell 2002.

During termination of cancer cell 2002 in FIG. 86A, FIG. 86B and FIG. 86C, lysis of cancer cell 2002 occurs and genetic material, including tumor DNA and RNA, within cancer cell 2002 is released and will finally enter blood stream of PUT. In this invention, cell 2001 with receptor 2003 of FIG. 86A, antibody 2056 and antigen 2055 of FIG. 86B, cell 2008 with antigen 2004 of FIG. 86C, will be categorially referred to as "anti-tumor agent", which may be administered externally to a PUT and causing a target type of cancer cell 2002, if existing in PUT, to terminate and release genetic material into blood stream of PUT.

FIG. 87 illustrates first method of this invention to achieve pre-symptom early stage tumor detection, which includes the sequential steps of: (step 1001) administer anti-tumor agent to a person-under-test (PUT) to cause termination and lysis of target tumor cells, if existing in PUT, and release of genetic material into blood stream of PUT; (step 1002) collect peripheral blood from PUT; (step 1003) obtain cell-free plasma from the collected peripheral blood; (step 1004) perform PCR on the cell-free plasma to amplify quantity of known DNA or RNA sequences that identify target tumor cells, resulting in PCR sample; (step 1005) perform DNA or RNA sequencing on PCR sample and ascertain existence of known DNA or RNA sequence that identifies target tumor cells.

In step 1001 anti-tumor agent may be one of, or a combination of, anti-tumor agents described in FIG. 86A, FIG. 86B and FIG. 86C. Anti-tumor agent may be in sufficiently small amount that does not eliminate target tumor cells in PUT, but will cause lysis of a plurality of target tumor cells to release genetic material to be collected in step 1003, amplified in step 1004 and detected in step 1005. With anti-tumor agent being in sufficiently small amount, adverse effects of FIG. 86A, FIG. 86B and FIG. 86C processes, including cytokine release syndrome, neurotoxicity, or off-tumor aplasia, may be limited to not causing clinical conditions of PUT requiring medical attention. FIG. 87 method implies that the DNA or RNA sequencing of step 1004 and step 1005 is generic to the type of target tumor cells and is independent of PUT.

PUT of FIG. 87 may be a person without prior history of tumor, or without showing symptom of tumor, or without showing any physical sign or results of tumor through conventional medical examination methods. PUT may be a person at risk of target tumor, for example due to genetic mutation, family history, age, environment, or occupation. PUT may be a person who has been treated for target tumor, but needs monitor of recurrence of target tumor. PUT may or may not carry target tumor cells. In the case that step 1005 confirms existence of known DNA or RNA sequence that identifies target tumor cells, it may be concluded that PUT carries target tumor, where the amount of DNA or RNA detected in step 1005 may be used to project stage and severity of tumor in PUT. Due to the specificity of known DNA or RNA sequence that identifies target tumor, existence of such DNA or RNA may also confirm simultaneously most probable location of occurrence of such tumor when PUT is a pre-symptom and very early stage patient. In the case that step 1005 does not detect known DNA or RNA sequence that identifies target tumor cells, or does not detect such DNA or RNA sequence at an amount that is above a confidence threshold value, it may be concluded that PUT does not carry target tumor.

In practice, a time lapse may be needed after administering anti-tumor agent in step 1001, and before tumor genetic material may be released into blood stream of PUT after tumor cell lysis for collection in step 1002. Therefore, a scheduled waiting period, or a peripheral blood collection time window, may be implemented between step 1001 and step 1002. Said scheduled waiting period may be between 15 minutes and 30 minutes in one embodiment, between 30 minutes and 1 hour in another embodiment, between 1 hour and 2 hours in yet another embodiment, between 2 hours and 6 hours in yet another embodiment, between 6 hours and 12 hours in yet another embodiment, between 12 hours and 24 hours in yet another embodiment, between 1 day and 2 days in yet another embodiment, between 2 days and 4 days in yet another embodiment, between 4 days and 10 days in yet another embodiment, between 10 days and 15 days in yet another embodiment, and between 15 days and 30 days in yet another embodiment. Said collection time window has a start time and an end time after the time of said administering of said anti-tumor agent, where the start time and end time may respectively be 15 minutes and 30 minutes in one embodiment, 30 minutes and 1 hour in another embodiment, 30 minutes and 1 hour in yet another embodiment, 1 hour and 2 hours in yet another embodiment, 2 hours and 6 hours in yet another embodiment, 6 hours and 12 hours in yet another embodiment, 12 hours and 24 hours in yet another embodiment, 1 day and 2 days in yet another embodiment, 2 days and 4 days in yet another embodiment, 4 days and 10 days in yet another embodiment, 10 days and 15 days in yet another embodiment, and 15 days and 30 days in yet another embodiment. Additionally, a multiple-cycled repeated step 1002 to step 1005 process may be performed as shown by procedure 1009, where procedure 1009 may include a scheduled waiting period, such that existence of target tumor cells in PUT may be monitored and ascertained during an extended amount of time for a more complete anti-tumor agent action on target tumor cells. Said scheduled waiting period in procedure 1009 may be between 6 hours and 12 hours in one embodiment, between 12 hours and 24 hours in another embodiment, between 1 day and 2 days in yet another embodiment, between 2 days and 4 days in yet another embodiment, between 4 days and 10 days in yet another embodiment, between 10 days and 15 days in yet another embodiment, and between 15 days and 30 days in yet another embodiment.

Advantages of FIG. 87 method are: (1) PUT may be a person carrying tumor at early stage but without tumor indication in conventional tests, thus enabling pre-symptom early stage cancer intervention; (2) by administering anti-tumor agent targeting a specific tumor, for example breast cancer, pancreatic cancer, lung cancer, detection of corresponding tumor DNA or RNA signal also confirms type and origin of such cancer, enabling fast and targeted treatment; (3) by administering anti-tumor agent targeting a specific tumor, released DNA or RNA in blood stream may spike in a well-defined time window afterwards, which provides an enhanced signal-to-noise ratio (SNR) of tumor DNA or RNA detection and may enable high sensitivity and high accuracy detection even when the actual amount of tumor cells in PUT is still much lower than being detectable by conventional tests; (4) this method may allow a panel of multiple anti-tumor agents targeting multiple types of tumors being applied simultaneously to PUT to detect existence of multiple types of target tumors at the same time, as described in FIG. 89. Although FIG. 87 method targets pre-symptom early stage tumor, it is possible to implement same method against dormant tumor, which may not show fast growth, but has genetic mutation that has high risk of malignancy.

FIG. 88 illustrates a second method of tumor detection. FIG. 88 process is same as FIG. 87 process in every other aspect, except that: after step 1001, instead of collecting peripheral blood as in step 1002 of FIG. 87, step 1006 of FIG. 88 collects body fluid from around organ of PUT where target tumor may occur, in which such body fluid would be where released DNA or RNA by lysed target tumor cells may be found, for example urine for bladder cancer, or prostate secretion for prostate cancer; then step 1007 replaces step 1003 of FIG. 87, and obtains cell-free fluid from the collected body fluid of step 1006; and then step 108 replaces step 1004 of FIG. 87, and performs PCR on cell-free fluid to amplify quantity of known DNA or RNA sequences that identify target tumor cells, resulting in PCR sample. PCR sample of step 1008 then undergoes same step 1005 as in FIG. 87.

FIG. 89 illustrates a third method of tumor detection. FIG. 89 process is same as FIG. 87 process, but expanding tumor detection from one target tumor to multiple types of tumor. FIG. 89 process includes the sequential steps of: (step 3001) administer anti-tumor agents to PUT to cause lysis of a plurality types of target tumor cells to release genetic material into blood stream of PUT; (step 1002) collect peripheral blood from PUT; (step 1003) obtain cell-free plasma from the collected peripheral blood; (step 3004) perform PCR on the cell-free plasma to amplify quantity of known DNA or RNA sequences that identify each type of the plurality types of target tumor cells, resulting in PCR sample; (step 3005) perform DNA or RNA sequencing on PCR sample and ascertain existence of known DNA or RNA sequence that identifies each type of the plurality types of target tumor cells. In FIG. 89, ascertaining existence of any of the multiple types of tumors may be performed at same time in PUT. Anti-tumor agents in step 3001 may be one of anti-tumor agents described in FIG. 86A, FIG. 86B and FIG. 86C, which lyses multiple types of tumors simultaneously. Anti-tumor agents in step 3001 may be a combination of more than one anti-tumor agents described in FIG. 86A, FIG. 86B and FIG. 86C, where each different anti-tumor agent lyses one type, or a sub-set of types, of the plurality types of tumors. Steps 1002 and 1003 of FIG. 89 may be replaced by steps 1006 and 1007 of FIG. 88 to collect body fluids, where step 3004 may correspondingly be updated with performing PCR on cell-free fluid from step 1007.

FIG. 90, FIG. 91, and FIG. 92 illustrate embodiments of process flows to utilize MAG and UFL devices to obtain cell-free plasma from peripheral blood. For simplicity of description, terms UFL and MAG are used in these figures for explanation. However, UFL may be any of UFL 600, 620, 630, 640 of FIG. 40A, FIG. 41A, FIG. 42A, FIG. 43, while MAG may be any of MAG 121, 122, 123, 124, 124,125, 126, 127, 128, 129 with corresponding channel types as described in prior figures without limitation and without sacrifice of performance.

FIG. 90 illustrates embodiment of first process flow to obtain cell-free plasma of step 1003 from collected peripheral blood in step 1002. After collection of peripheral blood in step 1002, peripheral blood may be centrifuged as in step 5001, and result of centrifuge may contain cell-free plasma that may directly achieve step 1003 as indicated by path 5005. Alternatively, after centrifuge step 5001, blood plasma may be depleted of certain blood cells, for example red blood cells, but may not have enough purity for later stage PCR process. Plasma from step 5001 may then be sent along path 5008 to undergo a UFL separation in step 5002, where UFL large entity output contains any remaining cells in plasma, while UFL small entity output contains DNA or RNA and may be more concentrated than plasma from step 5001. In yet another alternative path, peripheral blood from step 1002 may skip step 5001 and directly input into UFL separation step 5002 as shown by path 5007, where the UFL separates cells through large entity output while maintaining DNA and RNA in small entity output. Small entity output from UFL separation of step 5002 may then be used towards step 1003 as cell-free plasma according to path 5009. Further alternatively, magnetic labels hybridized with antibodies or ligands may be added to the plasma from UFL small entity output of step 5002 to bind to DNA or RNA within the plasma as in step 5003. MAG device may be used to separate the DNA and RNA bound with the magnetic labels in step 5004, and the resulting positive MAG sample containing DNA and RNA may then be regarded as the cell-free plasma of step 1003.

FIG. 91 illustrates embodiment of second process flow to obtain cell-free plasma of step 1003 from collected peripheral blood in step 1002. After collection of peripheral blood in step 1002, peripheral blood may be centrifuged as in step 5001, and resulting blood plasma may be depleted of certain blood cells, for example red blood cells. Then in step 5003, magnetic labels hybridized with antibodies or ligands may be added to the plasma from step 5001 to bind to DNA or RNA within the plasma. Alternatively, peripheral blood from step 1002 may be used directly in step 5003 without step 5001 centrifuge as shown by path 5015, and magnetic labels bind to the DNA or RNA in peripheral blood in step 5003. After step 5003, MAG device may be used to separate the DNA and RNA bound with the magnetic labels in step 5004, and the resulting positive MAG sample containing DNA and RNA may be regarded as the cell-free plasma of step 1003 as indicated by path 5013. Further alternatively, positive MAG sample of step 5004 may undergo a UFL separation in step 5002, where UFL large entity output contains any remaining cells in plasma, while UFL small entity output contains DNA or RNA that are bound with magnetic labels. Small entity output from UFL separation of step 5002 may then be used towards step 1003 as cell-free plasma according to path 5017.

FIG. 92 illustrates embodiment of third process flow to obtain cell-free plasma of step 1003 from collected peripheral blood in step 1002. After collection of peripheral blood in step 1002, peripheral blood may be centrifuged as in step 5001, and resulting blood plasma may be depleted of certain blood cells, for example red blood cells. Then in step 5023, magnetic labels hybridized with antibodies or ligands may be added to the plasma from step 5001 to bind to cells within the plasma. Alternatively, peripheral blood from step 1002 may be used directly in step 5003 without step 5001 centrifuge as shown by path 5015, and magnetic labels bind to the cells in peripheral blood in step 5023. After step 5023, MAG device may be used to separate the cells bound with the magnetic labels in step 5024 from the plasma that contains DNA or RNA, and the resulting negative MAG sample containing DNA and RNA may be regarded as the cell-free plasma of step 1003 as indicated by path 5013. Alternatively, negative MAG sample of step 5024 may undergo a UFL separation in step 5002, where UFL large entity output contains any remaining cells in plasma from step 5023, while UFL small entity output contains DNA or RNA. Small entity output from UFL separation of step 5002 may then be used towards step 1003 as cell-free plasma according to path 5017.

FIG. 93 illustrates a method to extend method of FIG. 89 for anti-aging purpose. For conditions relating to aging, for example Alzheimer's Disease, dementia, osteoporosis, and arthritis, human growth hormone or other anti-aging agents may be used to help cell growth to delay or alleviate symptom occurrence of the conditions. For aging in general, human growth hormone or other anti-aging agents may help to improve overall body conditions due to tissue or cell replenishment. However, in using such anti-aging agents, a possible limitation is increased risk of tumor occurrence. Due to the nature of tumor cells being fast growth and evasive to cell death by immune system, administering human growth hormone or anti-aging agent in presence of any tumor, especially pre-symptom tumor or dormant tumor, such hormone or agent may incur growth of these tumor cells. Thus, for low risk implementation of human growth hormone or anti-aging agent, a tumor free condition of PUT is desired. FIG. 93 initial flow steps of 3001, 1002, 1003, 3004 and 3005 are identical to FIG. 89, where existence of any of the multiple types of target tumors in PUT may be ascertained in step 3005. In FIG. 93, after step 3005, in the case that at least one type of tumor is confirmed to exist in PUT as in judgement 4001, corresponding tumor treatment may be performed in step 4002. After step 4002, another cycle of process from step 3001 to step 3005 may be performed to ascertain tumor absence after treatment of step 4002. In the case that step 3005 finds no tumor existence as in judgement 4003, growth hormone or anti-aging agent may be administered to the PUT as in step 4004. After step 4004, another cycle of step 3001 through step 3005 may be performed to ascertain no tumor was promoted by the step

4004. Flow from step 3001 to step 4004 may be repeated as many cycles as needed to achieve aging related condition treatment goal.

While the current invention has been shown and described with reference to certain embodiments, it is to be understood that those skilled in the art will no doubt devise certain alterations and modifications thereto which nevertheless include the true spirit and scope of the current invention. Thus the scope of the invention should be determined by the appended claims and their legal equivalents, rather than by examples given.

What is claimed is:

1. A magnetic device comprising:
   a soft magnetic center pole having a bottom end and a tapered tip end;
   first and second soft magnetic side poles disposed on opposite sides of the soft magnetic center pole and respectively having first and second bottom ends, the first and second soft magnetic side poles respectively having first and second top ends that are bent towards the soft magnetic center pole and are positioned above the tapered tip end;
   a magnetic flux source generating a magnetic flux in the soft magnetic center pole and the first and second soft magnetic side poles;
   a channel configured to flow a sample fluid containing biological entities, the channel being disposed in a gap formed between the tapered tip end and the first and second top ends,
   wherein the magnetic flux is concentrated from the bottom end to the tapered tip end of the soft magnetic center pole and is divided between the first and second top ends.

2. The magnetic device of claim 1, wherein the magnetic flux forms a first flux closure between the soft magnetic center pole and the first soft magnetic side pole and a second flux closure between the soft magnetic center pole and the second soft magnetic side pole.

3. The magnetic device of claim 1, wherein the magnetic flux source includes a soft magnetic shield and a permanent magnet disposed between the soft magnetic shield and the bottom end of the soft magnetic center pole, wherein the first and second bottom ends are disposed above the soft magnetic shield.

4. The magnetic device of claim 1, wherein the magnetic flux source includes a soft magnetic shield, a first permanent magnet disposed between the first bottom end and the soft magnetic shield, a second permanent magnet disposed between the second bottom end and the soft magnetic shield, and a third permanent magnet disposed between the bottom end of the soft magnetic center pole and the soft magnetic shield, wherein a magnetization direction of the third permanent magnet is opposite to magnetization directions of the first and second permanent magnets.

5. The magnetic device of claim 1, wherein the magnetic flux source includes a first permanent magnet disposed beneath the first bottom end, a second permanent magnet disposed beneath the second bottom end, and a third permanent magnet disposed beneath the bottom end of the soft magnetic center pole, wherein a magnetization direction of the third permanent magnet is opposite to magnetization directions of the first and second permanent magnets.

6. The magnetic device of claim 1, wherein the magnetic flux source includes a first permanent magnet disposed between the first soft magnetic side pole and the soft magnetic center pole and a second permanent magnet disposed between the second soft magnetic side pole and the soft magnetic center pole, wherein the first and second permanent magnets have opposite magnetization directions.

7. The magnetic device of claim 1, wherein the tapered tip end has a substantially higher magnetic flux density than the first and second top ends.

8. The magnetic device of claim 1, wherein the channel is in contact with at least one of the tapered tip end and the first and second top ends.

9. The magnetic device of claim 1, wherein the channel comprises a flexible tube.

10. The magnetic device of claim 1, further comprising a channel holder attached to the channel opposite the tapered tip end of the soft magnetic center pole.

11. The magnetic device of claim 10, wherein a cross section of the channel is flexible and the channel is compressed between the channel holder, the tapered tip end, and the first and second top ends.

12. The magnetic device of claim 1, wherein the soft magnetic center pole and the first and second soft magnetic side poles extend along a direction perpendicular to a cross section of the channel.

13. The magnetic device of claim 1, wherein the first and second top ends arch over the soft magnetic center pole and have a pincers shape.

14. A method for processing biological entities comprising the steps of:
    flowing a fluid sample containing biological entities attached with magnetic labels through a channel positioned in close proximity to a magnetic separation device to form a magnetic conglomerate on an internal surface of the channel;
    detaching the channel from the magnetic separation device; and
    vibrating the channel to dissociate the magnetic conglomerate,
    wherein the magnetic separation device comprises a soft magnetic center pole having a tapered tip end and two soft magnetic side poles disposed on opposite sides of the soft magnetic center pole, the two soft magnetic side poles respectively having two top ends that that are bent towards the soft magnetic center pole and are positioned above the tapered tip end.

15. The method of claim 14, wherein the channel is disposed in a gap formed between the tapered tip end and the two top ends.

16. The method of claim 14, wherein the channel comprises a flexible tube.

17. The method of claim 14, wherein a cross section of the channel is flexible and conforms to a gap formed between the tapered tip end and the two top ends under applied pressure.

18. The method of claim 14, wherein the step of vibrating the channel is carried out by a motor producing mechanical vibration.

19. The method of claim 14, wherein the step of vibrating the channel is carried out by a piezoelectric transducer producing ultrasound vibration.

20. A method for processing biological entities comprising the steps of:
    flowing a fluid sample containing biological entities attached with magnetic labels through a channel positioned in close proximity to a magnetic separation device to form a magnetic conglomerate on an internal surface of the channel;
    detaching the channel from the magnetic separation device; and deforming the channel by stretching, twisting, or compression to dissociate the magnetic conglomerate,
wherein the magnetic separation device comprises a soft magnetic center pole having a tapered tip end and two soft magnetic side poles disposed on opposite sides of the soft magnetic center pole, the two soft magnetic side poles respectively having two top ends that that are bent towards the soft magnetic center pole and are positioned above the tapered tip end.

* * * * *